(12) United States Patent
Judson et al.

(10) Patent No.: US 6,931,326 B1
(45) Date of Patent: Aug. 16, 2005

(54) METHODS FOR OBTAINING AND USING HAPLOTYPE DATA

(75) Inventors: Richard S. Judson, Guilford, CT (US); J. Claiborne Stephens, Guilford, CT (US); Andreas K. Windemuth, Woodbridge, CT (US)

(73) Assignee: Genaissance Pharmaceuticals, Inc., New Haven, CT (US)

( * ) Notice: Subject to any disclaimer, the term of this patent is extended or adjusted under 35 U.S.C. 154(b) by 434 days.

(21) Appl. No.: 10/019,342

(22) Filed: Dec. 21, 2001

Related U.S. Application Data

(63) Continuation of application No. PCT/US00/17540, filed on Jun. 26, 2000.
(60) Provisional application No. 60/141,521.

(51) Int. Cl.[7] .................. G06F 19/00; G01N 33/48; C12Q 1/68
(52) U.S. Cl. .................. 702/20; 702/19; 435/6
(58) Field of Search .................. 702/19, 20; 435/6

(56) References Cited

U.S. PATENT DOCUMENTS

| | | |
|---|---|---|
| 4,706,192 A | 11/1987 | Nasu et al. |
| 5,096,557 A | 3/1992 | Simons |
| 5,121,320 A | 6/1992 | Aoki et al. |
| 5,187,775 A | 2/1993 | Schroeder et al. |
| 5,192,659 A | 3/1993 | Simons |
| 5,297,288 A | 3/1994 | Hemminger et al. |
| 5,361,351 A | 11/1994 | Lenkov et al. |
| 5,502,773 A | 3/1996 | Tibbetts et al. |
| 5,559,944 A | 9/1996 | Ono |
| 5,561,754 A | 10/1996 | Oliver et al. |
| 5,612,179 A | 3/1997 | Simons |
| 5,618,672 A | 4/1997 | Stodola et al. |
| 5,632,041 A | 5/1997 | Peterson et al. |
| 5,648,482 A | 7/1997 | Meyer |
| 5,724,253 A | 3/1998 | Skovira |
| 5,762,876 A | 6/1998 | Lincoln et al. |
| 5,773,220 A | 6/1998 | Dekosky et al. |
| 5,789,568 A | 8/1998 | Simons |
| 5,811,235 A | 9/1998 | Jeffreys |
| 5,811,239 A | 9/1998 | Frayne |
| 5,834,183 A | 11/1998 | Orr et al. |
| 5,834,189 A | 11/1998 | Stevens et al. |
| 5,851,762 A | 12/1998 | Simons |
| 5,853,989 A | 12/1998 | Jeffreys et al. |
| 5,858,659 A | 1/1999 | Sapolsky et al. |
| 5,862,304 A | 1/1999 | Ravdin et al. |
| 5,866,404 A | 2/1999 | Bradshaw et al. |
| 5,867,402 A | 2/1999 | Schneider et al. |
| 5,874,256 A | 2/1999 | Bertina et al. |
| 5,876,933 A | 3/1999 | Perlin |
| 5,885,776 A | 3/1999 | Stone et al. |
| 5,891,633 A | 4/1999 | Gonzalez et al. |
| 5,912,120 A | 6/1999 | Goldstein et al. |
| 5,953,727 A | 9/1999 | Maslyn et al. |
| 5,966,711 A | 10/1999 | Adams |
| 5,966,712 A | 10/1999 | Sabatini et al. |
| 5,970,500 A | 10/1999 | Sabatini et al. |
| 5,972,604 A | 10/1999 | Santamaria et al. |
| 5,972,614 A | 10/1999 | Ruano et al. |
| 6,020,126 A | 2/2000 | Carlsson et al. |
| 6,022,683 A | 2/2000 | Poirer |
| 6,023,659 A | 2/2000 | Seilhamer et al. |
| 6,030,778 A | 2/2000 | Acton et al. |
| 6,043,040 A | 3/2000 | Acton |
| 6,081,786 A | 6/2000 | Barry et al. |
| 6,094,626 A | 7/2000 | Kephart et al. |
| 6,141,657 A | 10/2000 | Rothberg et al. |
| 6,175,830 B1 | 1/2001 | Maynard |
| 6,178,382 B1 | 1/2001 | Roederer et al. |
| 6,185,561 B1 | 2/2001 | Balaban et al. |
| 6,188,988 B1 | 2/2001 | Barry et al. |
| 6,189,013 B1 | 2/2001 | Maslyn et al. |
| 6,214,556 B1 | 4/2001 | Olek et al. |
| 6,219,674 B1 | 4/2001 | Classen |
| 6,222,559 B1 | 4/2001 | Asano et al. |
| 6,223,128 B1 | 4/2001 | Allex et al. |
| 6,537,759 B1 | 3/2003 | Stanton, Jr. |
| 6,664,062 B1 | 12/2003 | Stanton, Jr. |

FOREIGN PATENT DOCUMENTS

| | | |
|---|---|---|
| EP | 0336560 A2 | 10/1989 |
| EP | 0336560 A3 | 10/1989 |
| EP | 0404682 B1 | 12/1990 |
| EP | 0404682 A2 | 12/1990 |
| EP | 0408188 A3 | 1/1991 |
| EP | 0408188 B1 | 1/1991 |
| EP | 0408188 A2 | 1/1991 |
| EP | 0449494 A2 | 10/1991 |
| EP | 0449494 A3 | 10/1991 |
| EP | 0474944 A2 | 3/1992 |
| EP | 0481286 A2 | 4/1992 |
| EP | 0245466 B1 | 5/1994 |
| EP | 0612846 A1 | 8/1994 |
| EP | 0336560 B1 | 11/1994 |
| EP | 0494907 B1 | 5/1996 |
| EP | 0481286 B1 | 4/1997 |

(Continued)

OTHER PUBLICATIONS

Beaudet, Arthur I., "*1998 ASHG Presidential Address—Making Genomic Medicine a Reality*", American Journal of Human Genetics, vol. 64, pp. 1–13, 1999.

(Continued)

Primary Examiner—Marianne P. Allen

(57) ABSTRACT

Methods, computer program(s) and database(s) to analyze and make use of gene haplotype information. These include methods, program, and database to find and measure the frequency of haplotypes in the general population; methods, program, and database to find correlation's between an individual's haplotypes or genotypes and a clinical outcome; methods, program, and database to predict an individual's haplotypes from the individual's genotype for a gene; and methods, program, and database to predict an individual's clinical response to a treatment based on the individual's genotype or haplotype.

37 Claims, 62 Drawing Sheets

FOREIGN PATENT DOCUMENTS

| | | |
|---|---|---|
| EP | 0474944 B1 | 7/1997 |
| EP | 0812922 A2 | 12/1997 |
| EP | 0673523 B1 | 2/1999 |
| EP | 0449494 B1 | 8/1999 |
| EP | 0612846 B1 | 8/2000 |
| WO | WO 87/02802 | 5/1987 |
| WO | WO 91/05302 | 4/1991 |
| WO | WO 92/01066 | 1/1992 |
| WO | WO 95/10805 | 4/1995 |
| WO | WO 95/17524 | 6/1995 |
| WO | WO 97/40462 | 10/1997 |
| WO | WO 99/04038 A | 1/1999 |
| WO | WO 99/05323 | 2/1999 |
| WO | WO 99/05324 | 2/1999 |
| WO | WO 99/11822 | 3/1999 |
| WO | WO 99/54500 | 10/1999 |
| WO | WO 99/57308 | 11/1999 |
| WO | WO 99/64626 | 12/1999 |
| WO | WO 99/64627 | 12/1999 |
| WO | WO 00/33161 | 6/2000 |
| WO | WO 00/50639 A3 | 8/2000 |
| WO | WO 00/50639 A2 | 8/2000 |
| WO | WO 01/91026 | 11/2001 |
| WO | WO 02/064617 | 8/2002 |

OTHER PUBLICATIONS

Carter et al., "Genetic Control of Drug–Induced Recovery from Murine Visceral Leishmaniasis", J. Pharm. Pharmacol. 1994, 45:795–798.

Cashman, Siobhan M. et al., "The Irish Cystic Fibrosis Database", Journal of Medical Genetics, vol. 32, pp. 972–975, Jul. 1995.

Chakraborty, R, "A Class of Population Genetic Questions Formulated as the Generalized Occupancy Problem", Genetics, Jul. 1993, 134:953–958.

Chiano et al, "Fine Genetic Mapping Using Haplotype Analysis and the Missing Data Problem", Ann. Hum. Genet., 1998, 62:55–60.

Clark, Andrew G. et al., "Haplotype Structure and Population Genetic Inferences From Nucleotide–Sequence Variation in Human Lipoprotein Lipase", American Journal of Human Genetics, vol. 63, pp. 595–612, 1998.

Clark, Andrew G., "Inference of Haplotypes from PCR–amplified Samples of Diploid Populations", Mol. Biol. Evol., 7(2):111–122, 1990.

Cooper, Gillian et al., "Network Analysis of Human Y Microsatellite Haplotypes", Human Molecular Genetics, vol. 5, No. 11, pp. 1759–1766, 1996.

Dempster et al., "Maximum Likelihood from Incomplete Data via the EM Algorithm", J. Statistical Society, vol. 39, No. 1, pp. 1–38, 1977.

Drefus et al. "Etude des Reactions Croisees des Antigenes HLA A et B Chez 63 Patients Atteints de Polyarthrite Rhumatoide", Revuo du Rhumatisme, 1984, 51(4), 197–202.

Drysdale, "Complex promoter and coding region beta 2–adrenergic receptor haplotypes alter receptor expression and predict in vivo responsiveness", 2000, Proc. Natl. Acad. Sci. 97(19):10483–8.

Excoffier et al., "Incorporating Genotypes of Relatives into a Test of Linkage Disequilibrium", Am. J. Hum. Genet., 62:171–180, 1998.

Excoffier et al. "Maximum–Likelihood Esxtimation of Molecular Haplotype Frequencies in a Diploid Populations", Mol. Biol. Envol., 1995, 12(5):921–927.

Fisher, Lloyd D. et al., "Biostatistics: A Methodology for the Health Sciences", pp. 345–495, 692–762, John Wiley & Sons, Inc.

Gene et al., "Haplotype Frequencies of Eight Y–chromosome STR loci in Barcelona (North–East Spain)", International Journal of Legal Medicine, vol. 112, pp. 403–405, 1999.

Hartl, Daniel L. et al., "Genetic and Phenotypic Variation", Principles of Population Genetics, pp. 37–109, Singuer Associates, Inc., 3 ed.

Hawley et al., "HAPLO: A Program Using the EM Algorithm to Estimate the Frequencies of Multi–site Haplotypes", J. of Heredity, 86(5), pp. 409–411, 1995.

Hill et al., "Human Genetic Variation and Its Impact on Public Health and Medicine", pp. 62–74.

Hill, "Tests for Association of Gene Frequencies at Several LOCI in Random Mating Diploid Populations", Biometrics, 31, 881–888, 1975.

Hoang, Liem et al., "PAH Mutation Analysis Consortium Database: A Database for Disease–Producing and Other Allelio Variation at the Human PAH Locus", Nucleic Acids Research, vol. 24, No. 1, pp. 127–131, 1996.

Jackson et al., "Pharmacokinetic Pharmacogenetic Modelling in the Detection of Polymorphisims in Xenobiotic Metabolism", 1990, Ann. Occup. Hyg. 34(6):653–662.

Judosn et al., "The Predictive Power of Haplotypes in Clinical Response", 2000, pp. 1–12.

Judson, Richard, "Genetic Algorithms and Their Use in Chemistry", Reviews in Computational Chemistry, vol. 10, pp. 1–66, 1997.

Kalow et al., "The Science of Pharmacological Variability; An essay", Clin. Pharma, & Therapeutics, vol. 66, No. 5, pp. 445–447, 1999.

Kardia et al., "An Evolutionary Perspective on the Genetic Architecture of Susceptibility to Cardiovascular Disease", pp. 231–245.

Kleyn, Patrick W. et al., "Genetic Variation as a Guide to Drug Development", Science, vol. 281. pp. 1820–1821, Sep. 18, 1998.

Kwok et al., "Single Nucleotide Polymorphism Libraries: Why and How are We Building Them?", Mol. Med. Today, 1999, vol. 5, pp. 538–543.

Layton et al., "The Therapeutic Response to D–Penicillamine in Rheumatoid Arthritis: Influence of Glutatione S–transferase Polymorphisms", Rheumatology, 1999, 38:43–47.

Long et al., "An E–M Algorithm and Testing Strategy for Multiple–Locus Haplotypes", Am. J. Hum. Genet., 56:799–810, 1995.

MacLean et al., "Estimation of Myriad Haplotype Frequencies", Genetic Boidemiology, 2:263–272, 1985.

Magon, "Pharmacogenetic interactions in G6PD deficiency and development of an in vitro test to predict a drug's hemolytic potential", 1981, Prog. Clin. Biol. Res., 55:709–24.

Matise, T.C., "Genome Scanning for Complex Disease Genes Using the Transmission/Disequilibrium Test and Haplotype–based Haplotype Relative Risk", Genetic Epidemiology, vol. 12, pp. 641–645, 1995.

Meyer, Urs A., "Medically Relevant Genetic Variation of Drug Effects", pp. 41–49.

Michalatos–BeLion et al. "Molecular Haplotyping of Genetic Markers 10 kb Apart by Allele–Specific Long Range PCR", Nucleic Acids Research, 1996, 24(23):4841–4843.

Mori, Motomi et al., "Computer Program to Predict Likelihood of Finding an HLA–Matched Donor: Methodology, Validation, and Application", Biology of Blood and Marrow Transplantation, vol. 2, pp. 134–144, Oct. 1996.

Mori, Motomi et al., "HLA Gene and Haplotype Frequencies in the North American Population", Transplantation, vol. 64, No. 7, pp. 1017–1027, Oct. 15, 1997.

Neuman et al. "A Bit about Haplotypes: Using Binary Digital to Code Tightly Linked Loci", Hum. Hered.,1994 44:241–247.

Niu et al, "Bayesian Haplotype Inference for Multiple Linked Single–Nucleotide Polymorphisms", Am. J. Hum. Genet., 2002, 70:157–169.

Olsen et al., "Design and Sample–Size Considerations in the Detection of Linkage Disequilibrium with a Disease Locus", Am. J. Hum. Genet. 1994, 55:574–580.

Perlin, Mark et al., "Toward Fully Automated Genotyping: Allele Assignment, Pedigree Construction, Phase Determination, and Recombination Detection in Duchenne Muscular Dystrophy", American Journal of Human Genetics, vol. 55, pp. 777–787, Jun. 1994.

Press, William H. et al, "Numerical Recipes in C; The Art of Scientific Computing", pp. 394–455, Cambridge University Press, 2 ed.

Rich, Blaine et al., "Artificial Intelligence", pp. 514–519, McGraw–Hill, Inc., 2 ed.

Ruano et al. "Haplotype of Multiple Polymorphisms Resolved by Enzymatic Amplification of Single DNA Molecules", Aug. 1990, Proc. Natl. Acad, Sci., vol. 87, pp. 6296–6300.

R & D Directions Staff, "Beyond Genomics", R & D Directions, Apr. 1999 pp. 40–44.

Slatkin et al., "Testing for Linkage Disequilibrium in Genotypic Data Using the Expectation–Maximization Algorithm", Heredity, 76:377–383, 1996.

Staessen et al., "M235T Angiotensinogen Gene Polymorphism And Cardiovascular Renal Risk", J. Hypertension, Jan. 1999, 17(1):9–17.

J.C. Stephens et al., "Haplotype Variation and Linkage Disequilibrium in 313 Human Genes", Science, 2001.

Stephens, J. Claiborne, "Single–nucleotide Polymorphisms, Haplotypes, and Their Relevance to Pharmacogenetics", Molecular Diagnosis, vol. 4, No. 4, pp. 309–317, Dec. 1999.

Stephens et al., "A New Statistical Method for Hapolotype Reconstruction from Population Data", Am. J. Hum, Genet., 2001, 68:978–989.

Thayer, Ann M., "Bioinformatics for the Masses", C&EN, 19–32, 2000.

Tishkoff S. A. et al, "The Accuracy of Statistical Methods for Estimation of Haplotypes Frequencies: An Example from the CD4 Locus", American Journal of Human Genetics, vol. 67, pp. 518–522, Aug. 2000.

Appleby, "Pharmaceutical Labs Exploring Drugs Tailored to Ethnicity, DNA", Jan. 24, 1999, Las Vegas Review—Journal, Section A, p. 26A.

Birt, "Drugs Industry Predicted to Be 'Microsoft' For the New Millenium", Jun. 1, 1998, Birmingham Post, p. 29.

"Bursting with Innovation", Dec. 1997, Med Ad News.

Craig, "Answers for the Toughest Challenges", Apr. 19, 1999; Forbes, Supplement; Special Advertising Section; Biotechnology, p. 2.

Debaro, "California Spotlight: Incyte plans to conquer DNA mapping within year; Genetics: Part of the plan is to purchase British firm Hexagen for $41 million", Aug. 23, 1998, The Orange County Register, p. K01.

Furuta, "Race to Unlock Genetic Secrets Heats Up in Japan's Laboratories: Analysis of Genes Could Help Create Tailor–Made Medicines", Nov. 16, 1998, The Nikkei Weekly, p. 1.

"Genaissance Raises $10 Million in Private Placement; Accelorates Development of Personalized Medicines Through Pharmacogenomics", Aug. 27, 1998; PR Newswire, Financial News Section.

MacGregor, "Delay is Half The Cure: Nova's Merger With U.S. Firm Steps Up Research Aimed at Postponing Alzheimer's Until It No Longer Matters", Mar. 10, 1999, The Gazette (Montreal), Section D1.

"Mix/Match Analysis of Gene Diversity in Ethnic Cross-–Section Aims at Personalized Medicine", 2001, Bioworld Today, p. 5.

Regalado, "Inventing the Pharmacogenomics Business, Part 1", Sep. 1997, In Vivo the Business & Medicine Report, p. 52.

Sadoc, Wolfgang, "Using Genetic Information to Optimize Drug Therapy", Medscape Pharmacotherapy, 2000.

"Terrapin and Genaissance Establish Research and Development Collaboration Targeting Drug Candidates Based on Estrogen Receptor Modulators Identified in Genomics Research", Feb. 12, 1998, Business Wire.

The Genesis Group, "Will Pharmocogenomic Create a $2 Billion Market?", Jul. 1998, Genesis Report, 8(1); p. 26; 1061–2289.

"Valigon Acquires Berlin–Based Infogon and Phenotype Database", 2000, Worldwide Biotech.

"Variagenics, Inc. Acquires Exclusive Rights To Leading Pharmacogenomic Technologies for Neurological Disorders", Feb. 8, 1999, Canada Newswire.

Yasuhara, "Ethnic factors in evaluation of drug efficacy and safety", Aug. 1994, Nippon Yakurigaku Zasshi, 102(2): 67–78 (English Abstract).

Text of Apr. 17, 2001 press release to: Classen patent No. 6,219,674.

Fisher, LD and Van Belle, G, Biostatistics: A Methodology for the Health Sciences, John Wiley & Sons, Inc. (New York, US), p. 158–161; p. 844–865, (1993).

W. Siedlecki et al., "On automatic feature selection," Int. J. of Pattern Recognition and Artificial Intelligence, vol. 2 (No. 2), p. 197–220, (1988).

A. Jain & D. Zongker, "Feature Selection: Evaluation, Application, and Small Sample Performance," IEEE Transactions on Pattern Analysis and Machine Intelligence, IEEE Comput. Soc USA, vol. 19 (No. 2), p. 153–158, (Feb. 1997).

M. Dash & H. Liu, "Feature Selection for Classification," Intelligent Data Analysis, Elsevier USA, vol. 1 (No. 3), p. 131–156, (1997).

A. Sjalander et al., "p53 germ line haplotypes associated with increased risk for colorectal cancer," Carcinogenesis, vol. 16 (No. 7), p. 1461–1464, (Jul. 1995).

FIG. 3

DecoGen Browser: CYP2D6
File Edit Help

GENAISSANCE PHARMACEUTICAL

Pathways
Gene Description
Gene Structure
mRNA Structure
Protein Structure
HAP Frequencies
Population
Linkage
SNP Distribution
Phylogenetic Tree
Genotype Analysis
Clinical Distribution
Edit Pathway
MultiGene
Clinical Trial Cohorts
Expression
Assay Data
References Gene Description View

| Name | CYP2D6 |
| Definition | Human cytochrome P450 IID6 (CYP2D6) gene |
| Function | Metabolic enzyme |
| Organism | Homo Sapiens |
| Length | 9432 |
| No Features | 13 |
| Population Size | 46 |
| No. Haplotypes | 10 |
| Nucleotide Polymorphism (theta) | 5.6E-4 +/- 3.1E-4 |
| Nucleotide Diversity (pi) | 2.8E-4 +/- 1.8E-4 |

FIG. 8

DecoGen Browser: CYP2D6

File Edit Help

GENAISSANCE PHARMACEUTICAL

Pathways
Gene Description
Gene Structure
mRNA Structure
Protein Structure
HAP Frequencies
Population
Linkage
SNP Distribution
Phylogenetic Tree
Genotype Analysis
Clinical Distribution
Edit Pathway
MultiGene
Clinical Trial Cohorts
Expression
Assay Data
References Population View

| PID | Ethnicity | Age | Gender | HAP 1 | HAP 2 | Test |
|---|---|---|---|---|---|---|
| UP070 | CA | 99 | F | GCGCTGGGC | GCGCTGGGC | 0.1 |
| UP072 | CA | 99 | F | dCGCTGGGC | GCACTGGGC | 0.2 |
| UP074 | CA | 99 | F | GCGCTGGGC | GCACTGGGC | 0.2 |
| UP132 | CA | 99 | M | GTGCTGGGT | GTGCTGGGT | 0.3 |
| UP133 | CA | 99 | M | GCGCTGGGC | GTGCTGGGT | 0.2 |
| UP134 | CA | 99 | F | GCGCTGGGC | GCGCTGGGC | 0.1 |
| UP137 | CA | 99 | M | GTGCTGGGT | GTGCTGGGT | 0.1 |
| UP009 | CA | 99 | F | GCACTGGGC | GCACTGGGC | 0.3 |
| UP014 | CA | 99 | F | dCGCTGGGC | GCGCTGGAC | 0.3 |
| UP020 | CA | 99 | F | GTGCTGGGT | GTGCTGGGT | 0.2 |
| UP021 | CA | 99 | M | GCGTTGTGC | GCGCTGGGC | 0.4 |
| UP022 | CA | 99 | M | GCGCTGGAC | GCGCTGGAC | 0.3 |
| OR001 | AS | 99 | M | dCGCTGGGC | GCGTTGTGC | 0.2 |
| OR002 | AS | 99 | M | GCGCTGGGC | GCGCTGGGC | 0.3 |
| OR004 | AS | 99 | F | GCACTGGGC | GCCCTGGAC | 0.2 |
| OR006 | AS | 99 | F | GCGTTGGGC | GCGTTGTGC | 0.1 |
| WT003 | CA | 99 | M | GCGTTGTGC | GCGTTGGGC | 0.2 |
| WT005 | CA | 99 | M | GCGTTGTGC | GCGTTGTGC | 0.4 |
| WT007 | CA | 99 | F | GCCCTAGGC | GCGCTGGGC | 0.1 |
| UP012 | CA | 99 | M | GCACTGGGC | GCCCTGGAC | 0.2 |
| UP135 | CA | | | | | |

DecoGen ANOVA Modeler: Test

Clinical Measurements Regression Calculation

| Site | Slope   | Intercept | Variance | T(slope) | Significance Level |
|------|---------|-----------|----------|----------|--------------------|
| 1    | -0.083  | 0.316     | 0.05     | -0.59    | 0.7223             |
| 2    | 0.154   | 0.231     | 0.04     | 4.22     | 0.9999             |
| 3    | -0.08   | 0.326     | 0.05     | -1.16    | 0.8735             |
| 4    | -0.0080 | 0.313     | 0.06     | -0.14    | 0.5572             |
| 5    | 0.145   | 0.305     | 0.05     | 0.86     | 0.804              |
| 6    | -0.08   | 0.332     | 0.05     | -1.24    | 0.8902             |
| 7    | 0.0070  | 0.31      | 0.06     | 0.08     | 0.5303             |
| 8    | 0.158   | 0.222     | 0.04     | 4.34     | 1.0                |
| 9    | -0.043  | 0.322     | 0.05     | -0.76    | 0.7752             |

FIG. 21

*Legend of Figures:*

Rectangle Boxes: Tables in the database.

Rounded Boxes: Children tables that depend on their parent tables. This dependency requires that a parent record to be in existence before a child record can be created.

2: ——⊶⊀  Identifying parent / child relationship. It depicts the not nullable 1-to-0-or-many relationship.

4: )— — ⊶⊦  Non-identifying parent / child relationship. It represents the nullable 0-or-1-to-many relationship.

6: ——⊀  Identifying parent / child relationship. It depicts the not nullable 1-to-1-or-many relationship.

8: — — —⊀  Non-identifying parent / child relationship. It represents the not nullable 1-to-1-or-many relationship.

10: ⊢——  Identifying parent / child relationship. It depicts the not nullable 1-to-exact-1 relationship.

12: ⊖— — -  Non-identifying parent / child relationship. It represents the nullable 0-or-1-to-exact-1 relationship.

14: ⊢— — ⊶⊀  Non-identifying parent / child relationship. It represents the not nullable 0-or-1-to-many relationship.

Gene Description View

| Name | ADRB2 |
|---|---|
| Definition | adrenergic, beta-2-, receptor, surface |
| Function | Function |
| Organism | Human |
| Length | 3451 |
| No. Features | 5 |
| Population Size | 261 |
| No. Haplotypes | 12 |
| No. SNPs | 13 |
| Nucleotide Polymorphism (theta) | 7.9E-4 +/-3.9E-4 |
| Nucleotide Diversity (pi) | 4.6E-4 +/-2.8E-4 |

*Legend of Figures:*

 Rectangle Boxes: Tables in the database.

 Rounded Boxes: Children tables that depend on their parent tables. This dependency requires that a parent record to be in existence before a child record can be created.

2: Identifying parent / child relationship. It depicts the not nullable 1-to-0-or-many relationship.

4: Non-identifying parent / child relationship. It represents the nullable 0-or-1-to-many relationship.

6: Identifying parent / child relationship. It depicts the not nullable 1-to-1-or-many relationship.

8: Non-identifying parent / child relationship. It represents the not nullable 1-to-1-or-many relationship.

10: Identifying parent / child relationship. It depicts the not nullable 1-to-exact-1 relationship.

12: Non-identifying parent / child relationship. It represents the nullable 0-or-1-to-exact-1 relationship.

14: Non-identifying parent / child relationship. It represents the not nullable 0-or-1-to-many relationship.

FIG. 44F

METHODS FOR OBTAINING AND USING HAPLOTYPE DATA

RELATED APPLICATIONS

This application is a continuation of International Application PCT/US00/17540, filed Jun. 26, 2000, which claims priority to U.S. Provisional Application Ser. No. 60/141,521 filed Jun. 25, 1999, which is incorporated by reference herein.

FIELD OF THE INVENTION

The invention relates to the field of genomics, and genetics, including genome analysis and the study of DNA variation. In particular, the invention relates to the fields of pharmacogenetics and pharmacogenenomics and the use of genetic haplotype information to predict an individual's susceptibility to disease and/or their response to a particular drug or drugs, so that drugs tailored to genetic differences of population groups may be developed and/or administered to the appropriate population.

The invention also relates to tools to analyze DNA, catalog variations in DNA, study gene function and link variations in DNA to an individual's susceptibility to a particular disease and/or response to a particular drug or drugs.

The invention may also be used to link variations in DNA to personal identity and racial or ethnic background.

The invention also relates to the use of haplotype information in the veterinary and agricultural fields.

BACKGROUND OF THE INVENTION

The accumulation of genomic information and technology is opening doors for the discovery of new diagnostics, preventive strategies, and drug therapies for a whole host of diseases, including diabetes, hypertension, heart disease, cancer, and mental illness. This is due to the fact that many human diseases have genetic components, which may be evidenced by clustering in certain families, and/or in certain racial, ethnic or ethnogeographic (world population) groups. For example, prostrate cancer clusters in some families. Furthermore, while prostate cancer is common among all U.S. males, it is especially common among African American men. They are 35 percent more likely than Americans of European descent to develop the disease and more than twice as likely to die from it. A variation on chromosome 1 (PC 1) and a variation on the X chromosome (HPCX) appear to predispose men to prostrate cancer and a study is currently underway to test this hypothesis.

Likewise, it is clear that an individual's genes can have considerable influence over how that individual responds to a particular drug or drugs.

Individuals inherit specific versions of enzymes that affect how they metabolize, absorb and excrete drugs. So far, researchers have identified several dozen enzymes that vary in their activity throughout the population and that probably dictate people's response to drugs—which may be good, bad or sometimes deadly. For example, the cytochrome P450 family of enzymes (of which CYP 2D6 is a member) is involved in the metabolism of at least 20 percent of all commonly prescribed drugs, including the antidepressant Prozac™, the painkiller codeine, and high-blood-pressure medications such as captopril. Ethnic variation is also seen in this instance. Due to genetic differences in cytochrome P450, for example, 6 to 10 percent of Whites, 5 percent of Blacks, and less than 1 percent of Asians are poor drug metabolizers.

One very troubling observation is that adverse reactions often occur in patients receiving a standard dose of a particular drug. As an example, doctors in the 1950s would administer a drug called succinylcholine to induce muscle relaxation in patients before surgery. A number of patients, however, never woke up from anesthesia—the compound paralyzed their breathing muscles and they suffocated. It was later discovered that the patients who died had inherited a mutant form of the enzyme that clears succinylcholine from their system. As-another example, as early as the 1940s doctors noticed that certain tuberculosis patients treated with the antibacterial drug isoniazid would feel pain, tingling and weakness in their limbs. These patients were unusually slow to clear the drug from their bodies—isoniazid must be rapidly converted to a nontoxic form by an enzyme called N-acetyltransferase. This difference in drug response was later discovered to be due to differences in the gene encoding the enzyme. The number of people who would experience adverse responses using this drug is not small. Forty to sixty percent of Caucasians have the less active form of the enzyme (i.e., "slow acetylators").

Another gene encodes a liver enzyme that causes side effects in some patients who used Seldane™, an allergy drug which was removed from the market. The drug Seldane™ is dangerous to people with liver disease, on antibiotics, or who are using the antifungal drug Nizoral. The major problem with Seldane™ is that it can cause serious, potentially fatal, heart rhythm disturbances when more than the recommended dose is taken. The real danger is that it can interact with certain other drugs to cause this problem at usual doses. It was discovered that people with a particular version of a CYP450 suffered serious side effects when they took Seldane™ with the antibiotic erythromycin.

Sometimes one ethnic group is affected more than others. During the Second World War, for example, African-American soldiers given the antimalarial drug primaquine developed a severe form of anaemia. The soldiers who became ill had a deficiency in an enzyme called glucose-6-phosphate dehydrogenase (G6PD) due to a genetic variation that occurs in about 10 percent of Africans, but very rarely in Caucasians. G6PD deficiency probably became more common in Africans because it confers some protection against malaria.

Variations in certain genes can also determine whether a drug treats a disease effectively. For example, a cholesterol-lowering drug called pravastatin won't help people with high blood cholesterol if they have a common gene variant for an enzyme called cholesteryl ester transfer protein (CETP). As another example, several studies suggest that the version of the "ApoE" gene that is associated with a high risk of developing Alzheimer's disease in old age (i.e., APOE4) correlates with a poor response to an Alzheimer's drug called tacrine. As yet another example, the drug Herceptin™, a treatment for metastatic breast cancer, only works for patients whose tumors overproduce a certain protein, called HER2. A screening test is given to all potential patients to weed out those on whom the drug won't be effective.

In summary, it is well known that not all individuals respond identically to drugs for a given condition. Some people respond well to drug A but poorly to drug B, some people respond better to drug B, while some have adverse reactions to both drugs. In many cases it is currently difficult to tell how an individual person will respond to a given drug, except by having them try using it.

It appears that a major reason people respond differently to a drug is that they have different forms of one or more of the proteins that interact with the drug or that lie in the cascade initiated by taking the drug.

A common method for determining the genetic differences between individuals is to find Single Nucleotide Polymorphisms (SNPs), which may be either in or near a gene on the chromosome, that differ between at least some individuals in the population. A number of instances are known (Sickle Cell Anemia is a prototypical example) for which the nucleotide at a SNP is correlated with an individual's propensity to develop a disease. Often these SNPs are linked to the causative gene, but are not themselves causative. These are often called surrogate markers for the disease. The SNP/surrogate marker approach suffers from at least three problems:

(1) Comprehensiveness: There are often several polymorphisms in any given gene. (See Ref. 10 for an example in which there are 88 polymorphic sites). Most SNP projects look at a large number of SNPs, but spread over an enormous region of the chromosome. Therefore the probability of finding all (or any) SNPs in the coding region of a gene is small. The likelihood of finding the causative SNP(s) (the subset of polymorphisms responsible for causing a particular condition or change in response to a treatment) is even lower.

(2) Lack of Linkage: If the causative SNP is in so-called linkage disequilibrium (Ref 1, Chapter 2) with the measured SNP, then the nucleotide at the measured SNP will be correlated with the nucleotide at the causative SNP. However it is impossible to predict a priori whether such linkage disequilibrium will exist for a particular pair of measured and causative SNPs.

(3) Phasing: When there are multiple, interacting causative SNPs in a gene one needs to know what are the sequences of the two forms of the gene present in an individual. For instance, assume there is a gene that has 3 causative SNPs and that the remaining part of the gene is identical among all individuals. We can then identify the two copies of the gene that any individual has with only the nucleotides at those sites. Now assume that 4 forms exist in the population, labeled TAA, ATA, TTA and AAA. SNP methods effectively measure SNPs one at a time, and leave the "phasing" between nucleotides at different positions ambiguous. An individual with one copy of TAA and one of ATA would have a genotype (collection of SNPs) of [T/A, T/A, A/A]. This genotype is consistent with the haplotypes TTA/AAA or TAA/ATA. An individual with one copy of TTA and one of AAA would have exactly the same genotype as an individual with one copy of TAA and one copy of ATA. By using unphased genotypes, we cannot distinguish these two individuals.

A relatively low density SNP based map of the genome will have little likelihood of specifically identifying drug target variations that will allow for distinguishing responders from poor responders, non-responders, or those likely to suffer side-effects (or toxicity) to drugs. A relatively low density SNP based map of the genome also will have little likelihood of providing information for new genetically based drug design. In contrast, using the data and analytical tools of the present invention, knowing all the polymorphisms in the haplotypes will provide a firm basis for pursuing pharmacogenetics of a drug or class of drugs.

With the present invention, by knowing which forms of the proteins an individual possesses, in particular, by knowing that individual's haplotypes (which are the most detailed description of their genetic makeup for the genes of interest) for rationally chosen drug target genes, or genes intimately involved with the pathway of interest, and by knowing the typical response for people with those haplotypes, one can with confidence predict how that individual will respond to a drug. Doing this has the practical benefit that the best available drug and/or dose for a patient can be prescribed immediately rather than relying on a trial and error approach to find the optimal drug. The end result is a reduction in cost to the health care system. Repeat visits to the physician's office are reduced, the prescription of needless drugs is avoided, and the number of adverse reactions is decreased.

The Clinical Trials Solution (CTS™) method described herein provides a process for finding correlation's between haplotypes and response to treatment and for developing protocols to test patients and predict their response to a particular treatment.

The CTS™ method is partially embodied in the DecoGen™ Platform, which is a computer program coupled to a database used to display and analyze genetic and clinical information. It includes novel graphical and computational methods for treating haplotypes, genotypes, and clinical data in a consistent and easy-to-interpret manner.

SUMMARY OF THE INVENTION

The basis of the present invention is the fact that the specific form of a protein and the expression pattern of that protein in a particular individual are directly and unambiguously coded for by the individual's isogenes, which can be used to determine haplotypes. These haplotypes are more informative than the typically measured genotype, which retains a level of ambiguity about which form of the proteins will be expressed in an individual. By having unambiguous information about the forms of the protein causing the response to a treatment, one has the ability to accurately predict individuals' responses to that treatment. Such information can be used to predict drug efficacy and toxic side effects, lower the cost and risk of clinical trials, redefine and/or expand the markets for approved compounds (i.e., existing drugs), revive abandoned drugs, and help design more effective medications by identifying haplotypes relevant to optimal therapeutic responses. Such information can also be used, e.g., to determine the correct drug dose to give a patient.

At the molecular level, there will be a direct correlation between the form and expression level of a protein and its mode or degree of action. By combining this unambiguous molecular level information (i.e., the haplotypes) with clinical outcomes (e.g. the response to a particular drug), one can find correlations between haplotypes and outcomes. These correlations can then be used in a forward-looking mode to predict individuals' response to 8 drug.

The invention also relates to methods of making informative linkages between gene inheritance, disease susceptibility and how organisms react to drugs.

The invention relates to methods and tools to individually design diagnostic tests, and therapeutic strategies for maintaining health, preventing disease, and improving treatment outcomes, in situations where subtle genetic differences may contribute to disease risk and response to particular therapies.

The method and tools of the invention provide the ability to determine the frequency of each isogene, in particular, its haplotype, in the major ethno-geographic groups, as well as disease populations.

Similarly, in agricultural biotechnology, the method and tools of the invention can be used to determine the frequency of isogenes responsible for specific desirable traits, e.g., drought tolerance and/or improved crop yields, and reduce the time and effort needed to transfer desirable traits.

The invention includes methods, computer program(s) and database(s) to analyze and make use of gene haplotype information. These include methods, program, and database to find and measure the frequency of haplotypes in the general population; methods, program, and database to find-correlation's between an individuals' haplotypes or genotypes and a clinical outcome; methods, program, and database to predict an individual's haplotypes from the individual's genotype for a gene; and methods, program, and database to predict an individual's clinical response to a treatment based on the individual's genotype or haplotype.

The invention also relates to methods of constructing a haplotype database for a population, comprising:
(a) identifying individuals to include in the population;
(b) determining haplotype data for each individual in the population from isogene information;
(c) organizing the haplotype data for the individuals in the population into fields; and
(d) storing the haplotype data for individuals in the population according to the fields.

The invention also relates to methods of predicting the presence of a haplotype pair in an individual comprising, in order.
(a) identifying a genotype for the individual;
(b) enumerating all possible haplotype pairs which are consistent with the genotype;
(c) accessing a database containing reference haplotype pair frequency data to determine a probability, for each of the possible haplotype pairs, that the individual has a possible haplotype pair, and
(d) analyzing the determined probabilities to predict haplotype pairs for the individual.

The invention also relates to methods for identifying a correlation between a haplotype pair and a clinical response to a treatment comprising:
(a) accessing a database containing data on clinical responses to treatments exhibited by a clinical population;
(b) selecting a candidate locus hypothesized to be associated with the clinical response, the locus comprising at least two polymorphic sites;
(c) generating haplotype data for each member of the clinical population, the haplotype data comprising information on a plurality of polymorphic sites present in the candidate locus;
(d) storing the haplotype data; and
(e) identifying the correlation by analyzing the haplotype and clinical response data The invention also relates to methods for identifying a correlation between a haplotype pair and susceptibility to a disease comprising the steps of:
(a) selecting a candidate locus hypothesized to be associated with the condition or disease, the locus comprising at least two polymorphic sites;
(b) generating haplotype data for the candidate locus for each member of a disease population;
(c) organizing the haplotype data in a database;
(d) accessing a database containing reference haplotypes for the candidate locus;
(e) identifying the correlation by analyzing the disease haplotype data and the reference haplotype data wherein when a haplotype pair has a higher frequency in the disease population than in the reference population, a correlation of the haplotype pair to a susceptibility to the disease is identified.

The invention also relates to methods of predicting response to a treatment comprising:
(a) selecting at least one candidate gene which exhibits a correlation between haplotype content and at least two different responses to the treatment;
(b) determining a haplotype pair of an individual for the candidate gene;
(c) comparing the individual's haplotype pair with stored information on the correlation; and
(d) predicting the individual's response as a result of the comparing.

The invention also provides computer systems which are programmed with program code which causes the computer to carry out many of the methods of the invention A range of computer types may be employed; suitable computer systems include but are not limited to computers dedicated to the methods of the invention, and general-purpose programmable computers. The invention further provides computer-usable media having computer-readable program code stored thereon, for causing a computer to carry out many of the methods of the invention. Computer-usable media includes, but is not limited to, solid-state memory chips, magnetic tapes, or magnetic or optical disks. The invention also provides database structures which are adapted for use with the computers, program code, and methods of the invention.

TNFR1—Tissue Necrosis Factor 1
ADBR2—Beta-2 Adrenergic Receptor
IGERA—immunoglobulin E receptor alpha chain
IGERB—immunoglobulin E receptor beta chain
OCIF—osteoclastogenesis inhibitory factor
ERA—Estrogen alpha receptor
IL-4R—interleukin 4 receptor
5HT1A—5 hydroxytryptamine receptor 1A
DRD2—dopamine receptor D2
TNFA—tumor necrosis factor alpha
IL-1B—interleukin 1B
PTGS2—prostaglandin synthase 2 (COX-2)
IL4—interleukin 4
IL-13—interleukin 13
CYP2D6—cytochrome P450 2D6
HSERT—serotonin transporter
UCP3—uncoupling protein 3

FIG. 3. Gene Description View. This screen provides some of the basic information about the currently selected gene.

Figure 4A:
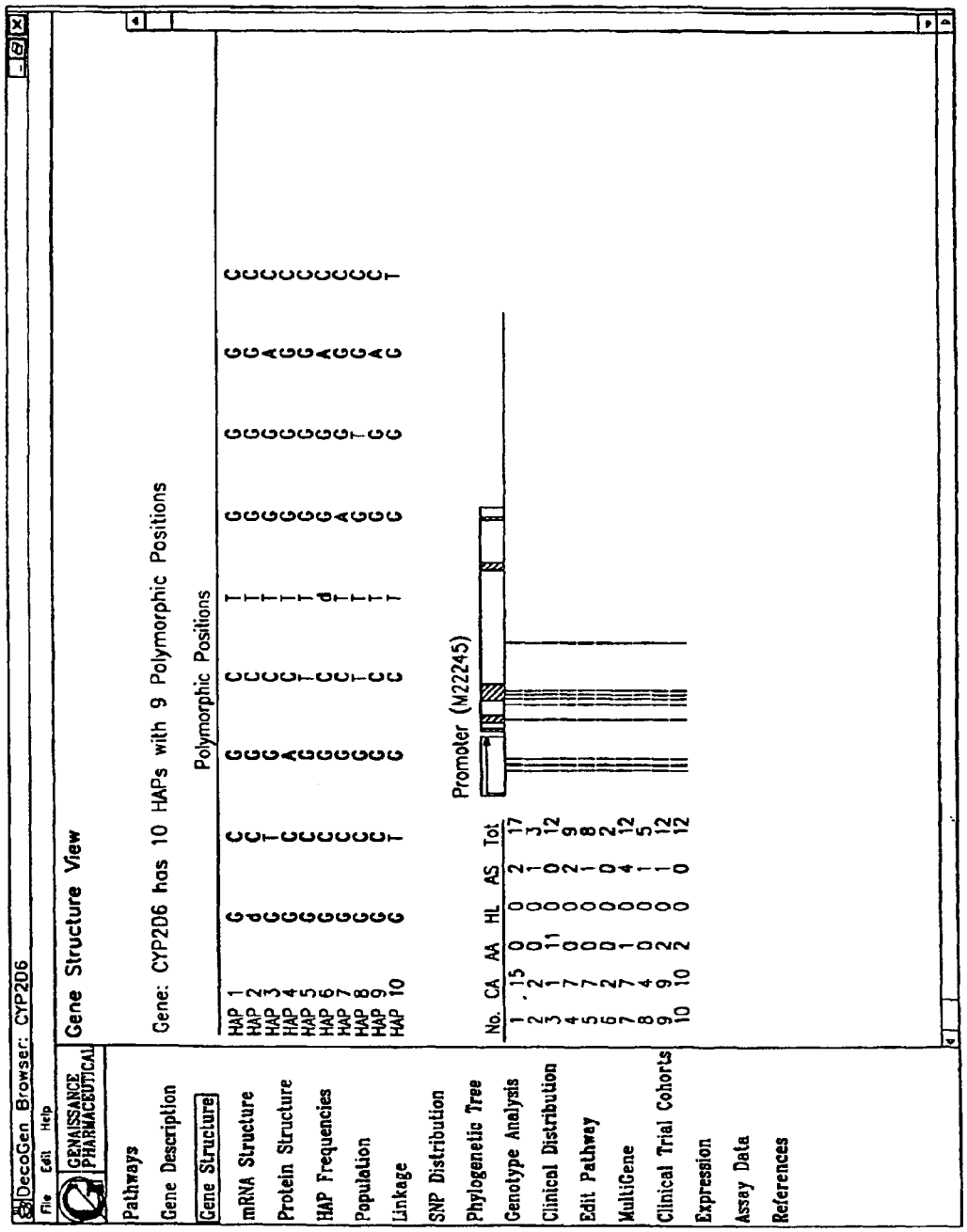

FIG. 4A. Gene Structure View. This screen shows the location of features in the gene (such as promoter, introns, exons, etc.), the location of polymorphic sites in the gene for each haplotype and the number of times each haplotype was seen in various world population groups.

Figure 4B:
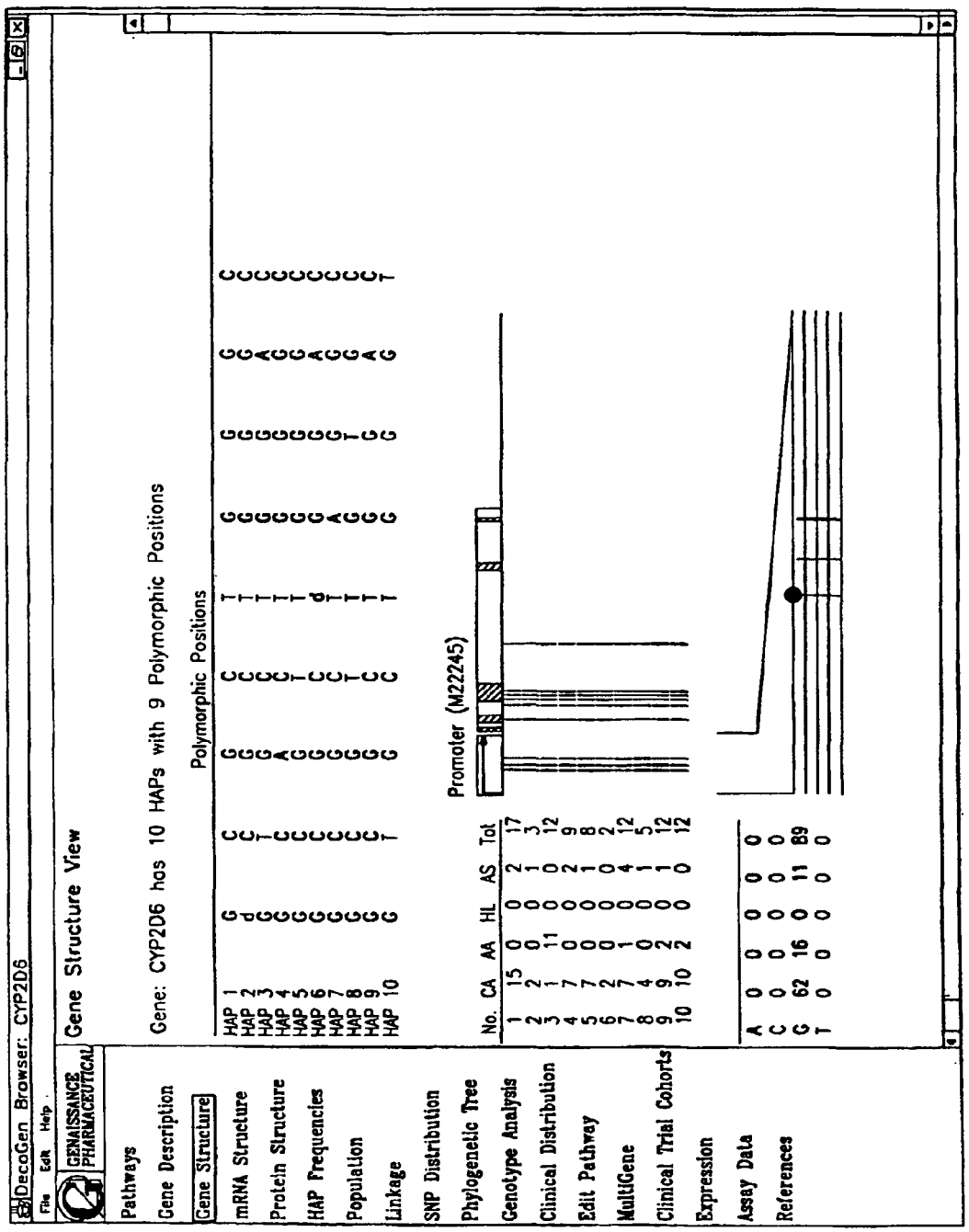

FIG. 4B. Gene Structure View (Cont.). This screen shows a screen which results after a gene feature is selected in the screen of FIG. 4A. An expanded view of the selected gene feature is shown at the bottom of the screen.

Figure 5:
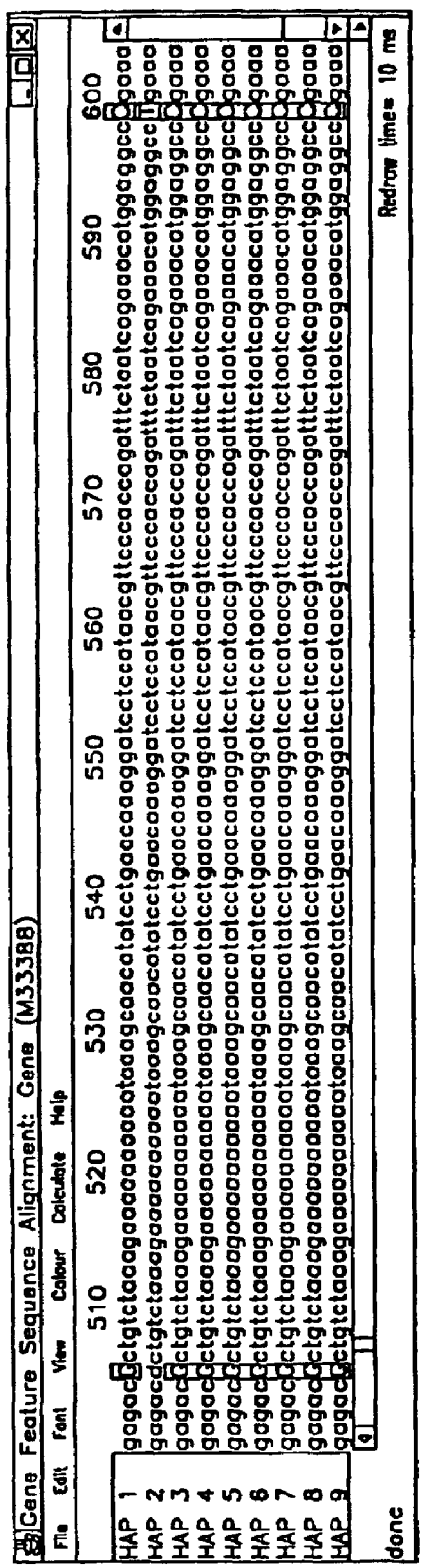

FIG. 5. Sequence Alignment View. This screen shows an alignment of the full DNA sequences for all the haplotypes (i.e., the isogenes) which appears in a separate window when one of the features in FIG. 4A or 4B is selected. The polymorphic positions are highlighted.

Figure 6:
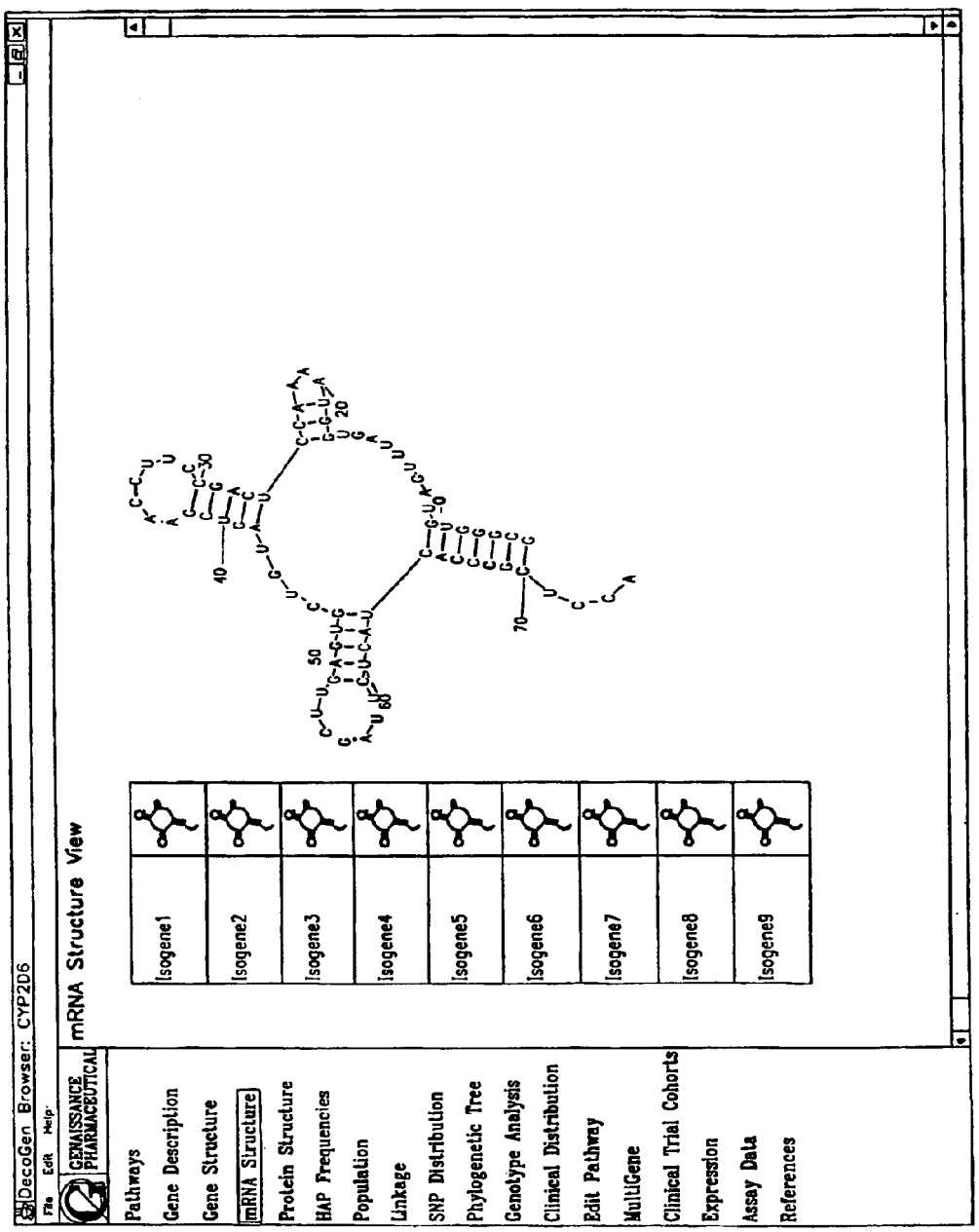

FIG. 6. mRNA Structure View. This screen shows the secondary structure of the RNA transcript for each isogene of the selected gene.

Figure 7:
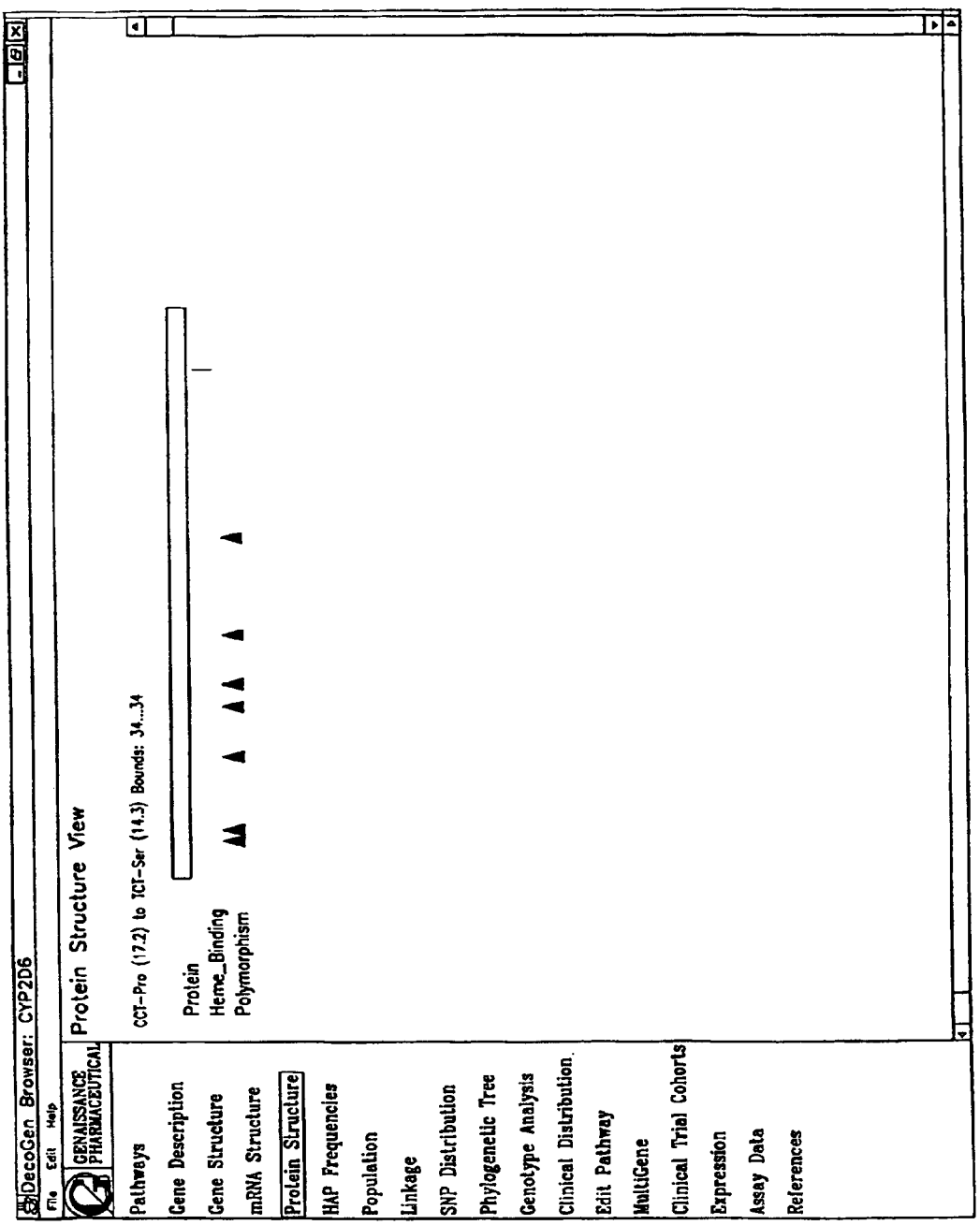

FIG. 7. Protein Structure View. This screen shows important motifs in the protein. The location of polymorphic sites in the protein is indicated by triangles. Selecting a triangle brings up information about the selected polymorphism at the top of the screen.

FIG. 8. Population View. This screen shows information about each of the members of the population being analyzed. PID is a unique identifier.

Figure 9:
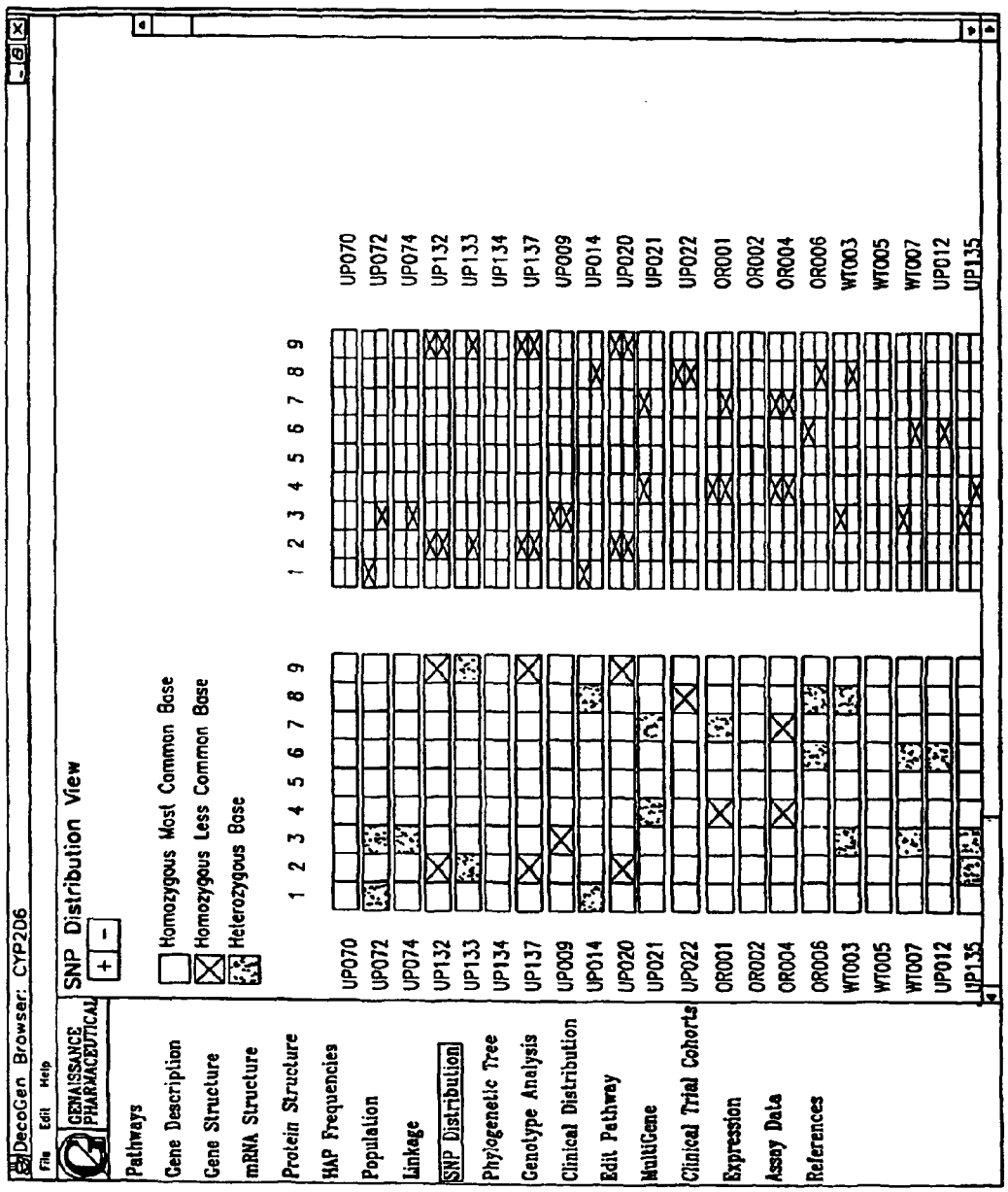

FIG. 9. SNP Distribution View. This screen shows the genotype to haplotype resolution of each of the individuals in the population being examined.

Figure 10:
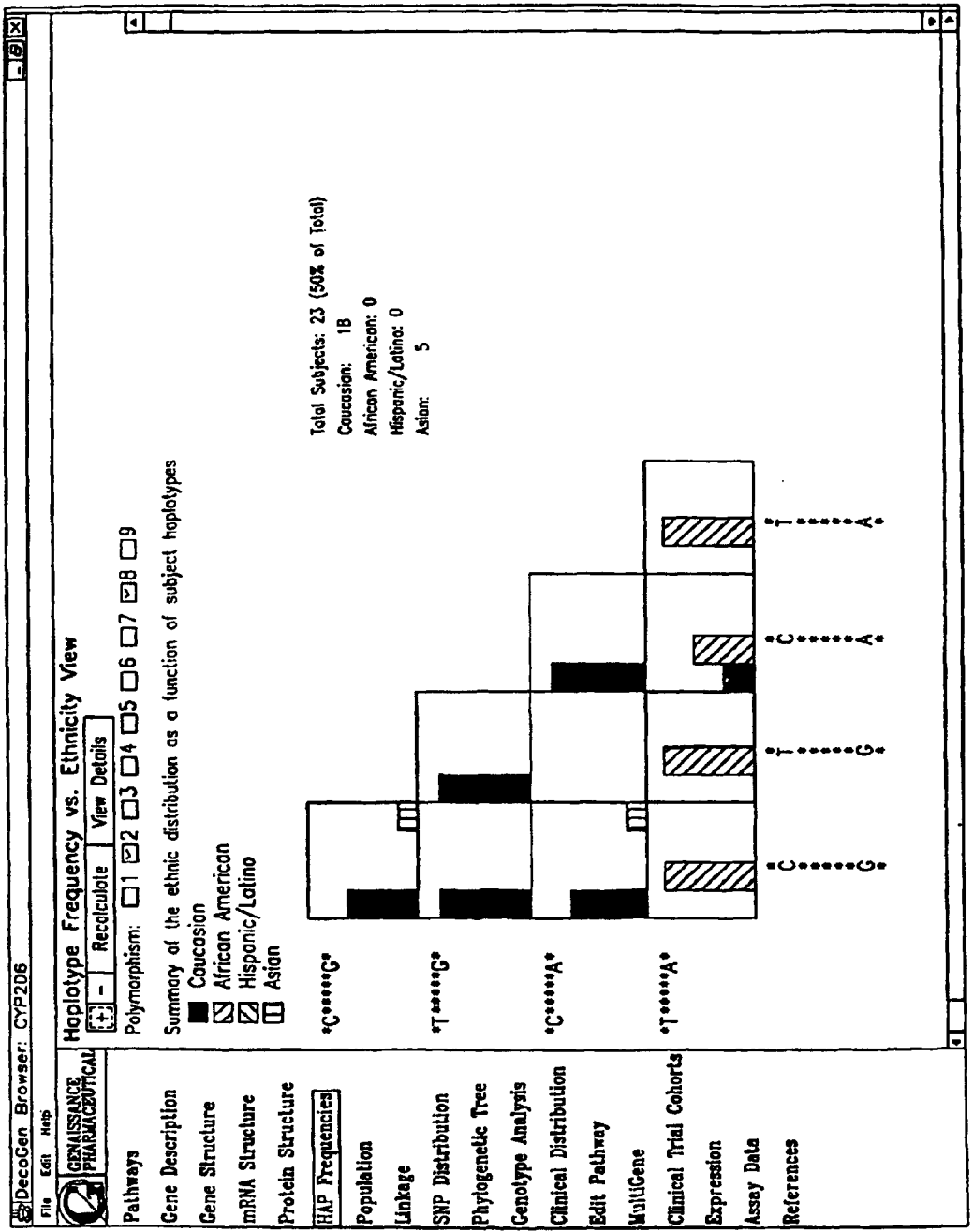

FIG. 10. Haplotype Frequencies (Summary View). This screen shows a summary of ethnic distribution as a function of haplotypes.

Figure 11:
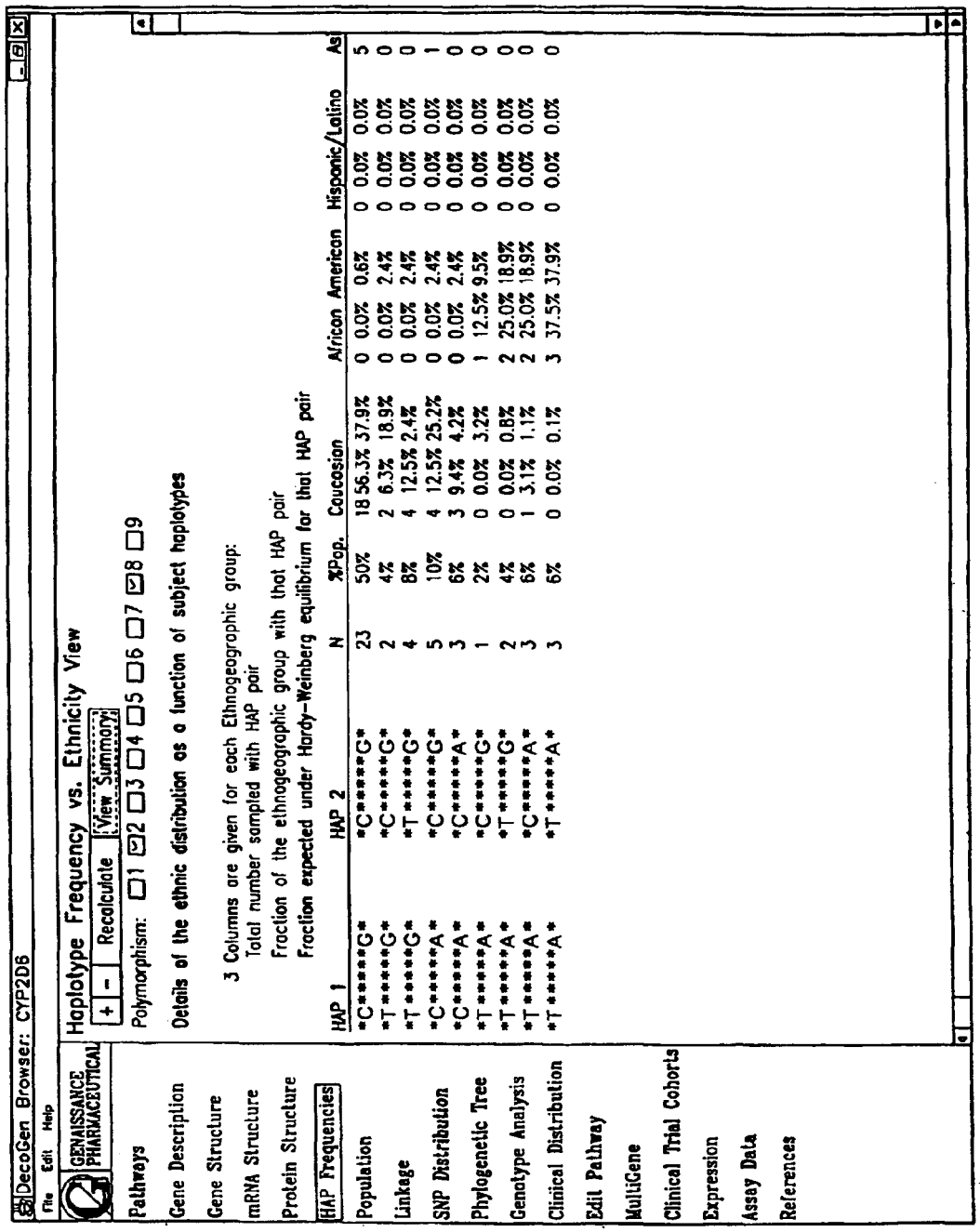

FIG. 11. Haplotype Frequencies (Detailed View). This screen shows details of ethnic distribution as a function of haplotype. Numerical data is provided.

Figure 12:
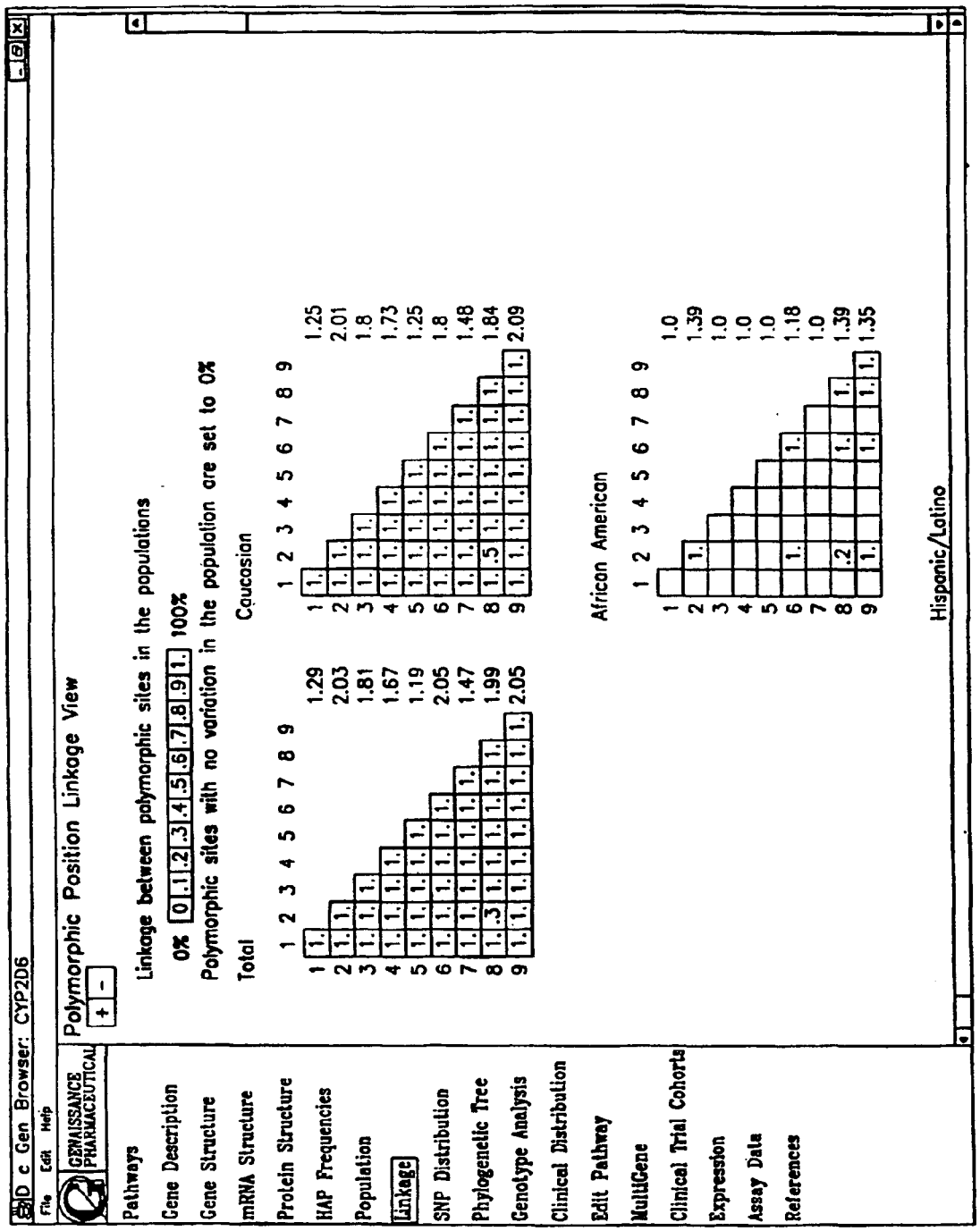

FIG. 12. Polymorphic Position Linkage View. This screen shows linkage between polymorphic sites in the population.

Figure 13:
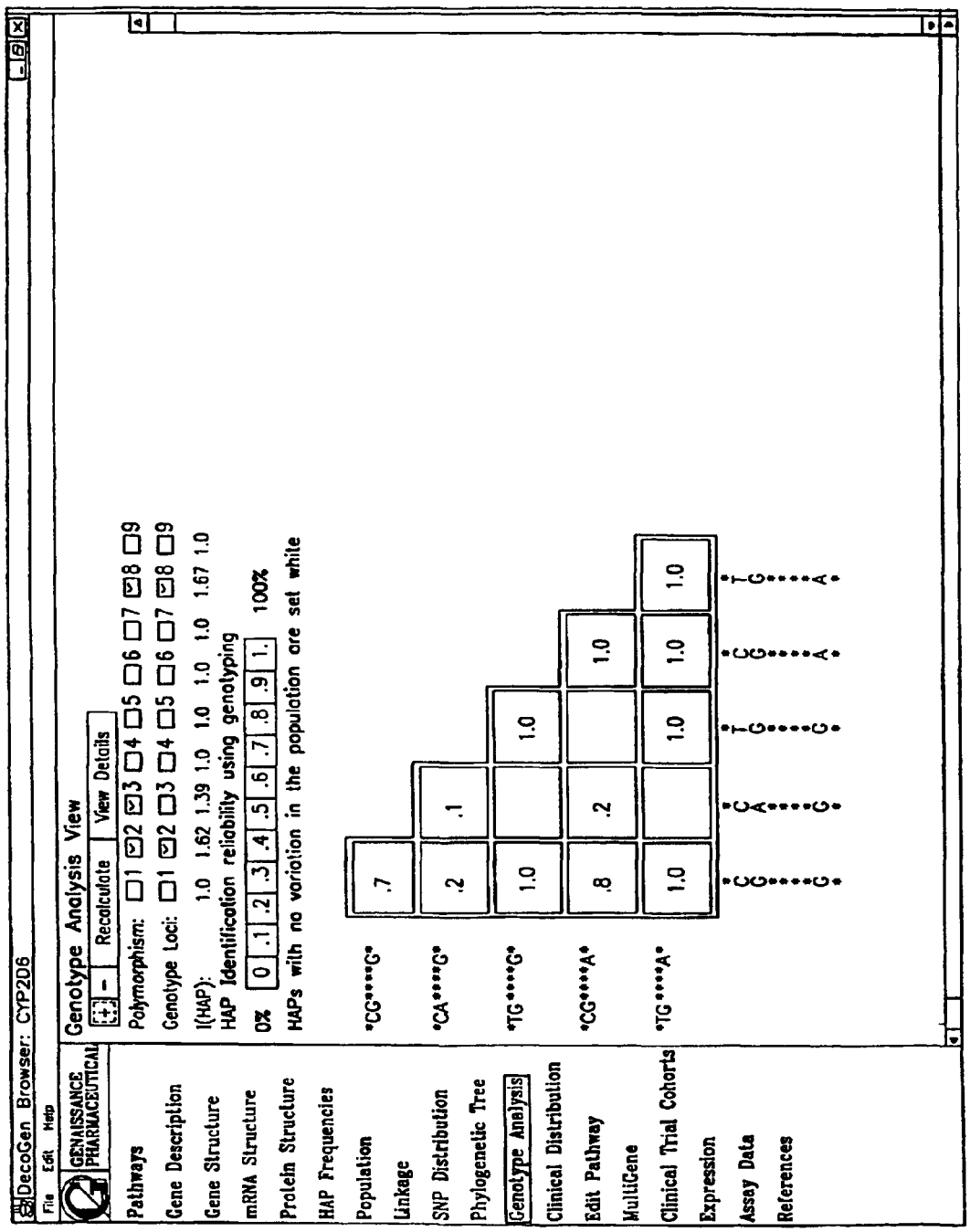

FIG. 13. Genotype Analysis View (Summary View). This screen shows haplotyping identification reliability using genotyping at selected positions.

Figure 14:
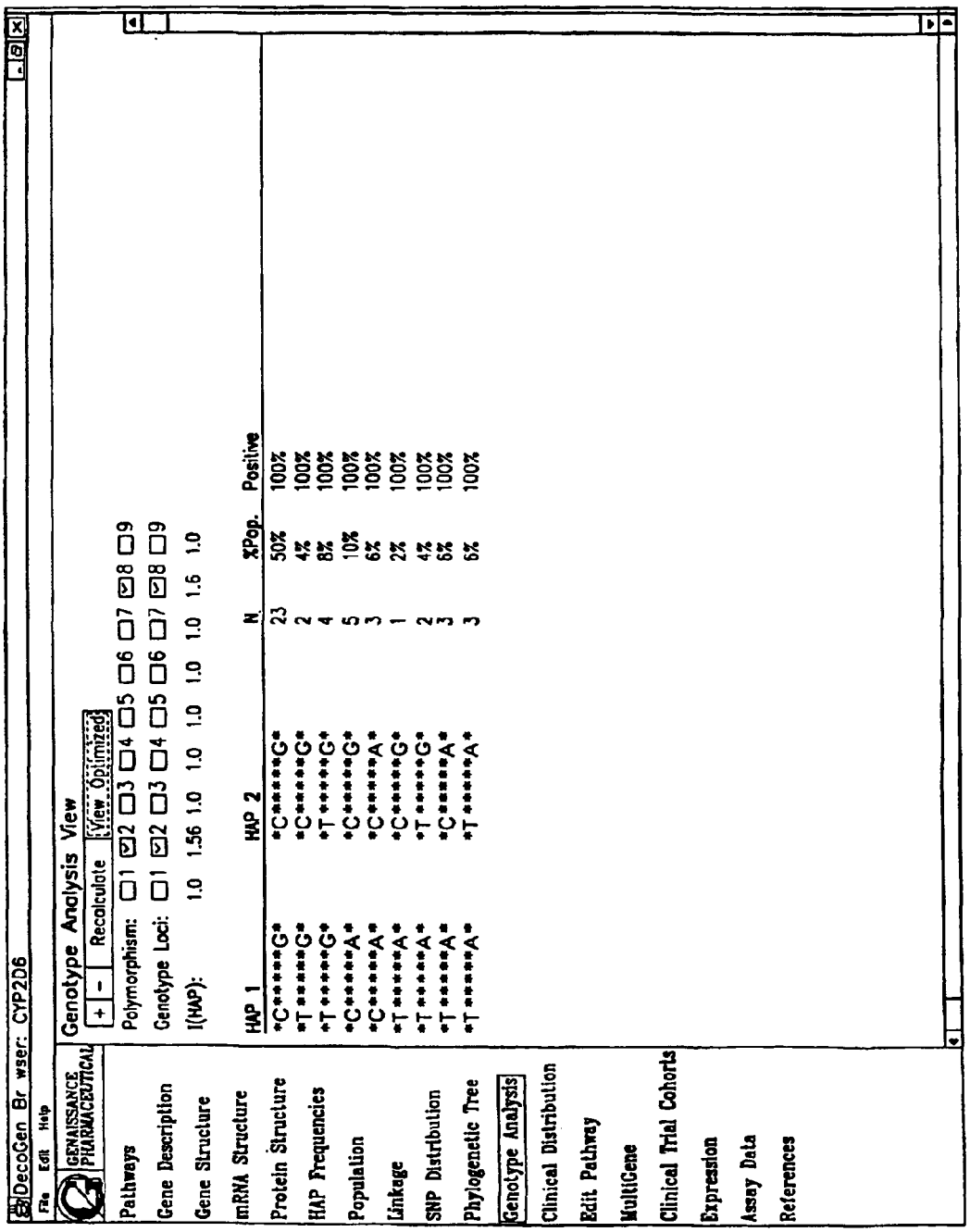

FIG. 14. Genotype Analysis View (Detailed View). This screen gives a number value for the graphical data presented in FIG. 13.

Figure 15:
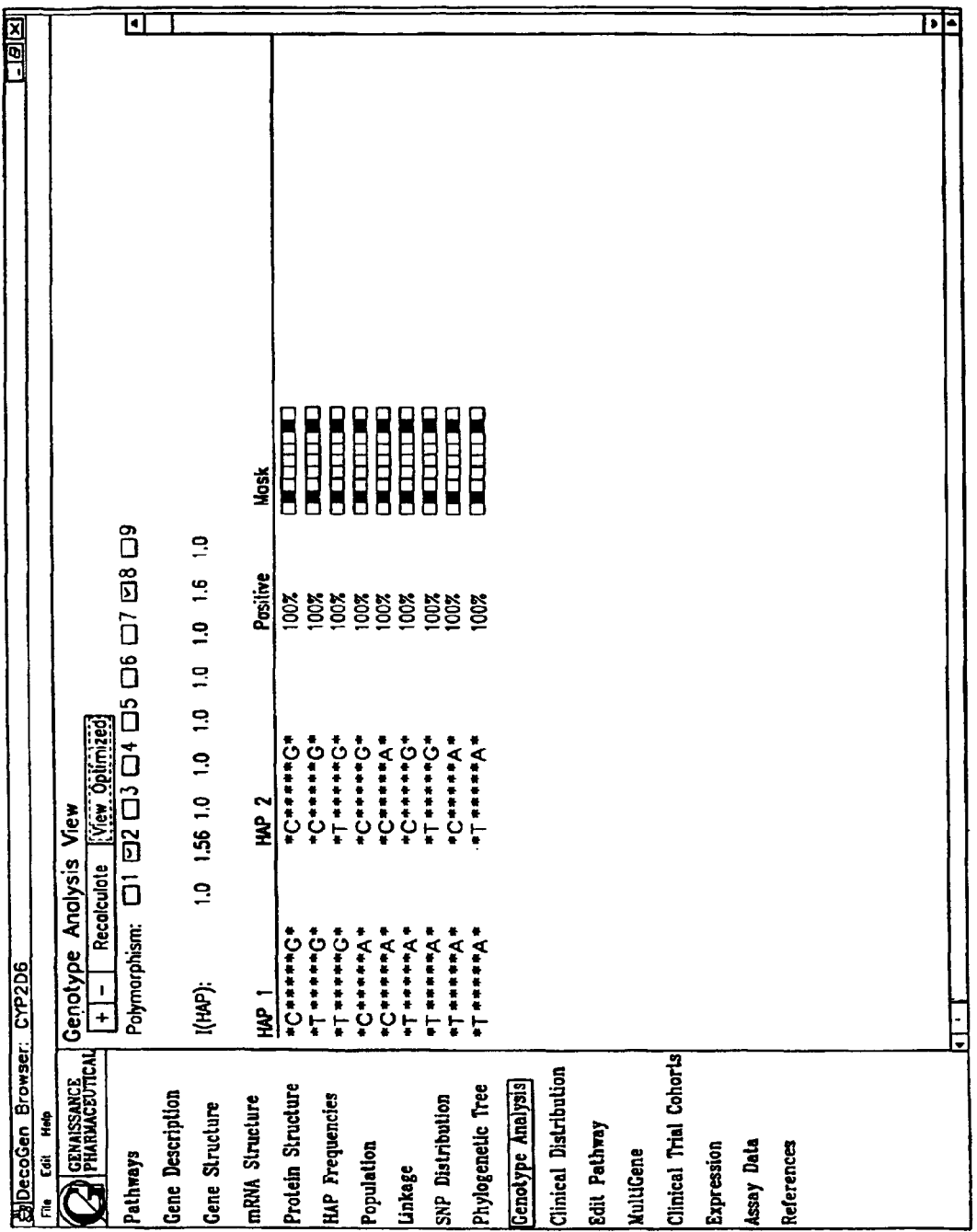

FIG. 15. Genotype Analysis View (Optimization View). This screen gives the results of a simple optimization approach to finding the simplest genotyping approach for predicting an individual's haplotypes.

Figure 16:
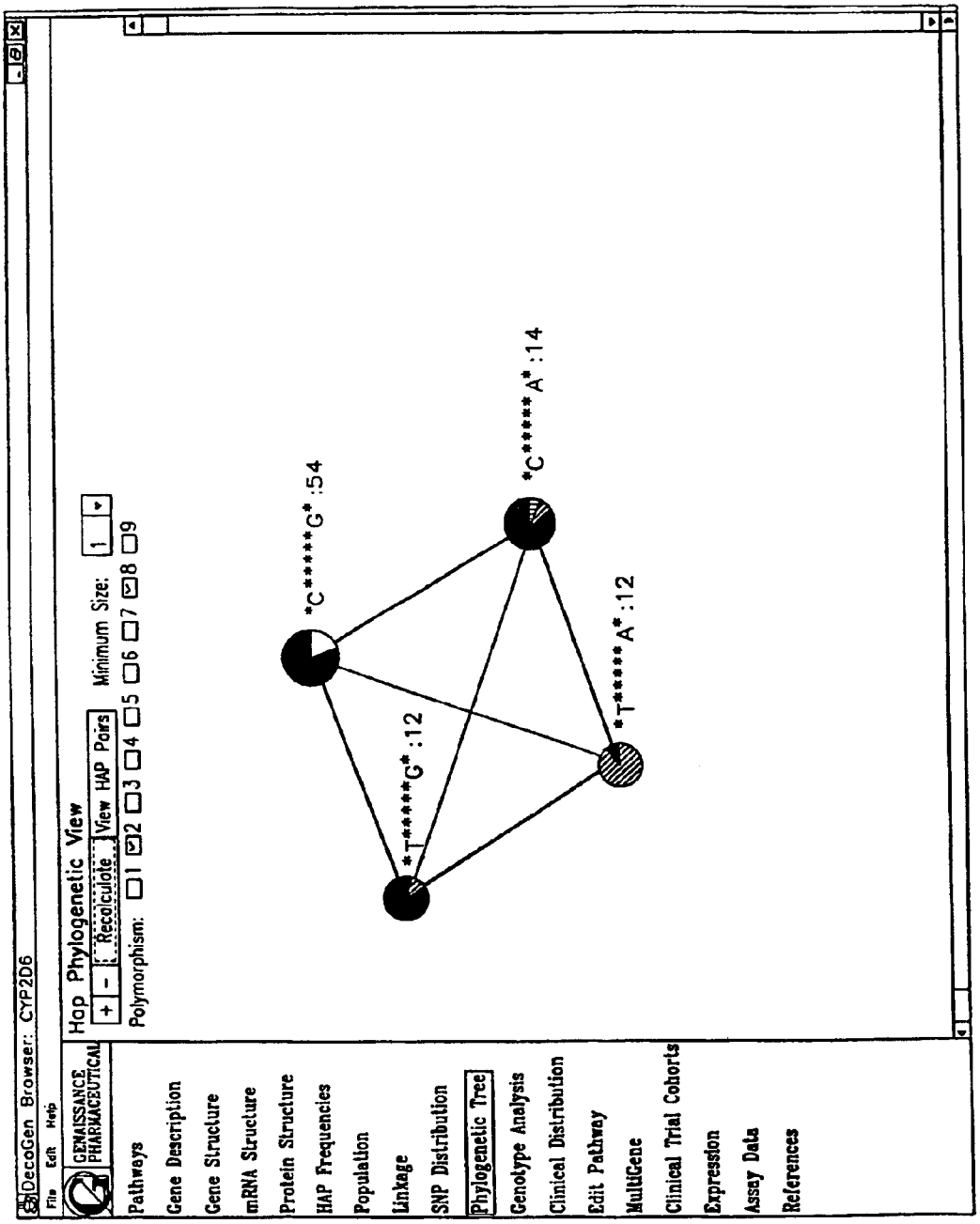
Figure 17:
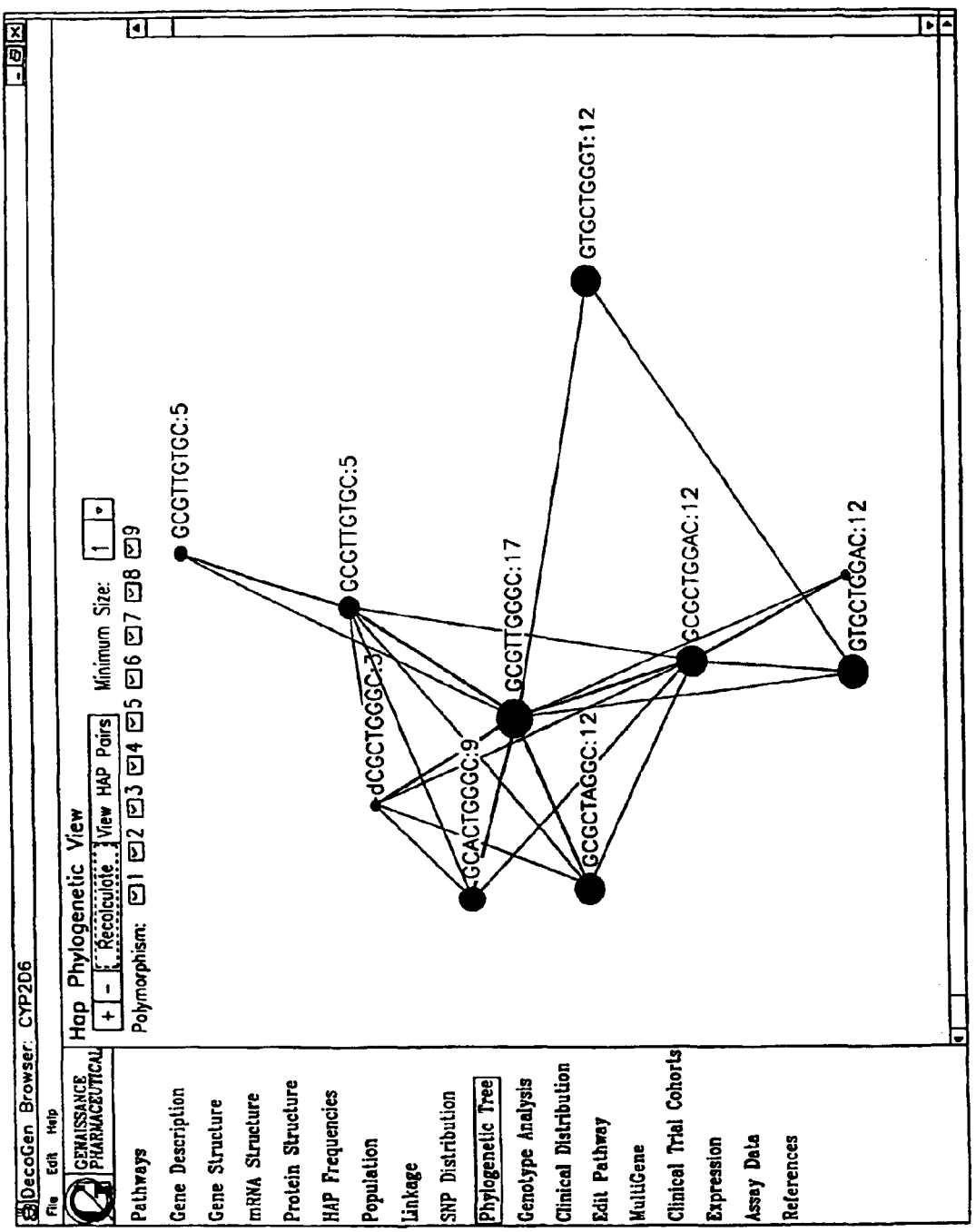

FIGS. 16 and 17. Haplotype Phylogenetic Views. These screens show minimal spanning networks for the haplotypes seen in the population.

Figure 18:
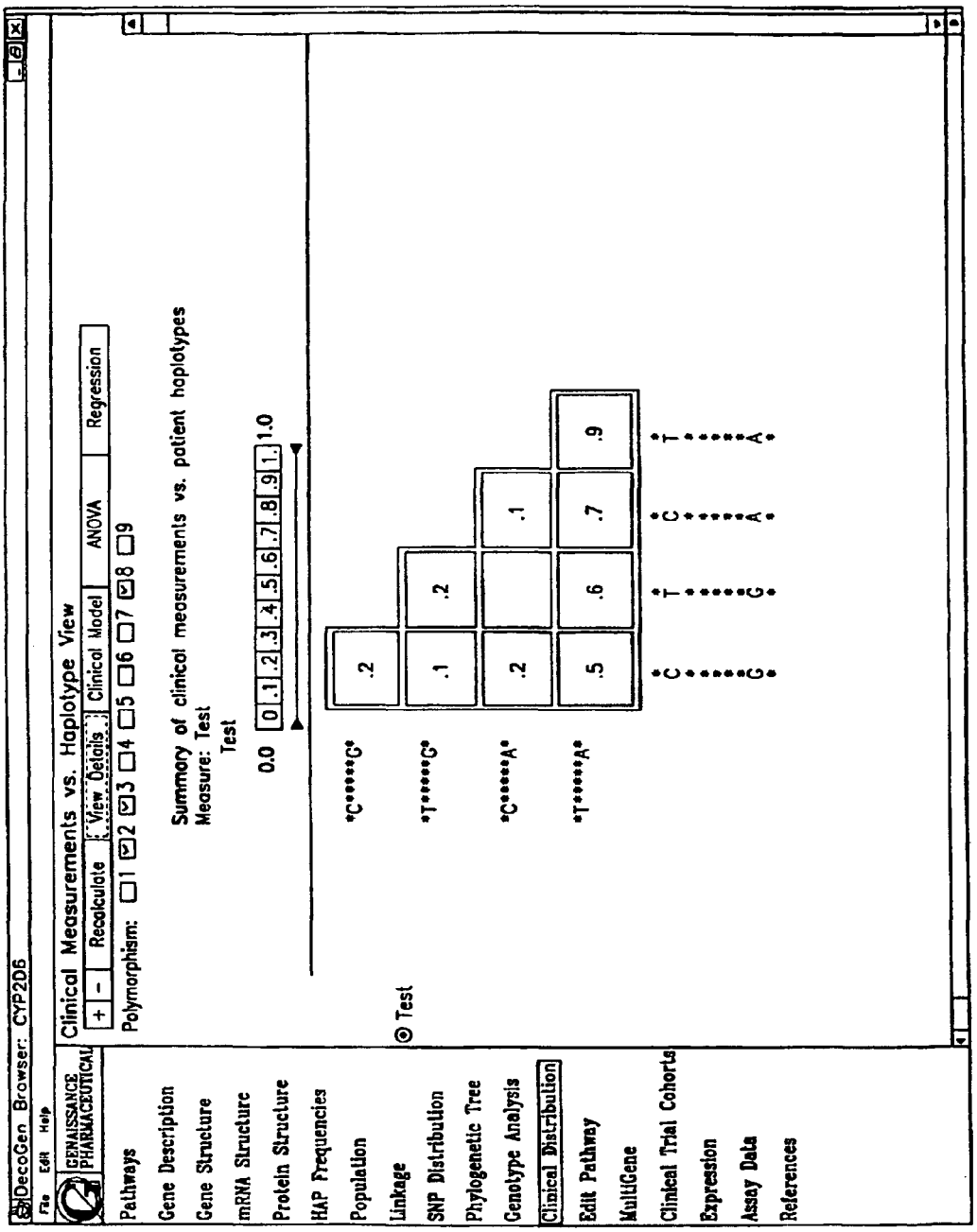

FIG. 18. Clinical Measurements vs. Haplotype View (Summary). This screen shows a matrix summarizing the correlation between clinical measurements and haplotypes.

Figure 19:
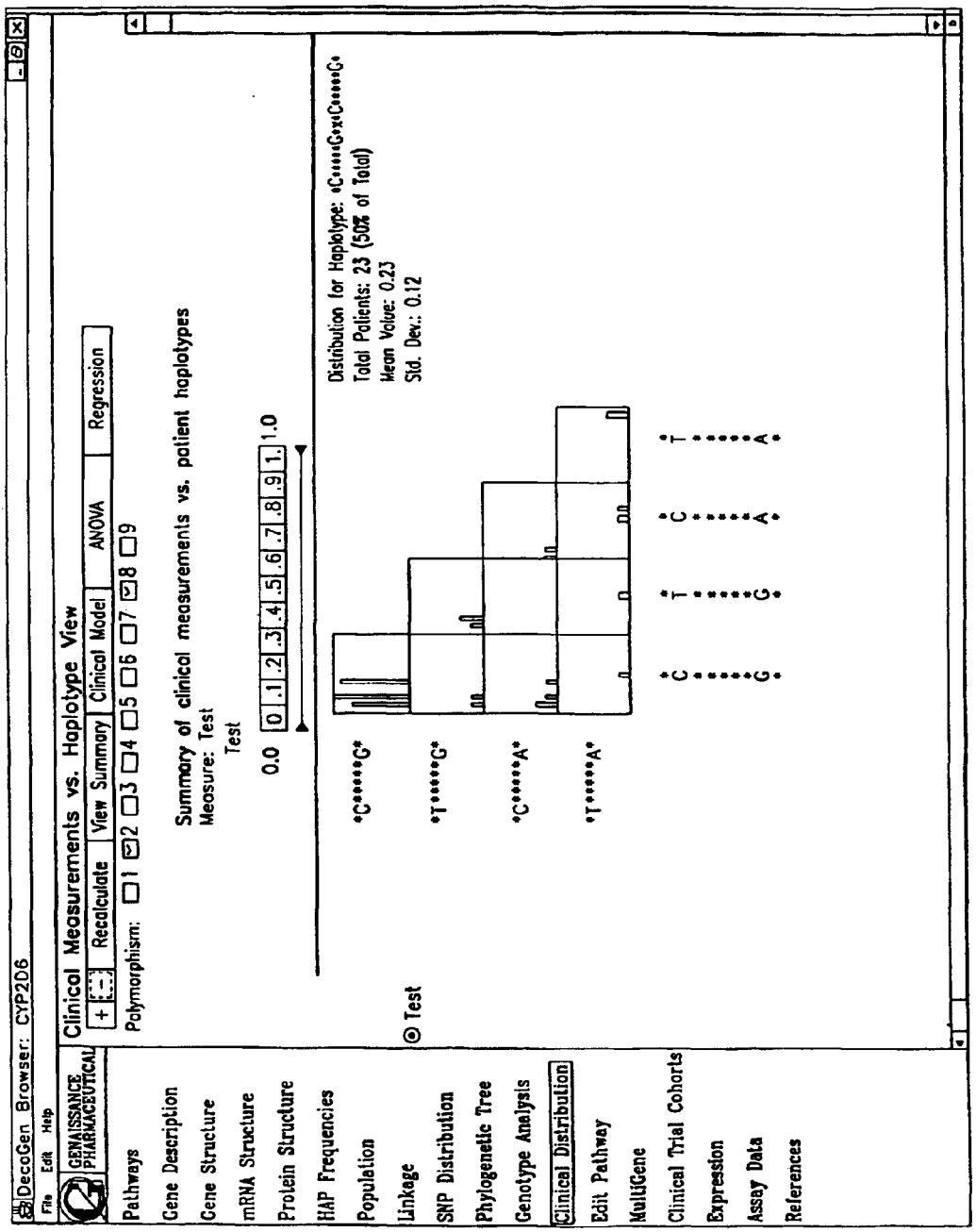

FIG. 19. Clinical Measurements vs. Haplotype View (Distribution View). This screen shows the distribution of the patients in each cell of the matrix of FIG. 18.

Figure 20:
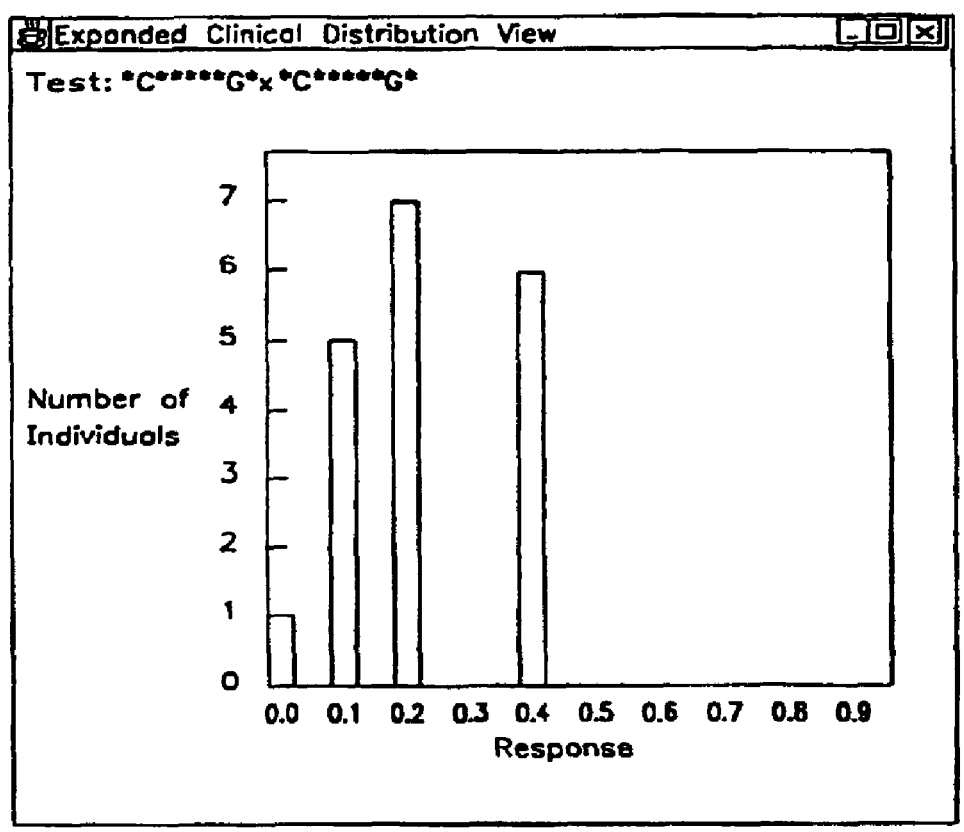

FIG. 20. Expanded view of one haplotype-pair distribution. This screen results when a user selects a cell in the matrix in FIG. 19. The screen shows the number of patients in the various response bins indicated on the horizontal axis.

FIG. 21. Linear Regression Analysis View. This screen shows the results of a dose-response linear regression calculation on each of the individual polymorphisms.

Figure 22:
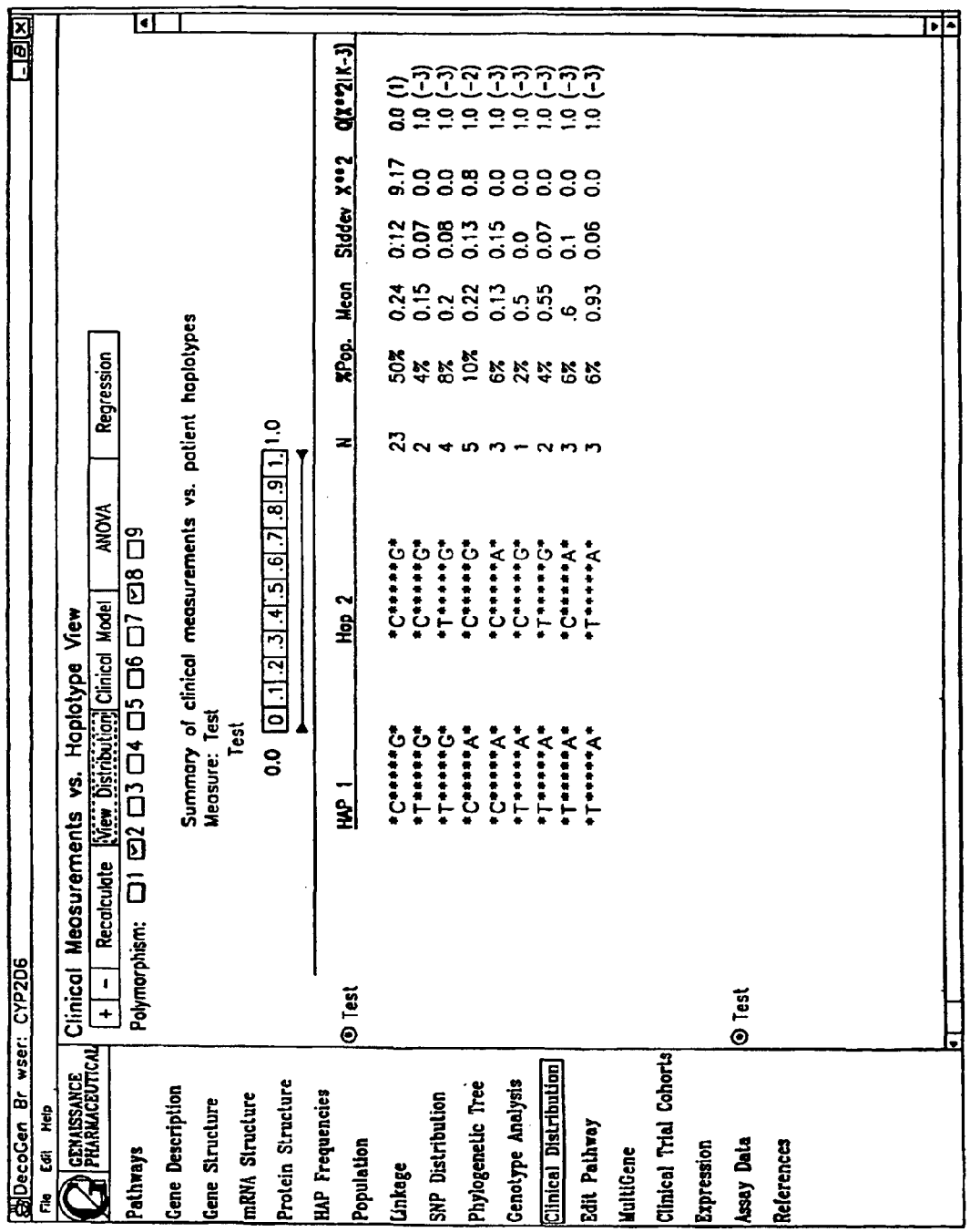

FIG. 22. Clinical Measurements vs. Haplotype View (Details). This screen gives the mean and standard deviation for each of the cells in FIG. 18.

Figure 23:
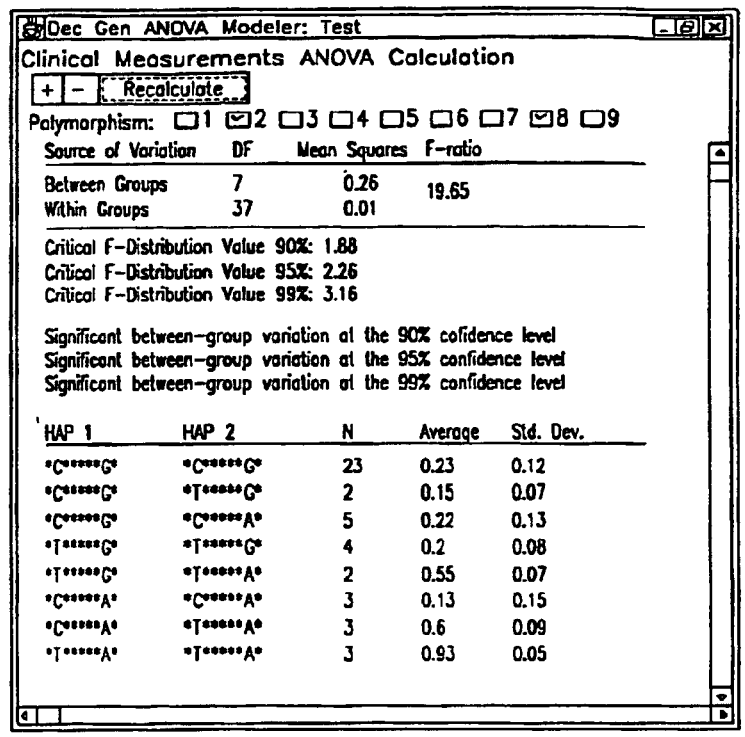

FIG. 23. Clinical Measurement ANOVA calculation. This screen shows the statistical significance between haplotype pair groups and clinical response.

Figure 24:
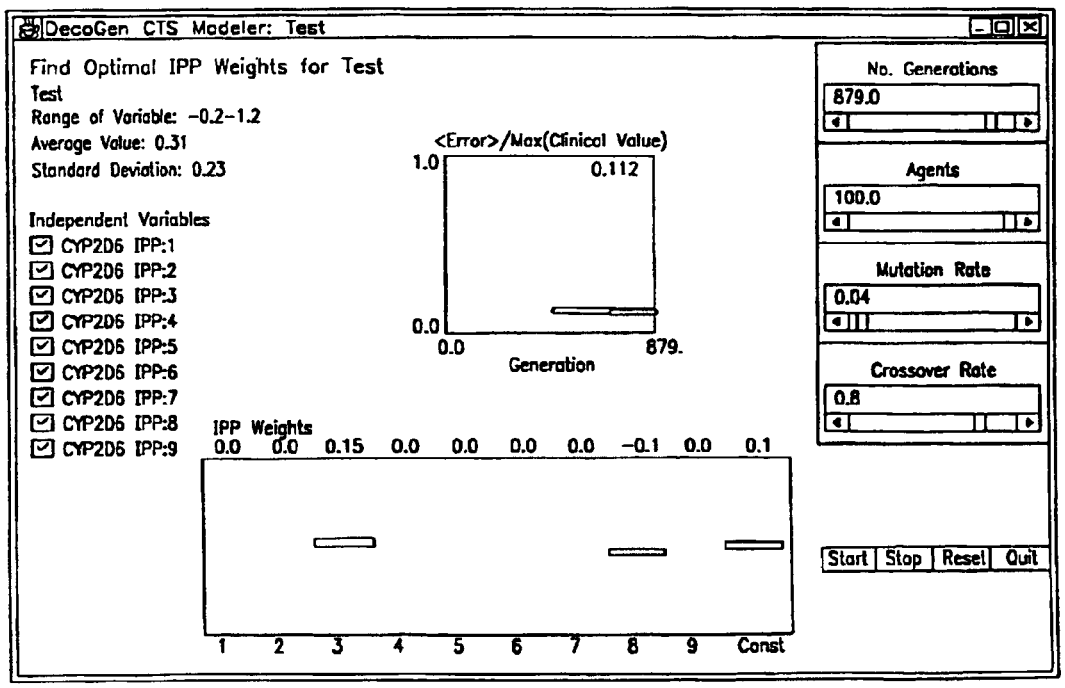

FIG. 24. Interface to the DecoGen CTS Modeler. As described in the text, a genetic algorithm (GA) is used to find an optimal set of weights to fit a function of the subject haplotype data to the clinical response. The controls at the right of the page are used to set the number of GA generations, the size of the population of "agents" that coevolve during the GA simulation, and the GA mutation and crossover rates. The GA population, and population parameters with those of the real human subjects, should not be confused. These are simply terms used in the computational algorithm which is the GA. The GA is an error-minimizing approach, where the error is a weighted sum of differences between the predicted clinical response and that which is measured. The graph in the top-middle shows the residual error as a function of computational time, measured in generations. The bar graph at the bottom center shows the weights from Equation 6 for the best solution found so far in the GA simulation.

Figure 25A:
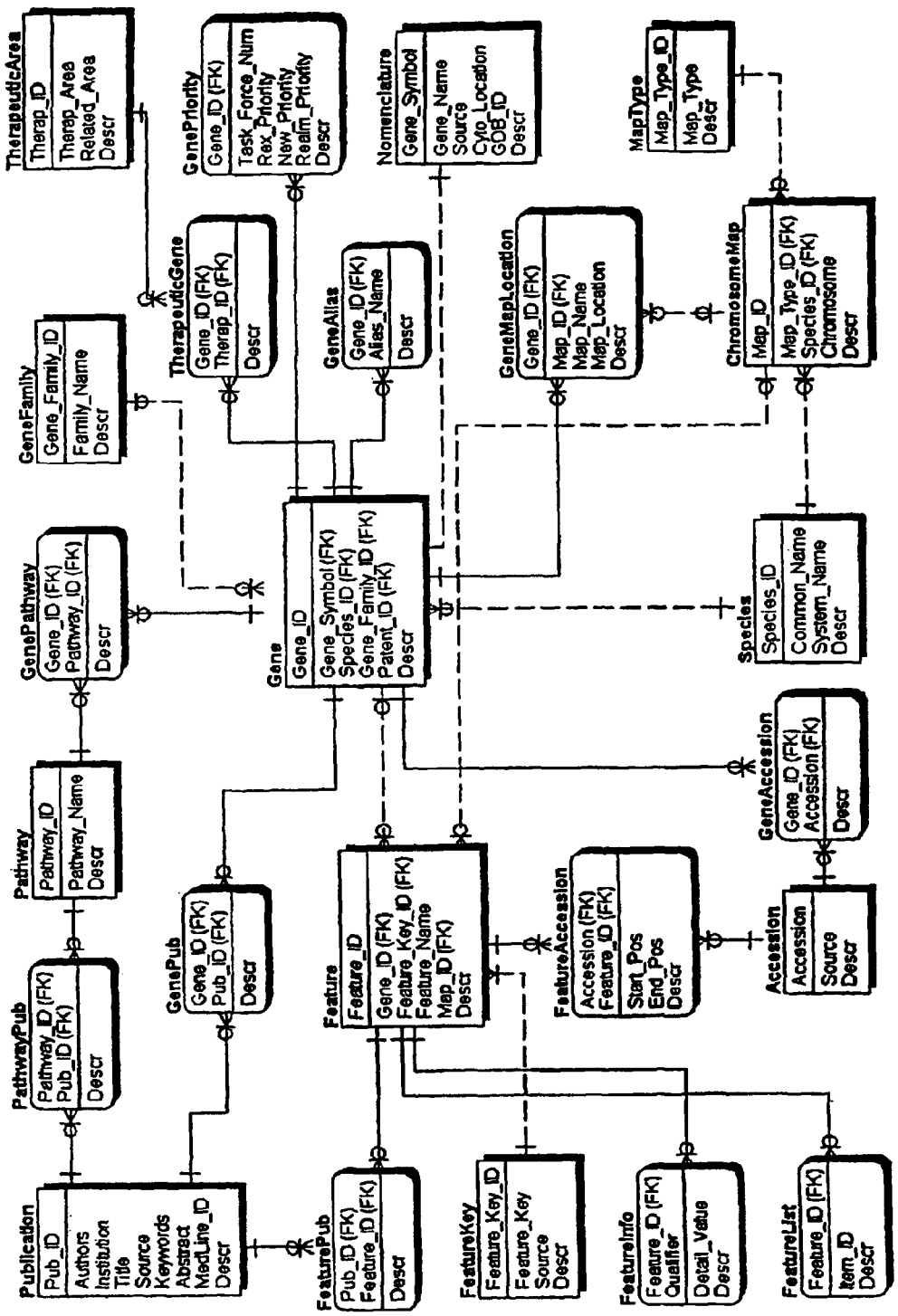

FIG. 25A. Gene Repository data submodel.

Figure 25B:
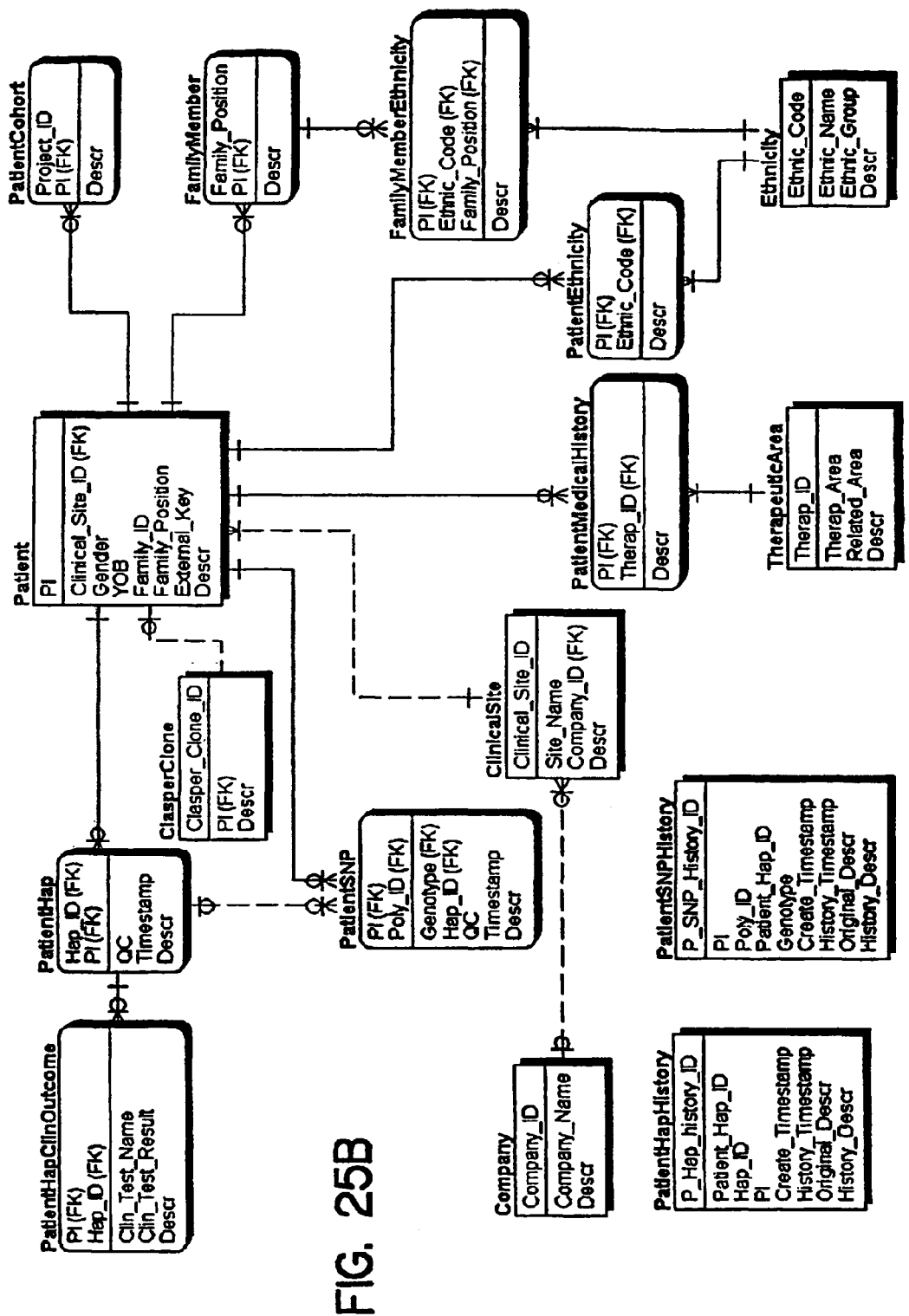

FIG. 25B. Population Repository data submodel.

Figure 25C:
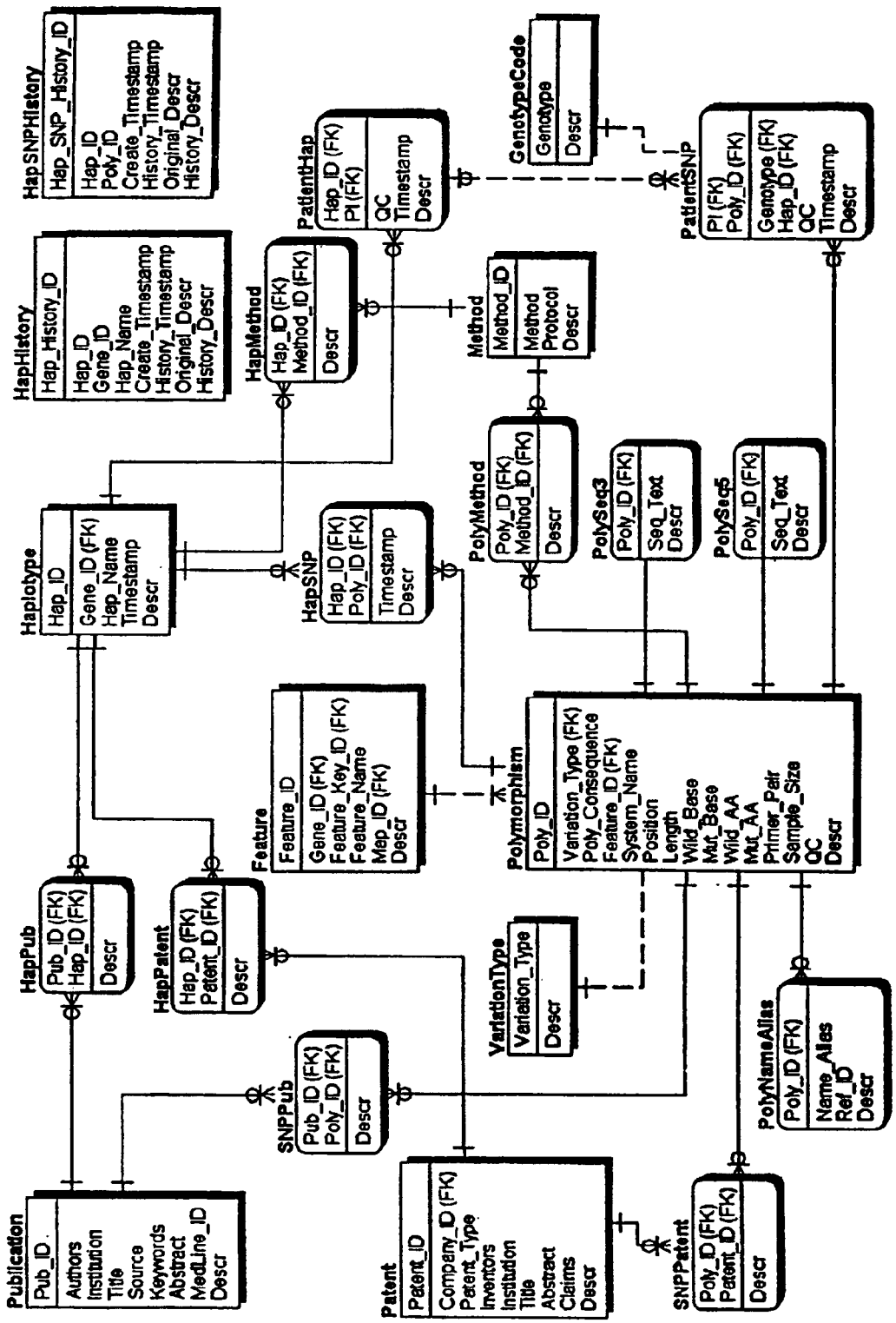

FIG. 25C. Polymorphism Repository data submodel.

Figure 25D:
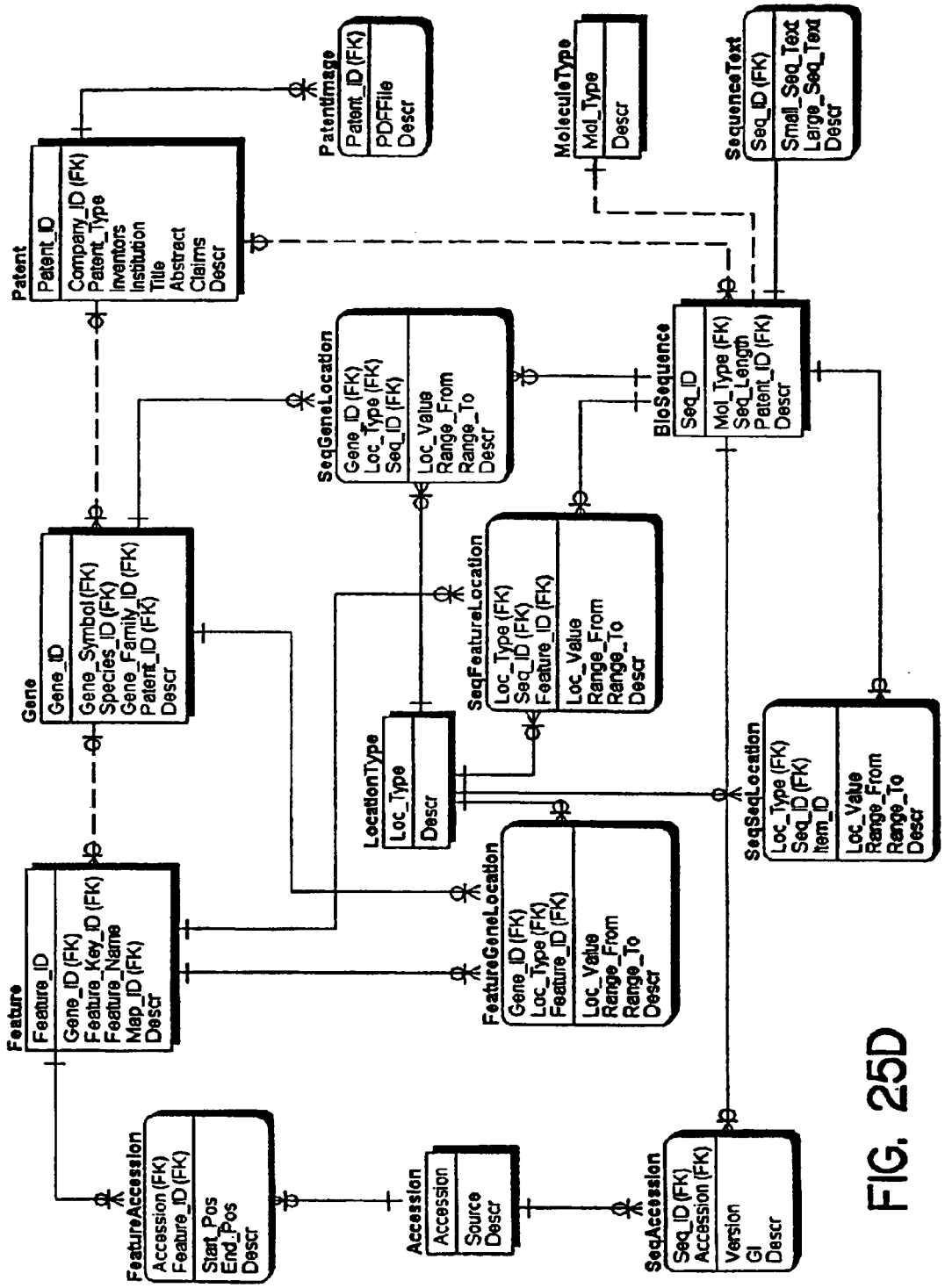

FIG. 25D. Sequence Repository data submodel.

Figure 25E:
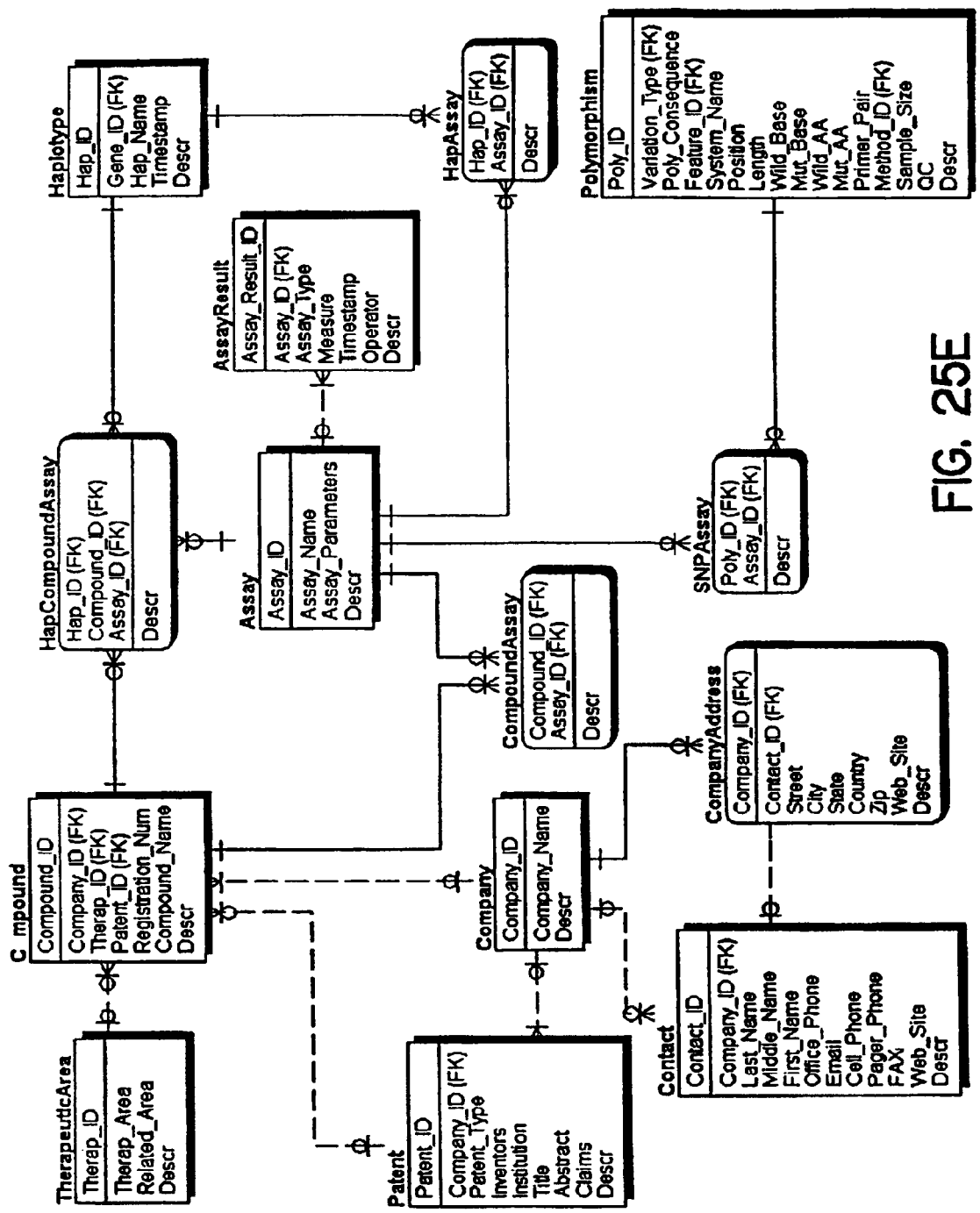

FIG. 25E. Assay Repository data submodel.

FIG. 25F. Legend of symbols in FIGS. 25A–E.

Figure 26:
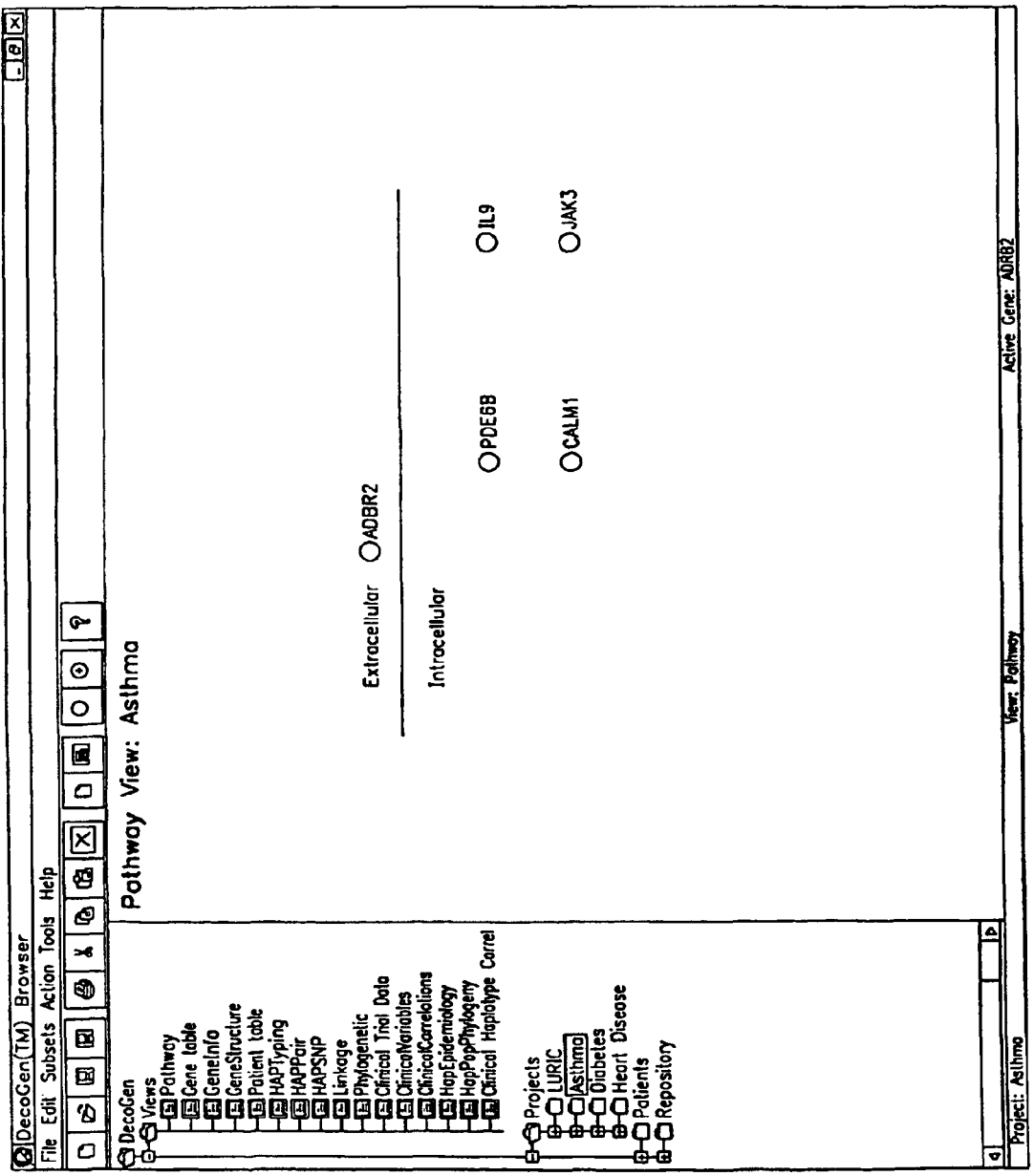

FIG. 26. Pathway View. This screen shows a schematic of candidate genes relevant to asthma from which a candidate gene may be selected to obtain further information. This view is an alternative way of showing information similar to that described in the Pathway/Gene Collection View shown in FIG. 2, with access to additional views, projects and other information, as well as additional tools. A menu on the left of the screen in FIG. 26 indicates some of the information about the candidate genes which may be accessed from a database. The candidates genes shown are ADBR2—Beta-2 Adrenergic Receptor IL-9—Interleukin 9

PDE6B—Phosphodiesterase 6B

CALM1—Calmodulin 1

JAK3—Janus Tyrosine Kinase 3

The following is a description about what happens (or could be made to happen) when each of the items on top of the screens (e.g., "File", "Edit", "Subsets", "Action", "Tools", "Help") are selected:

File:

New

Open

Save

Save As

Exit

"File" lets the viewer select the ability to open or save a project file, which contains a list of genes to be viewed.

Edit:

Cut

Copy

Paste

Subsets:

"Subsets" allows the user to create and select for analysis subsets of the total patient set. Once a subset has been defined and named, the name of the subset goes into the pulldown under this menu. Functions are available to select a subset of patients based on clinical value ("Select everyone with a choleserol level>200"), or ethnicity, or genetic makeup ("Select all patients with haplotype CAGGCTGG for gene DAXX"), etc.

Action:

Redo

"Redo" will cause displays to be regenerated when, for instance, the active set of SNPs has been changed.

Tools:

"Tools" will bring up various utilities, such as a statistics calculator for calculating $\chi^2$, etc.

Help:

"Help" will bring up on-line help for various functions.

The following is a description of the Standard Buttons that occur on all screens:

New (blank sheet)—standard windows button for creating new file—this creates a new project Open (open folder)—standard windows button for opening existing file—open an existing project Save (picture of floppy disk)—save the current project to a file Save $2^{nd}$ version—save the currently selected set of idividuals or genes to a collection that can be separately analyzed.

Print (picture of printer)—print the current page

Cut (scissors)—delete the selected items (could be a gene or genes, a person, a SNP, etc., depending on the context)

Copy—copy the selected item (as above) to the clipboard

Paste—paste the contents of the clipboard to the current view

X—currently not used

New 2 (next blank page icon)—create a subset (genes, people, etc) from the selected items in the view Recalculate (icon of calculator)—redo computation of statistics, etc., depending on the context.

Help (question mark)—bring up on-line help for the current view.

The following is a description of Buttons that show up on several views:

Expand (magnifying glass with + sign)—zoom in on the graphical display—increase in size Shrink (magnifying glass with - sign)—zoom out on the graphical display—decrease in size FIG. 27. GeneInfo View. This screen provides some of the basic information about the currently selected ADRB2 gene. This screen is an alternative way of showing information similar to that described in the Gene Description View in FIG. 3.

Figure 28A:
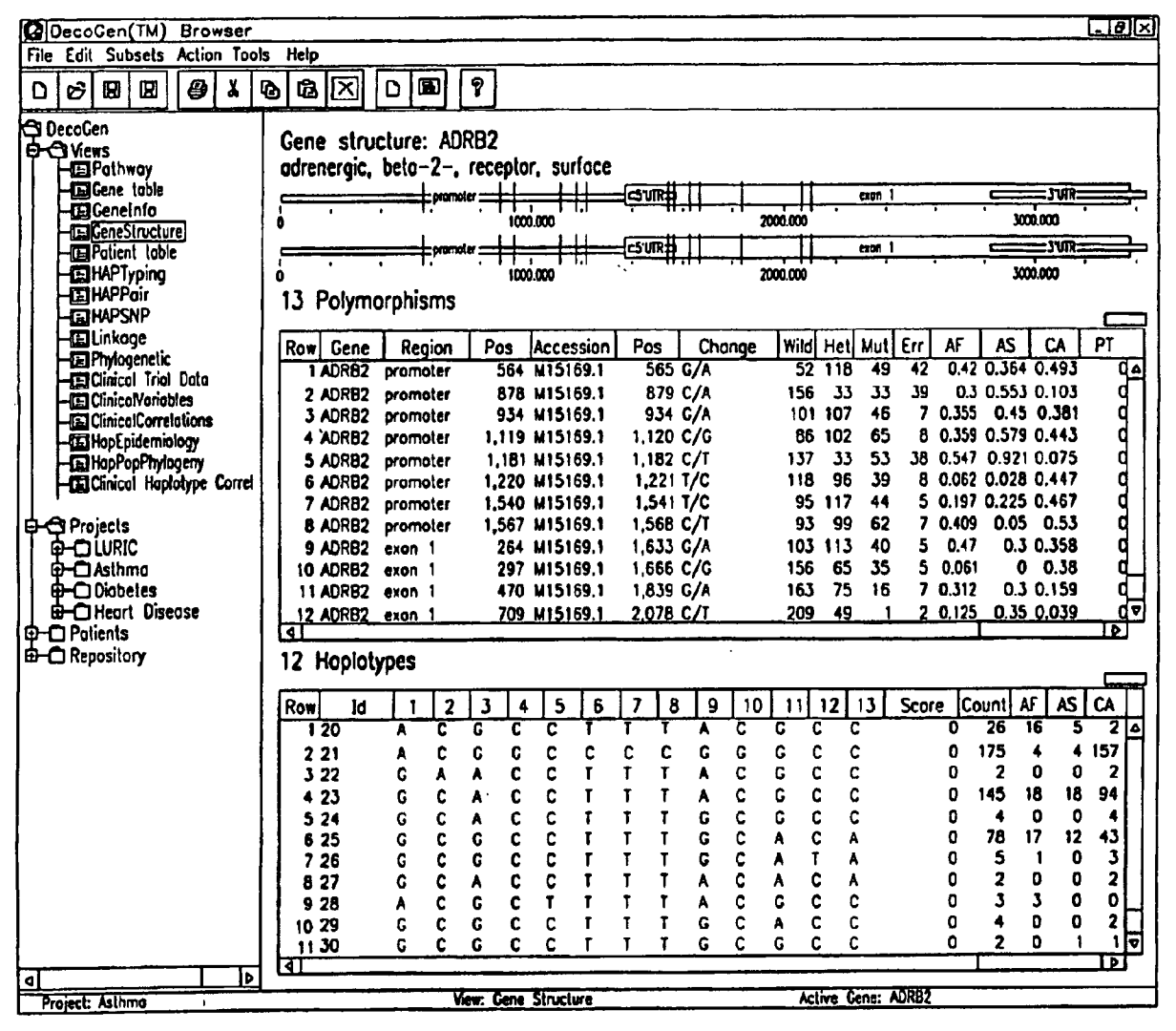

FIG. 28A. GeneStructure View. This screen shows the location of features in the gene (such as promoter, introns, exons, etc.), the location of polymorphic sites in the gene for each haplotype and the number of times each haplotype was seen in various world population groups for the ADRB2 gene. This screen is an alternative way of showing information similar to that described in the Gene Structure View in FIG. 4A.

Figure 28B:
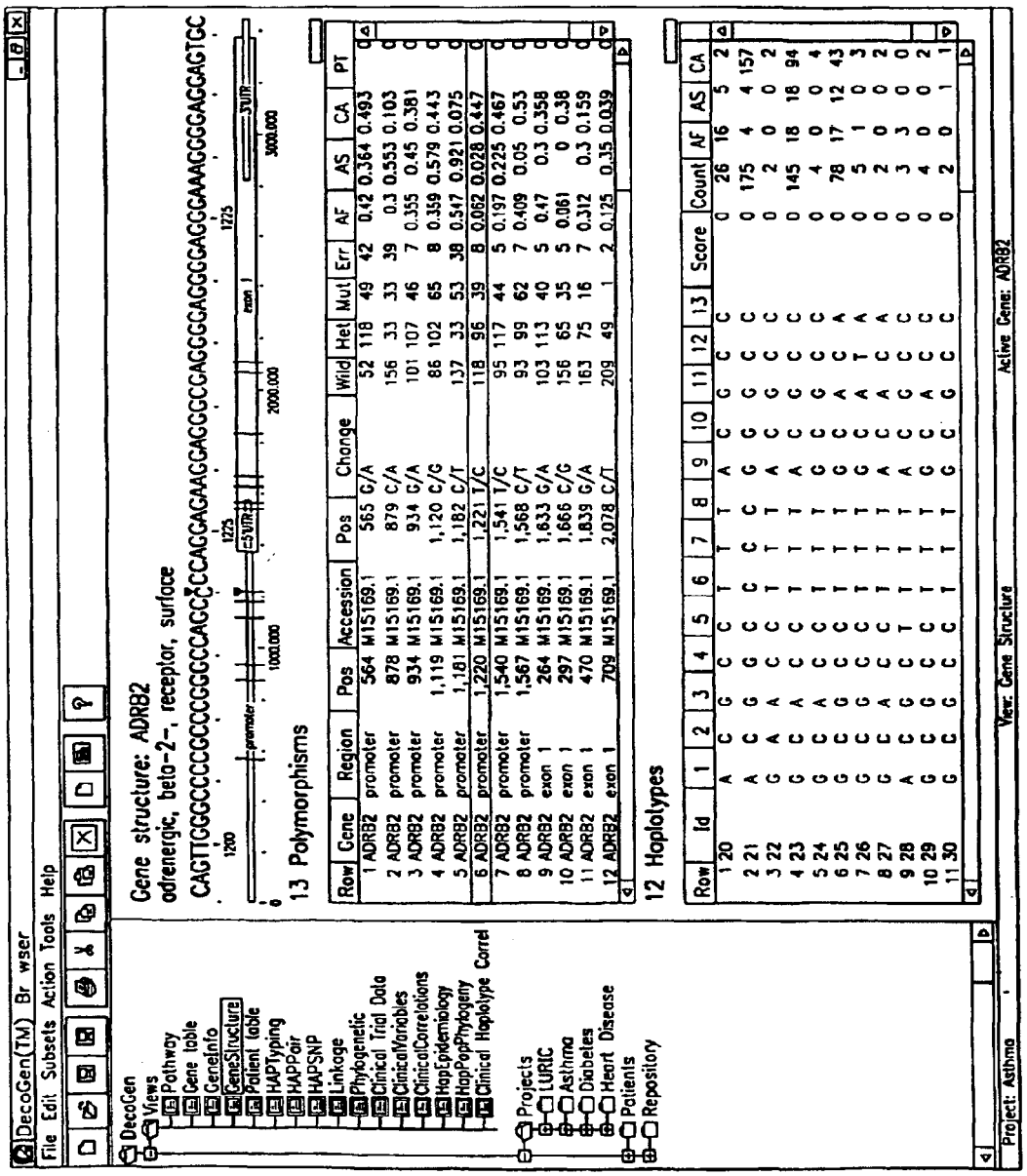

FIG. 28B. GeneStructure View (Cont.). This screen shows a screen which results after a gene feature is selected in the screen of FIG. 28A. This screen is an alternative way of showing information similar to that described in the Gene Structure View in FIG. 4B. An expanded view of the nucleotide sequence flanking the selected polymorphic site is shown at the top of the screen. This portion of the screen provides access to some of the same information as shown in FIG. 5 (Sequence Alignment View).

Figure 29A:
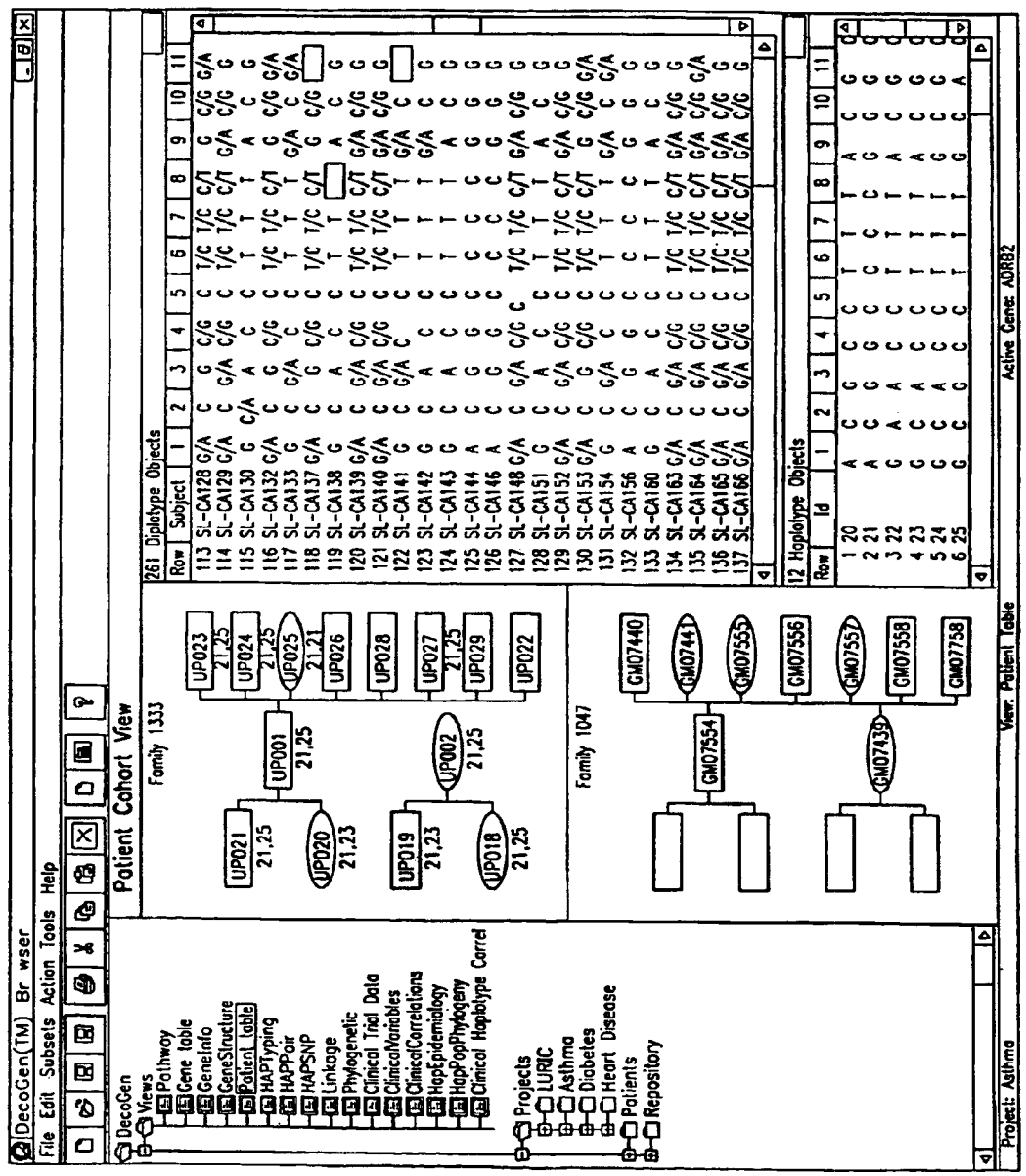

FIG. 29A. Patient Table View/Patient Cohort View. This screen shows genotype and haplotype information about each of the members of the patient population being analyzed. Family relationships are also shown, when such information is present. Families 1333 and 1047 shown in FIG. 29A are the families that were analyzed for this gene. In this particular screen, if other families had been analyzed, they would appear with those shown, but below, where one would scroll down. "Subject" is a unique identifier. The patients' genotypes are shown in the top right panel. At the far left of this panel (not seen until one scrolls over) are the indices for the two haplotypes that a patient has. These indices refer to the haplotype table at the bottom right. The left hand panel shows the haplotype Ids for families that have been analyzed as part of a cohort. The haplotypes must follow Mendelian inheritance pattern, i.e., one copy form his mother and one from his father. For instance if an individual's mother had haplotypes 1 and 2 and his father had haplotypes 3 and 4, then that individual must have one of the following pairs: (1,3), (1,4), (2,3) or (2,4). This panel is used to check the accuracy of the haplotype determination method used.

Figure 29B:
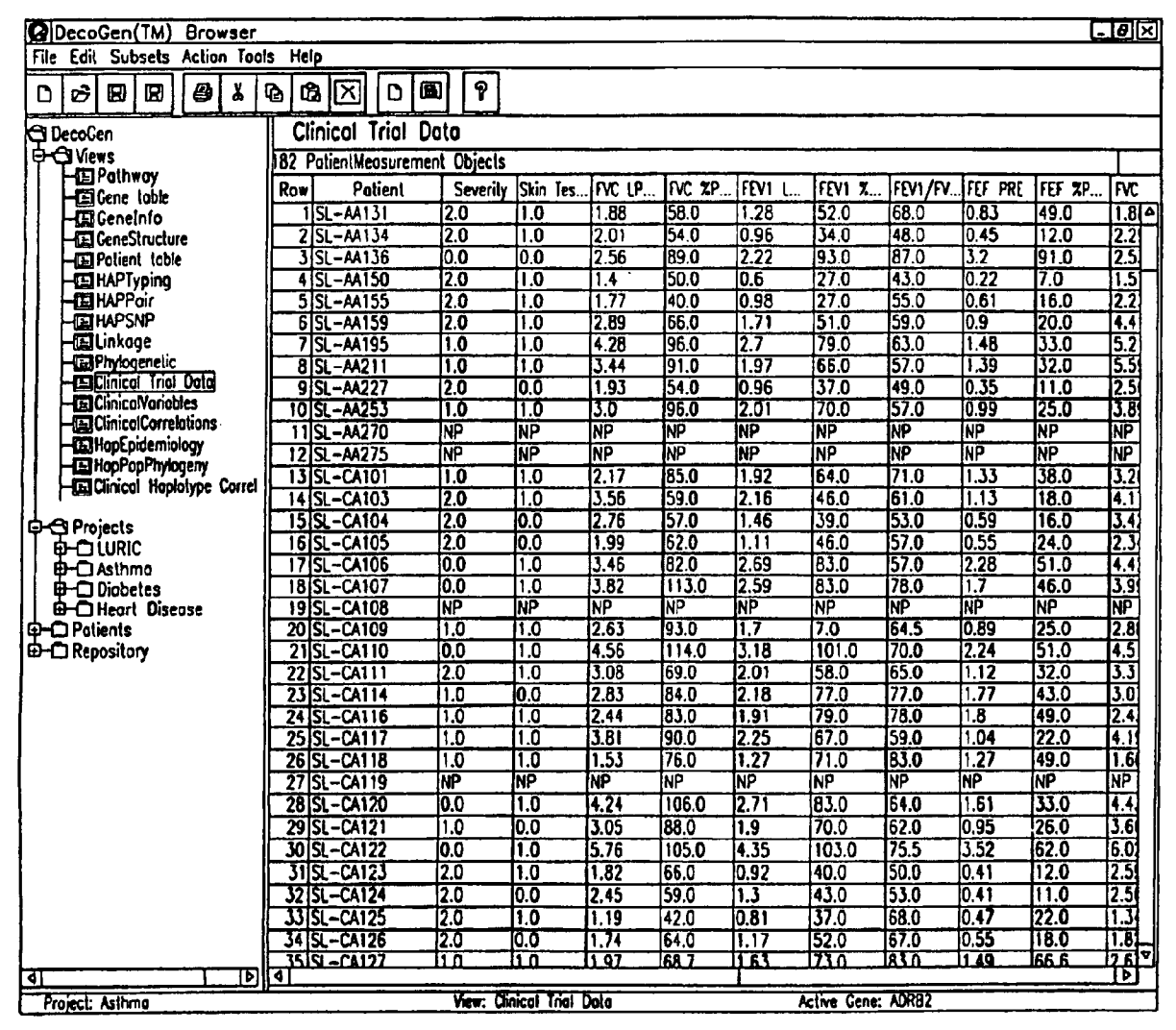

FIG. 29B. Clinical Trial Data View. This screen shows gives the values of all of the clinical measurements for each individual in FIG. 29A.

Figure 30:
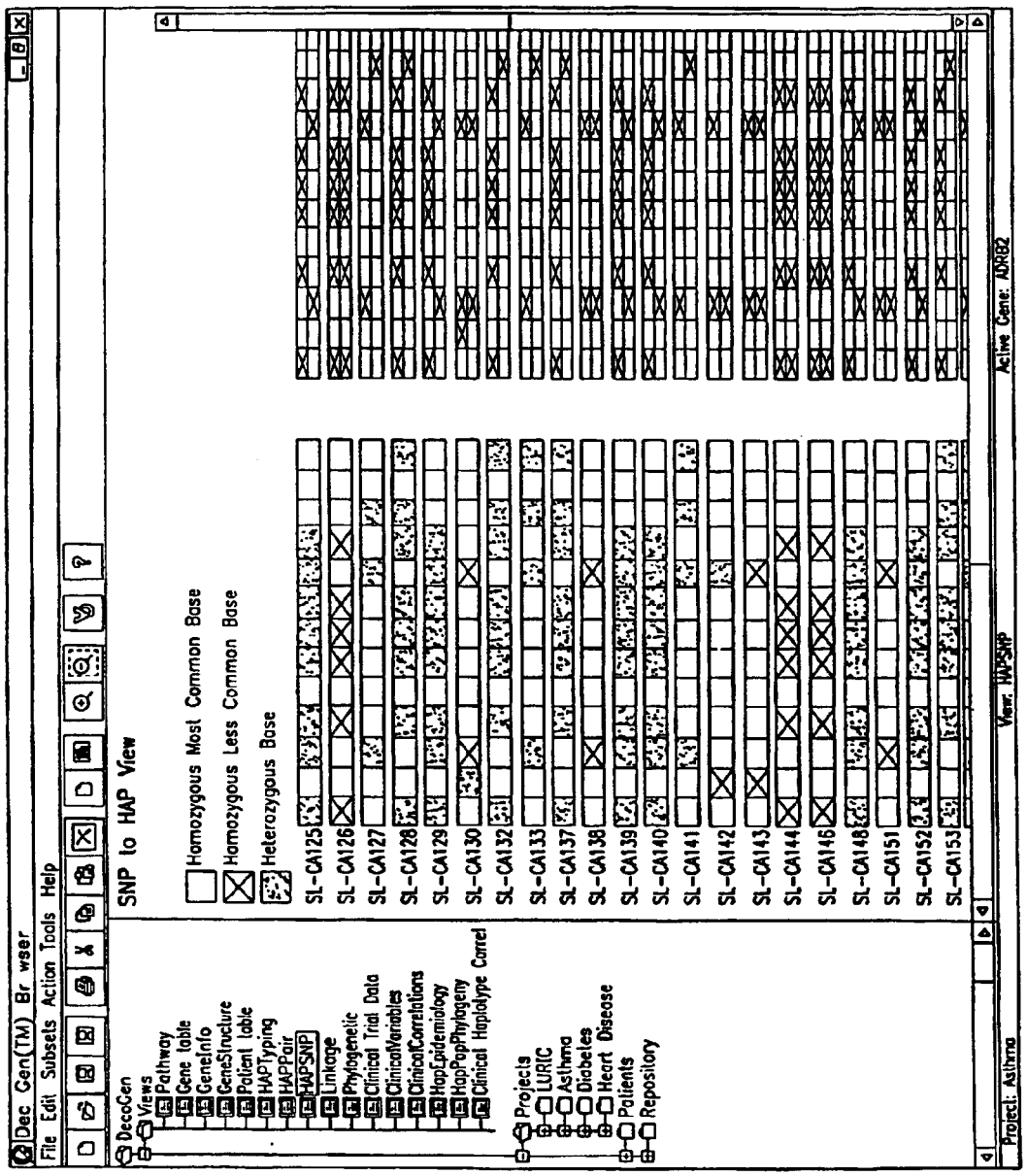

FIG. 30. HAPSNP View. This screen shows the genotype to haplotype resolution of the ADRB2 gene for each of the individuals in the population being examined. This view provides similar information as that shown in the SNP Distribution View of FIG. 9.

Figure 31:
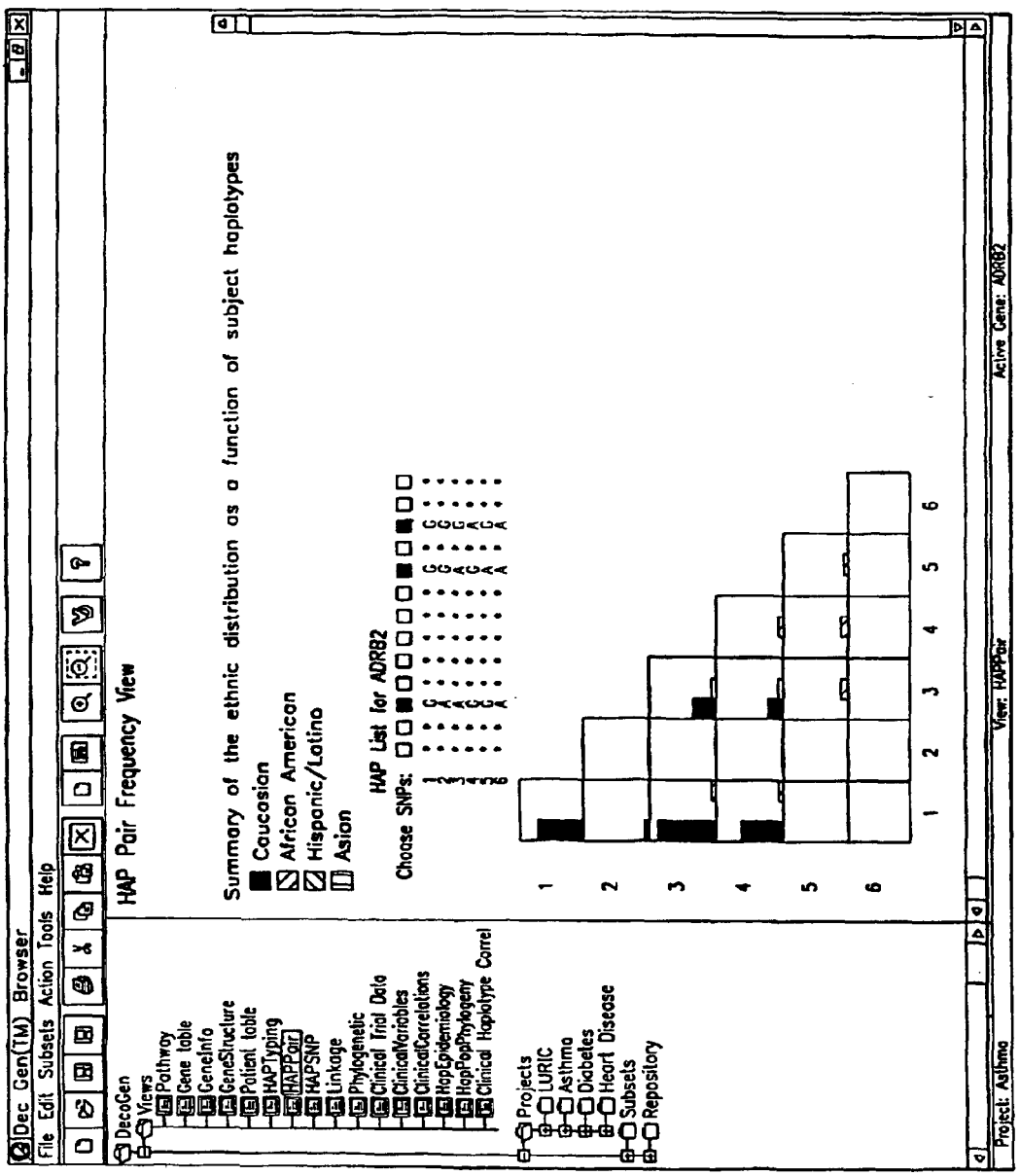

FIG. 31. HAPPair View. This screen shows a summary of ethnic distribution of haplotypes of the ADRB2 gene. This view is an alternative way of showing information similar to that shown in the Haplotype Frequencies (Summary View) of FIG. 10. The "V/D" (i.e., View Details) button in this view allows the user to toggle between the views shown in FIGS. 31 and 32.

Figure 32:
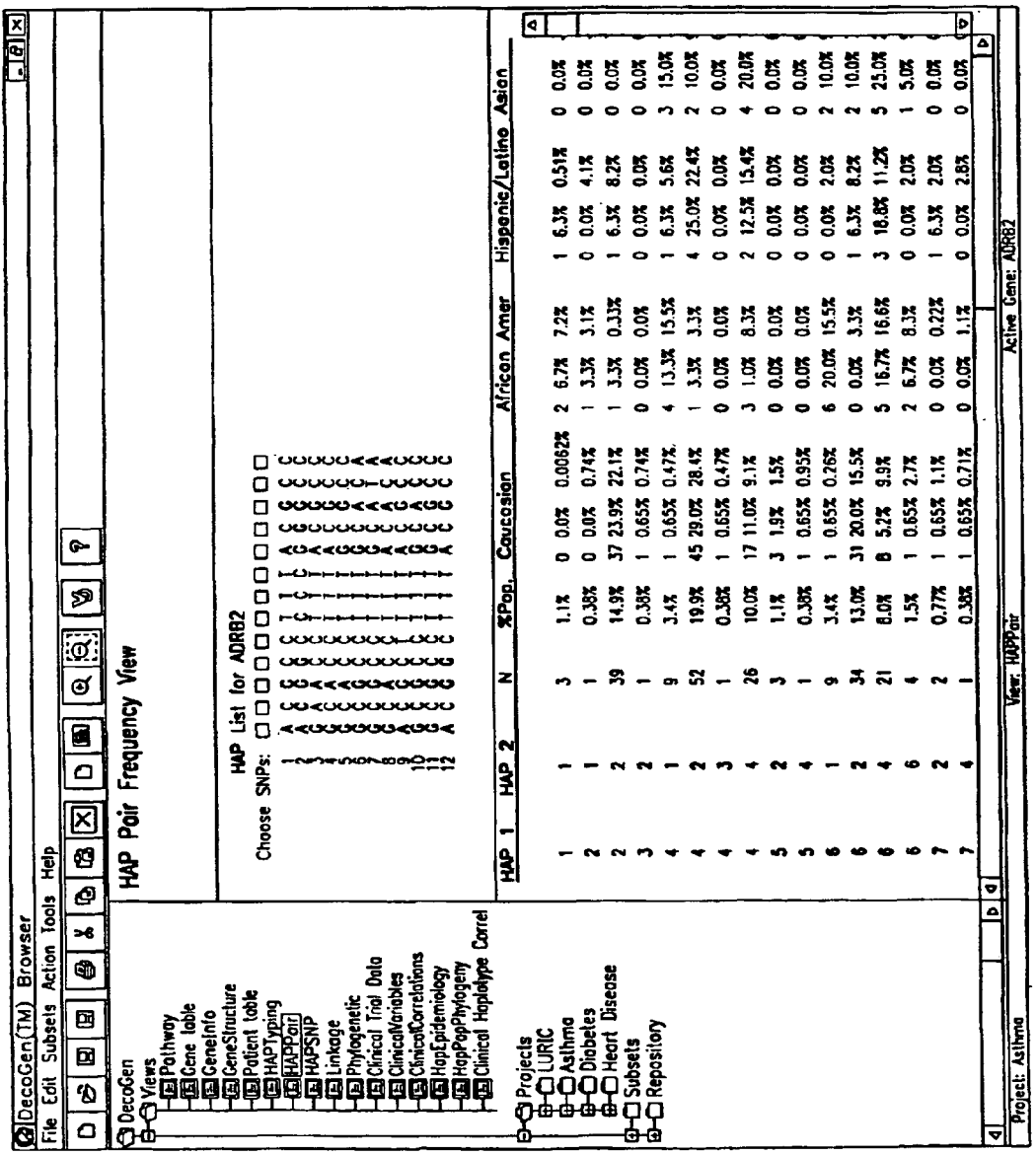

FIG. 32. HAP Pair View (HAP Pair Frequency View). This screen shows details of ethnic distribution as a function of haplotypes of the ADRB2 gene. Numerical data is provided. This view is an alternative way of showing information similar to that shown in the Haplotype Frequencies (Detailed View) of FIG. 11 for the CPY2D6 gene. The V/D button has the same function as in FIG. 31.

Figure 33:
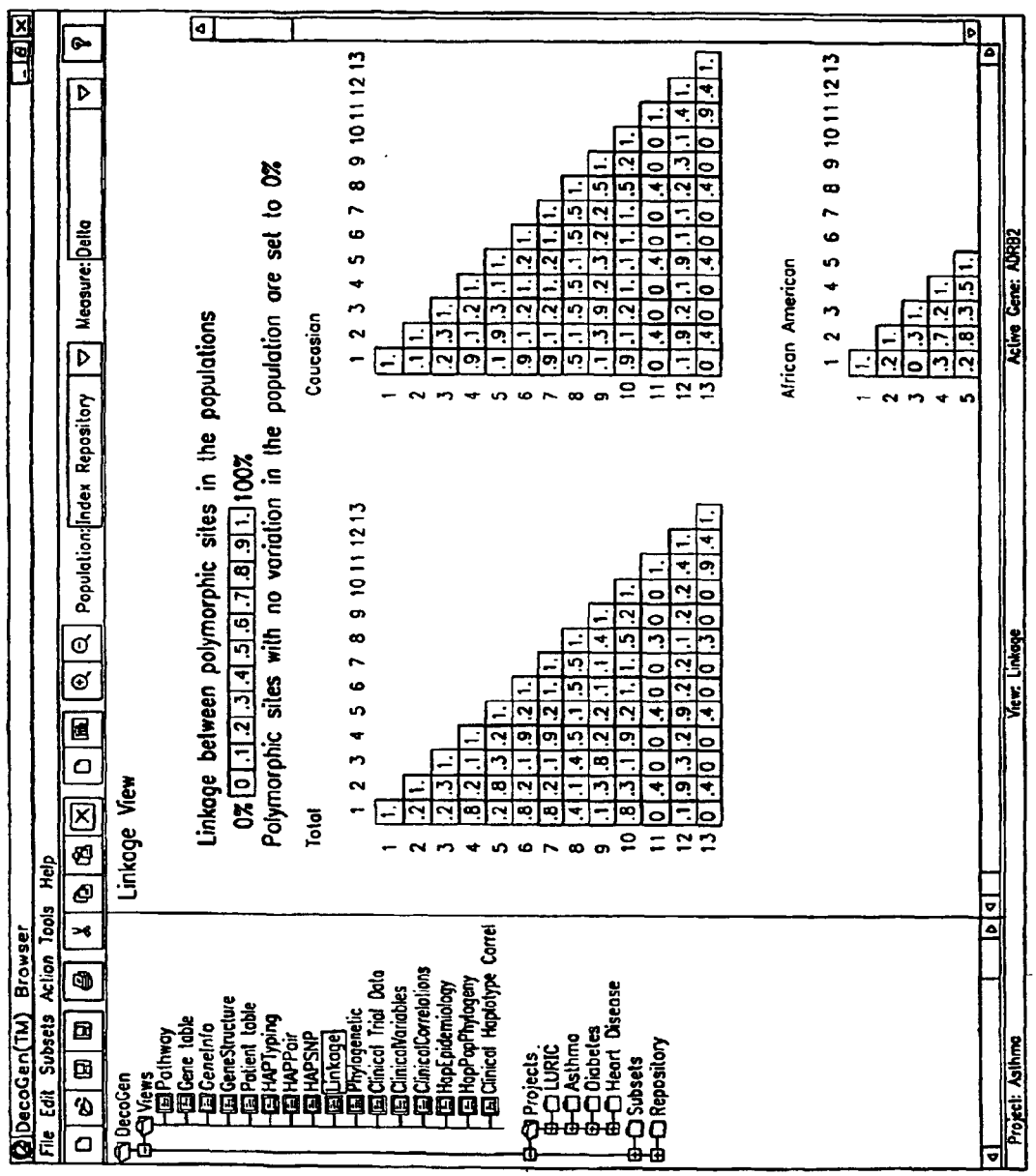

FIG. 33. Linkage View. This screen shows linkage between polymorphic sites in the population for the ADRB2 gene. This view is an alternative way of showing information similar to that shown in FIG. 12 for the CPY2D6 gene.

Figure 34:
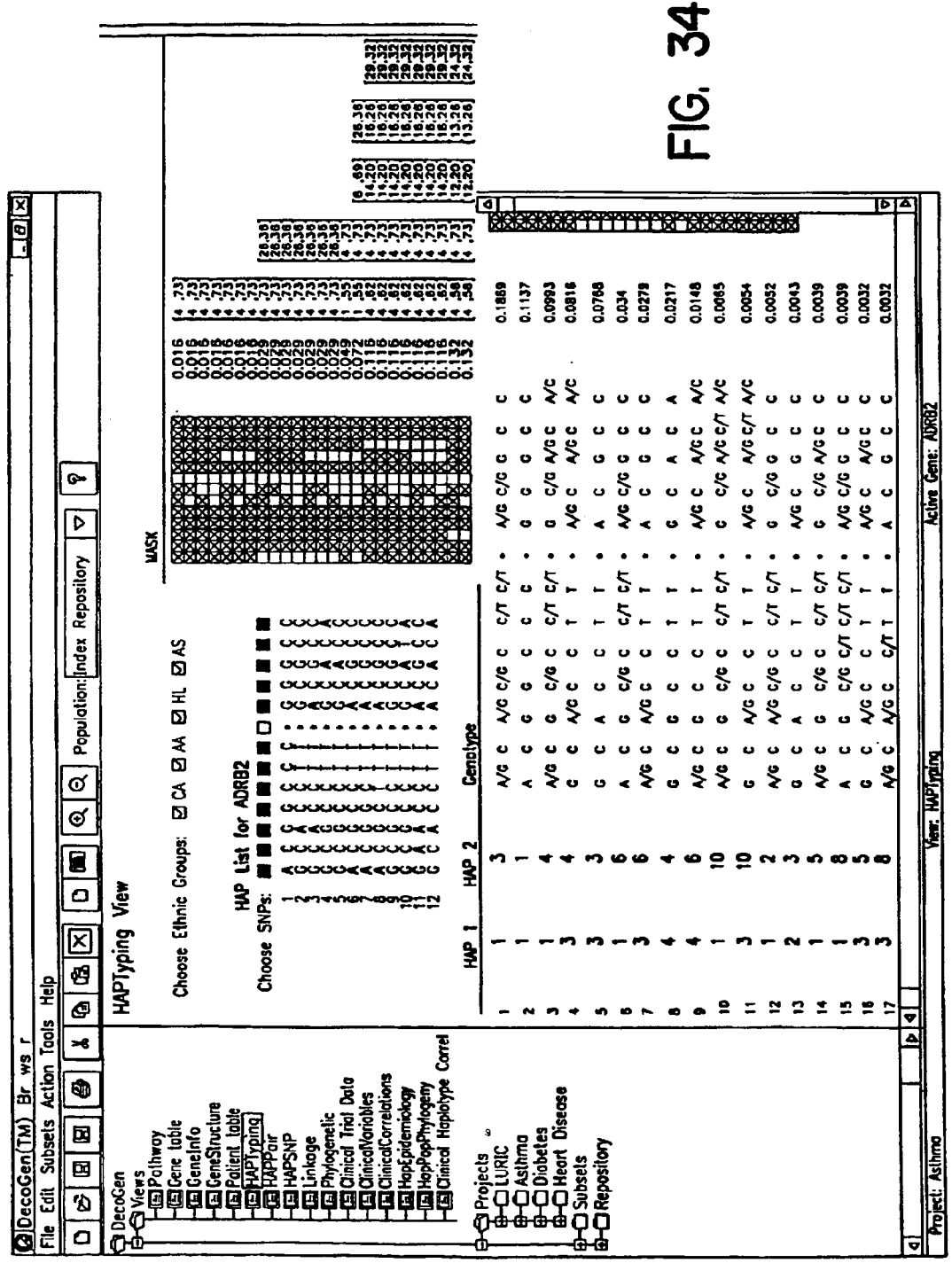

FIG. 34. HAPTyping View. This screen shows the reliability of haplotyping identification using genotyping at selected positions for the ADRB2 gene. This view is an alternative way of showing information similar to that shown in the Genotype Analysis Views of FIGS. 13, 14 and 15 for the CPY2D6 gene. This view is the interface to the automated method for determining the minimal number of SNPs that must be examined in order to determine the haplotypes for a population. See "Step 6", Section D(1) and Example 2, herein, for details of this method. The view shows all pairs of haplotypes and their corresponding genotypes and finally the frequency of the genotype. The inset (which one sees by scrolling to the right) shows the best scoring set of SNPs to score, along with a quality score (scores<1) are acceptable. The pairs of numbers in brackets are the genotypes that are still indistinguishable given this SNP set "Population" in the box in the top of the figure is equivalent to the, "Subset" selection menu described above. Populations and subsets are the same. One subset is the total analyzed population.

Figure 35:
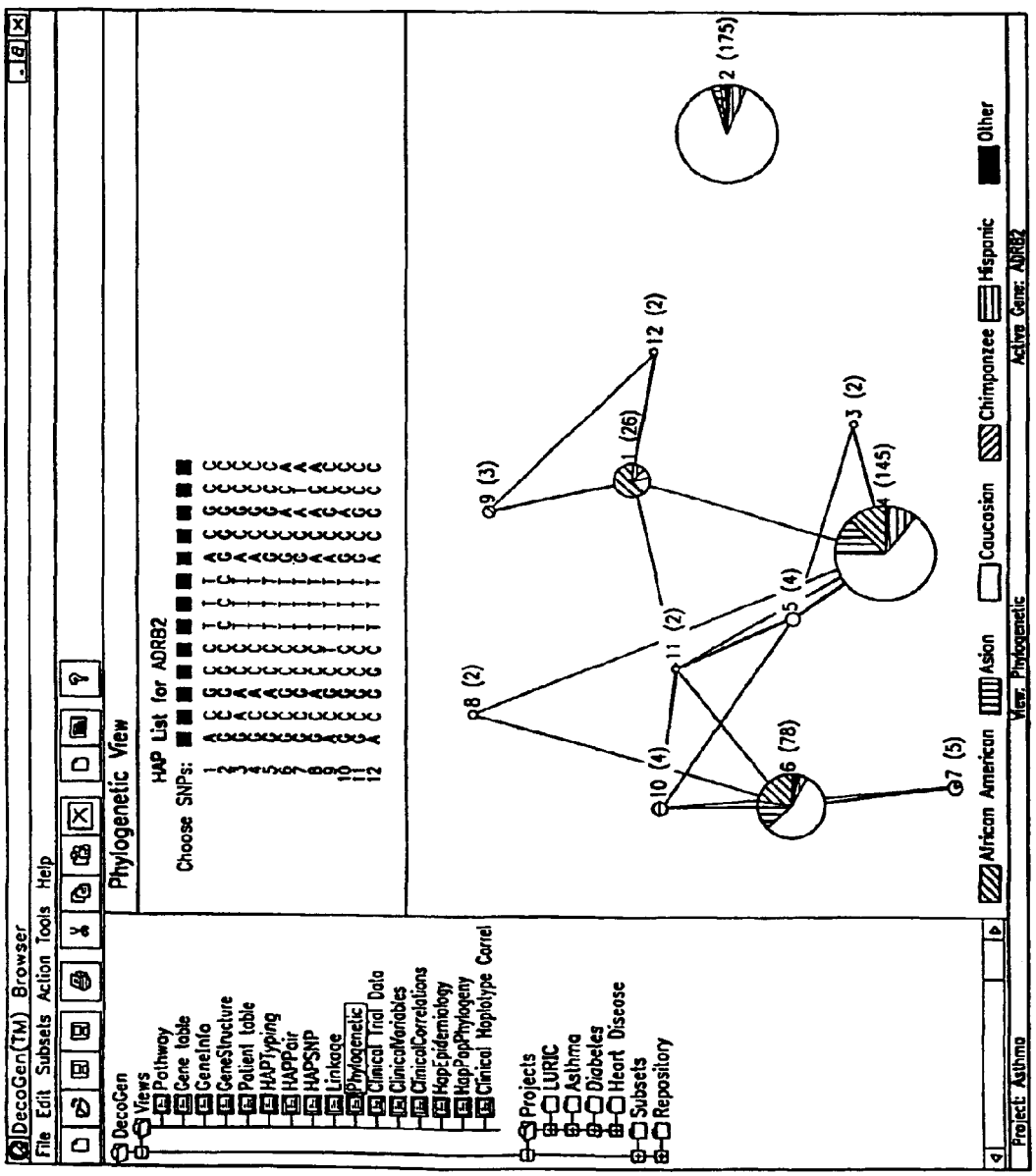

FIG. 35. Phylogenetic View. These screens show minimal spanning networks for the haplotypes seen in the population for the ADRB2 gene. This view is an alternative way of showing information similar to that shown in FIGS. 16 and 17 for the CPY2D6 gene. This view also provides a window containing haplotype and ethnic distribution information. The numbers next to the balls represent the haplotype number and the numbers inside the parentheses represent the number of people in the analyzed population that have that haplotype. The function of the calculator button (or a red/green flag button, not shown in this view) is the same as recalculate in FIGS. 16 and 17. In this case it arranges nodes according to evolutionary distance.

Figure 36:
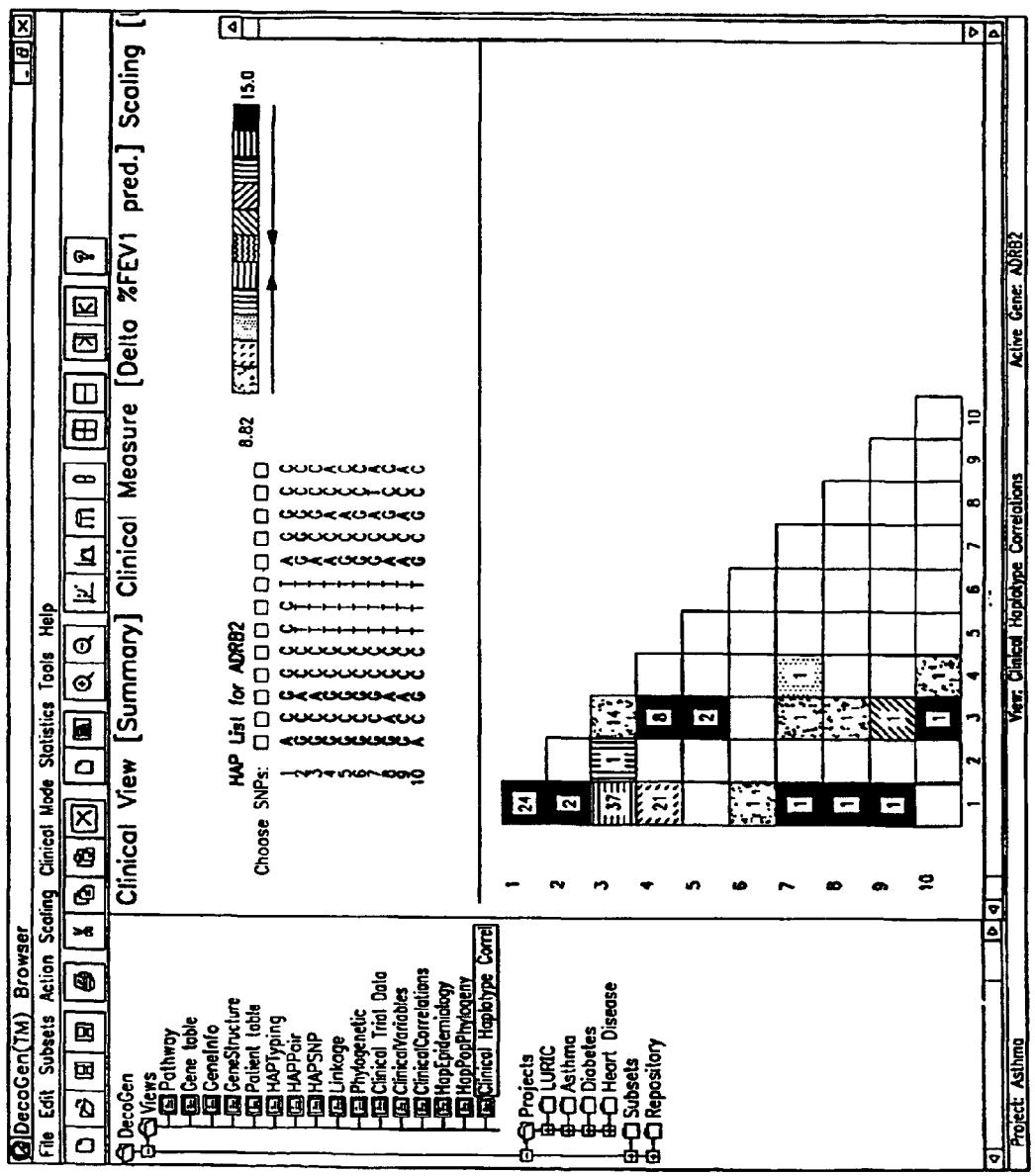

FIG. 36. Clinical Haplotype Correlations View (Summary). This screen shows a matrix summarizing the correlation between clinical measurements and haplotypes for the ADRB2 gene. This view is an alternative way of showing information similar to that shown in FIG. 18 for the CPY2D6 gene.

Figure 39A:
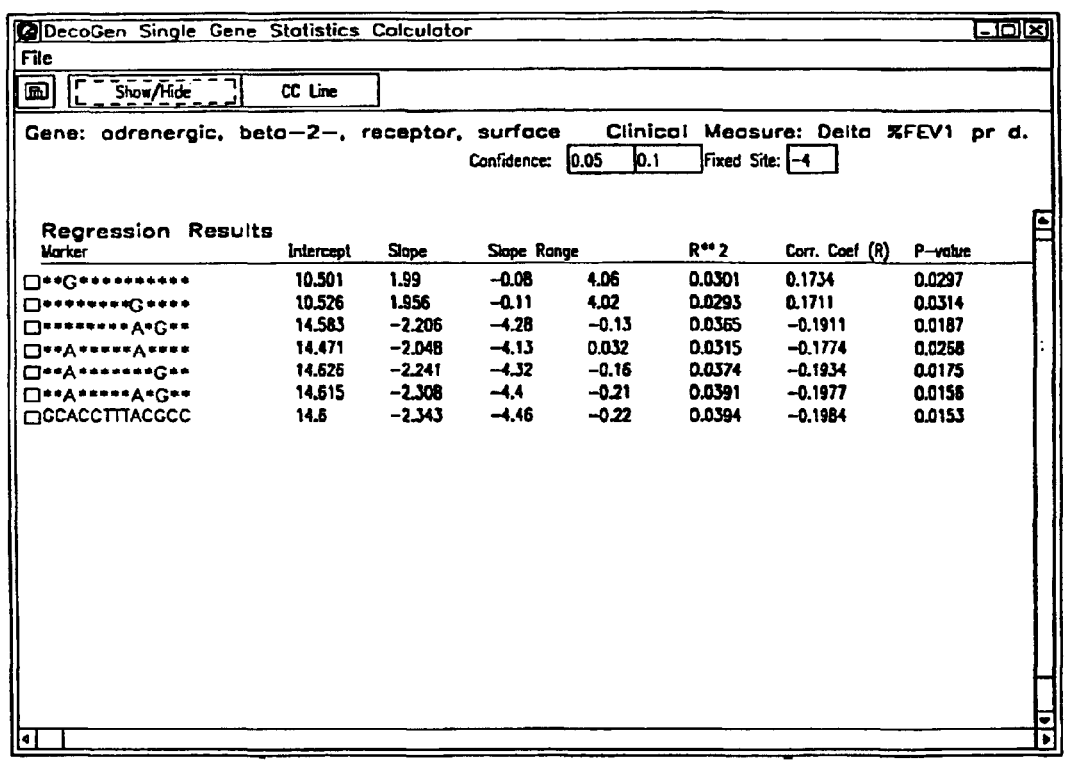

Buttons are as described for FIG. 26 and as follows:

Graph (icon of graph)—does a statistics calculation and brings up a statistics results window, such as FIG. 39A.

Normal (icon of bell curve)—does a HAPpair ANOVA calculation—a specialized statistical calculation.

3 finger down icon—displays a graph showing a histogram of clinical data for individuals with specific genetic markers.

Thermometer—shows a list of clinical variables for the user to select from for display and analysis.

Some of the viewing modes obtainable by selecting the following drop-down menus on this view (and the other views on which they appear) are:

Scaling:
Linear
Log
Log 10
Clinical Mode:
Summary
Distribution
Details
Quantile
Statistic:
Regression
ANOVA
Case Control
ANCOVA
Response Model FIG. 37. Clinical Measurements vs. Haplotype View (Distribution View). This screen shows the distribution of the patients in each cell of the matrix of FIG. 36. This view is an alternative way of showing information similar to that shown in FIG. 19 for the CPY2D6 gene. Drop-down menus and buttons are as described for FIG. 36.

Figure 37:
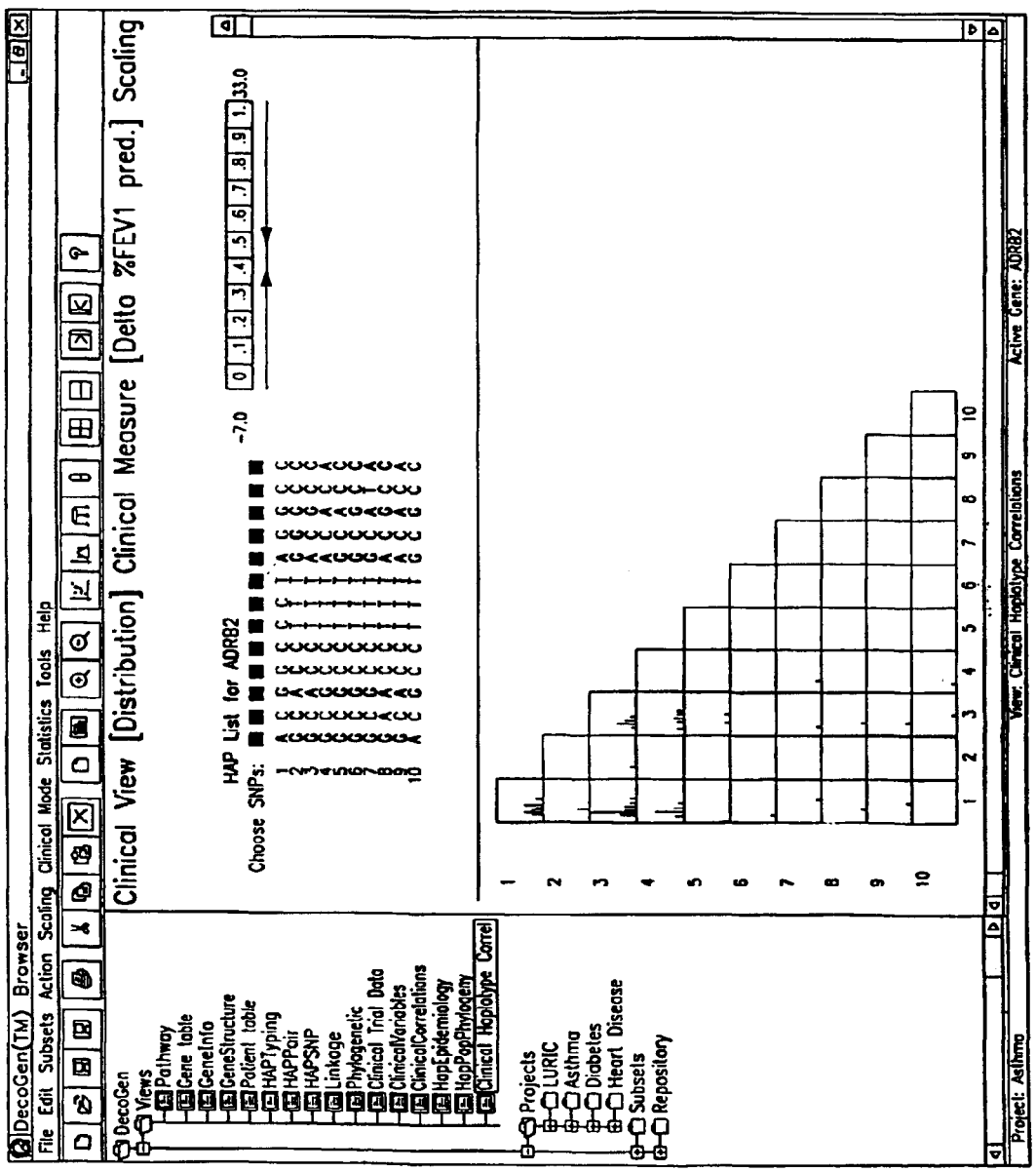
Figure 38:
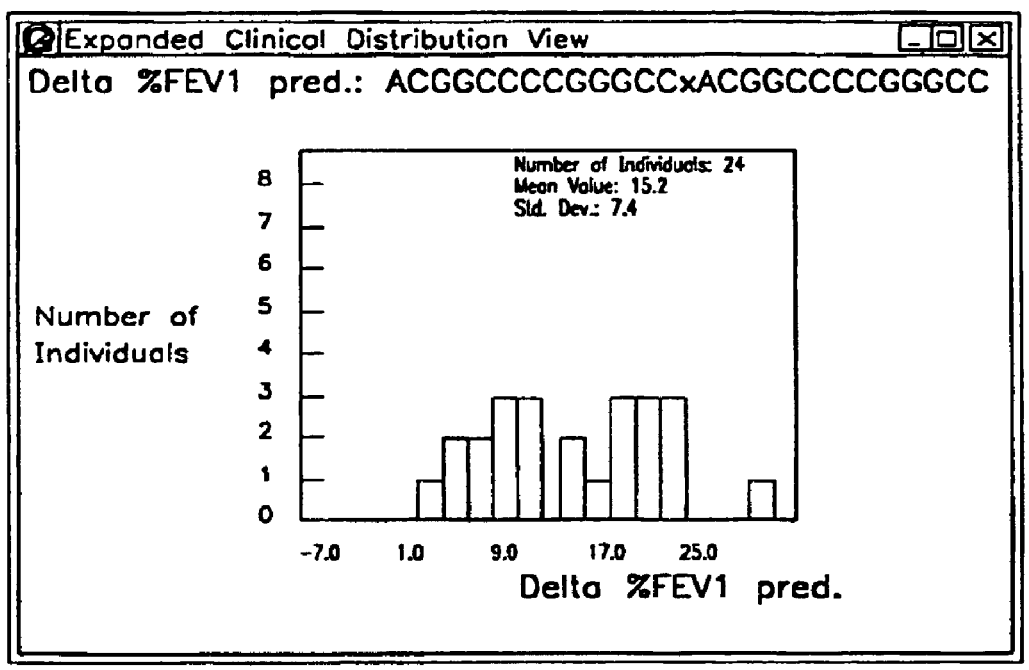

FIG. 38. Expanded Clinical Distribution View. This screen shows an expanded view of one haplotype-pair distribution. This screen results when a user selects a cell in the matrix in FIG. 37. The screen shows the number of patients in the various response bins indicated on the horizontal axis. This view is an alternative way of showing information similar to that shown in FIG. 20 for the CPY2D6 gene, and also displays additional information.

FIG. 39A. DecoGen Single Gene Statistics Calculator (Linear Regression Analysis View). This screen shows the results of a dose-response linear regression calculation on each of the shown individual polymorphisms or subhaplotypes with respect to the clinical measure "Delta % FEV1 pred." The SNPs and subhaplotypes shown are those selected as significant in the build-up procedure described below. This view is an alternative way of showing information similar to that shown in FIG. 21 for the CPY2D6 gene and the "test" measurement, with additional information. The numbers in the boxes next to "Confidence" and "Fixed Site" in FIG. 39A are default values for these parameters, but can be changed by the user. After they are changed, the user must click the "Redo" or "Recalculate" button (the little calculator icon) the regenerate the statistic with the new parameter. The first two boxes hold the tight and loose cutoffs for the snp-to-hap buildup procedure we have already discussed. The "Fixed site" value says how far the buildup can proceed a value of "4" says produce sub-haplotypes with no more that 4 non-* sites. The minus sign says to also do the full-haplotype build down procedure. Detecting the Show/Hide button allows the user to toggle between modes where all examined correlations are displayed and where only those passing the tight statistical criteria are displayed.

Figure 39B:
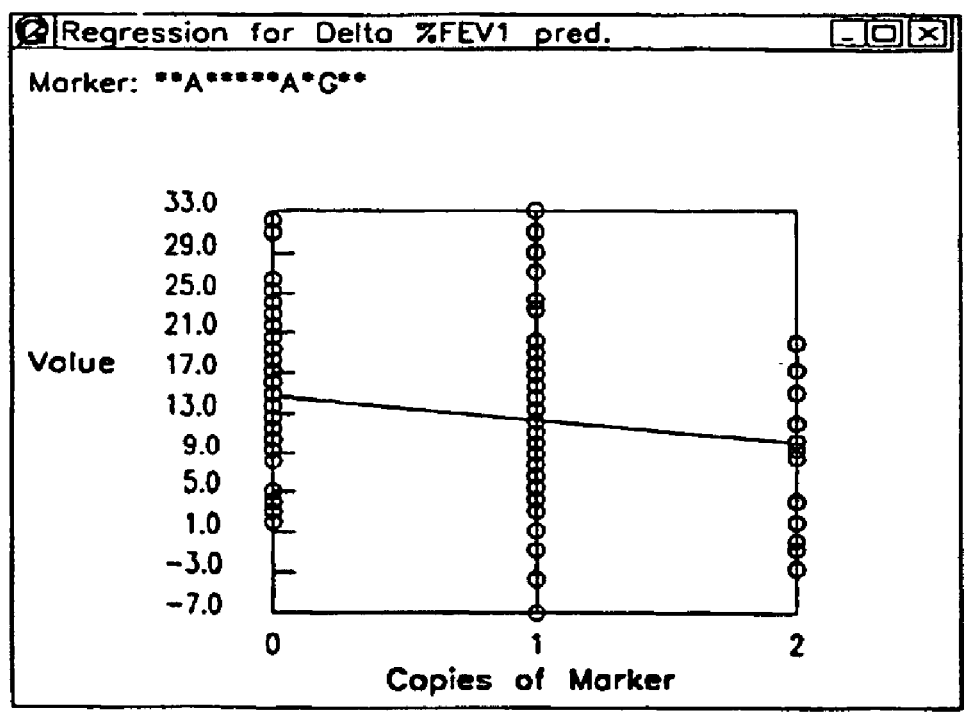

FIG. 39B. Regression for Delta % FEV1 Pred. View. This view shows the regression line response as a function of number of copies of haplotype A***A*G**.

Figure 40:
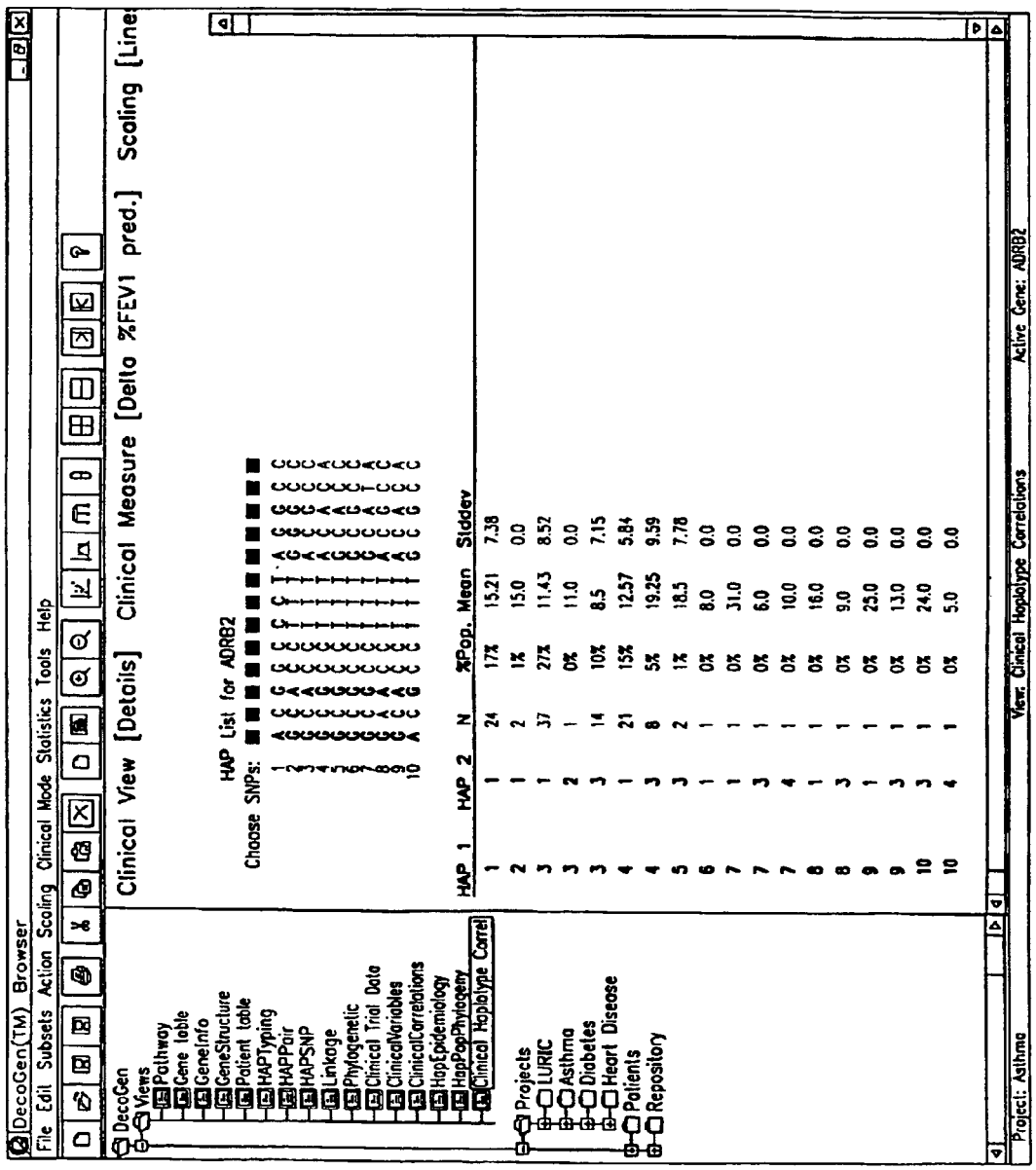

FIG. 40. Clinical Measurements vs. Haplotype View (Details). This screen gives the mean and standard deviation for each of the cells in FIG. 36. This view is an alternative way of showing some of the information similar to that shown in FIG. 22 for the CPY2D6 gene and the "test" measurement FIG. 41. Clinical Measurement ANOVA calculation. This screen shows the statistical significance between haplotype pair groups and clinical response for the Hap pairs for the ADRB2 gene. This view is an alternative way of showing some of the information similar to that shown in FIG. 23 for the CPY2D6 gene and the "test" measurement.

Figure 42:
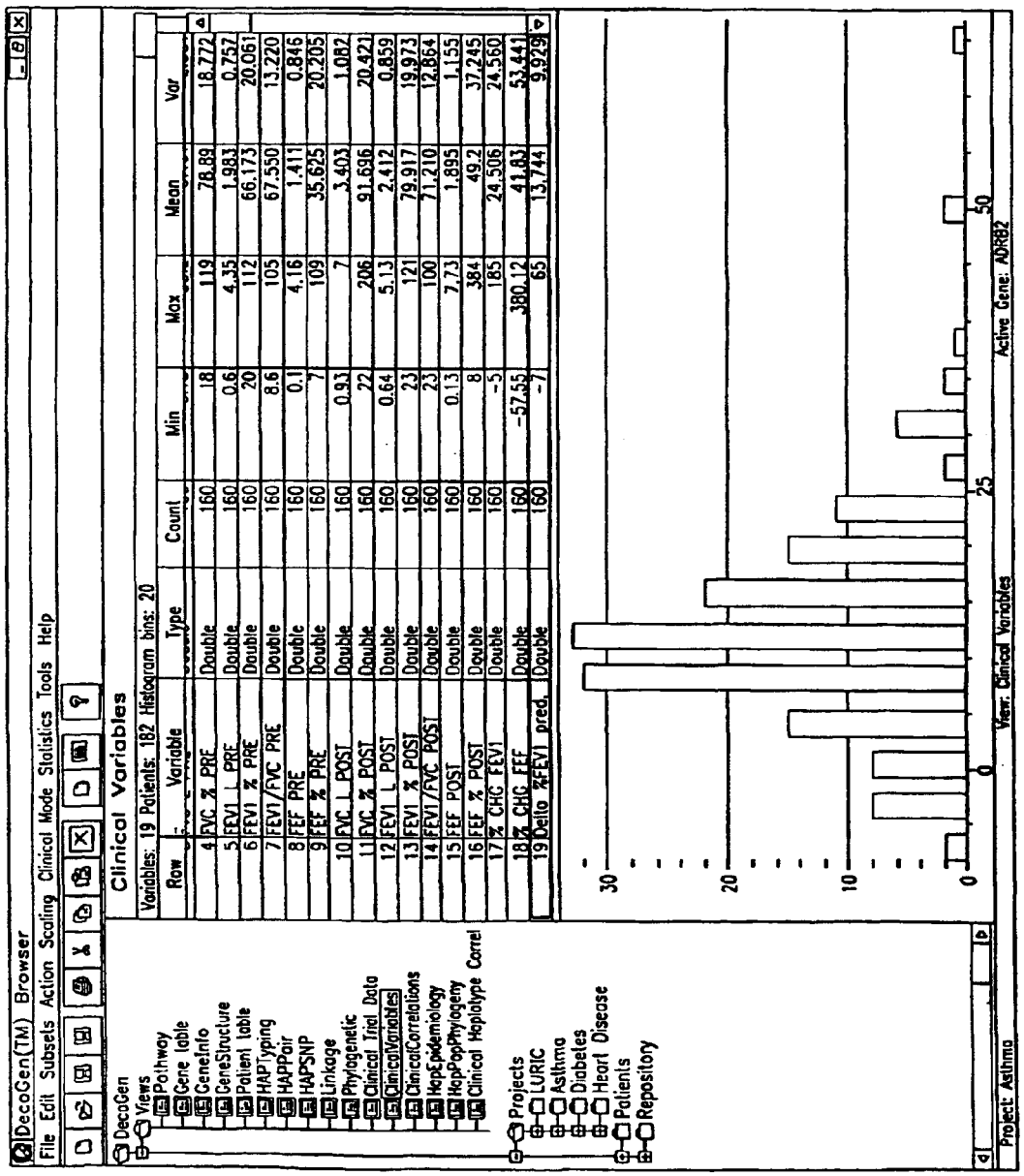

FIG. 42. Cinical Variables View. This figure simply shows histogram distributions for each of the clinical variables. This is the same as FIG. 38, but not selected by haplotype pair. A clinical measurement is chosen by selecting one of the lines in the top list FIG. 43. Clinical Correlations View. This view allows one to see the correlation between any pair of clinical measurements. The user selects one measurement from the list on the left, which becomes the x-axis, and one from the list on the right, which becomes the y-axis. Each point on the bottom graph represents one individual in the clinical cohort.

Figure 44A:
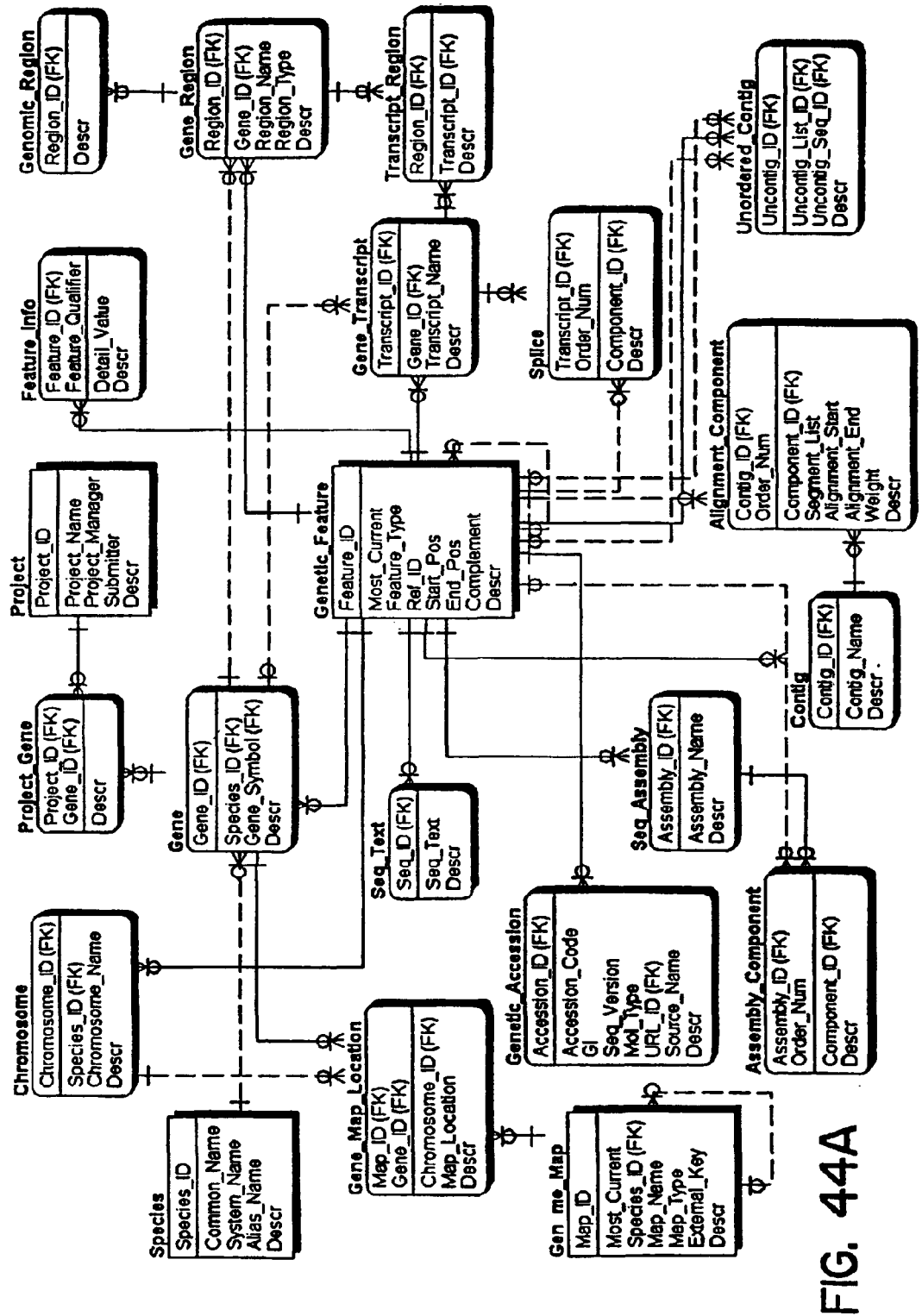

FIG. 44A. Genomic Repository data submodel. This is a preferred alternative model to the submodels shown in FIGS. 25A and 25D.

Figure 44B:
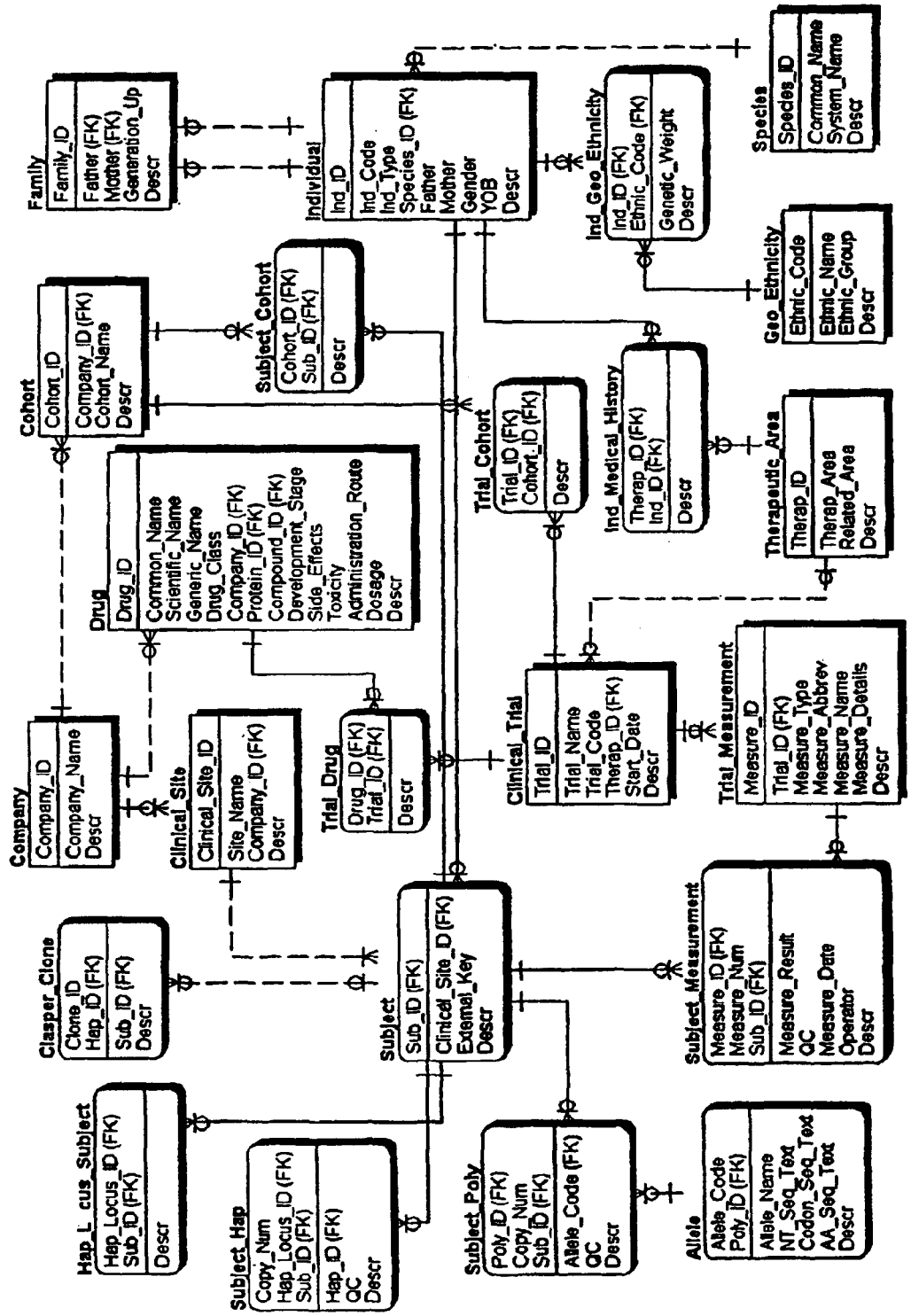

FIG. 44B. Clinical Repository data submodel. This is a preferred alternative submodel to that shown in FIG. 25B.

Figure 44C:
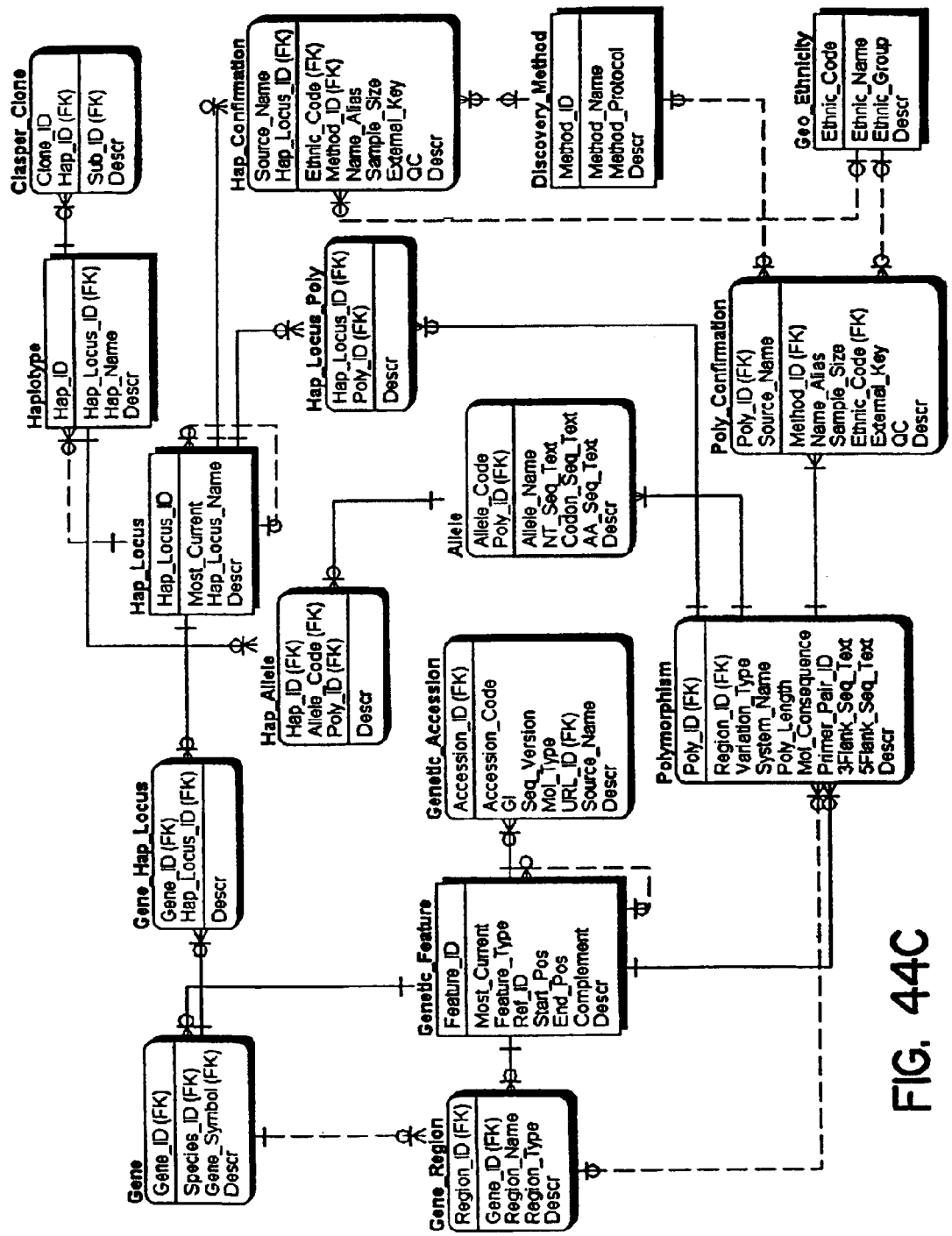

FIG. 44C. Variation Repository data submodel. This is an alternative submodel to that shown in FIG. 25C.

Figure 44D:
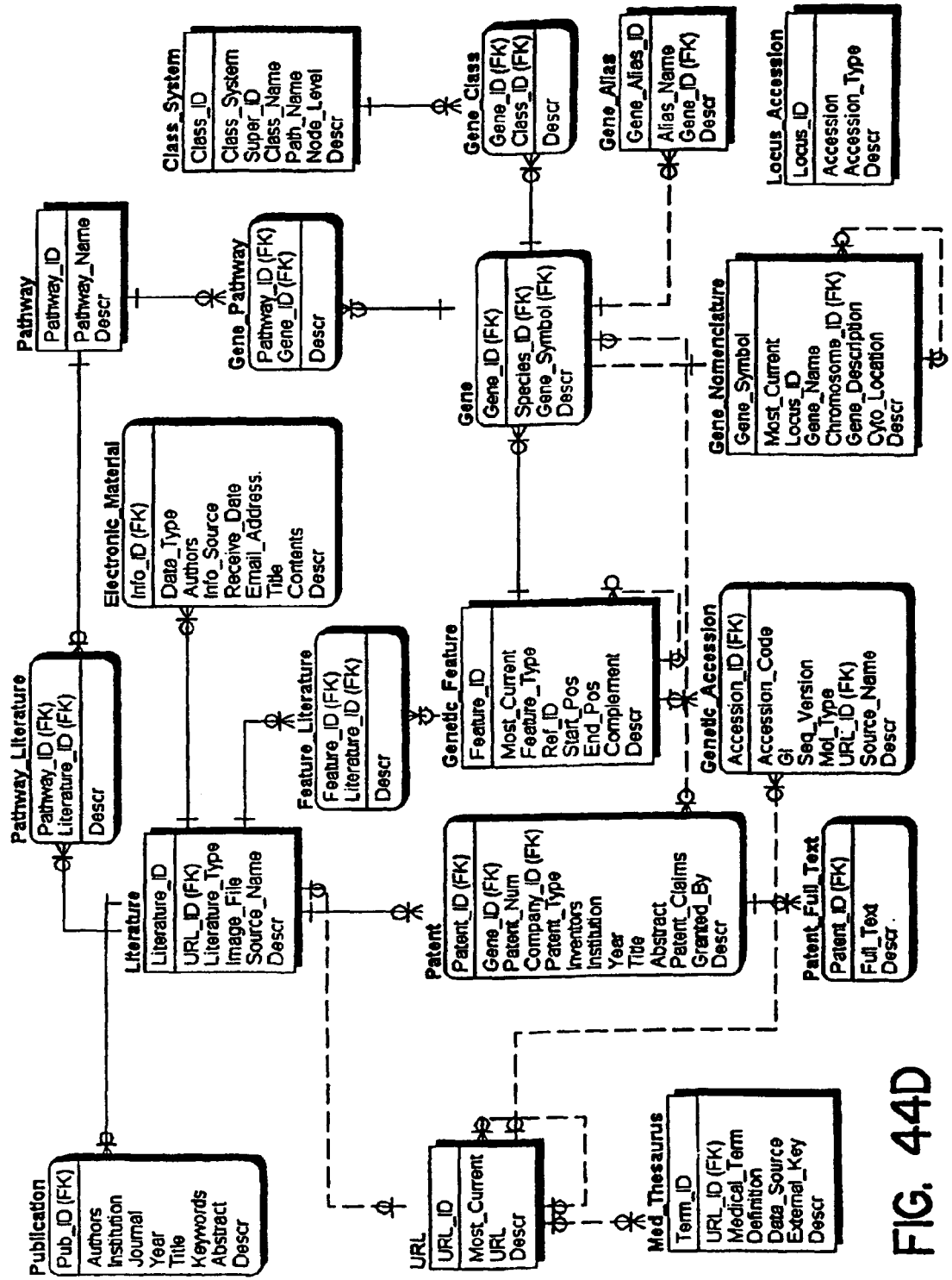

FIG. 44D. Literature Repository data submodel. This incorporates some of the tables from the gene repository submodel shown in FIG. 25A.

Figure 44E:
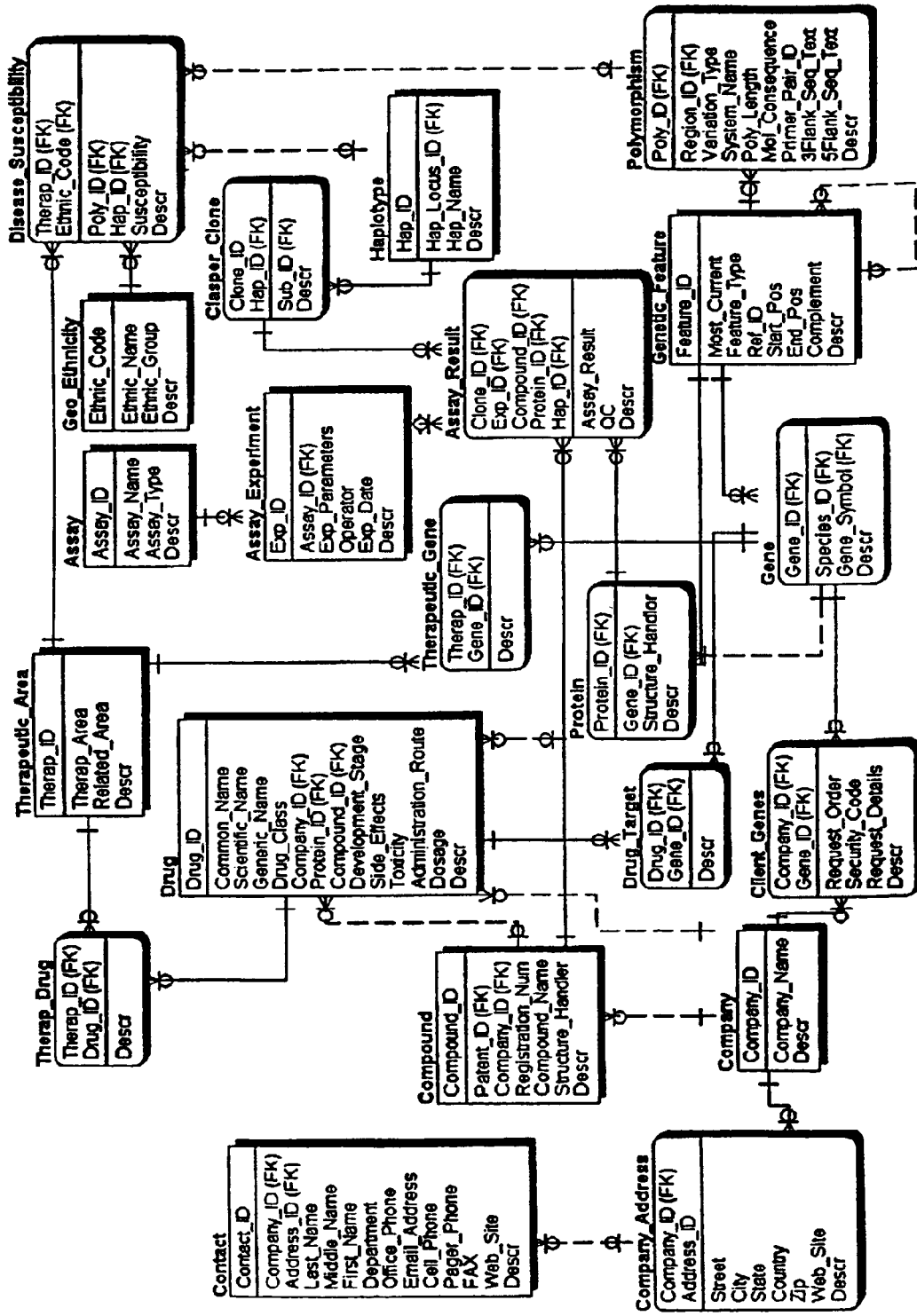

FIG. 44E. Drug Repository data submodel. This is an alternative submodel to that shown in FIG. 25E.

FIG. 44F. Legend of symbols in FIGS. 44A–E.

Figure 45:
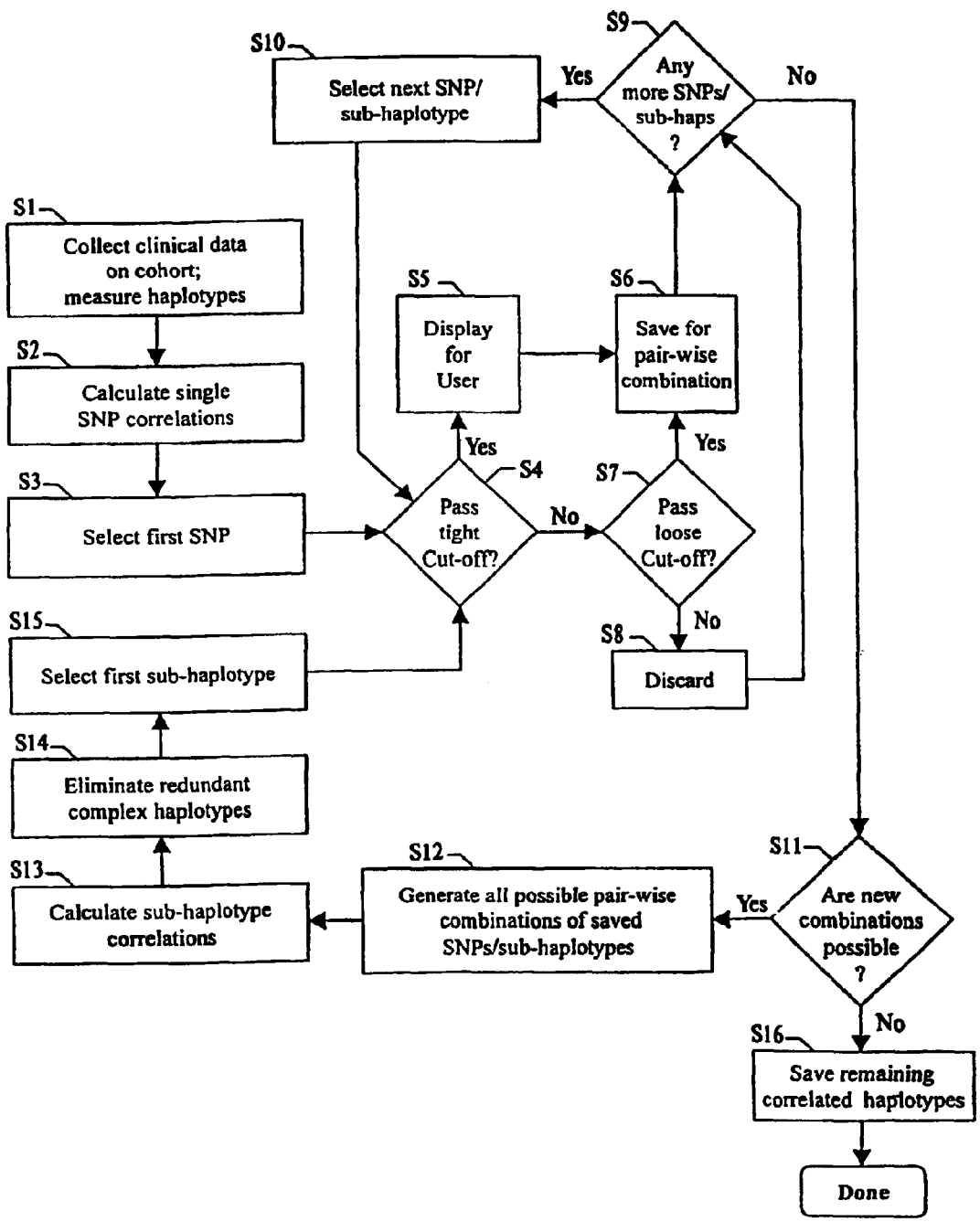

FIG. 45. Flow Chart. This is a flow chart for a multi-SNP analysis method of associating phenotypes (such as clinical outcomes) with haplotypes (also called a "build-up" procedure).

Figure 46:
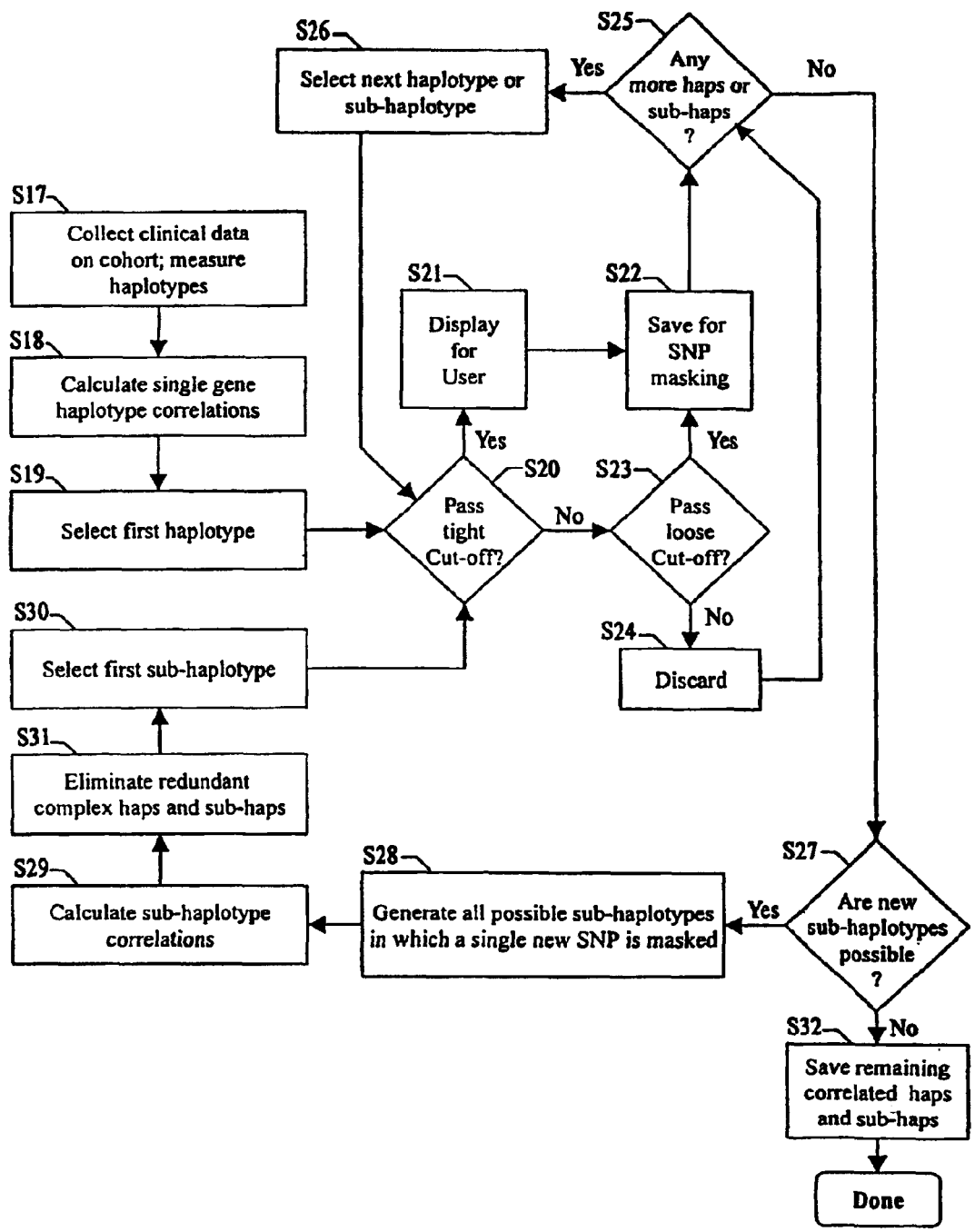

FIG. 46. Flow Chart. This is a flow chart for a reverse-SNP analysis method of associating phenotypes (such as clinical outcomes) with haplotypes (also called a "pare-down" procedure).

Figure 47:
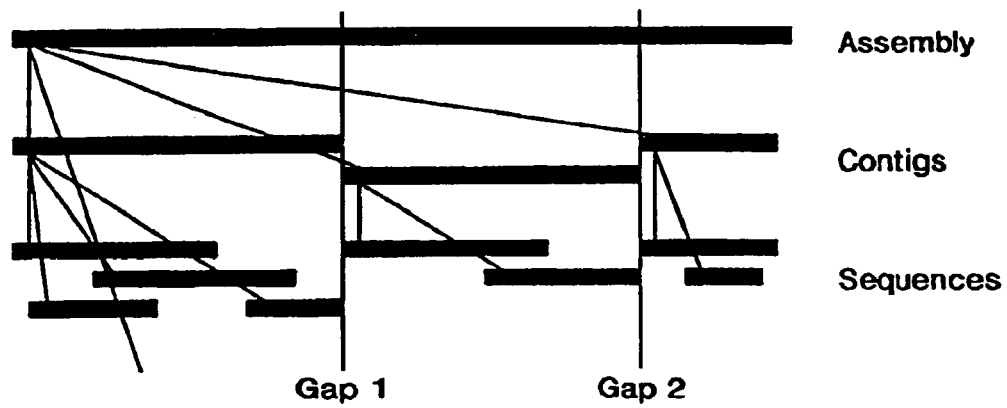

FIG. 47. Diagram of a process for assembling a genomic sequence by a human or a computer.

Figure 48:
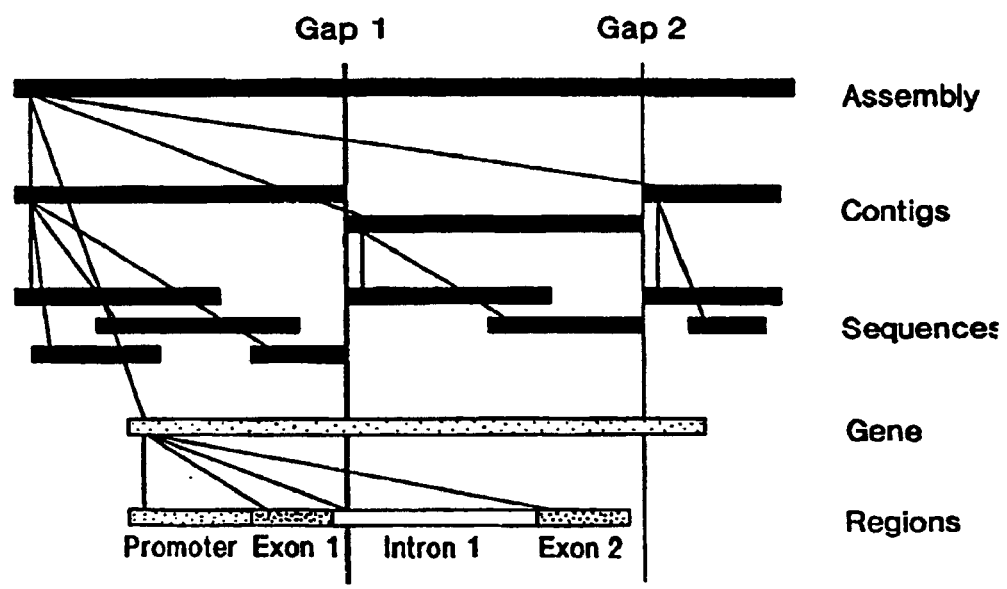

FIG. 48. Diagram of a process for generating and displaying a gene structure.

Figure 49:
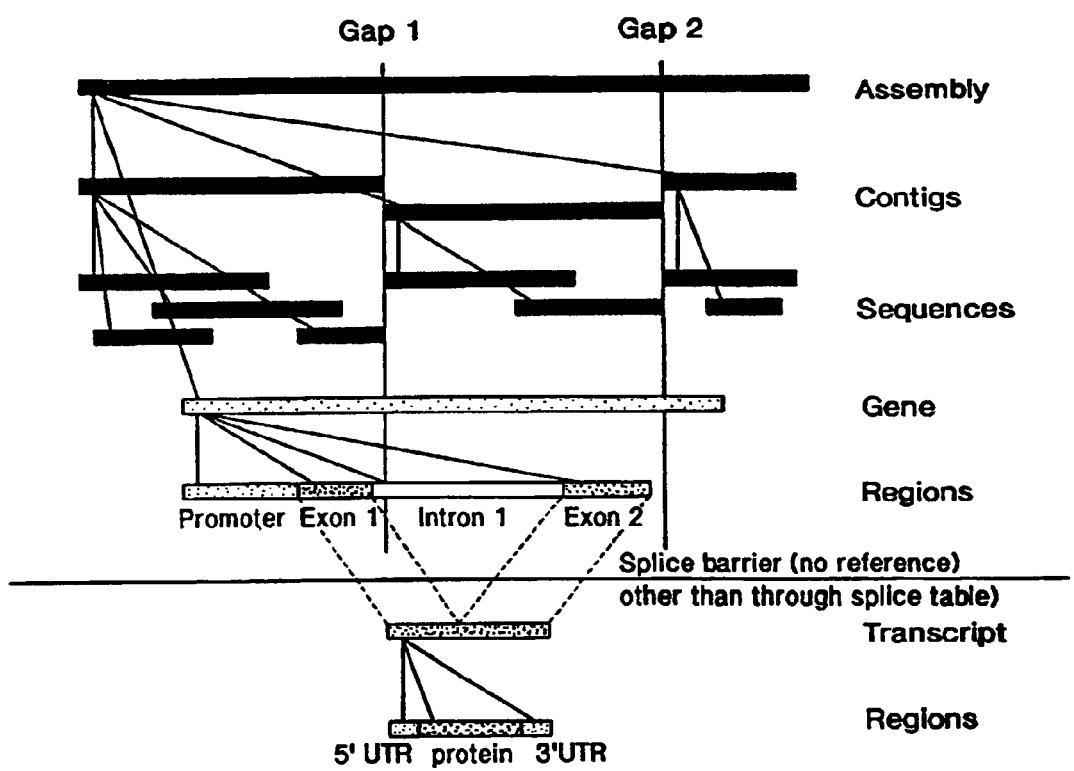

FIG. 49. Diagram of a process of generating and displaying a protein structure.

DETAILED DESCRIPTION OF THE INVENTION

A. Definitions

The following definitions are used herein:

Allele—A particular form of a genetic locus, distinguished from other forms by its particular nucleotide sequence.

Ambiguous polymorphic site—A heterozygous polymorphic site or a polymorphic site for which nucleotide sequence information is lacking.

Candidate Gene—A gene which is hypothesized or known to be responsible for a disease, condition, or the response to a treatment, or to be correlated with one of these.

Full Polymorphic Set—The polymorphic set whose members are a sequence of all the known polymorphisms.

Full-genotype—The unphased 5' to 3' sequence of nucleotide pairs found at all known polymorphic sites in a locus on a pair of homologous chromosomes in a single individual.

Gene—A segment of DNA that contains all the information for the regulated biosynthesis of an RNA product, including promoters, exons, introns, and other untranslated regions that control expression.

Gene Feature—A portion of the gene such as, e.g., a single exon, a single intron, a particular region of the 5' or 3'-untranslated regions. The gene feature is always associated with a continuous DNA sequence.

Genotype—An unphased 5' to 3' sequence of nucleotide pair(s) found at one or more polymorphic sites in a locus on a pair of homologous chromosomes in an individual. As used herein, genotype includes a full-genotype and/or a sub-genotype as described below.

Genotyping—A process for determining a genotype of an individual.

Haplotype—A member of a polymorphic set, e.g., a sequence of nucleotides found at one or more of the polymorphic sites in a locus in a single chromosome of an individual. (See, e.g., HAP 1 in FIG. 4A fill haplotype is a member of a full polymorphic set). A sub-haplotype is a member of a polymorphic subset.

Haplotype data—Information concerning one or more of the following for a specific gene: a listing of the haplotype pairs in each individual in a population; a listing of the different haplotypes in a population; frequency of each haplotype in that or other populations, and any known associations between one or more haplotypes and a trait.

Haplotype pair—The two haplotypes found for a locus in a single individual.

Haplotyping—A process for determining one or more haplotypes in an individual and includes use of family pedigrees, molecular techniques and/or statistical inference.

Isoform—A particular form of a gene, mRNA, cDNA or the protein encoded thereby, distinguished from other forms by its particular sequence and/or structure.

Isogene—One of the two copies (or isoforms) of a gene possessed by an individual or one of all the copies (or isoforms) of the gene found in a population. An isogene contains all of the polymorphisms present in the particular copy (or isoforms) of the gene.

Isolated—As applied to a biological molecule such as RNA, DNA, oligonucleotide, or protein, isolated means the molecule is substantially free of other biological molecules such as nucleic acids, proteins, lipids, carbohydrates, or other material such as cellular debris and growth media. Generally, the term "isolated" is not intended to refer to a complete absence of such material or to absence of water, buffers, or salts, unless they are present in amounts that substantially interfere with the methods of the present invention.

Locus—A location on a chromosome or DNA molecule corresponding to a gene or a physical or phenotypic feature.

Nucleotide pair—The nucleotides found at a polymorphic site on the two copies of a chromosome from an individual.

Phased—As applied to a sequence of nucleotide pairs for two or more polymorphic sites in a locus, phased means the combination of nucleotides present at those polymorphic sites on a single copy of the locus is known.

Polymorphic Set—A set whose members are a sequence of one or more polymorphisms found in a locus on a single chromosome of an individual. See, e.g., the set having members HAP 1 through HAP 10 in FIG. 4A.

Polymorphic site—A nucleotide position within a locus at which the nucleotide sequence varies from a reference sequence in at least one individual in a population. Sequence variations can be substitutions, insertions or deletions of one or more bases.

Polymorphic Subset—The polymorphic set whose members are fewer than all the known polymorphisms.

Polymorphism—The sequence variation observed in an individual at a polymorphic site. Polymorphisms include nucleotide substitutions, insertions, deletions and microsatellites and may, but need not, result in detectable differences in gene expression or protein function.

Polymorphism data—Information concerning one or more of the following for a specific gene: location of polymorphic sites; sequence variation at those sites; frequency of polymorphisms in one or more populations; the different genotypes and/or haplotypes determined for the gene; frequency of one or more of these genotypes and/or haplotypes in one or more populations; any known association(s) between a trait and a genotype or a haplotype for the gene.

Polymorphism Database—A collection of polymorphism data arranged in a systematic or methodical way and capable of being individually accessed by electronic or other means.

Polynucleotide—A nucleic acid molecule comprised of single-stranded RNA or DNA or comprised of complementary, double-stranded DNA.

Reference Population—A group of subjects or individuals who are representative of a general population and who contain most of the genetic variation predicted to be seen in a more specialized population. Typically, as used in the present invention, the reference population represents the genetic variation in the population at a certainty level of at least 85%, preferably at least 90%, more preferably at least 95% and even more preferably at least 99%.

Reference Repository—A collection of cells, tissue or DNA samples from the individuals in the reference population.

Single Nucleotide Polymorphism (SNP)—A polymorphism in which a single nucleotide observed in a reference individual is replaced by a different single nucleotide in another individual.

Sub-genotype—The unphased 5' to 3 sequence of nucleotides seen at a subset of the known polymorphic sites in a locus on a pair of homologous chromosomes in a single individual.

Subject—An individual (person, animal, plant or other eukaryote) whose genotype(s) or haplotype(s) or response to treatment or disease state are to be determined.

Treatment—A stimulus administered internally or externally to an individual.

Unphased—As applied to a sequence of nucleotide pairs for two or more polymorphic sites in a locus, unphased means the combination of nucleotides present at those polymorphic sites on a single copy of the locus (i.e., located on a single DNA strand) is not known.

World Population Group—Individuals who share a common ethnic or geographic origin.

B. Methods of Implementing the Invention

Figure 1A:
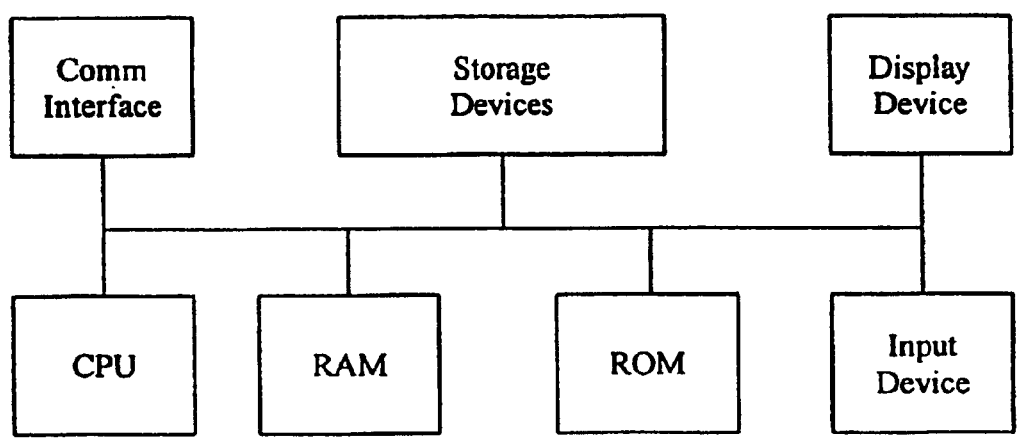
FIG. 1. System Architecture Schematic.

The present invention may be implemented with a computer, an example of which is shown in FIG. 1A. The computer includes a central processing unit (CPU) connected by a system bus or other connecting means to a communication interface, system memory (RAM), nonvolatile memory (ROM), and one or more other storage devices such as a hard disk drive, a diskette drive, and a CD ROM drive. The computer may also include an internal or external modem (not shown). The computer also includes a display device, such as a CRT monitor or an LCD display, and an input device, such as a keyboard, mouse, pen, touch-screen, or voice activation system. The computer stores and executes various programs such as an operating system and application programs. The computer may be embodied, for example, as a personal computer, work station, laptop, mainframe, or a personal digital assistant. The computer may also be embodied as a distributed multi-processor system or as a networked system such as a LAN having a server and client terminals.

The present invention uses a program referred to as the "DecoGen™ application", that generates views (or screens) displayed on a display device and which the user can interact with to accomplish a variety of tasks and analyses. For example, the DecoGen™ application may allow users to view and analyze large amounts of information such as gene-related data (e.g., gene loci, gene structure, gene family), population data (e.g., ethnic, geographical, and haplotype data for various populations), polymorphism data, genetic sequence data, and assay data. The DecoGen™ application is preferably written in the Java programming language. However, the application may be written using any conventional visual programming language such as C, C++, Visual Basic or Visual Pascal. The DecoGen™ application may be stored and executed on the computer. It may also be stored and executed in a distributed manner.

The data processed by the DecoGen™ application is preferably stored as part of a relational database (e.g., an instance of an Oracle database or a set of ASCII flat files). This data can be stored on, for example, a CD ROM or on one or more storage devices accessible by the computer. The data may be stored on one or more databases in communication with the computer via a network.

In one scenario, the data will be delivered to the user on any standard media (e.g., CD, floppy disk, tape) or can be downloaded over the internet. The DecoGen™ application and data may also be installed on a local machine. The DecoGen™ application and data will then be on the machine that the user directly accesses. Data can be transmitted in the form of signals.

Figure 1B:
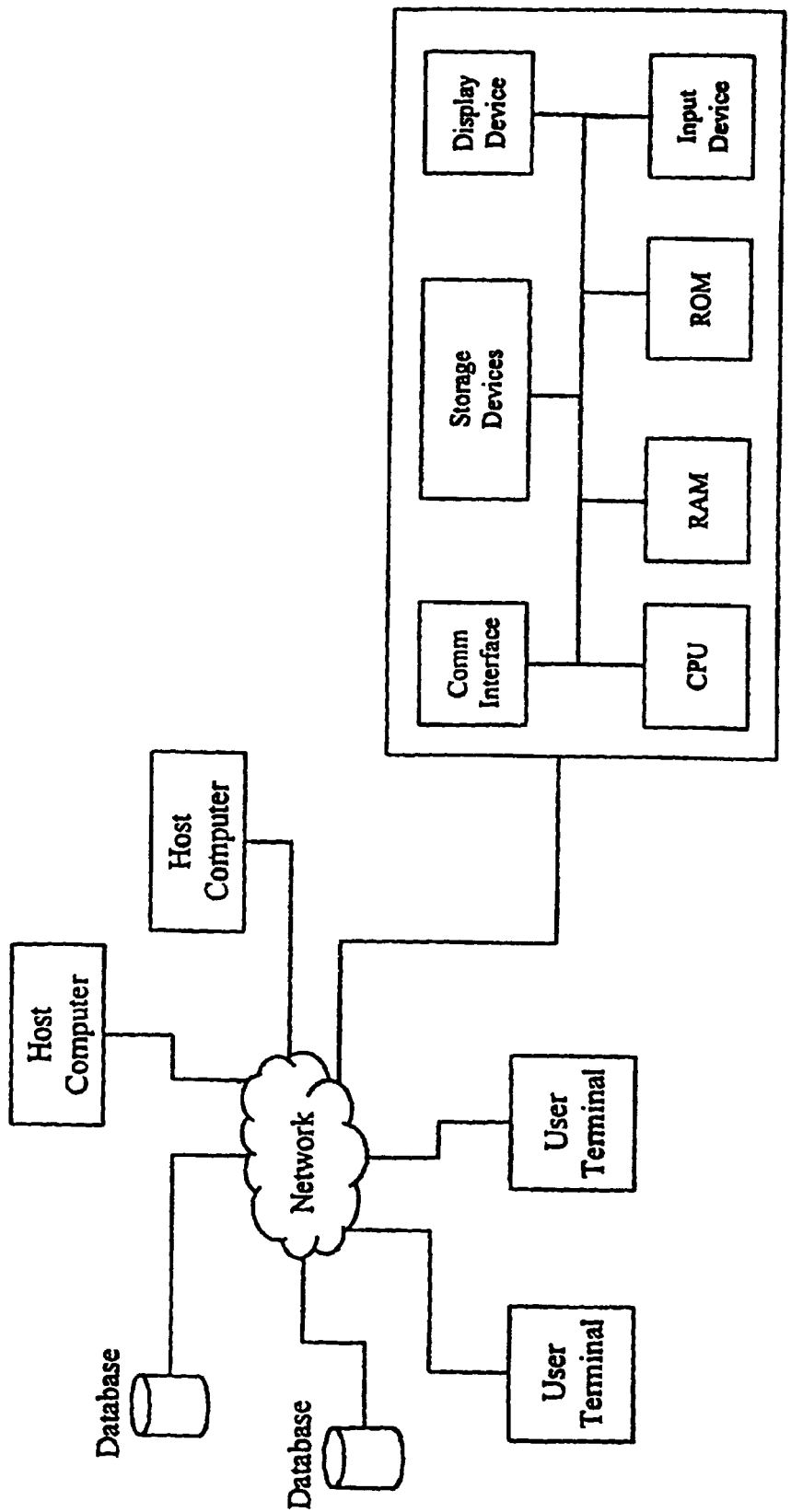

FIG. 1B shows an implementation where a network interconnects one or more host computers with one or more user terminals. The communication network may, for example, include one or more local area networks (LANs), metropolitan area networks (MANs), wide area networks (WANs), or a collection of interconnected networks such as the Internet. The network may be wired, wireless, or some combination thereof. The host computer may, for example, be a world wide web server ("web server"). The user terminal may, for example, be a client device such as a computer as shown in FIG. 1A.

A web server stores information documents called pages. A server process listens for incoming connections from clients (e.g., browsers running on a client device). When a connection is established, the client sends a request and the server sends a reply. The request typically identifies a page by its Uniform Resource Locator (URL) and the reply includes the requested page. This client-server protocol is typically performed using the hypertext transfer protocol ("http"). Pages are viewed using a browser program. They are written in a language called hypertext markup language ("html"). A typical page includes text and formatting comments called tags. Pages may also include links (pointers) to other pages. Strings of text or images that are links to other pages are called hyperlinks. Hyperlinks are highlighted (e.g., by shading, color, underlining) and may be invoked by placing the cursor on the highlighted area and selecting it (e.g., by clicking the mouse button). A page may also contain a URL reference to a portion of multimedia data such as an image, video segment, or audio file. Pages may also point to a Java program called an applet. When the browser connects to where the applet is stored, the applet is downloaded to the client device and executed there in a secure manner. Pages may also contain forms that prompt a user to enter information or that have active maps. Data entered by a user may be handled by common gateway interface (CGI) programs. Such programs may, for example, provide web users with access to one or more databases.

As shown in FIG. 1B the host computer may include a CPU connected by a system bus or other connecting means to a communication interface, system memory (RAM), nonvolatile (ROM), and a mass storage device. The mass storage device may, for example, be a collection of magnetic disk drives in a RAID system. The mass storage device may, for example, store the aforementioned web pages, applets, and the like. The host computer may also include an input device, such as a keyboard, and a display device to allow for control and management by an administrator. Additionally, the host computer may be connected to additional devices such as printers, auxiliary monitors or other input/output devices. The input device and display device may also be provided on another computer coupled to the host computer. The host computer may be embodied, for example, as one or more mainframes, workstations, personal computers, or other specialized hardware platforms. The functionality of the host computer may be centralized or may be implemented as a distributed system. As also shown in FIG. 1B, the host computer may communicate with one or more databases stored on any of a variety of hardware platforms.

In an Internet scenario, for example involving the system of FIG. 1B, the DecoGen™ application will be web-based and will be delivered as an applet that runs in a web browser. In this case, the data will reside on a server machine and will be delivered to the DecoGen application using a standard protocol (e.g., HTTP with cgi-bin). To provide extra security, the network connection could use a dedicated line. Furthermore, the network connection could use a secure protocol such as Secure Socket Layer (SSL) which only provides access to the server from a specified set of IP addresses.

In another scenario, the DecoGen™ application can be installed on a user machine and the data can reside on a separate server machine. Communication between the two machines can be handled using standard client-server technology. An example would be to use TCP/IP protocol to communicate between the client and an oracle server.

It may be noted that in any of the prior scenarios, some or all of the data used by the DecoGen™ application could be directly imported into the DecoGen™ application by the user. This import could be carried out by reading files residing on the user's local machine, or by cutting and pasting from a user document into the interface of the DecoGen™ application.

In yet a further scenario, some or all of the data or the results of analyses of the data could be exported from the DecoGen™ application to the user's local computer. This export could be carried out by saving a file to the local disk or by cutting and pasting to a user document.

In the present invention various calculations are performed to generate items displayed on a screen or to control items displayed on a screen. As is well known, some basic calculations may be performed using database query language (SQL), while other computations are performed by the DecoGen™ application (i.e., the Java program which, as previously mentioned, may be an applet downloaded over the internet.)

C. CTS™ Methods of the Invention

The CTS™ embodiment of present invention preferably includes the following steps:

1. A candidate gene or genes (or other loci) predicted to be involved in a particular disease/condition/drug response is determined or chosen.

2. A reference population of healthy individuals with a broad and representative genetic background is defined.

3. For each member of the reference population, DNA is obtained.

4. For each member of the reference population, the haplotypes for each of the candidate gene(s), (or other loci) are found.

5. Population averages and statistics for each of the gene(s) (loci)/haplotypes in the reference population are determined.

6. (Optional step) An optimal set of genotyping markers is determined. These markers allow an individual's haplotypes to be accurately predicted without using direct molecular haplotype analysis. The predictive haplotyping method relies on the haplotype distribution found for the reference population.

7. A trial population of individuals with the medical condition of interest is recruited.

8. Individuals in the trial population are treated using some protocol and their response is measured. They are also haplotyped, for each of the candidate gene(s), either directly or using predictive haplotyping based on the genotype.

9. Correlations between individual response and haplotype content are created for the candidate gene(s) (or other loci). From these correlations, a mathematical model is constructed that predicts response as a function of haplotype content.

10 (Optional) Follow-up trials are designed to test and validate the haplotype-response mathematical model.

11. (Optional) A diagnostic method is designed (using haplotyping, genotyping, physical exam, serum test, etc.) to determine those individuals who will or will not respond to the treatment.

These steps are now described in further detail below:

1. A candidate gene or genes (or other loci) for the disease/condition is determined.

In the CTS embodiment of the invention, candidate gene (s) (or other loci) are a subset of all genes (or other loci) that have a high probability of being associated with the disease of interest, or are known or suspected of interacting with the drug being investigated. Interacting can mean binding to the drug during its normal route of action, binding to the drug or one of its metabolic products in a secondary pathway, or modifying the drug in a metabolic process. Candidate genes can also code for proteins that are never in direct contact with the drug, but whose environment is affected by the presence of the drug. In other embodiments of the invention, candidate gene(s) (or other loci) may be those associated with some other trait, e.g., a desirable phenotypic trait. Such gene(s) (or other loci) may be, e.g., obtained from a human, plant, animal or other eukaryote. Candidate genes are identified by references to the literature or to databases, or by performing direct experiments. Such experiments include (1) measuring expression differences that result from treating model organisms, tissue cultures, or people with the drug; or (2) performing protein-protein binding experiments (e.g., antibody binding assays, yeast 2 hybrid assays, phage display assays) using known candidate proteins to identify interacting proteins whose corresponding nucleotide (genomic or cDNA) sequence can be determined.

Once the candidate gene(s) (or other loci) are identified, information about them is stored in a database. This information includes, for example, the gene name, genomic DNA sequence, intron-exon boundaries, protein sequence and structure, expression profiles, interacting proteins, protein function, and known polymorphisms in the coding and non-coding regions, to the extent known or of interest. This information can come from public sources (e.g. GenBank, OMIM (Online Inheritance of Man—a database of polymorphisms linked to inherited diseases), etc.) For genes that are not fully characterized, this step would generally require that the characterization be done. However, this is possible using standard mapping, cloning and sequencing techniques. The minimum amount of information needed is the nucleotide sequence for important regions of the gene. Genomic DNA or cDNA sequences are preferably used.

In the present invention, a person may use a user terminal to view a screen which allows the user to see all of the candidate genes associated with the disease project and to bring up further information. This screen (as well as all the other screens described herein) may, for example, be presented as a web page, or a series of web pages, from a web server. This web based use may involve a dedicated phone line, if desired. Alternatively, this screen may be served over the network from a non-web based server or may simply be generated within the user terminal. An example of such a screen referred to herein as a "Pathways" or "Gene Collection" screen is illustrated in FIG. 2.

1. Illustration Using the CYP2D6 Gene

Figure 2:
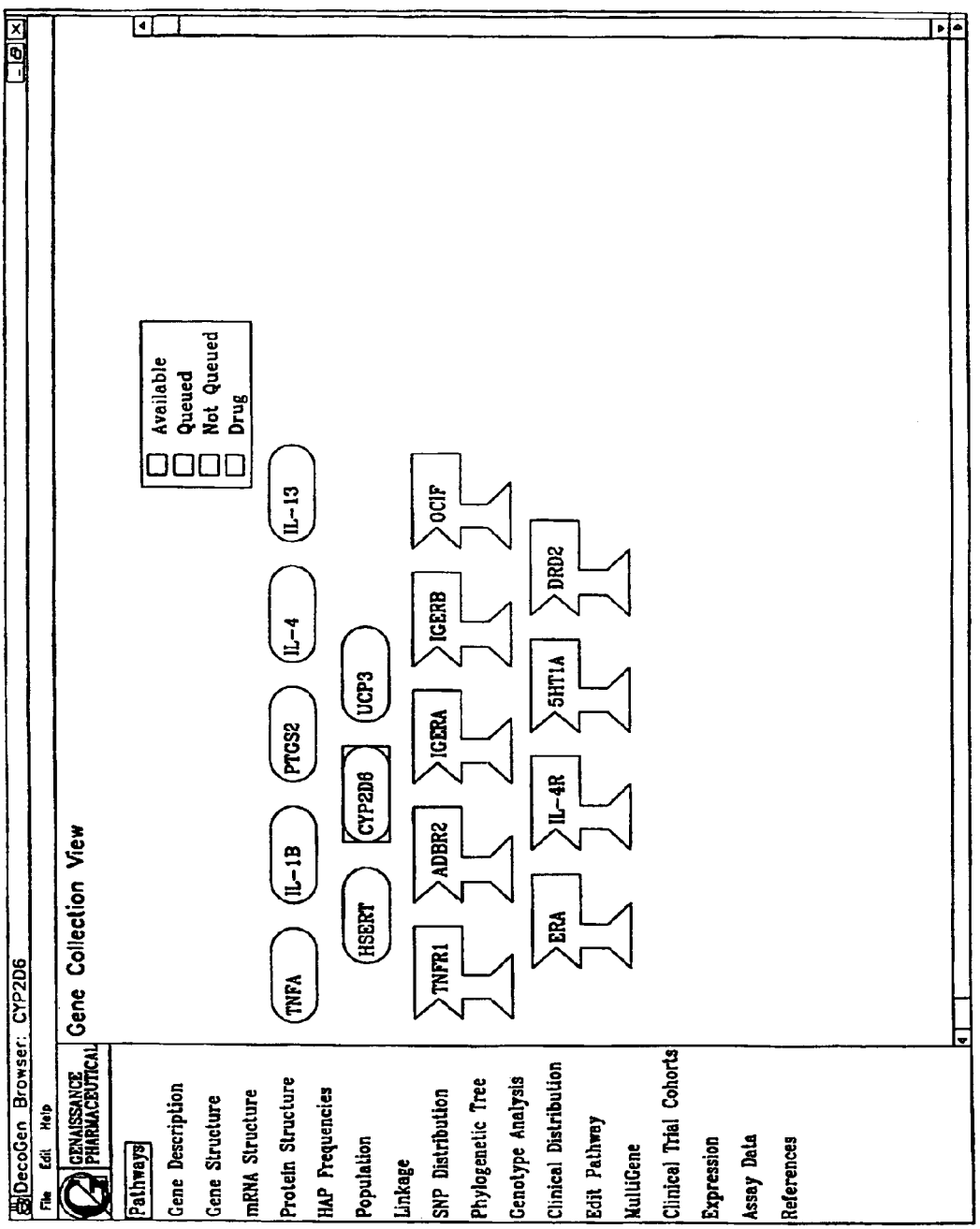
FIG. 2. Pathway/Gene Collection View. This screen shows a schematic of candidate genes from which a candidate gene may be selected to obtain further information. A menu on the left of the screen indicates some of the information about the candidate genes which may be accessed from a database.

FIG. 2 is an example of a screen showing the set of candidate genes whose polymorphisms potentially contribute to the response to a drug or to some other phenotype. The screen shows genes for which data is currently available in a database useful in the invention in green; those queued for processing (and for which data will appear in a database) would appear in one shade or color, e.g., yellow, and related but unqueued genes (those for which there is currently no plan to deposit data in a database) would appear in another shade or color, e.g., white. Drugs (typically ones that interact with one or more of the genes of interest) would be shown in a third shade or color, e.g., light blue. The user can select a gene to examine in detail by using the mouse (or other user-input device such as keyboard, roller ball, voice recognition, etc.) to select the corresponding icon. In the example depicted in FIG. 2, CYP2D6, a cytochrome P 450 enzyme, is selected, as indicated by the extra black box around the CYP2D6 icon. At the left of each screen is a menu that allows the user to navigate through different screens of the data.

A preferred embodiment of the present invention relates to situations in which patients have differential responses to the drug because they possess different forms of one or more of the candidate genes (or other loci). (Here different forms of the candidate gene(s) mean that the patients have different genomic DNA sequences in the gene locus). The method does not rely on these differences being manifested in altered amino acids in any of the proteins expressed by any candidate gene(s) (e.g., it includes polymorphisms that may affect the efficiency of expression or splicing of the corresponding mRNA). All that is required is that there is a correlation between having a particular form(s) of one or more of the genes and a phenotypic trait (e.g. response to a drug). Examples of salient information about the candidate genes is given in FIGS. 3–8.

FIG. 3 is an example of a screen showing basic information about the currently selected gene such as its name, definition, function, organism, and length. These pieces of information typically come from GenBank or other public data sources. The figure will typically also show the number of "gene features" (e.g. exons, introns, promoters, 3' untranslated regions, 5' untranslated regions, etc.) in the database, the size of the analyzed population (group of people whose DNA has been examined for this gene), the number of haplotypes found for this gene in this population, and some measures of polymorphism frequency. The information is stored in a database such as the one described herein, or calculated from information stored in such a database. Most of the information shown in later figures is specific to this analyzed population. Theta and Pi are standard measures of polymorphism frequency, described in Ref. 1, Chapter 2.

FIGS. 4A and 4B are examples of screens showing the genomic structure of the gene (generally showing the location of features of the gene, such as promoters, exons, introns, 5' and 3' untranslated regions), as well as haplotype information FIG. 4A shows the location of the features in the gene, the location of the polymorphic sites along the gene, the nucleotides at the polymorphic sites for each of the haplotypes, and the number of times each haplotype was seen in the representatives of each of 4 world population groups (CA=Caucasian, AA=African American, HL=Hispanic/Latino, AS=Asian) included in the population analyzed for this gene. All of this data resides in a database or is calculated from the data in a database. The top view shows the nucleotides at the polymorphic sites, i.e., the haplotypes. The middle cartoon shows the features of the gene. In this example the promoter is indicated by a dark shaded (or red) rectangular box and a line with an arrow, exons are shown by a gray shaded (or blue) rectangular box and introns are shown in white (or in yellow). When the mouse is held over a feature, the feature turns red and the name of the feature appears (e.g., in this case, Gene). The code in parenthesis (M22245) is the GenBank accession number for the selected feature. FIG. 4B is the same screen as FIG. 4A, after the user selects the gene feature. Under the cartoon of the features are vertical bars indicating the positions of the polymorphic sites, with one row per unique haplotype. The letter "d" indicates that there is a deletion. The table at the left gives the number of haplotype copies seen in each of the standard populations. For instance, this screen indicates that there are 10 copies of haplotype 10 in Caucasians, 2 copies in African Americans, and none in Hispanic/Latinos or Asians, for a total of 12 copies. Note that the total number of haplotypes is twice the number of individuals examined. At the very bottom is an expanded cartoon of the feature. One may display data concerning a particular polymorphism by selecting the corresponding vertical bar on the expanded cartoon. The selected bar may be identified, e.g., by a shaded or colored circle. The data for the polymorphism appears at the lower left of the screen. This gives the number of copies of each nucleotide (A, C, G or T) seen in each of the world population groups.

FIG. 5 is an example of a screen showing the actual DNA sequence of the genomic locus for the different haplotypes seen in the population (i.e., the sequence of the isogenes). This view appears in a separate window when one of the features in the Gene Structure Screen (FIG. 4A or 4B) is selected with the mouse or other input device. This shows an alignment between the full DNA sequences for all of the isogenes of the CYP2D6 gene in the database. The polymorphic positions are highlighted.

FIG. 6 is an example of a screen showing the predicted secondary structure of the mRNA transcript for each CYP2D6 isogene in the database. The secondary structure is predicted using a detailed thermodynamic model as implemented in the program RNA structure (REF. 2). This is useful because many of the polymorphisms detected do not change the amino acid composition of the resulting protein but still lie in the coding region of the gene. One result of such a silent mutation could be to alter the intermediate mRNA's structure in a way that could affect mRNA stability, or how (and if) the mRNA was spliced, transcribed or processed by the ribosome. Such a polymorphism could keep any of the protein from being expressed and from being available to carry out its functions. In this screen, the user can see thumbnail views of the structures for all of the isogenes and can see a selected one of these structures expanded on the right hand side of the screen. Changes in this structure caused by the polymorphisms seen in the isogenes can affect the expression into protein of the gene. The information presented in this screen can serve as an aid to the user to detect possible effects of these polymorphisms.

FIG. 7 is an example of a screen showing a schematic of the structure of the protein expressed by the gene, including important domains and the sites of the coding polymorphisms. The user gets to this screen by selecting the "Protein Structure" link at the left hand side of the display. This screen shows various important motifs found in the protein, and places the polymorphic sites in the context of these motifs. The user can get information on each motif or polymorphism by selecting the appropriate icon for the polymorphic site. In this example, the result of selecting the first polymorphic site (as indicated by the red shadow behind the icon) is shown. The text above at the top shows the reference codon and amino acid (CCT, Pro) and the resulting altered codon and amino acid (TCT, Ser). Also given are the codon frequencies in parentheses. These are calculated by looking at 10,000 codons in a variety of human genes and calculating how often that particular codon shows up. (REF. 3).

2. A reference population of healthy individuals with a broad and representative genetic background is defined.

Analysis of the candidate gene(s) (or other loci) requires an approximate knowledge of what haplotypes exist for the candidate gene(s) (or other loci) and of their frequencies in the general population. To do this, a reference population is recruited, or cells from individuals of known ethnic origin are obtained from a public or private source. The population preferably covers the major ethnogeographic groups in the U.S., European, and Far Eastern pharmaceutical markets. An algorithm, such as that described below may be used to choose a minimum number of people in each population group. For example, if one wants to have a q % chance of not missing a haplotype that exists in the population at a p % frequency of occurring in the reference population, the number of individuals (n) who must be sampled is given by $2n=\log(1-q)/\log(1-p)$ where p and q are expressed as fractions. For instance, if p is 0.05 (i.e., if one wants to find at least one copy of all haplotypes found at greater than 5% frequency) and q is 0.99 (i.e., one wants to be sure to the 99% level of confidence of finding the >5% frequency haplotypes), then n=0.5*log(0.01)/log(0.95)~--45. There is always a tradeoff between how rare a haplotype one wants to be guaranteed to see and the cost of experimentally determining haplotypes.

3. For each member of the population, DNA is obtained.

In the preferred embodiment, for each member of the reference population (called a subject), blood samples are drawn, and, preferably, immortalized cell lines are produced. The use of immortalized cell lines is preferred because it is anticipated that individuals will be haplotyped repeatedly, i.e., for each candidate gene (or other loci) in each disease project. As needed, a cell sample for a member of the population could be taken from the repository and DNA extracted therefrom. Genomic DNA or cDNA can be extracted using any of the standard methods.

4. For each member of the population, the haplotypes for each of the candidate gene(s) (or other loci) are found.

The 2 haplotypes for each of the subject's candidate gene(s) (or other loci) are determined. The most preferred method for haplotyping the reference population is that described in U.S. Application Ser. No. 60/198,340 (inventors Stephens et al.), filed Apr. 18, 2000, which is specifically incorporated by reference herein. Another, less preferred embodiment for haplotyping the reference population, uses the CLASPER System™ technology (Ref. U.S. Pat. No. 5,866,404), which is a technique for direct haplotyping. Other examples of the techniques for direct haplotyping include single molecule dilution ("SMD") PCR (Ref 9) and allele-specific PCR (Ref 10). However, for the purpose of this invention, any technique for producing the haplotype information may be used.

The information that is stored in a database, such as a database associated with the DecoGen application exemplified herein includes (1) the positions of one or more, preferably two or more, most preferably all, of the sites in the gene locus (or other loci) that are variable (i.e. polymorphic) across members of the reference population and (2) the nucleotides found for each individuals' 2 haplotypes at each of the polymorphic sites. Preferably, it also includes individual identifiers and ethnicity or other phenotypic characteristics of each individual.

In the preferred embodiment of the invention, the haplotypes and their frequencies are stored and displayed, preferably in the manner shown, e.g., in FIGS. 4A and 4B. Haplotypes and other information about each of the members of the population being analyzed can be shown, for example, in the manner shown in FIG. 8. The information shown in FIG. 8 includes a unique identifier (PID), ethnicity, age, gender, the 2 haplotypes seen for the individual, and values of all clinical measurements available for the individual. Quantitative values of clinical measures would ordinarily be seen by scrolling to the right. However, for the subjects seen in this view, there is no clinical data. This is because this is the reference population of healthy individuals.

The haplotype data may also be presented in the context of the entire DNA sequence. Examples of the sequences of the isogenes, with the polymorphisms highlighted, are shown in FIG. 5.

Because an individual has 2 copies of the gene (2 isogenes), and because these 2 copies are often different, some of the polymorphic sites will show 2 different nucleotides in a genotype, one from each of the isogenes. A genotype from an individual with haplotypes TAC and CAG would be (T/C),A,(C/G). This is consistent with the haplotypes TAC/CAG or TAG/CAC. The fact that we do not know which haplotypes gave rise to this genotype leads us to call this an "unphased genotype". If we haplotype this individual we then determine the "phased genotype", which describes which particular nucleotides go together in the haplotypes. Phasing is the description of which nucleotide at one polymorphic site occurs with which nucleotides at other sites. This information is left ambiguous (i.e., unphased) in a genotyping measurement but is resolved (i.e., phased) in a haplotype measurement.

FIG. 9 is an example of a screen showing the genotype to haplotype resolution for each of the individuals in the population being examined. At the left of the screen is a shaded (or color) matrix showing the genotype information at each of the polymorphic sites for each individual (sites across the top, individuals going down the page). The most and least common nucleotide at each site is defined by looking at both haplotypes of all individuals in the population at that particular site. The nucleotide that shows up most often is called the most common nucleotide. The one that shows up less often is termed the least common. In situations where more than 2 nucleotides are seen at a site (which is rare but not unknown in human genes) all nucleotides except the most common one are lumped together in the least common category. At the right is a shaded (or color) matrix showing the haplotype resolution. In the genotype view, a blue square indicates that the individual is homozygous for the most common nucleotide at that site. A yellow square indicates that the individual is homozygous for the least common base, and a red square indicates that the individual is heterozygous at the site. On the right hand side, a row for an individual is broken into a top and a bottom half, each representing one of the two haplotypes. The color scheme is the same as on the left except that all of the heterozygous sites have been resolved. The + and − buttons are for zooming in and out.

Unrelated individuals who are heterozygous at more than 1 site cannot be haplotyped without (1) using a direct molecular haplotyping method such as CLASPER System™ technology or (2) making use of knowledge of haplotype frequencies in the population, as described below or, preferably, as described in U.S. Application Ser. No. 60/198, 340 (inventors Stephens et al.), filed Apr. 18, 2000.

5. Population averages and statistics for each of the haplotypes in the reference population are determined.

Once the individual haplotypes of the reference population have been determined the population statistics may be calculated and displayed in a manner exemplified herein in FIG. 10. FIG. 10 is an example of one of several screens showing information about the pair of haplotypes for the candidate gene(s) (or other loci) found in an individual. In this screen, each cell of the matrix displays some information about the group of people who were found to have the haplotypes corresponding to the particular row and column. In all of these screens, subjects can be grouped together by pairs of haplotypes or sub-haplotypes, where a sub-haplotype is made up of a subset of the total group of polymorphic sites. For example, at the top of the screen in the figure are checkboxes allowing the user to select the subset of polymorphic sites to be examined (here sites 2 and 8 are chosen). The + and − buttons are for zooming in and out, which increases and decreases the viewing size of the matrix. The "Recalculate" button causes the statistics for the groups to be recalculated after a new subset of polymorphic sites has been selected. At the bottom is the matrix. The selected cell (outlined in green in this figure) displays information about subjects who are homozygous for C and G at sites 2 and 8. The text to the right gives summary numerical information about the subjects in that box. In particular, this screen shows the distribution of subjects in the different ethnogeographic groups with each of the haplotype pairs. In this example, 23 subjects (18 Caucasians and 5 Asians) were found to be homozygous for C and G at sites 2 and 8. In this example, the heights of the bars are normalized individually for each cell so that it is not possible in this example to see relative numbers of individuals cell to cell by looking at the heights. An alternative normalization (in which there is a consistent normalization for all boxes), is also possible. More detailed information is available by selecting the "View Details" button at the top (see FIG. 11).

FIG. 11 is a more detailed view of the information that is available from the summary view shown in FIG. 10. At the bottom, one row is shown for each haplotype pair found in the population being analyzed. Each row shows the corresponding 2 sub-haplotypes, the total number of individuals found with that sub-haplotype and the fraction of the total population represented by this number. Next to these are 3 columns for each ethnogeographic group. The first gives the number of individuals in that ethnogeographic group with that haplotype pair. The second gives the fraction of individuals (found in a database of the present invention) in that world population group who have that haplotype pair. The third column gives the expected number based on Hardy-Weinberg equilibrium.

The observed haplotype pair frequencies in the population in particular, the reference population, are preferably corrected for finite-size samples. This is preferably done when the data is being used for predictive genotyping. If it is assumed that each of the major population groups will be in Hardy-Weinberg equilibrium, this allows one to estimate the underlying frequencies for haplotype pairs in the reference population that are not directly observed. It is necessary to have good estimates of the haplotype-pair frequencies in the reference population in order to predict subjects' haplotypes from indirect measurements that will be used in a diagnostic context (see item 6). Preferably the reference population has been chosen to be representative of the population as a whole so that any haplotypes seen in a clinical population have already been seen in the reference population. Furthermore, it would be possible to determine whether certain haplotypes are enriched in the patient population relative to the reference population. This would indicate that those haplotypes are causative of or correlated with the disease state.

Hardy-Weinberg equilibrium (Ref. 1, Chapter 3) postulate that the frequency of finding the haplotype pair $H_1/H_2$ is equal to $p_{H-w}(H_1/H_2)=2p(H_1)p(H_2)$ if $H_1 \neq H_2$ and $p_{H-w}(H_1/H_2)=p(H_1)p(H_2)$ if $H_1=H_2$. Here, $p(H_i)$ (where i=1 or 2) is the probability of finding the haplotype $H_i$ in the population, regardless of whatever other haplotype it occurs with. Hardy-Weinberg equilibrium usually holds in a distinct ethnogeographic group unless there is significant inbreeding or there is a strong selective pressure on a gene. Actual observed population frequencies $p_{Obs}(H_1/H_2)$ and the corresponding Hardy-Weinberg predicted frequencies $p_{H-w}(H_1/H_2)$ are shown in FIG. 11, discussed above.

If large deviations from Hardy-Weinberg equilibrium are observed in the reference population, the number of individuals can be increased to see if this is a sampling bias. If it is not, then it may be assumed that the haplotype is either historically recent or is under selection pressure. A statistical test may be $$|P_{obs} - P_{n-w}| > \sqrt{\frac{P_{obs}^2}{N}}.$$

6. (Optional—this step can be skipped if direct molecular haplotyping will be used on all clinical samples.) An optimal set of genotyping markers is determined. These markers often allow an individual's haplotypes to be accurately predicted without using full haplotype analysis. This genotyping method relies on the haplotype distribution found directly from the reference population.

One of several methods to test subjects for the existence of a given pair of haplotypes in an individual can be used. These methods can include finding surrogate physical exam measurements that are found to correlate with haplotype pair; serum measurements (e.g., protein tests, antibody tests, and small molecule tests) that correlate with haplotype pair; or DNA-based tests that correlate with haplotype pair. An example that is used herein is to predict haplotype pair based on an (unphased) genotype at one or more of the polymorphic sites using an algorithm such as the one described further below.

For example, as discussed above, in the case where the two haplotypes are TAC and GAT, the genotyping information would only provide the information that the subject is heterozygous T/G at site 1, homozygous A at site 2 and heterozygous C/T at site 3. This genotype is consistent with the following haplotype pairs: TAC/GAT (the correct one) and GAC/TAT (the incorrect one). Assuming that the underlying probability (as measured in the reference population) for TAC/GAT is p % and for GAC/TAT is q %, subjects may be randomly assigned to the first group with a probability p/(p+q) and to the second group with a probability q/(p+q). If p>>q, then subjects will almost always be correctly assigned to the correct haplotype pair group if they are TAC/GAT, but the GAC/TAT individuals will always be mis-classified. However, the majority of individuals will be assigned to the correct haplotype-pair group. In the case that q=0, the correct assignment will always be made. For cases where p~q, this classification gives very low accuracy predictions, so other methods to resolve the subjects' haplotypes must be resorted to. One can always directly find the correct haplotypes using CLASPER System™ technology or other direct molecular haplotyping method.

The ability to use genotypes to predict haplotypes is based on the concept of linkage. Two sites in a gene are linked if the nucleotide found at the first site tends to be correlated with the nucleotide found at the second site. Linkage calculations start with the linkage matrix, which gives the probabilities of finding the different combinations of nucleotides at the two sites. For instance, the following matrix connects 2 sites, one of which can have nucleotide A or T and the other of which can have nucleotide G or C. The fraction of individuals in the population with A at site 1 and G at site 2 is 0.15.

|   | A | T |
|---|---|---|
| G | 0.15 | 0.40 |
| C | 0.40 | 0.05 |

In general, the matrix is given by

|  | Site 1 - Allele 1 | Site 1 - Allele 2 |  |
| --- | --- | --- | --- |
| Site 2 - Allele 1 | $p_{11}$ | $p_{12}$ | $p_{1+}$ |
| Site 2 - Allele 2 | $p_{21}$ | $p_{22}$ | $p_{2+}$ |
|  | $p_{+1}$ | $p_{+2}$ |  |

The values $p_{1+}$ and $p_{2+}$ give the sum of the respective rows while the values $p_{+1}$ and $p_{+2}$ give the sum over the respective columns. By definition, $p_{1+}+p_{2+}=p_{+1}+p_{+2}=1$. Three standard measures of linkage disequilibrium that are used are: (Ref. 1, Chapter 3)

$$D = p_{11} \times p_{22} - p_{12} \times p_{21} \quad (1)$$

$$\Delta = \frac{D}{(p_{11} \times p_{22} \times p_{12} \times p_{21})^{1/2}} \quad (2)$$

$$D' = \begin{cases} \frac{D}{\min(p_{1+} \times p_{+2},\ p_{+1} \times p_{2+})} & D > 0 \\ \frac{D}{\min(p_{1+} \times p_{+1},\ p_{+2} \times p_{2+})} & D < 0 \end{cases} \quad (3)$$

FIG. 12 is an example of a screen showing a measure of the linkage between different polymorphic sites in the gene. Measures of linkage tell how well we can predict the nucleotide at one polymorphic site given the nucleotide at another site. A high value of the linkage measure indicates a high level of predictive ability. This screen shows D'. The color of the square in the display at the intersection of site α and β indicates the value of the linkage measure. Red indicates strong linkage and blue indicates weak to non-existent linkage. White squares in a row indicate that the corresponding polymorphic site has no variation in the population being examined. Such sites are included because there is information about the presence of polymorphisms other than that provided by our haplotype analysis. This would be the case if a polymorphism was reported in the literature which we were not able to detect in our population. The values to the right of the matrix give $I_{HAP}$ for each of the sites. $I_{HAP}$ is a measure of the information content of the single site and is given by $$I_{HAP} = \sum_{i=1}^{2} \frac{\sum_{j=1}^{N_{HAP}} P(j\mid i)^2}{\sum_{j=1}^{N_{HAP}} P(j)^2} \quad (4)$$

where $N_{HAP}$ is the number of distinct haplotypes observed, P(j) is the probability of finding haplotype j, and P(j|i) is the conditional probability of finding haplotype j with nucleotide i. (The conditional probability P(j|i) is the probability of finding haplotype j in the subset of all observations where nucleotide i is seen.) High values of $I_{HAP}$ (~2.0) indicate that at least some pairs of observed haplotypes can be distinguished by looking at that single site. Small values (1.0) indicate that the particular site is not informative for distinguishing any pair of haplotypes. This same method can be used for sub-haplotypes. These values are useful for choosing sites for genotyping, as described above. The + and − boxes are for zooming in and out.

FIGS. 13, 14, and 15 show views of a tool for performing an analysis of which polymorphic sites may be genotyped in order to determine an individual's haplotypes by the method of predictive haplotyping, rather than using more expensive direct haplotyping methods, such as the CLASPER-System™ method of haplotyping. In these screens, one chooses a subset of polymorphic sites of interest (the entire haplotype or a sub-haplotype can be examined) and then a subset of sites at which the subject is to be genotyped. The colors in the haplotype-pair boxes then indicate the fraction of individuals in that box who are correctly haplotyped based on the statistical model described in the previous paragraph. FIG. 14 gives the predicted values and FIG. 15 shows a tool for directly finding the optimal set of genotyping sites.

The purpose of the three screens in FIGS. 13, 14 and 15 is to provide an example of the tools to find the simplest genotyping experiment that could detect an individual's haplotypes. The basic layout of the screen in FIG. 13 is the same as described in FIG. 10. The top row of checkboxes is used to the haplotype or subhaplotype which is desired to be determined. There is one other row of checkboxes beneath those for choosing the haplotype or sub-haplotype. This second row, labeled "Genotype Loci", allows the user to select a subset of positions at which to genotype. The color of the square in the matrix indicates the fraction of individuals who are actually in that category who would be correctly categorized using this sub-genotype. For example, this screen shows that individuals homozygous for TGG at positions 2, 3, and 8 would be correctly haplotyped by genotyping at positions 2 and 8. Selection of optimal genotyping sites is aided by information from the Linkage View (FIG. 12). Typically one will only need to genotype one site of a pair of polymorphic sites that are in strong linkage.

The screen in FIG. 14 gives a numerical view of the data show in FIG. 13. One can see that if we genotype at sites 2 and 8, one could assign individuals to the TGG/TGG group with 100% confidence (based on the data obtained for the reference population). However, one would have low confidence in the ability to assign individuals to the CAG/CGG group.

FIG. 15 is an example of a screen showing the results of a tool for directly finding the optimal genotyping sites. This screen gives the results of a simple optimization approach to finding the simplest genotyping approach for predicting an individual's haplotypes. For each haplotype pair, the predictive abilities of all single site genotyping experiments are calculated. If any of these has a predictive ability of greater than some cutoff (say 90%), then that single-site genotype test is shown. A single-site genotype test is one in which an individual's nucleotide(s) is found at that single site. This can be done using any of several standard methods including DNA sequencing, single-base extension, allele-specific PCR, or TOF-mass spec. (In the figure, a red box indicates that individuals should be genotyped at that site, and a white box indicates that the individual should not be genotyped there.) If no single-site test has a predictive ability of greater than the cutoff, then the calculated predictive ability of all 2-site genotyping tests are examined by the computer program. The first 2-site test whose predictive ability exceeds the cutoff is then displayed. If no 2-site test is successful, then the predictive ability of all 3-sites tests are examined by the computer program, and so on. The mask at the right hand side of this display shows the first test found that exceeded the cutoff value.

An improved method for finding optimal genotying sites is described in section D, below.

FIGS. 16 and 17 are examples of screens demonstrating another tool for analyzing linkage. This tool is a minimal spanning network which shows the relatedness of the haplotypes seen in the population (Ref. 8). Haplotypes are amenable to modes of analysis that are not available for isolated variants (e.g., SNPs). In particular, a sample of haplotypes reflects the actual phylogenetic history of the genetic locus. This history includes the divergence patterns among the haplotypes, the order of mutational and recombinational events, and a better understanding of the actual variation among the different populations comprising the sample. These considerations are important in the assessment of a locus's involvement in a particular phenotype (e.g., differential response to a drug or adverse side effects). The phylogenetic algorithms included in the DecoGen™ application are both exploratory and analytical tools, in that they allow consideration of partial haplotypes as well as those based on the full set of haplotypes in the context of clinical data. The checkboxes and recalculate button shown in FIGS. 16 and 17 serve the purpose of selecting sub-haplotypes as described under FIG. 10. The results of the calculations are shown in real time, i.e., the sizes and positions of the balls, as well as the length of the lines, change as the calculation progresses. Here a circle represents a haplotype. The distance between haplotypes is a rough measure of the number of nucleotides that would have to be flipped to change one haplotype into the other. Pairs of haplotypes separated by one nucleotide flip are connected with black lines. Pairs connected by 2 flips are connected with light blue lines. The size of the haplotype ball increases with the frequency of that haplotype in the population. Each haplotype or sub-haplotype ball is labeled with the relevant nucleotide string. The user can toggle the labels off and on by selecting the haplotype ball, e.g., with a mouse. The + and − boxes are for zooming in and out. The "View Hap Pairs" box serve the purpose of showing the pairing information for haplotypes. The lines shown in this figure are replaced with lines connecting pairs of haplotypes seen in each individual. The colors in the balls, and the pie shaped pieces, represent the fraction of that haplotype found in the major ethnogeographic group. Red represents Caucasian, blue African-American, Light Blue Asian, Green Hispanic/Latino. The Minimum Size checkbox allows the user to select sub-haplotypes as in earlier Figures (FIG. 10).

This aspect of the invention relates to a graphical display of the haplotypes (including sub-haplotypes) of a gene grouped according to their evolutionary relatedness. As used herein, "evolutionary relatedness" of two haplotypes is measured by how many nucleotides have to be flipped in one of the haplotypes to produce the other haplotype.

In one embodiment, the display is a minimal spanning network in which a haplotype is represented by a symbol such as a circle, square, triangle, star and the like. Symbols representing different haplotypes of a gene may be visually distinguished from each other by being labeled with the haplotype and/or may have different colors, different shading tones, cross-hatch patterns and the like. Any two haplotype symbols are separated from each other by a distance, referred to as the ideal distance, that is proportional to the evolutionary relatedness between their represented haplotypes. For example, if displaying a group of haplotypes related by one, two or three nucleotide flips, the proportional distances between the haplotype symbols could be one inch, two inches, and three inches, respectively. The haplotype symbols may be connected by lines, which may have different appearances, i.e., different colors, solid vs. dotted vs. dashed, and the like, to help visually distinguish between one nucleotide flip, two nucleotide flips, three nucleotide flips, etc.

In a preferred embodiment, the method is implemented by a computer and the graphical display is produced by an algorithm that connects haplotype symbols by springs whose equilibrium distance is proportional to the ideal distance. Preferably, the size of a particular haplotype symbol is proportional to the frequency of that haplotype in the population. In addition, the haplotype symbol may be divided into regions representing different characteristics possessed by members of the population, such as ethnicity, sex, age, or differences in a phenotype such as height, weight, drug response, disease susceptibility and the like. The different regions in a haplotype symbol may be represented by different colors, shading tones, stippling, etc. In a particularly preferred embodiment, generation of the graphical display is shown in real time, i.e., the positions and sizes of haplotype symbols, as well as the lengths of their connecting springs, change as the algorithm-directed organization of the haplotypes of a particular gene proceeds.

The resulting display provides a visual impression of the phylogenetic history of the locus, including the divergence patterns among the haplotypes for that locus, as well as providing a better understanding of the actual variation among the different populations comprising the sample. These considerations are important in the assessment of the encoded protein's involvement in a particular phenotype (e.g., differential response to a drug or adverse side effects). In addition, a spanning network generated for haplotypes in a clinical population using the same algorithm may be superimposed on the spanning network for the reference population to analyze whether the haplotype content of the clinical population is representative of the reference population.

7. A trial population of individuals who suffer from the condition of interest is recruited.

The end result of the CTS method is the correlation of an underlying genetic makeup (in the form of haplotype or sub-haplotype pairs for one or more genes or other loci) and a treatment outcome. In order to deduce this correlation it is necessary to run a clinical trial or to analyze the results of a clinical trial that has already been run. Individuals who suffer from the condition of interest are recruited. Standard methods may be used to define the patient population and to enroll subjects.

Individuals in the trial population are optionally graded for the existence of the underlying cause (disease/condition) of interest. This step will be important in cases where the symptom being presented by the patients can arise from more than one underlying cause, and where treatment of the underlying causes are not the same. An example of this would be where patients experience breathing difficulties that are due to either asthma or respiratory infections. If both sets were included in a trial of an asthma medication, there would be a spurious group of apparent non-responders who did not actually have asthma. These people would degrade any correlation between haplotype and treatment outcome.

This grading of potential patients could employ a standard physical exam or one or more lab tests. It could also use haplotyping for situations where there was a strong correlation between haplotype pair and disease susceptibility or severity.

8. Individuals in the trial population are treated using some protocol and their response is measured. In addition, they are haplotyped, either directly or using predictive genotyping.

This step is straightforward. If patients are to be haplotyped for the candidate genes, a direct molecular haplotyping method could be used. If they are to be indirectly haplotyped, a method such as the one described above in item 6 could be used. Clinical outcomes in response to the treatment are measured using standard protocols set up for the clinical trial.

9. Correlations between individual response and haplotype content are created for the candidate genes. From these correlations, a mathematical model is constructed that predicts response as a function of haplotype content.

Correlations may be produced in several ways. In one method averages and standard deviations for the haplotype-pair groups may be calculated. This can also be done for sub-haplotype-pair groups. These can be displayed in a color coded manner with low responding groups being colored one way and high responding groups colored another way (see, e.g., FIG. 18). Distributions in the form of bar graphs can also be displayed (see, e.g., FIG. 19), as can all group means and standard deviations (see, e.g., FIG. 20).

The information in FIGS. 18–24 may be used to determine whether haplotype information for the gene being examined can be used to predict clinical response to the treatment. One question that can be answered is whether there is a significant difference in response between groups of individuals with different haplotype pairs. FIGS. 18–22 show screens of the data that connect haplotypes with clinical outcomes. The example shown in FIG. 18 and the next several screens gives the results of a simulated clinical trial run to test the link between patients' haplotypes for CYP2D6 and a phenotypic response called "Test". The main layout of this page is the same as described in FIG. 10. At the left side of this view is a list of the clinical measurements performed on the patients. This list is completely generic as far as the invention is concerned. Selecting the relevant radio button will bring up data for any of the clinical measurements. (Only one "Test" radio button shown here, but there may be many, corresponding to different tests, with appropriate labels.) In this view, the color in a cell of the matrix indicates the mean value of the measurement for the individuals in that haplotype pair group. When one of the cells is selected, text appears at the right, giving the 2 haplotypes, the number of patients in the cell, the mean value and standard deviation for individuals in the cell. A slide bar is present below the color boxes near the top of the screen indicating 0% to 100/o so that moving, e.g., one or both of the ends of the bar will change the color scale in the color boxes at the top of the screen as well as the colors in the matrix. (Note that a slide bar may be used with ay screen with similar colored (or otherwise graded) boxes). FIG. 19 is a screen showing the distribution of the patients in each cell of the clinical measurement matrix of FIG. 18. In this case, the histograms are collectively normalized so that the user can directly compare frequencies from one cell to the next. The screen in FIG. 20 is brought up when the user selects any of the cells in the haplotype-pair matrix in FIG. 19. This shows the number of patients in the various response bins indicated on the horizontal axis. A response bin simply counts the number of individuals whose response is within a particular interval. For instance, there are 7 individuals in the response bin from 0.2 to 0.25 in FIG. 20.

The result of regression calculation shown in FIG. 21 (which calculation is described below) allows the user to see which polymorphic sites give the most significant contribution to the differences in phenotype. This display comes up in a separate window when the user pushed the "Regression" button on the "Clinical Measurements vs. Haplotype View" (FIG. 18, 19, or 21). Shown are the results of a dose-response linear regression calculation on each of the individual polymorphisms (REF 4, Chapter 9). In this case, sites 2 and 8 are most predictive, as indicated by their large values of the significance level. This fact would lead the user to examine the site 2/8 sub-haplotypes as in FIG. 22. This screen gives a detailed view of the mean and standard deviation values for each of the cells in FIG. 18. Also shown are the Chi-squared value for the distributions. These values indicate how close the distributions in each haplotype-pair group are to normal. The function Q(chi-squared) gives a level of statistical significance. If Q>0.05 the user could not reject the hypothesis that the distribution is normal. FIG. 22 shows that groups having different 2/8 sub-haplotypes can have very different mean values of the Test phenotype. To see if this group-to-group variation is significant, the user could ask the DecoGen™ application to perform an ANOVA (Analysis of Variation) calculation. The results of an ANOVA calculation are shown in FIG. 23. Selecting the ANOVA button on any of the earlier Clinical Measurements views brings up this display. This view uses standard calculation methods to see if the variation in clinical response between haplotype-pair groups is statistically significant. The methods used are described in Ref. 4, Chapter 10. FIG. 23 shows that the variation between different 2/8 sub-haplotype groups is statistically significant at the 99% confidence level.

The regression model used in FIG. 21 starts with a model of the form $$r = r_0 + S \times d \qquad (5)$$

where r is the response, $r_0$ is a constant called the "intercept", S is the slope and d is the dose. As discussed previously, the most-common nucleotide at the site and the least common nucleotide are defined. For each individual in the population, we calculate his "dose" as the number of least-common nucleotides he has at the site of interest. This value can be 0 (homozygous for the least-common nucleotide), 1 (heterozygous), or 2 (homozygous for the most common nucleotide). An individual's "response" is the value of the clinical measurement. Standard linear regression methods are then used to fit all of the individuals' dose and response to a single model. The outputs of the regression calculation are the intercept $r_0$, the slope S, and the variance (which measures how well the data fits this simple linear model). The Students t-test value and the level of significance can then be calculated. This figure shows the relevant variables (site, slope S, intercept $r_0$, variance, Student's t-test value and level of significance) for each of the sites.

From the results shown in FIG. 21, the user would see that the nucleotides at site 2 and 8 have significant contributions to the Test variable. This result would be interpreted as follows. Averaging over all variables other than the nucleotides at site 2, the Test variable can be predicted by $$\text{Test} = 0.231 + 0.154 \times (\text{number of T's at site 2}).$$

On average, an individual homozygous for C at site 2 will have a response of 0.231. Heterozygous individuals have an average response of 0.385, and individuals homozygous for T have an average response of 0.539. This trend is significant at the 99.9% confidence level. It is important to note that the calculation of significance (the Student's t-test) is based on the assumption that the distribution of responses for individuals (such as seen in FIG. 20) are normally distributed. The present invention can incorporate any of the standard methods for calculating statistical significance for non-normal distributions. Furthermore, the present invention can include more complex dose-response calculations that examine multiple sites simultaneously. See, e.g., Ref. 4.

A second method for finding correlations uses predictive models based on error-minimizing optimization algorithms. One of many possible optimization algorithms is a genetic algorithm. (Ref. 5). Simulated annealing (Ref. 6, Chapter 10), neural networks (Ref. 7, Chapter 18), standard gradient descent methods (Ref. 6, Chapter 10), or other global or local optimization approaches (See discussion in Ref. 5) could also be used. As an example (one that is currently implemented in the DecoGen™ application) a genetic algorithm approach is described herein. This method searches for optimal parameters or weights in linear or non-linear models connecting haplotype loci and clinical outcome. One model is of the form $$C = C_0 + \sum_{a}\left(\sum_{i} w_{i,a} R_{i,a} + \sum_{i} w'_{i,a} L_{i,a}\right) \quad (6)$$

where C is the measured clinical outcome, i goes over all polymorphic sites, $\alpha$ over all candidate genes, $C_0$, $w_{i,\alpha}$ and $w'_{i,\alpha}$ are variable weight values, $R_{i,\alpha}$ is equal to 1 if site i in gene $\alpha$ in the first haplotype takes on the most common nucleotide and –1 if it takes on the less common nucleotide. $L_{i,\alpha}$ is the same as $R_{i,\alpha}$ except for the second haplotype. The constant term $C_0$ and the weights $w_{i,\alpha}$ and $w'_{i,\alpha}$ are varied by the genetic algorithm during a search process that minimizes the error between the measured value of C and the value calculated from Equation 6. Models other than the one given in Equation 6 can be easily incorporated. The genetic algorithm is especially suited for searching not only over the space of weights in a particular model but also over the space of possible models. (Ref. 5).

Correlations can also be analyzed using ANOVA techniques to determine how much of the variation in the clinical data is explained by different subsets of the polymorphic sites in the candidate genes. The DecoGen™ application has an ANOVA function that uses standard methods to calculate significance (Ref. 4, Chapter 10). An example of an interface to this tool is shown in FIG. 23.

ANOVA is used to test hypotheses about whether a response variable is caused by or correlated with one or more traits or variable that can be measured. These traits or variables are called the independent variables. To carry out ANOVA, the independent variable(s) are measured and people are placed into groups or bins based on their values of the variables. In this case, each group contains those individuals with a given haplotype (or sub-haplotype) pair. The variation in response within the groups and also the variation between groups is then measured. If the within-group variation is large (people in a group have a wide range of responses) and the variation between groups is small (the average responses for all groups are about the same) then it can be concluded that the independent variables used for the grouping are not causing or correlated with the response variable. For instance, if people are grouped by month of birth (which should have nothing to do with their response to a drug) the ANOVA calculation should show a low level of significance. Here, as shown in FIG. 23, each haplotype-pair group is made up of the individuals in the population who have that haplotype pair. The table at the bottom shows the number of individuals in the group, the average response ("Test") of those individuals, and the standard deviation of that response. At the top is a table showing information comparing the "Between Group" calculation and the "Within Group" calculations. The details are given in the reference. [Ref 4] If the variation (the "Mean Squares" column) is larger for the "Between Groups" than for the "Within Groups" set, we will have an F-ratio (="Between Groups" divided by "Within Groups") greater than one. Large values of the F-ratio indicate that the independent variable is causing or correlated with the response. The calculated F-ratio is compared with the critical F-distribution value at whatever level of significance is of interest. If the F-ratio is greater than the Critical F-distribution value, then the user may be confident that the independent variable is predictive at that level. In this example, the user may would see that grouping by haplotype-pair for sites 2 and 8 for CYP2D6 gives significant probability at the 99% confidence level. The conclusion from this is that an individual's haplotypes at these positions in this gene is at least partially responsible for, or is at least strongly correlated with the value of Test.

FIG. 24 shows a screen which is an example interface to the modeling tool (i.e., the CTS™ Modeler) described herein. At the right are controls to set the parameters for the genetic algorithm (Ref 5). In the center is a graph showing the residual error of the model as a function of the number of genetic algorithm generations. At the bottom is a bar graph showing the current best weights for Eq. 6. In this example, the linear model described in Eq. 4 is used to find optimal weights for the polymorphic sites. The final parameters arrived at are $C_0=0.1$ and $w_{3,CYP2D6}=0.15$ and $w'_{8,CYP2D6}=-0.1$. This says that the response variable "Test" can be predicted from the formula:

Test=0.1+[0.15×(Number of Cs in position z)+0.1×(Number of As in position 8)]×2 where "number" refers to the number in the two haplotypes for an individual.

10. Preferably, follow-up trials are designed to test and validate the haplotype-response mathematical model.

The outcome of Step 9 is a hypothesis that people with certain haplotype pairs or genotypes are more likely or less likely on average to respond to a treatment. This model is preferably tested directly by running one or more additional trials to see if this hypothesis holds.

11. A diagnostic method is designed (using one or more of haplotyping, genotyping, physical exam, serum test, etc.) to determine those individuals who will or will not respond to the treatment.

The final outcome of the CTS™ method is a diagnostic method to indicate whether a patient will or will not respond to a particular treatment. This diagnostic method can take one of several forms—e.g., a direct DNA test, a serological test, or a physical exam measurement. The only requirement is that there is a good correlation between the diagnostic test results and the underlying haplotypes or sub-haplotypes that are in turn correlated with clinical outcome. In the preferred embodiment, this uses the predictive genotyping method described in item 6.

2. Illustration with ADRB2 Gene

FIG. 26 is the opening screen for the Asthma project. This screen appears after the "Asthma" folder has been selected from among the projects shown at the left. Selecting a folder causes the genes associated with that project to become active. Genes known or suspected of being involved in asthma are shown in the screen in "Extracellular" and "Intracellular" compartments. The text "Active Gene: DAXX" is a default value; "DAXX" will be replaced with the name of whatever gene is selected from this window. Selecting ADRB2, and then "Geneinfo" from the menu at left, brings up FIG. 27.

FIG. 27 presents data and statistics related to the ADBR2 gene. Selecting "GeneStructure" from the menu at left brings up FIG. 28A.

FIG. 28A is a screen showing the genomic structure of the ADBR2 gene (showing the location of features of the gene, such as promoters, exons, introns, 5' and 3' untranslated regions), polymorphism and haplotype information, and the number of times each haplotype was seen in the representatives of each of 4 world population groups. The column "Wild" contains the number of individuals homozygous for the more common nucleotide at each polymorphic site, "Mut" contains the number homozygous for the less common nucleotide, and "Het" is the number of heterozygous individuals. Overlaid on the two graphical gene representations at the upper part of the screen are vertical bars, indicating the positions of the polymorphic sites elaborated in the middle box. The user may scroll through the lower boxes to bring different portions of the polymorphism and haplotype data into view. Selecting row 6 in the middle window results in FIG. 28B.

FIG. 28B is a screen where a particular polymorphic site has been selected in the middle box. The upper graphical representation of the gene has been replaced by a textual representation, presented as a nucleotide sequence aligned with the lower graphical representation at the point of the selected polymorphic site (indicated by the black triangles). At the polymorphic site, the two observed nucleotides (T and C) are displayed. Selecting "Patient table" from the menu at left brings up FIG. 29A.

FIG. 29A presents genealogical information and diplotype and haplotype data for individuals within the database. Shaded rectangles within the table represent missing data. Within the rectangles and ovals are the ID numbers of the individuals; below each of these in the upper genealogical chart are the two haplotypes of the ADBR2 gene present in that individual, identified by number. The nucleotides comprising these haplotypes are displayed in the box at the lower right Selecting "Clinical Trial Data" from the menu at left brings up FIG. 29B.

FIG. 29B presents the clinical data sorted by individual patient. Severity scores, Skin Test results, and the clinically measured parameters described elsewhere are set out in columns. "NP" stands for "No data Point", and represents data missing for any reason. Selecting "HAPSNP" from the menu at left brings up FIG. 30.

FIG. 30 presents, for each patient, a row of color-coded (or shaded) squares representing the heterozygosity of the patient at each polymorphic site. These are adjacent to a row of split squares, where the same information is presented in a two-color (or shaded) format Selecting the HAPPair command from the menu at the left brings up FIG. 31.

FIG. 31 presents the "HAP Pair Frequency View" in which the world population distribution of haplotype or sub-haplotype pairs can be investigated. In this window, polymorphic sites 3, 9, and 11 have been selected by checking the corresponding boxes above the haplotypes. Each cell in the matrix below corresponds to a haplotype pair identified by the HAP numbers on the x and y axes. The height of the color-coded (or shaded) bars within each cell corresponds to the number of individuals of each population group having that haplotype pair. Clicking on the V/D button at the top of the screen toggles between FIGS. 31 and 32.

FIG. 32 shows the same data in tabular form. In this figure all SNPs have been selected, so the haplotypes being evaluated consist of thirteen polymorphic sites. Each row in the table corresponds to a haplotype pair (the two haplotypes which comprise the pair are identified in the first two columns), followed by the number of individuals in the database having that pair, and the percentage of the total population this number represents. Under each population group three columns presenting the number of individuals in the population group with that pair, the percentage of the population group that has that pair, and the percentage predicted by Hardy-Weinberg equilibrium. Selecting "Linkage" from the menu at left brings up FIG. 33.

FIG. 33 displays separate matrices for the total population and for each population group. Each cell is color-coded (or shaded) to indicate the extent to which the two haplotypes occur together in individuals, i.e., the degree to which they are linked. Selecting "HAPTyping" from the menu at left brings up the screen in FIG. 34.

FIG. 34 presents the ambiguity scores that result from masking one or more SNPs or polymorphisms in the genotype. The ambiguity scores are calculated by taking the sum of the geometric means of all pairs of genotypes rendered ambiguous by the mask, and multiplying by ten. All population groups have been chosen for inclusion in this figure by checking off the boxes at the upper left of the screen. The list of haplotype pairs has been sorted by the calculated Hardy-Weinberg frequency, and the pairs have been numbered consecutively, as shown in the first column.

A mask that causes SNP 8 to be ignored in all cases has been imposed by deselecting the appropriate box in the "Choose SNP" row above the haplotype list. Additional masking has been imposed by deselecting the appropriate boxes in the mask to the right of the Genotype table. (The mask is to the right of the table and may be accessed by scrolling horizontally; in the figure it has been relocated to bring it into view.) In the first mask, only SNP 8 is ignored, which results in haplotype pairs 4 and 73 both being consistent with the genotype observed. (In other words, the genotypes derived from haplotype pairs 4 and 73 differ only at SNP 8, and cannot be distinguished if it is not measured). An ambiguity score of 0.016 is associated with this first mask. The frequency of haplotype pair 4 is much greater than that of haplotype pair 73 (recall that the list is sorted by frequency), so one could resolve this ambiguity with some confidence simply by choosing haplotype pair 4. (In an alternative embodiment, the probability of each choice being the correct one could be displayed.) For the present application, in general, the mask with the largest number of ignored SNPs that retains an ambiguity score of about 1.0 or less will be preferred. The ambiguity score cut-off that is chosen may vary depending on the intended use of the inferred haplotypes. For example, if haplotype pair information is to be used in prescribing a drug, and certain haplotype pairs are associated with severe side effects, the acceptable ambiguity score may be reduced. In such a situation masks that do not render the haplotype pairs of interest ambiguous would be preferred as well. Selecting "Phylogenetic" from the menu at left brings up FIG. 35.

FIG. 35 presents haplotype data in a phylogenetic minimal spanning network. Each disk corresponds to a haplotype, the haplotype number is to the immediate right of each disk. The size of each disk is proportional to the number of individuals having that haplotype; that number is displayed in parentheses to the right of each disk. Haplotypes that are closely related, that is they differ at only one polymorphic site, are connected by solid lines. Haplotypes that differ at two sites are connected by light lines, and are spaced farther apart. The colored (or shaded) wedges represent the fraction of individuals having that haplotype that are from different population groups. Selecting "Clinical Haplotype Correlation" brings up the screen in FIG. 36.

FIG. 36 presents the association between a clinical outcome value (in this case, "delta % FEV1 pred" which is the change in FEV1 observed after administration of albuterol, corrected for size, age, and gender. The SNPs one wishes to test for association may be selected by checking off the appropriate box above the HAP list table. The value of delta % FEV1 is represented in grayscale or by a color scale. Each cell in the matrix corresponds to a given haplotype pair, defined by the haplotype numbers on the x and y axes. The number in each cell is the number of patients having that haplotype pair, and the color (or shading) of each cell reflects the response of those patients to albuterol. In this case, groups of people with haplotype pairs shown in the red (or darkly shaded) boxes have the highest average response, e.g. haplotype pairs 3,4 and 3,5. (See also FIG. 41, which presents numerical results showing that individuals with these haplotype pairs have a high average response to albuterol.) Under the "Clinical Mode" menu heading at the top of the screen is a command that the user may use to toggle among FIGS. 36, 37, 38, and 40.

Switching to FIG. 37 in this manner displays a collection of histograms, one in each cell of a haplotype pair matrix. Selecting the 1,1 cell enlarges it, bringing up FIG. 38.

FIG. 38 is a histogram showing the number of individuals having the 1,1 haplotype pair who exhibited the response to albuterol shown on the x axis. The bars in the histogram are color-coded (or shaded) as well, as an additional indication of the degree of response.

In either FIG. 36 or FIG. 37, there is a button with an icon of a small scatter plot (just below the Help menu at the top of the screen.) Selecting this button brings up FIG. 39A. This figure displays the regression calculations employed in the multi-SNP analysis, or "Build-up" process. Given the confidence values shown, which are the default values for the "tight cutoff" and "loose cutoff", the program generates pairwise combinations of SNPs, tests their p-values for correlation with "delta % FEV1 pred" against the cutoff values, and, from those subhaplotypes that pass the cut-offs, re-calculates and tests new pairwise combinations, until the number of SNPs in the subhaplotypes reaches the limit shown in the "Fixed Site" box. In the example shown, no four-SNP subhaplotype passed the loose cutoff, thus there are only 1-, 2-, and 3-SNP sub-haplotypes shown in this screen. New values may be entered in the Confidence and Fixed site fields; clicking on the calculator button (under the File menu) re executes the Build-up and Build-down processes with the entered values.

A reverse SNP analysis, or "Build down" process, may also be carried out; the presence of the minus sign in the "Fixed Site" box indicates that this process is being requested. (In the example given, only a single "Build-down" round was executed, so as to ensure that the full haplotype is present for comparison.)

For each "marker" (SNP, subhaplotype, or haplotype) in the left column, a regression analysis of the correlation of the number of copies of that marker with the value of "delta % FEV1 pred" is generated, and selected statistical information is presented in the columns to the right (A negative correlation coefficient (R) indicates that response to albuterol decreases with increasing copy number of the indicated marker.) The SNPs or subhaplotypes exhibiting the lowest p values are identified as the ones that should most preferably be measured in patients in order to predict response to albuterol. Selecting the box to the left of the A***A*G** sub-haplotype brings up FIG. 39B.

FIG. 39B presents in a graphic form the calculation of regression parameters displayed in FIG. 39A. The values of "delta % FEV1 pred" for patients with 0, 1, and 2 copies of the A***A*G** subhaplotype are plotted vertically at three ordinates. A line is drawn through the three means, and the slope of the line is taken as an indication of the degree of correlation. The intercept, slope, slope range, R and $R^2$ values, and the p value associated with this line, are all listed in FIG. 39A. The "slope range" is a pair of limits, reflecting the standard deviation in the values of "delta % FEV1 pred". Mathematically, the p value listed in FIG. 39A is the probability that the slope is actually zero, i.e. it is the probability that there is in fact no correlation. A lower value of p thus indicates greater reliability.

FIG. 40 (reached through the "Clinical Mode" menu) displays the observed haplotype pairs, their distribution in the population, and the mean clinical response (delta % FEV1 pred.) of the patients having those haplotype pairs. Selecting the "normal" button (to the right of the scatter plot button) brings up FIG. 41.

Figure 41:
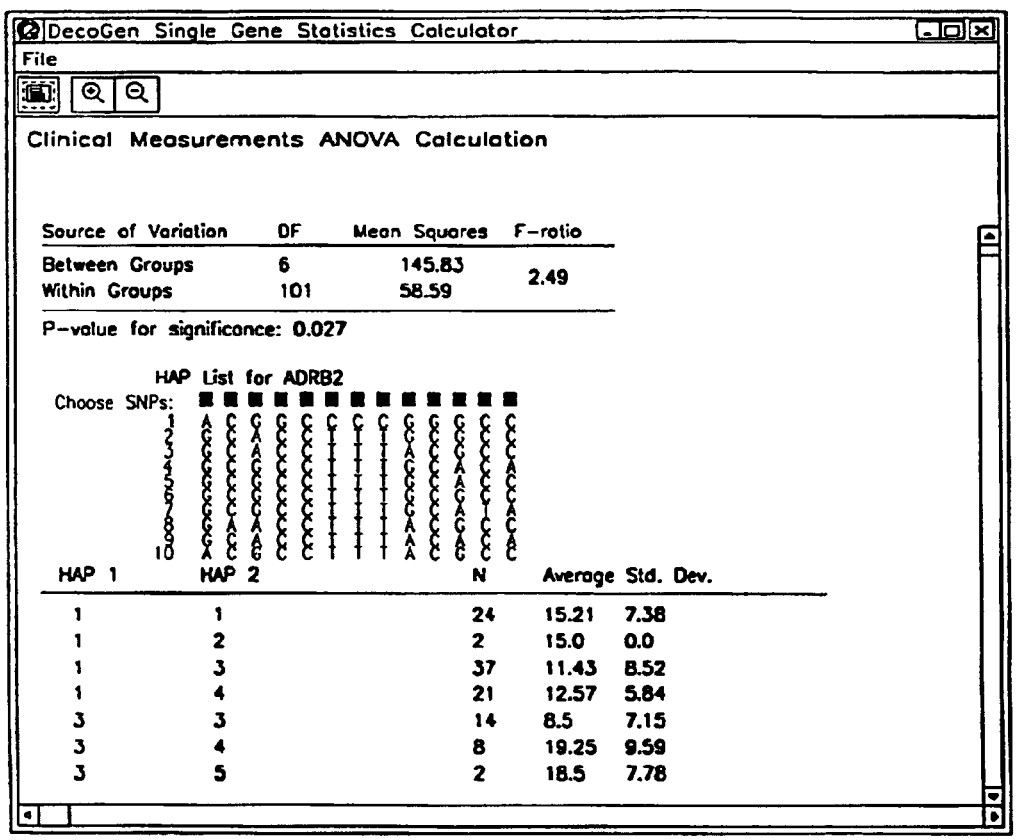

FIG. 41 shows a screen that displays the results of an ANOVA calculation in which patients were grouped according to haplotype pails, and the average value of "delta % FEV1 pred." was analyzed both within the groups and between the groups. This permits one to determine which pairs of haplotypes are associated with the observed clinical response. All SNPs in the ADBR2 gene have been selected in the row of boxes labeled "Choose SNPs", thus the groups are the same as the cells in the matrix in FIG. 36. Groups containing one patient were ignored, leaving the seven groups listed at the bottom of the screen. This left six degrees of freedom (the parameter "DF") for inter-group comparisons. The variation ("Mean Squares") is larger between groups than within groups, and the ratio of the two (F-ratio) is greater than one. (A large F-ratio indicates that the independent variable—the haplotype pair group—is correlated with the response.) There is a significant difference (p=0.027) between the mean square value of the clinical response between groups compared to that within groups. It is found in this example that being homozygous for haplotype 3 results in a significantly lower response (average 8.5%), while individuals with haplotype pair 3,4 (i.e., GCACCTTTACGCC and GCGCCTTTGCACA) show a good response to albuterol (average delta % FEV1 pred= 19.25%). This information is displayed in a more visual presentation in FIG. 36.

FIG. 42 is arrived at by selecting the "ClinicalVariables" command from the menu to the left of most of the previous screens. This is the same information displayed in FIG. 38, except that it is for the entire cohort rather than for a selected haplotype pair. The number of patients is plotted against the value of "delta % FEV1 pred". Note the outliers at 500% and 65% response. Selecting "ClinicalCorrelations" from the menu to the left brings up FIG. 43.

Figure 43:
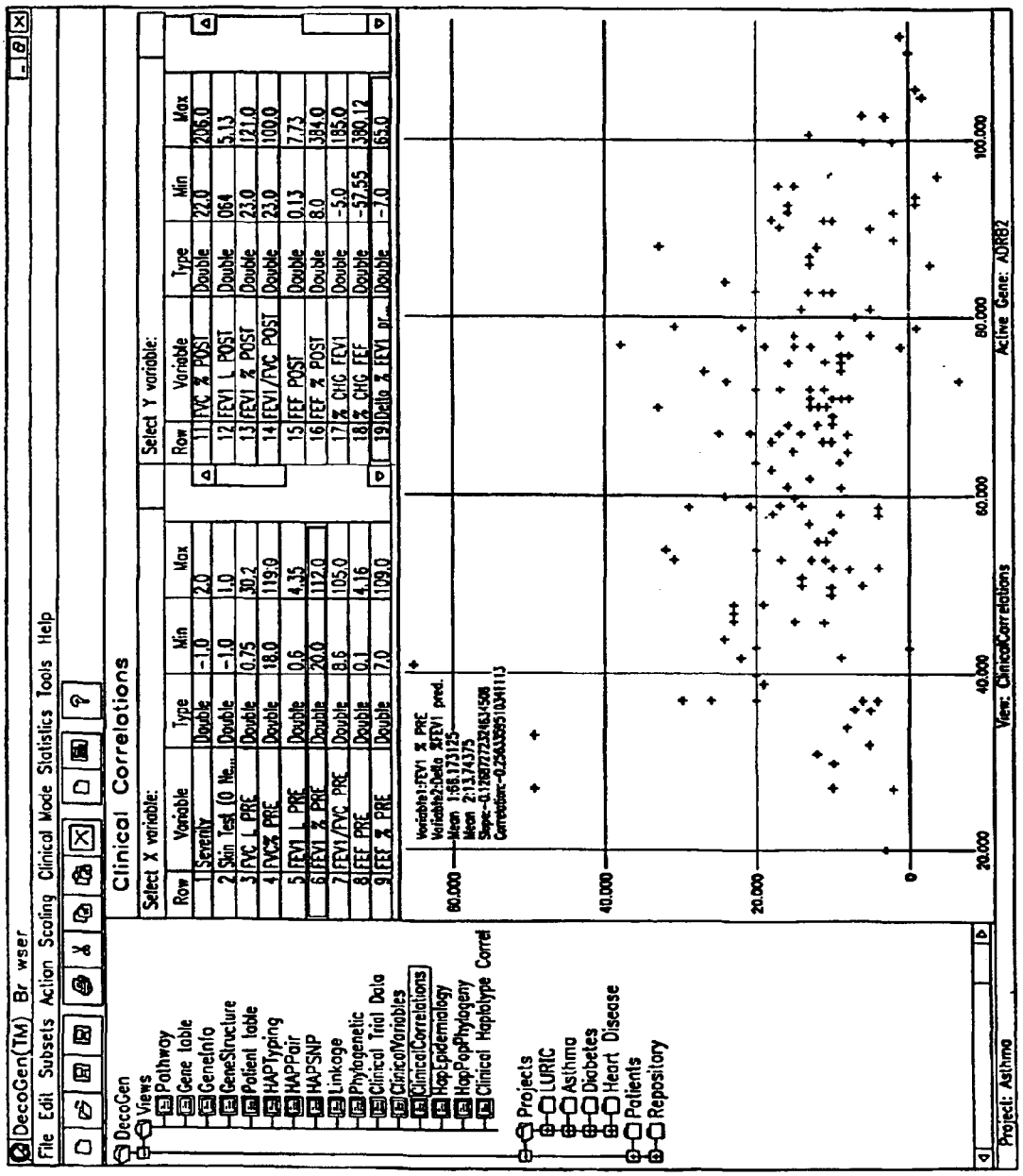

FIG. 43 is a plot of each patient's "FEV1% PRE" (the normalized value of FEV1 prior to administration of albuterol) against "delta % FEV1 pred". These variables are selected in the upper part of the screen. It is seen in this example that the response does not correlate with the initial value of FEV1.

D. Improved Methods

1. Improved Method for Finding Optimal Genotyping Sites

This aspect of the invention provides a method for determining an individual person's haplotypes for any gene with reduced cost and effort. A haplotype is the specific form of the gene that the individual inherited from either mother or father. The 2 copies of the gene (one maternal and one paternal) usually differ at a few positions in the DNA locus of the gene. These positions are called polymorphisms or Single Nucleotide Polymorphisms (SNPs). The minimal information required to specify the haplotype is the reference sequence, and the set of sites where differences occur among people in a population, and nucleotides at those sites for a given copy of the gene possessed by the individual. For the rest of this discussion, we assume that the reference sequence is given, and we represent the haplotype as a string of letters specifying the nucleotides at the variable sites. In almost all cases, only two of the possible 4 nucleotides will occur at any position (e.g. A or T, C or G), so for generality we can represent the two values for alleles as 1 and 0. Therefore a haplotype can be represented as a string of 1s and 0s such as 001010100. In practicing this invention, one may make use of known methods for discovering a representative set of the haplotypes that exist in a population, as well as their frequencies. One begins by sequencing large sections of the gene locus in a representative set of members in the population. This provides (1) a determination of all of the sites of variation, and (2) the mixed (unphased) genotype for each individual at each site. For instance in a sample of 4 individuals for a gene with 3 variable sites, the mixed genotypes could be:

| Individual | Genotype site 1 | Genotype site 2 | Genotype site 3 | Haplotype of $1^{st}$ allele | Haplotype of $2^{nd}$ allele |
|---|---|---|---|---|---|
| 1 | 1/1 | 1/0 | 1/0 | 3 | 4 |
| 2 | 0/0 | 0/0 | 0/0 | 1 | 1 |
| 3 | 1/0 | 1/0 | 0/0 | 1 | 2 |
| 4 | 1/1 | 0/0 | 1/0 | 3 | 5 |

This mixed set of genotypes could be derived from the following haplotypes:

| Haplotype No. | Haplotype | Frequency in population |
|---|---|---|
| 1 | 000 | 3 |
| 2 | 110 | 1 |
| 3 | 100 | 2 |
| 4 | 111 | 1 |
| 5 | 101 | 1 |

A method for deriving the haplotypes from the genotypes is described in a separate patent filing.

The haplotypes arm a fundamental unit of human evolution and their relationships can be described in terms of phylogenetics. One consequence of this phylogenetic relationship is the property of linkage disequilibrium. Basically this means that if one measures a nucleotide at one site in a haplotype, one can often predict the nucleotide that will exist at another site without having to measure it. This predictability is the basis of this aspect of the invention. Elimination of sites that do not need to be measured results in a reduced set of sites to be measured.

Information from a previously measured set of individuals (who were measured at all sites) may be used to determine the minimum number (or a reduced number) of sites that need to be measured in a new individual in order to predict the new individual's haplotypes with a desired level of confidence. Since the measurement at each site is expensive, the invention can lead to great cost reduction in the haplotyping process.

Step 1: Measure the full genotypes of a representative cohort of individuals.

Step 2: Determine their haplotypes directly, or indirectly) (e.g., using one of several algorithms.

Step 3: Tabulate the frequencies for each of these haplotypes.

Note that Steps 1–3 are optional. The remaining steps only require that a database of haplotypes with frequencies exists. There are several ways to achieve this, but the above set of steps is the preferred route.

Step 4: Construct the list of all full genotypes that could come from the observed haplotypes. Note that only a subset of these will actually be observed in a typical sample, for example 100–200 individuals.

Step 5: Predict the frequency of these genotypes from the Hardy-Weinberg equilibrium. If two haplotypes Hap1 and Hap2 have frequencies f1 and f2, the expected frequency of the mix is 2×f1×f2, or f1×f2 if Hap1 and Hap2 are identical.

Step 6: Go through this list and find all sites that, if they were not measured, would still allow one to correctly determine each pair of haplotypes. For example, take the case where the three haplotypes A (1111), B (1110), and C (0000) exist in a population. The six genotypes that could be observed are derived from the six different pairs that are possible:

| Hap Pair | Polymorphic Site | | | |
|---|---|---|---|---|
| | 1 | 2 | 3 | 4 |
| 1. A, A | 1/1 | 1/1 | 1/1 | 1/1 |
| 2. A, B | 1/1 | 1/1 | 1/1 | 1/0 |
| 3. A, C | 1/0 | 1/0 | 1/0 | 1/0 |
| 4. B, B | 1/1 | 1/1 | 1/1 | 0/0 |
| 5. B, C | 1/0 | 1/0 | 1/0 | 0/0 |
| 6. C, C | 0/0 | 0/0 | 0/0 | 0/0 |

Not measuring any one of the sites 1–3 would still permit one to correctly assign a haplotype pair to an individual. From this we can see that any one of the first three positions, together with the fourth, carries all of the information required to determine which pair of haplotypes an individual has.

Step 7: Extend the analysis of Step 6 as follows. Create a set of masks of the same length as the haplotype. A mask may be represented by a series of letters, e.g., Y for yes and N for no, to indicate whether the marked site is to be measured. For example, using the mask YNNY in the previous example, one would measure only sites 1 and 4, and one could use the information that only haplotypes 1111, 1110, and 0000 exist to infer the haplotypes for the individuals. Masks NYNY and NNYY would give equivalent information. If there are n sites, all combinations of Y and N produce $2^n$ masks, of which $2^n-1$ need to be examined (the all-N mask provides no information).

Step 8: For each mask, evaluate how much ambiguity exists from this measurement of incomplete information. For example, one measure of ambiguity would be to take all pairs of genotypes that are identical when using the mask, and multiply their frequencies. The product may be converted to the geometric mean. Then, for each mask, add up all such products for all ambiguous pairs to obtain an ambiguity score, which is used as a penalty factor in evaluating the value of the mask. The consequence of this would be to highly penalize masks that fail to resolve likely-to-be-seen genotypes into correct haplotypes, and masks that leave large numbers of genotypes ambiguous, such as the mask NNNY in the above example. This would give greater weight to masks that only confuse low frequency, low probability genotypes. A variety of other scoring schemes could be devised for this purpose.

This approach is most preferably implemented by means of a computer program that allows a user to view the ambiguity score for each mask, and calculate the tradeoff between reduced cost and reduced certainty in the determination of the haplotypes.

Step 8: Genotype new individuals using the optimal set of m sites (the optimal mask). In the example above, there are three equivalent optimal masks, YNNY, NYNY and NNYY, which require that only two of the four polymorphic sites be measured. (These masks have zero ambiguity.)

Step 9: Derive these individuals' full n-site haplotypes by matching their m-site genotypes to the appropriate m-site genotypes derived from the n-site haplotypes of the initial cohort. If there is an ambiguity in the choice, the more common haplotype may be chosen, but preferably a haplotype pair will be chosen based on a weighted probability method as follows:

If two haplotype pairs A and B exist that could explain a given genotype, the Hardy-Weinberg equilibrium will predict probabilities $p_A$ and $p_B$, where $p_A+p_B=1$. One chooses a random number between 0 and 1. If the number is less than or equal to $p_A$, the first haplotype pair A is assumed. If the number is greater than $p_A$, the second pair is assumed. There are more complex variants of this algorithm, but this simple, unbiased approach is preferred.

2. Improved Methods for Correlating Haplotypes with Clinical Outcome Variable(s)

The following methods are described for correlating haplotypes, or haplotype pairs, with a clinical outcome variable. However, these methods are applicable to correlating haplotypes, and/or haplotype pairs, to any phenotype of interest, and is not limited to a clinical population or to applications in a clinical setting.

a. Multi-SNP Analysis Method (Build-Up Process)

This process is outlined in the flow chart shown in FIG. 45. The first step (S1) is the collection of haplotype information and clinical data from a cohort of subjects. Clinical data may be acquired before, during, or after collection of the haplotype information. The clinical data may be the diagnosis of a disease state, a response to an administered drug, a side-effect of an administered drug, or other manifestation of a phenotype of interest for which the practitioner desires to determine correlated haplotypes. The data is referred to as "clinical outcome values." These values may be binary (e.g., response/no response, survival at 5 months, toxicity/no toxicity, etc.) or may be continuous (e.g. liver enzyme levels, serum concentrations, drug half-life, etc.)

The collection of haplotype information is the determination (e.g., by direct sequencing or by statistical inference) of a pattern of SNPs for each allele of a pre-selected gene or group of genes, for each individual in the cohort. The gene or group of genes selected may be chosen based on any criteria the practitioner desires to employ. For example, if the haplotype data is being collected in order to build a general-purpose haplotype database, a large number of clinically and pharmacologically relevant genes are likely to be selected. Where a retrospective analysis of a cohort from an ongoing or completed clinical study is being carried out, a smaller number of genes judged to be relevant might be selected.

The next step (S2) is the finding of single SNP correlations. Each individual SNP is statistically analyzed for the degree to which it correlates with the phenotype of interest. The analysis may be any of several types, such as a regression analysis (correlating the number of occurrences of the SNP in the subject's genome, i.e. 0, 1, or 2, with the value of the clinical measurement), ANOVA analysis (correlating a continuous clinical outcome value with the presence of the SNP, relative to the outcome value of individuals lacking the SNP), or case-control chi-square analysis (correlating a binary clinical outcome value with the presence of the SNP, relative to the outcome value of individuals lacking the SNP).

In one embodiment, a "tight cut-off" criterion is next applied to each SNP in turn. A first SNP is selected (S3) and its correlation with the clinical outcome is tested against a tight cut-off (S4). A typical value for the tight cut-off will be in the range p=0.01 to 0.05, although other values may be chosen on empirical or theoretical grounds. If the SNP correlation meets the tight cut-off it is displayed to the user of the system (S5) (or, alternatively, stored for later display), and stored for later combination (S6). If the SNP correlation does not meet the tight cut-off it is tested against a "loose cut-off" (S7), typically in the range p=0.05 to 0.1. Again, other cut-off values may be chosen if desired for any reason. (User-selected tight and loose cut-off values are entered in the two boxes labeled "confidence" in FIG. 39a.) A SNP whose correlation meets the loose cut-off is stored for later combination (S6). Any SNP whose correlation does not meet either cut-off is discarded (S8) i.e., it is not considered further in the process. If there are SNPs remaining to be tested against the cut-offs (S9) they are selected (S10) and tested (S4) in turn.

In an alternative embodiment, a tight cut-off is not applied, and each SNP's correlation is tested directly against the loose cut-off, and the SNP is either saved or discarded. In this embodiment, correlations of pair-wise generated sub-haplotypes (see below) are also tested directly against the loose cut-off. If desired, SNPs and sub-haplotypes which are saved at the end of this alternative process may be measured against a tight cut-off and those that pass may be displayed.

When all SNPs have had their correlations tested, the next step of the process consists of generating all possible pair-wise combinations (sub-haplotypes) of the saved SNPs. If novel (i.e. untested) sub-haplotypes are possible (S11), which will be the case on the first iteration, they are generated by pair-wise combination of all saved SNPs (S12). The correlations of the newly generated sub-haplotypes with the clinical outcome values are calculated (S13), as was done for the SNPs. A first sub-haplotype is selected (S15) and its correlation is tested against the tight and loose cut-offs (S4, S7) as described above for the SNP correlations. Each sub-haplotype is tested in turn, as described above, discarding any sub-haplotypes that do not pass the cut-off criteria and saving those that do pass.

When all sub-haplotypes have been examined, the process generates new pair-wise combinations among the originally saved SNPs and the newly saved sub-haplotypes, and among all saved sub-haplotypes as well. The process may be iterated until no new combinations are being generated; alternatively the practitioner may interrupt the process at any time. In a preferred embodiment, the practitioner may set a limit to the number of SNPs permitted in the generated sub-haplotypes. (See FIG. 39a, where "fixed site=4" is a 4-SNP limit). In this embodiment the system would then determine if new combinations within the limit are possible prior to each pairwise combination step.

In a preferred embodiment, complex redundant sub-haplotypes are removed from the pair-wise generated sub-haplotypes (S14). Complex redundant sub-haplotypes are those which are constructed from smaller sub-haplotypes, where the smaller sub-haplotypes have correlation values that are at least as significant as that of the complex sub-haplotype, i.e. they have correlation values that account for the correlation value of the complex redundant sub-haplotype. In such cases the complex haplotype provides no additional information beyond what the component sub-haplotypes provide, which makes it redundant. The non-redundant haplotypes and sub-haplotypes that remain are those that have the strongest association with the clinical outcome values. These are saved for future use (S16).

b. Reverse SNP Analysis Method (Pare-Down Process)

This aspect of the invention provides a method for discovering which particular SNPs or sub-haplotypes correlate with a phenotype of interest, when one has in hand single gene haplotype correlation values. The process is outlined in the flow chart illustrated in FIG. 46.

The first step (S17) is the collection of haplotype information and clinical data from a cohort of subjects. Clinical data may be acquired before, during, or after collection of the haplotype information. The clinical data may be the diagnosis of a disease state, a response to an administered drug, a side-effect of an administered drug, or other manifestation of a phenotype of interest for which the practitioner desires to determine correlated haplotypes. The data is referred to as "clinical outcome values." These values may be binary (e.g., response/no response, survival at 5 months, toxicity/no toxicity, etc.) or may be continuous (e.g. liver enzyme levels, serum concentrations, drug half-life, etc.)

The collection of haplotype information is the determination (e.g., by direct sequencing or by statistical inference) of a pattern of SNPs for each allele of each of a pre-selected group of genes, for each individual in the cohort. The group of genes selected may be chosen based on any criteria the practitioner desires to employ. For example, if the haplotype data is being collected in order to build a general-purpose haplotype database, a large number of clinically and pharmacologically relevant genes are likely to be selected. Where a retrospective analysis of a cohort from an ongoing or completed clinical study is being carried out, a smaller number of genes judged to be relevant might be selected.

The next step (S18) is the finding of single-gene haplotype correlations. Each individual haplotype of each gene is statistically analyzed for the degree to which it correlates with the phenotype or clinical outcome value of interest. The analysis may be any of several types, such as a regression analysis (correlating the number of occurrences of the haplotype in the subject's genome, i.e. 0, 1, or 2, with the value of the clinical measurement), ANOVA analysis (correlating a continuous clinical outcome value with the presence of the haplotype, relative to the outcome value of individuals lacking the haplotype), or case-control chi-square analysis (correlating a binary clinical outcome value with the presence of the haploytype, relative to the outcome value of individuals lacking the haplotype).

In one embodiment, a "tight cut-off" criterion is next applied to each haplotype in turn. A first haplotype is selected (S19) and its correlation with the clinical outcome value is tested against a tight cut-off (S20). A typical value for the tight cut-off will be in the range $p=0.01$ to $0.05$, although other values may be chosen on empirical or theoretical grounds. If the haplotype correlation meets the tight cut-off it is displayed to the user of the system (S21) (or, alternatively, stored for later display), and stored for later combination (S22). If the haplotype correlation does not meet the tight cut-off it is tested against a "loose cut-off" (S23), typically in the range $p=0.05$ to $0.1$. Again, other cut-off values may be chosen if desired for any reason. A haplotype meeting the loose cut-off is stored for later combination (S22). Any haplotype whose correlation does not meet either cut-off is discarded (S24), i.e., it is not considered further in the process. If there are haplotypes remaining to be tested against the cut-offs (S25) they are selected (S26) and tested (S20) in turn.

In an alternative embodiment, a tight cut-off is not applied. The correlation of each haplotype is tested directly against the loose cut-off, and the haplotype is either saved or discarded. In this embodiment, correlations of sub-haplotypes generated by masking (see below) are also tested directly against the loose cut-off. If desired, sub-haplotypes which are saved at the end of this alternative process may be measured against a tight cut-off, and those that pass may be displayed.

When all haplotypes have had their correlations tested, the next step of the process consists of generating all possible sub-haplotypes in which a single SNP is masked, i.e. its identity is disregarded. If novel (i.e. untested) sub-haplotypes are possible (S27), which will be the case on the first iteration, they are generated by systematically masking each SNP of all saved haplotypes (S28). The correlations of the newly generated sub-haplotypes with the clinical outcome value are calculated (S29), as was done for the haplotypes themselves. A first sub-haplotype is selected (S30) and its correlation is tested against the tight and loose cut-offs (S20, S23) as described above for the haplotype correlations. Each sub-haplotype is tested in turn, as described above, discarding any sub-haplotypes that do not pass the cut-off criteria and saving those that do pass.

Optionally, in a preferred embodiment, complex redundant haplotypes and sub-haplotypes are discarded after correlations are calculated for the sub-haplotypes and SNPs generated by the masking step (S31). Complex redundant haplotypes and sub-haplotypes are those which are constructed from smaller sub-haplotypes or SNPs, where the smaller sub-haplotypes or SNPs have correlation values that are at least as significant as that of the complex sub-haplotype, i.e. they have correlation values that account for the correlation value of the complex redundant sub-haplotype. In such cases the complex haplotype or sub-haplotype provides no additional information beyond what its component sub-haplotypes or SNPs provide, which makes it redundant.

When all sub-haplotypes have been examined, the process generates new sub-haplotypes by masking SNPs among the newly saved sub-haplotypes. The process is preferably iterated until no new sub-haplotypes are being generated; this may occur only when the sub-haplotypes have been reduced to individual SNPs. Alternatively the practitioner may interrupt the process at any time.

The non-redundant sub-haplotypes and SNPs that remain are those that have the strongest association with the clinical outcome values. These are saved for future use (S32).

E. Tools of the Invention

The methods of the invention preferably use a tool called the DecoGen™ Application.

The tool consists of:

a. One or more databases that contain (1) haplotypes for a gene (or other loci) for many individuals (i.e., people for the CTS™ method application, but it would include animals, plants, etc. for other applications) for one or more genes and (2) a list of phenotypic measurements or outcomes that can be but are not limited to: disease measurements, drug response measurements, plant yields, plant disease resistance, plant drought resistance, plant interaction with pest-management strategies, etc. The databases could include information generated either internally or externally (e.g. GenBank).

b. A set of computer programs that analyze and display the relationships between the haplotypes for an individual and its phenotypic characteristics (including drug responses).

Specific aspects of the tool which are novel include:

a. A method of displaying measurements (such as quantitative phenotypic responses) for groups of individuals with the same group of haplotypes or sub-haplotypes, and thereby easily showing how responses segregate by haplotype or sub-haplotype composition. In the example herein, the display shows a matrix where the rows are labeled by one haplotype and the columns by a second. Each cell of the matrix is labeled either by numbers, by colors representing numbers, by a graph representing a distribution of values for the group or by other graphical controls that allow for further data mining for that group.

b. A minimal spanning tree display (see e.g., Ref. 8) showing the phylogenetic distance between haplotypes. Each node, which represents a haplotype, is labeled by a graphic that shows statistics about the haplotype (for example, fraction of the population, contribution to disease susceptibility).

c. Numerical modeling tools that produce a quantitative model linking the haplotype structure with any specific phenotypic outcome, which is preferably quantitative or categorical. Examples of outcomes include years of survival after treatment with anticancer drugs and increase in lung city after taking an asthma medication. This model can use a genetic algorithm or other suitable optimization algorithm to find the most predictive models. This can be extended to multiple genes using the current method (see Equation 5). Techniques such as Factor Analysis (Ref. 4, Chapter 14) could be used to find the minimal set of predictive haplotypes.

d. A genotype-to-haplotype method that allows the user to find the smallest number of sites to genotype in order to infer an individual's haplotypes or sub-haplotypes for a given gene. An individual's haplotypes provide unambiguous knowledge of his genetic makeup and hence of the protein variations that person possesses. As described earlier, the individual's genotype does not distinguish his haplotypes so there is ambiguity about what protein variants the individual will express. However, using current technology, it is much more expensive to directly haplotype an individual than it is to genotype him. The method described above allows one to predict an individual's haplotypes, and therefore to make use of the predictive haplotype-to-response correlation derived from a clinical trial. The steps required for this to work are (a) determine the haplotype frequencies from the reference population directly; (b) correct the observed frequencies to conform to Hardy-Weinberg equilibrium (unless it is determined that the derivation is not due to sampling bias as discussed above); and (c) use the statistical approach described in the third paragraph of item 6 above to predict individuals' haplotypes or sub-haplotypes from their genotypes.

F. Data/Database Model

The present invention uses a relational database which provides a robust, scalable and releasable data storage and data management mechanism. The computing hardware and software platforms, with 7×24 teams of database administration and development support, provide the relational database with advantageous guaranteed data quality, data security, and data availability. The database models of the present invention provide tables and their relationships optimized for efficiently storing and searching genomic and clinical information, and otherwise utilizing a genomics-oriented database.

A data model (or database model) describes the data fields one wishes to store and the relationships between those data fields. The model is a blueprint for the actual way that data is stored, but is generic enough that it is not restricted to a particular database implementation (e.g., Sybase or Oracle). In the preferred embodiment of the present invention, the model stores the data required by the DecoGen application.

1. Database Model Version 1 a. Submodels

In one embodiment, the database comprises 5 submodels which contain logically related subsets of the data. These are described below.

1. Gene Repository (FIG. 25A): This submodel describes the gene loci and its related domains. It captures the information on gene, gene structure, species, gene map, gene family, therapeutic applications of genes, gene naming conventions and publication literature including the patent information on these objects.

2. Population Repository (FIG. 25B): This submodel encapsulates the patient and population information. It covers entities such as patient, ethnic and geographical background of patient and population, medical conditions of the patients, family and pedigree information of the patients, patient haplotype and polymorphism information and their clinical trial outcomes.

3. Polymorphism Repository (FIG. 25C): This submodel stores the haplotypes and the polymorphisms associated with genes and patient cohorts used in clinical trials. The polymorphisms may include SNPs, small insertions/deletions, large insertions/deletions, repeats, frame shifts and alternative splicing.

4. Sequence Repository (FIG. 25D): Genetic sequence information in the form of genomic DNA, cDNA, mRNA and protein is captured by this data submodel. What is more important in this model is the location relationship between the gene structural features and the sequences. Patent information on sequences is also covered.

5. Assay Repository (FIG. 25E): This submodel captures client companies, contact information, compounds used in the different disease areas and assay results for such compounds in regards to polymorphisms and haplotypes in target genes.

A model or sub-model is a collection of database tables. A table is described by its columns, where there is one column for each data field. For instance the table COMPANY contains the following 3 columns: COMPANY_ID, COMPANY_NAME, and DESCR. COMPANY_ID is a unique number (1, 2, 3, etc.) assigned to the company. COMPANY_NAME holds the name (e.g., "Genaissance") and DESCR holds extra descriptive information about the company (e.g., "The HAP Company"). There will be one row in this table for each company for which data exists in the database. In this case COMPANY_ID is the "primary key" which requires that no two companies have the same value of COMPANY_ID, i.e., that it is unique in the table. Tables are connected together by "relationships". To understand this, refer to FIG. 25E which shows the table COMPANYADDRESS. It has fields COMPANY_ID, STREET, CITY, etc. In this table the field COMPANY_ID refers back to the table COMPANY. If a company has several locations, there will be several rows in the table COMPANYADDRESS, each with the same value of COMPANY_ID. For each of these we can get the name and description of the company by referring back to the COMPANY TABLE.

b. Abbreviations

The following abbreviations are used in FIGS. 25A–E and the tables describing the database model depicted therein:

AA: amino acid
Clin: clinical
Descr: description
FK: foreign key
Geo: geographical
Hap: Haplotype
ID: identifier
Loc: location
Mol: molecule
NT: nucleotide
PK: primary key
Poly: polymorphism
Pos: position
Pub: publication
QC: quality control
Seq: sequence
SNP: single nucleotide polymorphism
Therap: therapeutic c. Tables In this embodiment of the present invention, the database contains 76 tables as follows:

1) Accession
2) Assay
3) AssayResult
4) BioSequence
5) ChromosomeMap
6) ClasperClone
7) ClinicalSite
8) Company
9) CompanyAddress
10) Compound
11) CompoundAssay
12) Contact
13) FamilyMember
14) FamilyMemberEthnicity
15) Feature
16) FeatureAccession
17) FeaturGeneLocation
18) FeatureInfo
19) FeatureKey
20) FeatureList
21) FeaturePub
22) Gene
23) GeneAccession
24) GeneAlias
25) GeneFamily
26) GeneMapLocation
27) GenePathway
28) GenePriority
29) GenePub
30) GenotypeCode
31) Ethnicity
32) HapAssay
33) HapCompoundAssay
34) HapHistory
35) Haplotype
36) HapMethod
37) HapPatent
38) HapPub
39) HapSNP
40) HapSNPHistory
41) LocationType
42) MapType
43) Method
44) MoleculeType
45) Nomenclature
46) Patent
47) PatentImage
48) Pathway
49) PathwayPub
50) PolyMethod
51) Polymorphism
52) PolyNameAlias
53) PolySeq3
54) PolySeq5
55) Publication
56) SeqAccession
57) SeqFeatureLocation
58) SeqGeneLocation
59) SeqSeqLocation
60) SequenceText
61) SNPAssay
62) SNPPatent
63) SNPPub
64) Species
65) Patient
66) PatientCohort
67) PatientEthnicity
68) PatientHap
69) PatientHapClinOutcome
70) PatientHapHistory
71) PatientMedicalHistory
72) PatientSNP
73) PatientSNPHistory
74) TherapetuicArea
75) TherapeuticGene
76) VariationType Additional tables (not shown) may include Allele, FeatureMapLocation, PubImage, TherapCompound.

d. Fields

FIGS. 25A–E show the fields of each table in the database. The following are descriptions of the fields found in the database as well as for fields and tables that could be added to the database:

|  | Name | Null? | Type | Comments |
|---|---|---|---|---|
| table Accession | ACCESSION | NOT NULL | VARCHAR2(20) | a unique ID for a sequence in the commonly used public domain databases; becomes de facto standard for sequence data access in the academia and industry |
|  | SOURCE |  | VARCHAR2(20) | who issued the ID |
|  | DESCR |  | VARCHAR2(200) | other descriptions |
|  | INSERTED_BY |  | VARCHAR2(30) | who inserted the record |
|  | INSERT_TIME |  | DATE | when |
|  | UPDATED_BY |  | VARCHAR2(30) | who updated the record |
|  | UPDATE_TIME |  | DATE | when |
| table Allele | ALLELE_NAME | NOT NULL | NUMBER(4) | allele is the one member of a pair or series of genes that occupy a specific position on a specific chromosome |
|  | POLY_ID | NOT NULL | NUMBER | Foreign key to the polymorphism record |
|  | NT_SEQ_TEXT |  | VARCHAR2(4000) | Nucleotide sequence string |
|  | AA_SEQ_TEXT |  | VARCHAR2(1000) | Amino acid sequence string |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table Assay | ASSAY_ID | NOT NULL | NUMBER | Primary key for the assay table |
|  | ASSAY_NAME |  | VARCHAR2(50) |  |
|  | ASSAY_PARAMETERS |  | VARCHAR2(200) |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table AssayResult | ASSAY_ID | NOT NULL | NUMBER |  |
|  | ASSAY_TYPE |  | VARCHAR2(100) |  |
|  | MEASURE |  | VARCHAR2(200) | measurement of the assay parameters |
|  | TIMESTAMP |  | DATE | time of operation |
|  | OPERATOR |  | VARCHAR2(50) | who did it |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table BioSequence | SEQ_ID | NOT NULL | NUMBER | sequence ID (PK) |
|  | MOL_TYPE | NOT NULL | VARCHAR2(20) | molecular type |
|  | SEQ_LENGTH |  | NUMBER | sequence length |
|  | PATENT_ID |  | NUMBER | FK to the patent record |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table Chromosome Map | MAP_ID | NOT NULL | NUMBER(4) | unique genetic map ID |
|  | MAP_TYPE_ID | NOT NULL | NUMBER(4) | FK to MapType |
|  | SPECIES_ID | NOT NULL | NUMBER | FK to species |
|  | CHROMOSOME |  | VARCHAR2(2) |  |
|  | MAP_NAME |  | VARCHAR2(50) |  |
|  | EXTERNAL_KEY |  | VARCHAR2(50) | ID used by external sources |
|  | KEY_SOURCE |  | VARCHAR2(20) | which source |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table ClasperClone | CLASPER_CLONE_ID | NOT NULL | NUMBER | Unique ID for each Clasper done |
|  | PI |  | VARCHAR2(50) | Subject ID; It is the FK to Subject table |
|  | DESCR |  | VARCHAR2(200) |  |

-continued

|  | Name | Null? | Type | Comments |
|---|---|---|---|---|
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table ClinicalSite | CLINICAL_SITE_ID | NOT NULL | NUMBER(4) |  |
|  | SITE_NAME |  | VARCHAR2(50) |  |
|  | COMPANY_ID |  | NUMBER |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table Company | COMPANY_ID | NOT NULL | NUMBER |  |
|  | COMPANY_NAME |  | VARCHAR2(50) |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table Company Address | COMPANY_ID | NOT NULL | NUMBER |  |
|  | CONTACT_ID | NOT NULL | NUMBER |  |
|  | STREET |  | VARCHAR2(50) |  |
|  | CITY |  | VARCHAR2(50) |  |
|  | STATE |  | VARCHAR2(50) |  |
|  | COUNTRY |  | VARCHAR2(100) |  |
|  | ZIP |  | VARCHAR2(20) |  |
|  | WEB_SITE |  | VARCHAR2(200) |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table Compound | COMPOUND_ID | NOT NULL | NUMBER |  |
|  | COMPANY_ID |  | NUMBER |  |
|  | THERAP_ID |  | NUMBER |  |
|  | PATENT_ID |  | NUMBER |  |
|  | REGISTRATION_NUM |  | VARCHAR2(50) | Compound registration number is generally the unique ID for the compound in that company |
|  | COMPOUND_NAME |  | VARCHAR2(200) |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table Compound Assay | COMPOUND_ID | NOT NULL | NUMBER |  |
|  | ASSAY_ID | NOT NULL | NUMBER |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table Contact | CONTACT_ID | NOT NULL | NUMBER |  |
|  | COMPANY_ID | NOT NULL | NUMBER |  |
|  | ADDRESS_ID |  | NUMBER |  |
|  | LAST_NAME |  | VARCHAR2(50) |  |
|  | MIDDLE_NAME |  | VARCHAR2(20) |  |
|  | FIRST_NAME |  | VARCHAR2(50) |  |
|  | OFFICE_PHONE |  | VARCHAR2(20) |  |
|  | EMAIL |  | VARCHAR2(100) |  |
|  | CELL_PHONE |  | VARCHAR2(20) |  |
|  | PAGER_PHONE |  | VARCHAR2(20) |  |
|  | FAX |  | VARCHAR2(20) |  |
|  | WEB_SITE |  | VARCHAR2(200) |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table FamilyMember | PI | NOT NULL | VARCHAR2(50) | FK to Patient |
|  | FAMILY_POSITION | NOT NULL | VARCHAR2(20) | examples are sibblings, parents, grandparents, etc. |
|  | DESCR |  | VARCHAR2(200) |  |
|  | INSERTED_BY |  | VARCHAR2(30) |  |

-continued

|  | Name | Null? | Type | Comments |
|---|---|---|---|---|
|  | INSERT_TIME |  | DATE |  |
|  | UPDATED_BY |  | VARCHAR2(30) |  |
|  | UPDATE_TIME |  | DATE |  |
| table | PI | NOT NULL | VARCHAR2(50) |  |
| FamilyMember | FAMILY_POSITION | NOT NULL | VARCHAR2(20) |  |
| Ethnicity | ETHNIC_CODE | NOT NULL | VARCHAR2(20) | FK pointing to the Ethnicity table |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table Feature | FEATURE_ID | NOT NULL | NUMBER | a feature is defined as either a genomic structure of a gene, or a fragment of DNA on a chromosome in the genome. |
|  | GENE_ID |  | NUMBER | FK pointing to the Gene table in case of feature of a gene |
|  | FEATURE_NAME |  | VARCHAR2(50) |  |
|  | FEATURE_KEY_ID | NOT NULL | NUMBER(3) | FK pointing to the FeatureKey table to allow only validated feature types |
|  | MAP_ID |  | NUMBER |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table | ACCESSION | NOT NULL | VARCHAR2(20) |  |
| Feature | FEATURE_ID | NOT NULL | NUMBER |  |
| Accession | START_POS |  | NUMBER | the start position of the feature in the sequence identified by that accession |
|  | END_POS |  | NUMBER | the end position |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table | GENE_ID | NOT NULL | NUMBER | FK |
| Feature | LOC_TYPE | NOT NULL | VARCHAR2(20) | location type determines what type of structural relationship we are going to build in the particular case between the gene and the feature |
| GeneLocation |  |  |  |  |
|  | FEATURE_ID | NOT NULL | NUMBER | FK |
|  | LOC_VALUE |  | NUMBER | if the location type requires only one value, here it goes |
|  | RANGE_FROM |  | NUMBER | if the location type is a range, then this is the start position |
|  | RANGE_TO |  | NUMBER | and this is the end position |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table | FEATURE_ID | NOT NULL | NUMBER |  |
| FeatureInfo | QUALIFIER | NOT NULL | VARCHAR2(50) | a free set of annotations to a feature |
|  | DETAIL_VALUE |  | VARCHAR2(2000) | the values of the qualifier annotation |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |

-continued

|  | Name | Null? | Type | Comments |
|---|---|---|---|---|
| table FeatureKey | FEATURE_KEY_ID | NOT NULL | NUMBER(3) | feature key validates the feature types allowed |
|  | FEATURE_KEY |  | VARCHAR2(20) |  |
|  | SOURCE |  | VARCHAR2(20) | who defined the key |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table FeatureList | FEATURE_ID | NOT NULL | NUMBER | PK1 |
|  | ITEM_ID | NOT NULL | NUMBER | PK2. This structure is used to build the relationship between 2 features |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table FeatureMap Location | FEATURE_ID | NOT NULL | NUMBER |  |
|  | MAP_ID | NOT NULL | NUMBER(4) |  |
|  | MAP_LOCATION |  | NUMBER | gene or genome map location of the feature |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table FeaurePub | PUB_ID | NOT NULL | NUMBER | publication ID is the PK & FK |
|  | FEATURE_ID | NOT NULL | NUMBER | so is the feature ID. This table builds the many-to-many relationship between the tables of Publication and Feature |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table Gene | GENE_ID | NOT NULL | NUMBER | unique ID for a gene |
|  | GENE_SYMBOL | NOT NULL | VARCHAR2(20) | standardized gene symbols used in the most simplistic manner to refer to a gene |
|  | GENE_FAMILY_ID |  | NUMBER | the family cluster a gene belongs to |
|  | SPECIES_ID | NOT NULL | NUMBER | the species which has this gene |
|  | PATENT_ID |  | NUMBER | the patent associated with this gene |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table GeneAccession | GENE_ID | NOT NULL | NUMBER |  |
|  | ACCESSION | NOT NULL | VARCHAR2(20) | gene and the sequence association through the unique accession |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table GeneAlias | GENE_ID | NOT NULL | NUMBER |  |
|  | ALIAS_NAME | NOT NULL | VARCHAR2(500) | table to handle the various alias names for a gene |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table GeneFamily | GENE_FAMILY_ID | NOT NULL | NUMBER(4) |  |
|  | FAMILY_NAME |  | VARCHAR2(50) |  |
|  | DESCR |  | VARCHAR2(200) |  |

-continued

|  | Name | Null? | Type | Comments |
|---|---|---|---|---|
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table GeneMap Location | GENE_ID | NOT NULL | NUMBER |  |
|  | MAP_ID | NOT NULL | NUMBER(4) |  |
|  | MAP_LOCATION |  | NUMBER | genome map location |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table GenePathway | PATHWAY_ID | NOT NULL | NUMBER(4) | the biological pathway in which the gene plays a role |
|  | GENE_ID | NOT NULL | NUMBER |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table GenePriority | GENE_ID | NOT NULL | NUMBER |  |
|  | TASK_FORCE_NUM |  | NUMBER(6) | internal info for gene project prioritization |
|  | REX_PRIORITY |  | VARCHAR2(5) |  |
|  | NEW_PRIORITY |  | VARCHAR2(5) |  |
|  | REALM_PRIORITY |  | VARCHAR2(5) |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table GenePub | PUB_ID | NOT NULL | NUMBER | publications concerning a gene |
|  | GENE_ID | NOT NULL | NUMBER |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table GenotypeCode | GENOTYPE | NOT NULL | CHAR(1) | genotyping code for the polymorphism |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table Ethnicity | ETHNIC_GROUP |  | VARCHAR2(20) | the major ethnic groups such as Caucasian, Asian, etc. |
|  | ETHNIC_CODE | NOT NULL | VARCHAR2(20) | the Ethnic code that specifies the detailed geographical and ethnic background of the subject (patient, or genetic sample donor) |
|  | ETHNIC_NAME |  | VARCHAR2(100) | the name description of the code |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table HapAssay | HAP_ID | NOT NULL | NUMBER | unique ID for the haplotype |
|  | ASSAY_ID | NOT NULL | NUMBER |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table HapCompound Assay | HAP_ID | NOT NULL | NUMBER | association table where the haplotype of a gene and a compound meet in a specific assay |
|  | COMPOUND_ID | NOT NULL | NUMBER |  |
|  | ASSAY_ID | NOT NULL | NUMBER |  |

-continued

|  | Name | Null? | Type | Comments |
|---|---|---|---|---|
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table HapHistory | HAP_HISTORY_ID | NOT NULL | NUMBER | history table to keep track of the knowledge progress concerning a haplotype |
|  | HAP_ID |  | NUMBER |  |
|  | GENE_ID |  | NUMBER |  |
|  | CREATE_TIMESTAMP |  | DATE | when created |
|  | HAP_NAME |  | VARCHAR2(50) |  |
|  | HISTORY_TIMESTAMP |  | DATE | when put into history |
|  | ORIGINAL_DESCR |  | VARCHAR2(200) |  |
|  | HISTORY_DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table Haplotype | HAP_ID | NOT NULL | NUMBER |  |
|  | GENE_ID |  | NUMBER |  |
|  | TIMESTAMP |  | DATE |  |
|  | HAP_NAME |  | VARCHAR2(50) |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table HapMethod | HAP_ID | NOT NULL | NUMBER |  |
|  | METHOD_ID | NOT NULL | NUMBER | method used in haplotyping |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table HapPatent | HAP_ID | NOT NULL | NUMBER |  |
|  | PATENT_ID | NOT NULL | NUMBER | patent relates to a haplotype |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table HapPub | PUB_ID | NOT NULL | NUMBER | publication relates to a haplotype |
|  | HAP_ID | NOT NULL | NUMBER |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table HapSNP | HAP_ID | NOT NULL | NUMBER |  |
|  | POLY_ID | NOT NULL | NUMBER | haplotype consists of SNPs |
|  | TIMESTAMP |  | DATE |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table HapSNPHistory | HAP_SNP_HISTORY_ID | NOT NULL | NUMBER(4) | history about the progress of the SNPs that are used in a haplotype construction |
|  | HAP_ID | NOT NULL | NUMBER |  |
|  | POLY_ID | NOT NULL | NUMBER |  |
|  | CREATE_TIMESTAMP |  | DATE |  |
|  | HISTORY_TIMESTAMP |  | DATE |  |
|  | ORIGINAL_DESCR |  | VARCHAR2(200) |  |
|  | HISTORY_DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |

-continued

| | Name | Null? | Type | Comments |
|---|---|---|---|---|
| table LocationType | LOC_TYPE | NOT NULL | VARCHAR2(20) | location type for the various genetic objects in the genome |
| | DESCR | | VARCHAR2(200) | |
| | INSERTED_BY | | VARCHAR2(30) | |
| | INSERT_TIME | | DATE | |
| | UPDATED_BY | | VARCHAR2(30) | |
| | UPDATE_TIME | | DATE | |
| table MapType | MAP_TYPE_ID | NOT NULL | NUMBER(4) | validation tool for the possible types of genome maps |
| | MAP_TYPE | | VARCHAR2(20) | |
| | DESCR | | VARCHAR2(200) | |
| | INSERTED_BY | | VARCHAR2(30) | |
| | INSERT_TIME | | DATE | |
| | UPDATED_BY | | VARCHAR2(30) | |
| | UPDATE_TIME | | DATE | |
| table Method | METHOD_ID | NOT NULL | NUMBER | |
| | METHOD | NOT NULL | VARCHAR2(50) | the lab experimental method |
| | PROTOCOL | | VARCHAR2(2000) | the detailed protocol for a method |
| | DESCR | | VARCHAR2(200) | |
| | INSERTED_BY | | VARCHAR2(30) | |
| | INSERT_TIME | | DATE | |
| | UPDATED_BY | | VARCHAR2(30) | |
| | UPDATE_TIME | | DATE | |
| table MoleculeType | MOL_TYPE | NOT NULL | VARCHAR2(20) | molecular type for which a sequence is known |
| | DESCR | | VARCHAR2(200) | |
| | INSERTED_BY | | VARCHAR2(30) | |
| | INSERT_TIME | | DATE | |
| | UPDATED_BY | | VARCHAR2(30) | |
| | UPDATE_TIME | | DATE | |
| table Nomenclature | GENE_SYMBOL | NOT NULL | VARCHAR2(20) | |
| | GENE_NAME | | VARCHAR2(500) | used to standardize the naming of a gene. HUGO official name takes precedence in the naming scheme |
| | SOURCE | | VARCHAR2(20) | |
| | CYTO_LOCATION | | VARCHAR2(50) | cytogenetic location of a gene; this is the best way to map various gene names onto a single gene |
| | GDB_ID | | VARCHAR2(50) | ID by other public data source |
| | DESCR | | VARCHAR2(200) | |
| | INSERTED_BY | | VARCHAR2(30) | |
| | INSERT_TIME | | DATE | |
| | UPDATED_BY | | VARCHAR2(30) | |
| | UPDATE_TIME | | DATE | |
| table Patent | PATENT_ID | NOT NULL | NUMBER | |
| | PATENT_TYPE | | VARCHAR2(20) | patent type can be issued, pending, etc. |
| | COMPANY_ID | | NUMBER | |
| | INVENTORS | | VARCHAR2(200) | |
| | ABSTRACT | | VARCHAR2(1000) | |
| | INSTITUTION | | VARCHAR2(200) | |
| | CLAIMS | | VARCHAR2(4000) | the claims of the patent |
| | TITLE | | VARCHAR2(200) | |
| | DESCR | | VARCHAR2(200) | |
| | INSERTED_BY | | VARCHAR2(30) | |
| | INSERT_TIME | | DATE | |
| | UPDATED_BY | | VARCHAR2(30) | |
| | UPDATE_TIME | | DATE | |
| table PatentImage | PATENT_ID | NOT NULL | NUMBER | |
| | PDFFILE | | BLOB | the multi-media image file of the patent |
| | DESCR | | VARCHAR2(20) | |
| | INSERTED_BY | | VARCHAR2(30) | |
| | INSERT_TIME | | DATE | |
| | UPDATED_BY | | VARCHAR2(30) | |
| | UPDATE_TIME | | DATE | |

-continued

| | Name | Null? | Type | Comments |
|---|---|---|---|---|
| table Pathway | PATHWAY_ID | NOT NULL | NUMBER(4) | biological pathways |
| | PATHWAY_NAME | | VARCHAR2(50) | |
| | DESCR | | VARCHAR2(200) | |
| | INSERTED_BY | | VARCHAR2(30) | |
| | INSERT_TIME | | DATE | |
| | UPDATED_BY | | VARCHAR2(30) | |
| | UPDATE_TIME | | DATE | |
| table PathwayPub | PATHWAY_ID | NOT NULL | NUMBER(4) | publications concerning a pathway |
| | PUB_ID | NOT NULL | NUMBER | |
| | DESCR | | VARCHAR2(200) | |
| | INSERTED_BY | | VARCHAR2(30) | |
| | INSERT_TIME | | DATE | |
| | UPDATED_BY | | VARCHAR2(30) | |
| | UPDATE_TIME | | DATE | |
| table PolyMethod | POLY_ID | NOT NULL | NUMBER | method used in discovering a polymorphism |
| | METHOD_ID | NOT NULL | NUMBER | |
| | DESCR | | VARCHAR2(200) | |
| | INSERTED_BY | | VARCHAR2(30) | |
| | INSERT_TIME | | DATE | |
| | UPDATED_BY | | VARCHAR2(30) | |
| | UPDATE_TIME | | DATE | |
| table Polymorphism | POLY_ID | NOT NULL | NUMBER | PK for a polymorphism |
| | FEATURE_ID | NOT NULL | NUMBER | where the polymorphism occurs in a genetic feature |
| | VARIATION_TYPE | NOT NULL | VARCHAR2(3) | what type of polymorphism |
| | POLY_CONSEQUENCE | | VARCHAR2(200) | the consequence or mechanism of the polymorphism |
| | SYSTEM_NAME | | VARCHAR2(50) | the systematic name for the polymorphism |
| | START_POS | | NUMBER | starting position of the polymorphism in the feature |
| | END_POS | | NUMBER | ending position |
| | LENGTH | | NUMBER | length of the changing structure |
| | PRIMER_ID | | VARCHAR2(50) | FK to a table in another in-house database where the primers used in the polymorphism discovery was kept |
| | SAMPLE_SIZE | | NUMBER | the number of subject being used in the discovery of the polymorphism |
| | QC | | VARCHAR2(20) | quality control information |
| | DESCR | | VARCHAR2(200) | |
| | INSERTED_BY | | VARCHAR2(30) | |
| | INSERT_TIME | | DATE | |
| | UPDATED_BY | | VARCHAR2(30) | |
| | UPDATE_TIME | | DATE | |
| table PolyNameAlias | POLY_ID | NOT NULL | NUMBER | |
| | NAME_ALIAS | | VARCHAR2(50) | other names for the polymorphism |
| | EXTERNAL_KEY | | VARCHAR2(50) | unique ID by other data sources |
| | KEY_SOURCE | | VARCHAR2(20) | |
| | DESCR | | VARCHAR2(200) | |
| | INSERTED_BY | | VARCHAR2(30) | |
| | INSERT_TIME | | DATE | |
| | UPDATED_BY | | VARCHAR2(30) | |
| | UPDATE_TIME | | DATE | |
| table PolySeq3 | POLY_ID | NOT NULL | NUMBER | the 3' DNA sequence that flanks the polymorphic site |
| | SEQ_TEXT | NOT NULL | VARCHAR2(250) | sequence string of this piece of DNA |
| | DESCR | | VARCHAR2(200) | |
| | INSERTED_BY | | VARCHAR2(30) | |
| | INSERT_TIME | | DATE | |
| | UPDATED_BY | | VARCHAR2(30) | |
| | UPDATE_TIME | | DATE | |

-continued

|  | Name | Null? | Type | Comments |
|---|---|---|---|---|
| table PolySeq5 | POLY_ID | NOT NULL | NUMBER | the 5' DNA sequence that flanks the polymorphic site |
|  | SEQ_TEXT | NOT NULL | VARCHAR2(250) |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table PubImage | PUB_ID | NOT NULL | NUMBER |  |
|  | PDFFILE |  | BLOB | image file of the publication |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table Publication | PUB_ID | NOT NULL | NUMBER | PK for a publication |
|  | AUTHORS |  | VARCHAR2(200) |  |
|  | TITLE |  | VARCHAR2(500) |  |
|  | INSTITUTION |  | VARCHAR2(200) |  |
|  | SOURCE |  | VARCHAR2(200) |  |
|  | KEYWORDS |  | VARCHAR2(500) |  |
|  | ABSTRACT |  | VARCHAR2(4000) |  |
|  | EXTERNAL_KEY |  | VARCHAR2(50) |  |
|  | KEY_SOURCE |  | VARCHAR2(20) |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table SeqAccession | SEQ_ID | NOT NULL | NUMBER | PK for sequence |
|  | ACCESSION | NOT NULL | VARCHAR2(20) | unique ID from the public sequence databases |
|  | VERSION |  | NUMBER | version of the sequence |
|  | GI |  | NUMBER | gene ID Issues by NCBI national database |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table SeqFeature Location | LOC_TYPE | NOT NULL | VARCHAR2(20) | sequence and feature location relationship |
|  | SEQ_ID | NOT NULL | NUMBER |  |
|  | FEATURE_ID | NOT NULL | NUMBER |  |
|  | LOC_VALUE |  | NUMBER |  |
|  | RANGE_FROM |  | NUMBER |  |
|  | RANGE_TO |  | NUMBER |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table SeqGene Location | GENE_ID | NOT NULL | NUMBER | sequence and gene location relationship |
|  | LOC_TYPE | NOT NULL | VARCHAR2(20) |  |
|  | SEQ_ID | NOT NULL | NUMBER |  |
|  | LOC_VALUE |  | NUMBER |  |
|  | RANGE_FROM |  | NUMBER |  |
|  | RANGE_TO |  | NUMBER |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table SeqSeq Location | LOC_TYPE | NOT NULL | VARCHAR2(20) | sequence and sequence location relationship |
|  | SEQ_ID | NOT NULL | NUMBER |  |
|  | ITEM_ID | NOT NULL | NUMBER |  |
|  | LOC_VALUE |  | NUMBER |  |
|  | RANGE_FROM |  | NUMBER |  |
|  | RANGE_TO |  | NUMBER |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table SequenceText | SEQ_ID | NOT NULL | NUMBER | the actual sequence text in a string of characters if the sequence is less than 4000 characters, it |
|  | SMALL_SEQ_TEXT |  | VARCHAR2(4000) |  |

-continued

|  | Name | Null? | Type | Comments |
|---|---|---|---|---|
|  | LARGE_SEQ_TEXT |  | LONG | is stored in this field if larger than 4K, stored as a LONG datatype in this field which has much limitation in terms of processing capacities by the DBMS. This division is caused by the fact that a Oracle VARCHAR2 data type can store only 4000 characters. |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table SNPAssay | POLY_ID | NOT NULL | NUMBER | polymorphism in an assay |
|  | ASSAY_ID | NOT NULL | NUMBER |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table SNPPatent | POLY_ID | NOT NULL | NUMBER | polymorphism related patent |
|  | PATENT_ID | NOT NULL | NUMBER |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table SNPPub | PUB_ID | NOT NULL | NUMBER | a polymorphism related publications |
|  | POLY_ID | NOT NULL | NUMBER |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table Species | SPECIES_ID | NOT NULL | NUMBER | a biological species |
|  | SYSTEM_NAME |  | VARCHAR2(50) | its scientific systematic name |
|  | COMMON_NAME |  | VARCHAR2(20) | its common name |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table Patient | CLINICAL_SITE_ID | NOT NULL | NUMBER(4) |  |
|  | PI | NOT NULL | VARCHAR2(50) | patient ID as the unique identifier for a person |
|  | GENDER |  | CHAR(1) |  |
|  | YOB |  | DATE | year of birth |
|  | FAMILY_ID |  | VARCHAR2(20) | family ID if known |
|  | FAMILY_POSITION |  | VARCHAR2(20) | the generation information in a family based genetic study |
|  | EXTERNAL_KEY |  | VARCHAR2(20) | the ID used by other sources |
|  | KEY_SOURCE |  | VARCHAR2(20) |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table PatientCohort | PROJECT_ID | NOT NULL | NUMBER | the patient set used in a particular project |
|  | PI | NOT NULL | VARCHAR2(50) |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table PatientEthnicity | PI | NOT NULL | VARCHAR2(50) | Ethnic background of a person |
|  | ETHNIC_CODE | NOT NULL | VARCHAR2(20) |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |

-continued

|  | Name | Null? | Type | Comments |
| --- | --- | --- | --- | --- |
| table PatientHap | PI | NOT NULL | VARCHAR2(50) | Haplotyping information of a person |
|  | HAP_ID | NOT NULL | NUMBER |  |
|  | QC |  | VARCHAR2(20) |  |
|  | TIMESTAMP |  | DATE |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table PatientHapClinOutcome | SI | NOT NULL | VARCHAR2(50) | the clinical measurement against a particular haplotype in a person |
|  | HAP_ID | NOT NULL | NUMBER |  |
|  | CLIN_TEST_NAME |  | VARCHAR2(50) |  |
|  | CLIN_TEST_RESULT |  | VARCHAR2(20) |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table SubjectHapHistory | S_HAP_HISTORY_ID | NOT NULL | NUMBER | history record of the haplotype information for a subject |
|  | HAP_ID |  | NUMBER |  |
|  | QC |  | VARCHAR2(20) |  |
|  | SI |  | VARCHAR2(50) |  |
|  | CREATE_TIMESTAMP |  | DATE |  |
|  | HISTORY_TIMESTAMP |  | DATE |  |
|  | ORIGINAL_DESCR |  | VARCHAR2(200) |  |
|  | HISTORY_DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table SubjectMedicalHistory | SI | NOT NULL | VARCHAR2(50) | medical conditions of a subject when the genetic sample is collected |
|  | THERAP_ID | NOT NULL | NUMBER | FK pointing to a therapeutic area which maps to a disease |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table SubjectSNP | SI | NOT NULL | VARCHAR2(50) |  |
|  | POLY_ID | NOT NULL | NUMBER |  |
|  | GENOTYPE | NOT NULL | CHAR(1) | the genotyping information of a person at a given polymorphic site |
|  | HAP_ID |  | NUMBER | the polymorphism may be a part of a haplotype |
|  | QC |  | VARCHAR2(20) |  |
|  | TIMESTAMP |  | DATE |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table SubjectSNPHistory | S_SNP_HISTORY_ID | NOT NULL | NUMBER | history record for a polymorphism in a person |
|  | SI |  | VARCHAR2(50) |  |
|  | POLY_ID |  | NUMBER |  |
|  | HAP_ID |  | NUMBER |  |
|  | GENOTYPE |  | CHAR(1) |  |
|  | CREATE_TIMESTAMP |  | DATE |  |
|  | QC |  | VARCHAR2(20) |  |
|  | HISTORY_TIMESTAMP |  | DATE |  |
|  | ORIGINAL_DESCR |  | VARCHAR2(200) |  |
|  | HISTORY_DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |
| table TherapCompound | COMPOUND_ID | NOT NULL | NUMBER | a compound used in the treatment of a disease |
|  | THERAP_ID | NOT NULL | NUMBER |  |
|  | DESCR |  | VARCHAR2(200) |  |
|  | INSERTED_BY |  | VARCHAR2(30) |  |
|  | INSERT_TIME |  | DATE |  |
|  | UPDATED_BY |  | VARCHAR2(30) |  |
|  | UPDATE_TIME |  | DATE |  |

-continued

| | Name | Null? | Type | Comments |
|---|---|---|---|---|
| table Therapeutic Area | THERAP_AREA<br>THERAP_ID<br>RELATED_AREA<br><br>DESCR<br>INSERTED_BY<br>INSERT_TIME<br>UPDATED_BY<br>UPDATE_TIME | NOT NULL | VARCHAR2(50)<br>NUMBER<br>NUMBER(4)<br><br>VARCHAR2(200)<br>VARCHAR2(30)<br>DATE<br>VARCHAR2(30)<br>DATE | the disease name<br><br>its relation to other diseases |
| table Therapeutic Gene | GENE_ID<br>THERAP_ID<br>DESCR<br>INSERTED_BY<br>INSERT_TIME<br>UPDATED_BY<br>UPDATE_TIME | NOT NULL<br>NOT NULL | NUMBER<br>NUMBER<br>VARCHAR2(200)<br>VARCHAR2(30)<br>DATE<br>VARCHAR2(30)<br>DATE | the target gene for a disease |
| table VariationType | VARIATION_TYPE<br><br>DESCR<br>INSERTED_BY<br>INSERT_TIME<br>UPDATED_BY<br>UPDATE_TIME | NOT NULL | VARCHAR2(3)<br><br>VARCHAR2(200)<br>VARCHAR2(30)<br>DATE<br>VARCHAR2(30)<br>DATE | the validated types of polymorphism |

With reference to FIGS. 25A–E, and as is apparent to one of skill in the art, rectangular boxes represent parent tables in the database, while rounded boxes represent children tables that depend on their parent tables. This dependency requires that a parent record be in existence before a child record can be created. Within the tables the primary keys are shown at the top and are partitioned off from the other fields by a line. Repeat instances of primary keys are indicated by "(FK)" meaning foreign key.

FIG. 25F describes the relational symbols used in FIGS. 25A–E. A relational symbol such as indicated by reference numeral 2 represents an identifying parent/child relationship. It depicts the not nullable 1-to-0-or-many relationship. Not nullable means that one cannot create a record in the child unless a corresponding record (indicated by the particular relating field) exists or is created in the parent A relational symbol such as indicated by reference numeral 4 represents a non-identifying parent/child relationship. It represents the nullable 0-or-1-to-many relationship. A relational symbol such as indicated by reference numeral 6 represents an identifying parent/child relationship. It depicts the not nullable 1-to-1-or-many relationship. A relational symbol such as indicated by reference 8 represents a non-identifying parent/child relationship. It represents the not nullable 1-to-1-or-many relationship. A relational symbol such as indicated by reference numeral 10 represents an identifying parent/child relationship. It depicts the not nullable 1-to-exact-1 relationship. A relational symbol such as indicated by reference numeral 12 represents a non-identifying parent/child relationship. It represents the nullable 0-or-1-to-exact-1 relationship. A relational symbol such as indicated by reference numeral 14 represents a non-identifying parent/child relationship. It depicts the not nullable 0-or-1-to-many relationship.

2. Database Model Version 2

A preferred embodiment of the database model of the invention contains 5 sub-models and 83 tables. This model is organized at three levels of detail: sub-model, table and fields of tables.

a. Submodels

The five submodels of this preferred embodiment are depicted in FIGS. 44A–E and are described below.

Genomic Repository (FIG. 44A): This submodel organizes genomic information by spatial relationships. The central element of the genomic repository submodel is the Genetic_Feature object, which is an abstract template for any object having a nucleotide sequence that can be mapped to the nucleotide sequence of other objects by providing a start and stop position. Genetic objects (also referred to herein as genetic features) that are organized by the genomic repository submodel include, but are not limited to, chromosomes, genomic regions, genes, gene regions, gene transcripts and polymorphisms.

Some of these genetic objects contain nucleotide sequences identified in the public domain while others represent some derived final state of a calculation as described below for generating an assembly and gene structure. In object parlance, Genetic_Feature is the base class from which these other objects are extended from. In relational terms, the primary keys for each of these genetic objects are foreign keys to the primary key of the Genetic_Feature table. Each genetic feature is represented by a unique Feature_ID that is generated by the database management system's sequence generator. The principal properties of a genetic feature are start position, stop position and reference. The start and stop positions indicate the extent of that genetic feature relative to another given genetic feature, which is the reference and is represented by another unique Feature_ID generated by the database management system's sequence generator. The reference serves as the parent in this table by the self pointing foreign key of Ref_ID. The Feature_Type attribute gives the database model the possibility to determine what type of spatial relationship is legal among what types of genetic features at a given time in a given context. For example, the system will allow a gene to map on to a sequence assembly by defining the start and end position of the gene in the assembly. A gene region is mapped on to a gene through a similar mechanism. The mapping of the gene region onto the assembly will therefore be made possible through the transverse of links between the Seq_Assembly and Gene tables and between the Gene and Gene_Region tables. Similarly, a polymorphism is mapped on to a sequence that will be a building block for the assembly, which in turn determines the reference sequence for the gene being analyzed for genetic variation.

This centralized organization of the positional relationships of various genetic features through one parent table is believed to be novel and offers significant advantages over known database designs by reducing the cost of maintaining the database and increasing the efficiency of querying the database. In addition, organization of genetic features by this novel relative positional referencing approach allows this information to readily be organized into genomic sequences, gene and gene transcript structures and also into diagrams mapping genetic features to the assembled genomic and gene sequences. The design and use of the genomic repository submodel are described in more detail below.

The most important genetic features are defined below, with the names of the tables containing information specific to each genetic feature indicated in parentheses if different.

Genome: The ultimate root feature for all genetic features. Its reference link is always null, i.e. it is itself not mapped to anything. As long as there is not a complete genomic sequence, there is little reason to actually have a table for this.

Chromosome: The highest unit of contiguous genomic sequence. The reference for chromosomes would be the genome. Because there is no overlap between chromosomes, the genome is a disjoint assembly of all the chromosomes, in a particular order, with gaps between all neighboring chromosomes.

Assembly (Seq_Assembly): An assembly is defined as a set of one or more contigs, ordered in a certain way. In the absence of genome or chromosome features, the assembly will be the root of the genomic sequence mapping tree. Its reference is then null.

Contig: A contiguous assembly of overlapping sequences that are ordered 5'to 3'. A contig is preferably referenced to its assembly.

Unordered Contig: A collection of contiguous sequences that are not ordered and may or may not have gaps between them. An unordered contig, which is represented by an external accession number, is broken down and used in building the sequence assembly as a normal contig.

Sequence (Genetic_Accession): A stretch of nucleotide sequence data. This data is represented by a unique accession number and a version number. Sequence data can include YACs, BACs, Gene sequences and ESTs. Typically, the source of sequence data will be GenBank and other sequence databases, but any piece of sequence is allowed. A sequence is normally referenced to its contig.

Gap: The gap is a zero length feature which indicates that there is an unknown amount of additional sequence to be inserted at this point. It is merely an indication of lack of knowledge and has no physical counterpart. Gaps are usually referenced to the Assembly in which they separate the contigs. They would also be used with the genome as reference to separate the chromosomes.

Gene: This defines the gene locus in terms of base pairs. The start and stop positions of the gene are not usually well defined. A gene starts somewhere between the end of the previous gene and the beginning of the first recognized promoter element. A gene ends somewhere between the end of the last exon and the beginning of the next gene. In practice, including at least four kilobase pairs of promoter region are desirable. A gene is preferably referenced to an assembly.

Gene Region: A particular region of the gene. Gene regions are classified according to their transcriptional or translational roles. For a gene sequence, there are promoters, introns and exons. In a transcribed sequence, different gene regions include 5' and 3' untranslated regions (UTRs) as well as protein-coding regions.

Polymorphism: A part of the genome that is polymorphic across different individuals in a population. The most common polymorphisms are SNPs, the length of which is one base pair. All polymorphisms are preferably referenced to the sequence with respect to which they were found.

Primer: A short region of about 20 base pairs corresponding to an oligonucleotide for priming PCR reactions and/or primer extension reactions in a variety of polymorphism detection assays. Primers are preferably referenced to the sequence they were designed from.

Transcript: The result of a splice operation of the gene sequence. There can be several transcripts per gene, to indicate splice variants. The transcript is mapped to genetic features via the Splice table, but does not map to anything the conventional way, i.e., its reference is always null. The transcript starts another branch of positional mapping of genetic features related to protein sequences.

While the above definitions sets forth the preferred reference for certain kinds of genetic features (such as polymorphisms should be referenced to sequences), it is important to realize that the schema design allows the reference for any particular genetic feature to be flexible and the reference may be changed as circumstances warrant. Whenever the user asks for a start or stop position, he should ask "what is the position of X relative to Y", rather than "what is the position of X", which is an ambiguous question. The correct question can be answered with a simple tree traversal routine. The answer will not depend on which genetic feature serves as the direct reference for X.

All start and stop positions are preferably given in nucleotide positions, even for protein features. This retains the uniformity of the mapping scheme, and the translation to amino acid positions is trivial. The first position in a sequence has the position 1. The stop position is one more than the position of the last base, such that length=abs(stop−start). The stop position can be less than the start position, in which case a reverse complement needs to be taken on the reference sequence to get the feature sequence. However, in another embodiment, a different physical map could be generated that would be expressed in something other than base pair positions, e.g. centimorgans.

Another level of hierarchy could be added to the genomic repository submodel by implementing each gene region type as its own subclass extending the Gene_Region (i.e., creating separate tables for different gene region types with the primary key linked as foreign key to the Gene_Region table). Alternatively, the hierarchy could be flattened by eliminating the Gene_Region object and have individual gene region types directly subclassing Genetic_Feature.

In addition, other genetic features may be added as the database develops. For example, it is contemplated that an additional useful genetic feature is a secondary structure region of a protein, e.g., alpha-helix, beta-sheet, turn and coil regions. For each new genetic feature, a new genetic feature type needs to be created, and a table to contain information specific to the new genetic feature type needs to be added. Some genetic features will not have additional information (Gap, for example), and thus no table is necessary in such cases. The primary key of the genetic feature type specific table always needs to double as a foreign key to the Genetic_Feature table. This design enables the database submodel to be flexible and extendable enough to accommodate the rapid evolution and increase in volume of genomic information.

Assembly of a genomic sequence typically starts with a gene name and comprises performance of the following steps by a human and/or computer operator:

(a) Identify sequences related to this gene by searching GenBank and/or other sequence databases
(b) Generate contigs and alignments from the identified sequences using a commercial sequence alignment program such as Phrap.
(c) Store the assembly, contigs, and sequences as selected by the operator in the database (see Table A).

The results of this process are one assembly made up out of one or more contigs, which in turn are made out of potentially many sequences. This is illustrated in the diagram shown in FIG. 47 and Table A below.

TABLE A

| Feature Id | Feature Name | Feature Type | Reference | Start | Stop |
|---|---|---|---|---|---|
| 1 | Assembly | Assembly | — | — | — |
| 2 | Contig 1 | Contig | 1 | 1 | 400 |
| 3 | Gap 1 | Gap | 1 | 400 | 400 |
| 4 | Contig 2 | Contig | 1 | 400 | 750 |
| 5 | Gap 2 | Gap | 1 | 750 | 750 |
| 6 | Contig 3 | Contig | 1 | 750 | 1000 |
| 7 | A2345 | Sequence | 2 | 1 | 250 |
| 8 | A3724 | Sequence | 2 | 30 | 180 |
| 9 | M28384 | Sequence | 2 | 100 | 350 |
| 10 | EST283729 | Sequence | 2 | 300 | 400 |
| 11 | A2445 | Sequence | 4 | 1 | 250 |
| 12 | M24783 | Sequence | 4 | 200 | 350 |
| 13 | M9485 | Sequence | 6 | 1 | 250 |
| 14 | EST374886 | Sequence | 6 | 80 | 220 |

If there is more than one contig, the assembly will be disjoint, indicating that an unknown amount of sequence is missing in one or more places. Each such place is marked by a gap feature, which is referenced to the assembly feature.

The assembly may be used in conjunction with additional information on the location of gene regions, i.e., promoters, exons and introns and the like, to generate a gene structure. Information on gene regions may be private or found in the public domain. Preferably, information on the gene regions is stored in the database and the gene structure is displayed to the user. An example of how such a display would typically appear is shown in FIG. 48. The corresponding additions to Table A are shown in Table B below.

TABLE B

| Feature Id | Feature Name | Feature Type | Reference | Start | Stop |
|---|---|---|---|---|---|
| 15 | EXAMPLE | Gene | 1 | 120 | 800 |
| 16 | Promoter | Gene Region | 15 | 1 | 180 |
| 17 | Exon 1 | Gene Region | 15 | 180 | 280 |
| 18 | Intron 1 | Gene Region | 15 | 280 | 500 |
| 19 | Exon 2 | Gene Region | 15 | 500 | 680 |

The genomic repository database submodel of the present invention also allows referencing of gene transcripts to other genetic features. The relationship between a transcript and a genomic sequence is not a simple start/stop mapping, but requires the concatenation of separate regions of the genomic sequence into one combined sequence, the gene transcript. In the present submodel, this is represented by a Splice table, which provides an ordered list of splice elements (usually exon regions) for each splice product (usually a transcript). Although the splice product is a feature, it is not mapped to anything else, i.e. it is the root of its own mapping tree. Components of this tree can be 5' and 3' UTRs, a protein, and features related to that protein such as secondary structure or signal sequences. The diagram in FIG. 49 shows the full mapping example down to the protein regions. The Splice table for this example is set forth in Table C below, which incorporates the EXAMPLE information from Table B:

TABLE C

| Splice Id | Order No | Region Id | Product Id |
|---|---|---|---|
| 1 | 1 | 17 | 20 |
| 1 | 2 | 19 | 20 |

Also, Table A would have the following additions:

| Feature Id | Feature Name | Feature Type | Reference | Start | Stop |
|---|---|---|---|---|---|
| 20 | EXAMPLE trans | Transcript | — | — | — |
| 21 | 5' UTR | Region | 20 | 1 | 40 |
| 22 | CETP prot | Protein | 20 | 40 | 240 |
| 23 | 3' UTR | Region | 20 | 240 | 280 |

2. Clinical Repository (FIG. 44B): This submodel encapsulates polymorphism and clinical information about subjects and reference individuals used in clinical trials. The Subject_Hap table associates a given haplotype (identified by the field of Hap_Id) with each patient subject having that haplotype (identified by the field of Sub_ID (Subject ID)). Associations between polymorphisms in a locus (including SNPs and haploytpes) and different clinical phenotypes (such as disease association and drug response) are captured by the Measure_ID and Measure_Result fields in the Subject_Measurement table.

3. Variation Repository (FIG. 44C): This submodel covers the haplotypes and the polymorphisms associated with genes and patient cohorts used in clinical trial studies. Polymorphisms may include SNPs, small insertions/deletions, large insertions/deletions, repeats, frame shifts and alternative splicing. The Haplotype table has the basic fields of Hap_ID, Hap_Locus_ID and Hap_Name that identify a unique haplotype of a given gene or locus. A haplotype is further defined by the set of SNPs that it comprises, which are listed in the Hap_SNP table. This association table uses data fields named Hap_ID (haplotype ID) and Poly_ID (polymorphism ID) to allow the mapping of the many-to-many relationship between haplotype and the polymorphism (s) that constitute the specific haplotype. The haplotype and SNP information may be used in clinical trial and drug assay studies. Data from such studies are stored in the clinical repository and drug repository submodels.

4. Literature Repository (FIG. 44D): This submodel enables annotation of the genetic features in the genomic repository and the variation information in the variation repository with public domain information relating to these objects. Annotation information useful in the invention may be found in peer-reviewed scientific publications, patent documents, or by searching on-line electronic databases. The relationship between the annotated objects and their referencing information are linked through the various association tables.

5. Drug Repository (FIG. 44E): This submodel captures client companies, contact information, compounds used in different disease areas and assay results for such compounds in regards to polymorphisms and haplotypes of target genes. Associations between polymorphisms in a drug target and activity of a candidate drug are captured by the following data fields: Hap_ID (Hap_Locus table); Compound_ID (Compound table), and the Assay_ID (Assay, Assay_Experiment, and Assay_Result tables).

b. Abbreviations

The following abbreviations are used extensively in the data model described herein below, both in the table schema and in the diagram drawings shown in FIGS. 44A–E.

AA: amino acid
Clin: clinical
Descr: description
FK: foreign key
Geo: geographical
HAP: Haplotype
ID: identifier
Info: information
Loc: location
Med: medical
Mol: molecule
NT: nucleotide
PK: primary key
Poly: polymorphism
Pos: position
ub: publication
QC: quality control
Seq: sequence
SNP: single nucleotide polymorphism
Sub: subject
Therap: therapeutic c. Tables This preferred embodiment of a database of the present invention contains 83 tables as follows:

1) Alignment_Component
2) Allele
3) Assay
4) Assay_Experiment
5) Assay_Result
6) Assembly_Component
7) Chromosome
8) Clasper_Clone
9) Class_System
10) Client_Genes
11) Clinical_Site
12) Clinical_Trial
13) Cohort
14) Company
15) Company_Address
16) Compound
17) Contact
18) Contig
19) Discovery_Method
20) Disease_Susceptibility
21) Drug
22) Drug_Target
23) Electronic_Material
24) Family
25) Feature_Info
26) Feature_Literature
27) Gene
28) Gene_Alias
29) Gene_Class
30) Gene_Hap_Locus
31) Gene_Map_Location
32) Gene_Nomenclature
33) Gene_Pathway
34) Gene_Region
35) Gene_Transcript
36) Genetic_Accession
37) Genetic_Feature
38) Genome_Map
39) Genomic_Region
40) Geo_Ethnicity
41) Hap_Allele
42) Hap_Configuration
43) Hap_Locus
44) Hap_Locus_Poly
45) Hap_Locus_Subject
46) Haplotype
47) Ind_Geo_Ethnicity
48) Ind_Medical_History
49) Individual
50) Literature
51) Locus_Accession
52) Med_Thesaurus
53) Patent
54) Patent_Full_Text
55) Pathway
56) Pathway_Literature
57) Poly_Confirmation
58) Poly_Patent
59) Poly_Pub
60) Polymorphism
61) Project
62) Project_Gene
63) Protein
64) Publication
65) Seq_Accession
66) Seq_Assembly
67) Seq_Text
68) Species
69) Splice
70) Subject
71) Subject_Cohort
72) Subject_Hap
73) Subject_Measurement
74) Subject_Poly
75) Therap_Drug
76) Therapeutic_Area
77) Therapeutic_Gene
78) Transcript_Region
79) Trial_Cohort
80) Trial_Drug
81) Trial_Measurement
82) Unordered_Contig
83) URL d. Fields FIGS. 44A–E show the fields of each of the tables in the currently used database. The following are descriptions of the fields in the database:

| Table Name | Field Name | PK | FK | Comments | Relationship Explanation |
|---|---|---|---|---|---|
| Alignment_Component | Descr | No | No | free note text about the record; occurs in all tables | |
| | Weight | No | No | weight for a component to take in alignment decision making | |
| | Alignment_End | No | No | end of the align of component in the contig | |
| | Alignment_Start | No | No | start of the align of component in the contig | |
| | Segment_List | No | No | the actual consensus alignment text with gaps | |
| | Component_ID | No | Yes | component used in the alignment | |
| | Order_Num | Yes | No | order of the component in the alignment | An Alignment_Component is associated with exactly one Contig. |
| | Contig_ID | Yes | Yes | contig constructed by the alignment | An Alignment_Component is associated with exactly one Genetic_Feature. |
| Allele | Descr | No | No | | |
| | AA_Seq_Text | No | No | amino acid sequence for the allele | |
| | Codon_Seq_Text | No | No | codon sequence | |
| | NT_Seq_Text | No | No | nucleotide sequence | |
| | Allele_Name | No | No | descriptive name | |
| | Poly_ID | Yes | Yes | id of the polymorphism | A Hap_Allele is associated with one to many Allele. |
| | Allele_Code | Yes | No | name that reveals the allele the allele, usually the same as NT_Seq_Text | A Subject_Poly is associated with exactly one Allele. An Allele is associated with exactly one Polymorphism. |
| Assay | Descr | No | No | | |
| | Assay_Type | No | No | | |
| | Assay_ID | Yes | No | id for an assay | An Assay_Experiment is associated with exactly one Assay. |
| | Assay_Name | No | No | descriptive name | |
| Assay_Experiment | Descr | No | No | | |
| | Exp_Date | No | No | date of experiment | |
| | Operator | No | No | | |
| | Exp_Parameters | No | No | parameters used in the experiment | |
| | Assay_ID | No | Yes | the assay where the experiment belongs | |
| | Exp_ID | Yes | No | id for an experiment | An Assay_Result is associated with exactly one Assay_Experiment. An Assay_Experiment is associated with exactly one Assay. |
| Assay_Result | Descr | No | No | | |
| | QC | No | No | quality control of the experiment | |
| | Assay_Result | No | No | free test of the assay result | |
| | Hap_ID | Yes | Yes | HAP in study | |
| | Protein_ID | Yes | Yes | protein in study + E70 | An Assay_Result is associated with exactly one Clasper_Clone. |
| | Compound_ID | Yes | Yes | compound in study | An Assay_Result is associated with exactly one Assay_Experiment. |
| | Exp_ID | Yes | Yes | the experiment | An Assay_Result is associated with exactly one Compound. |
| | Clone_ID | Yes | Yes | clone involved | An Assay_Result is associated with exactly one Protein |
| Assembly_Component | Component_ID | No | Yes | component used in the assembly | |
| | Descr | No | No | | |
| | Order_Num | Yes | No | order of the component in the assembly | An Assembly_Component is associated with exactly one Seq_Assembly. |
| | Assembly_ID | Yes | Yes | id for the assembly | An Assembly_Component is associated with zero or one Genetic Feature. |
| Chromosome | Descr | No | No | | |
| | Chromosome_Name | No | No | descriptive name | |
| | Species_ID | No | Yes | the species of the genome | A Gene_Map_Location is |

-continued

| Table Name | Field Name | PK | FK | Comments | Relationship Explanation |
|---|---|---|---|---|---|
| | | | | | associated with exactly one Chromosome. |
| | Chromosome_ID | Yes | Yes | id for a chromosome | A Gene_Nomenclature is associated with zero or one Chromosome. |
| | | | | | A Chromosome is associated with exactly one Genetic_Feature. |
| | | | | | A Chromosome is associated with zero or one Species. |
| Clasper_Clone | Clone_ID | Yes | No | id for a clone | |
| | Hap_ID | Yes | Yes | HAP the clone represents | |
| | Descr | No | No | | |
| | Sub_ID | No | Yes | the individual from which the clone is obtained | An Assay_Result us associated with exactly one Clasper_Clone. |
| | | | | | A Clasper_Clone is associated with zero or one Subjects. |
| | | | | | A Clasper_Clone is associated with exactly one Haplotype. |
| Class_System | Path_Name | No | No | the specific path a class is defined | |
| | Descr | No | N | | |
| | Class_Name | No | No | descriptive name | |
| | Node_Level | N | N | level at which the class is located | |
| | Super_ID | N | N | the parent of the current class | |
| | Class_ID | Yes | N | id for a class | A Gene_Class is associated with exactly one Class_System. |
| | Class_System | No | No | the system used to define the class | |
| Client_Genes | Request_Details | No | No | details of the request | |
| | Security_Code | No | No | security level of the request | |
| | Descr | No | No | | |
| | Request_Order | No | No | the physical order of the request | |
| | Company_ID | Yes | Yes | id for company that makes the request | A Client_Genes is associated with exactly one Gene. |
| | Gene_ID | Yes | Yes | id of the gene | A Client_Genes is associated with exactly one Company. |
| Clinical_Site | Descr | No | No | | |
| | Company_ID | No | Yes | | |
| | Site_Name | No | No | descriptive name | |
| | Clinical_Site_ID | Yes | No | A Clinical_Site R/41 at least one Subject. | A Subject is associated with exactly one Clinical_Site. |
| | | | | | A Clinical_site is associated with exactly one Company. |
| Clinical_Trial | Descr | No | No | | A Clinical_Trial is associated with one to many Trial_Drug. |
| | Therap_ID | No | Yes | id for the therapeutic area | A Clinical_Trial is associated with one to many Trial_Cohort. |
| | Start_Date | No | No | when the trial started | A Clinical_Trial is associated with one to many Trial_Measurement. |
| | Trial_ID | Yes | No | id | A Trial_Drug is associated with exactly one to many Clinical_Trial. |
| | Trial_Code | No | No | code for identification purpose | A Trial_Cohort is associated with exactly one Clinical_Trial. |
| | Trial_Name | No | No | descriptive name | A Trial_Measurement is associated with exactly one Clinical_Trial. |
| | | | | | A Clinical_Trial is associated with one Therapeutic_Area. |
| Cohort | Descr | No | No | | A Cohort is associated with one to many Trial_Cohort. |
| | Cohort_Name | No | No | descriptive name | A Cohort is associated with one to many Subject_Cohort. |
| | Cohort_ID | Yes | No | id | A Trial_Cohort is associated |

-continued

| Table Name | Field Name | PK | FK | Comments | Relationship Explanation |
|---|---|---|---|---|---|
| | Company_ID | No | Yes | company who owns the trial | with exactly one Cohort.<br>A Subject_Cohort is associated with exactly one Cohort.<br>A Cohort is associated with exactly one Company. |
| Company | | | | | A Compound is associated with exactly one Company.<br>A Company_Address is associated with exactly one Company.<br>A Clinical_Site is associated with exactly one Company.<br>A Client_Genes is associated with exactly one Company. |
| | Descr | No | N | | A Cohort is associated with exactly one Company. |
| | Company_Name | No | No | descriptive name | A Patent is associated with one Company. |
| | Company_ID | Yes | No | id | A Drug is associated with exactly one Company.<br>A Company is associated with one to many Compound.<br>A Company is associated with on to many Company_Address.<br>A Company is associated with one to many Clinical_Site.<br>A Company is associated with one to many Client_Gene.<br>A Company is associated with one to many Cohort.<br>A Company is associated with one to many Patent.<br>A Company is associated with one to many Drug. |
| Company_Address | Descr | No | No | | |
| | Web_Site | No | No | | |
| | Zip | No | No | | |
| | Country | No | No | | |
| | Street | No | No | | |
| | City | No | No | | |
| | State | No | No | | |
| | Address_ID | Yes | No | | A Company_Address is associated with one to many Contact.<br>A Contact is associated with zero or one Company_Address.<br>A Company_Address is associated with exactly one Company. |
| | Company_ID | Yes | Yes | | |
| Compound | Compound_Name | No | No | descriptive name | |
| | Structure_Handler | No | No | a handler for accessing the structure info | |
| | Descr | No | No | | |
| | Company_ID | No | Yes | company who owns the compound | A Compound is associated with one to many Assay_Result.<br>A Compound is associated with one to many Drug. |
| | Registration Num | No | No | registration number of the compound | |
| | Compound_ID | Yes | No | id | An Assay_Result is associated with exactly one Compound. |
| | Patent_ID | No | Yes | patent on the compound | A Drug is associated with zero or one Compound.<br>A Compound is associated with zero or one Patent.<br>A Compound is associated with exactly one Company. |

-continued

| Table Name | Field Name | PK | FK | Comments | Relationship Explanation |
|---|---|---|---|---|---|
| Contact | Office_Phone | No | N | | |
| | Email_Address | N | No | | |
| | Cell_Phone | No | No | | |
| | FAX | N | N | | |
| | Web_Site | No | No | | |
| | Descr | No | No | | |
| | Pager_Phone | No | No | | |
| | Department | No | No | | |
| | Contact_ID | Yes | No | | A Contig is associated with zero or one Company_Address. |
| | Company_ID | No | Yes | | |
| | Address_ID | No | Yes | | |
| | Last_Name | No | No | | |
| | Middle_Name | No | No | | |
| | First_Name | No | No | | |
| Contig | Descr | No | No | a contig is a continuous piece of DNA sequence | |
| | Contig_Name | No | No | descriptive name | A Contig is associated with one to many Alignment_Component. |
| | Contig_ID | Yes | Yes | id | A Alignment_Component is associated with exactly one Contig. A Contig is associated with exactly one Genetic_Feature. |
| Discovery_ Method | Descr | No | No | | A Discovery_Method is associated with one to many Hap_Confirmation. |
| | Method_ Protocol | No | No | detailed protocol | A Discovery_Method is associated with one to many Poly_Confirmation. |
| | Method_Name | No | No | descriptive name | A Hap_Confirmation is associated with zero or one Discovery_Method. |
| | Method_ID | Yes | No | id | A Poly_Confirmation is associated with zero or one Discovery_Method. |
| Disease_ Susceptibil-ity | Poly_ID | No | Yes | polymorphism in study | |
| | Ethnic_Code | Yes | Yes | ethnic group code | |
| | Therap_ID | Yes | Yes | therapeutic area in study | A Disease_Susceptibility is associated with zero or one Polymorphism. |
| | Descr | No | No | | A Disease_Susceptibility is association with exactly one Therapeutic_Area. |
| | Hap_ID | No | Yes | HAP in study | A Disease_Susceptibility is associated_with exactly one Geo_Ethnicity. |
| | Susceptibility | No | No | measurement of susceptibility | A Disease_Susceptibility is associated with or one Haplotype. |
| Drug | Compound_ID | No | Yes | being a compound with an ID | |
| | Development_ Stage | No | No | stage | |
| | Side_Effects | No | No | | |
| | Toxicity | N | N | | |
| | Administration_ Route | N | No | | |
| | Descr | N | N | | A Drug is associated with one to many Trial_Drug. |
| | Dosage | No | No | | A Drug is associated with one to many Drug_Target. |
| | Protein_ID | No | Yes | protein ID if drug is a protein | A Drug is associated with one to many Therap_Drug. |
| | Drug | Yes | No | id | A Trial_Drug is associated with exactly one Drug. |
| | Common_Name | No | No | | A Drug_Target is associated with exactly one Drug. |
| | Scientific_ Name | No | No | | A Therap_Drug is associated with exactly one Drug. |
| | Generic_Name | No | No | | A Drug is associated with zero or one Protein. |
| | Drug_Class | No | No | classification of the drug | A Drug is associated with |

-continued

| Table Name | Field Name | PK | FK | Comments | Relationship Explanation |
|---|---|---|---|---|---|
| | Company_ID | No | Yes | company who owns the drug | zero or one Compound.<br>A Drug is associated with exactly one Company. |
| Drug_Target | Descr | No | No | | |
| | Gene_ID | Yes | Yes | the gene that the drug works on | A Drug_Target is associated with exactly one Drug. |
| | Drug_ID | Yes | Yes | drug in study | A Drug_Target is associated with exactly one Gene. |
| Electronic_Material | Receive_Date | No | No | captures the referencing material distributed electronically | |
| | Descr | No | No | | |
| | Title | No | No | | |
| | Contents | No | No | | |
| | Email_Address | No | No | | |
| | Info_Source | No | No | | |
| | Info_ID | Yes | Yes | | An Electronic_Material is associated with exactly one Literature. |
| | Data_Type | No | No | | |
| | Authors | No | No | | |
| Family | Descr | No | No | | |
| | Generation_Up | No | No | number of generation into the ancestry | |
| | Mother | No | Yes | | |
| | Father | No | Yes | | A Family is associated with exactly one Individual. |
| | Family_ID | Yes | No | id | A Family is associated with exactly one Individual. |
| Feature_Info | Descr | No | No | | |
| | Detail_Value | No | No | feature info value | |
| | Feature_Qualifier | Yes | No | feature info category | |
| | Feature_ID | Yes | Yes | | A Feature_Info is associated with exactly one Genetic Feature. |
| Feature_Literature | Descr | No | No | feature to literature association | |
| | Literature_ID | Yes | Yes | | A Feature_Literature is associated associated with exactly one Genetic_Feature. |
| | Feature_ID | Yes | Yes | | A Feature_Literature is associated with exactly one Literature. |
| Gene | | | | | A Gene_MapLocation is associated with exactly one Gene.<br>A Client_Genes is associated with exactly one Gene.<br>A Seq_Gene_Location is associated with exactly one Gene.<br>A Feature_Gene_Location is associated with exactly one Gene.<br>A Therapeutic_Gene is associated with exactly one Gene.<br>A Gene_Pathway is associated with exactly one Gene.<br>A Drug_Target is associated with exactly one Gene. |
| | Gene_Symbol | No | Yes | standard symbol | A Patent is associated with zero or one Gene. |
| | Descr | No | No | | A Project_Gene is associated with exactly one Gene. |
| | Species_ID | No | Yes | species in which the gene is located | A Gene_Hap_Locus is associated with exactly one Gene. |
| | Gene_ID | Yes | Yes | id | A Gene_Transcript is associated with zero or one Gene.<br>A Gene_Region is associated with exactly one Gene.<br>A Gene_Alias is associated |

-continued

| Table Name | Field Name | PK | FK | Comments | Relationship Explanation |
|---|---|---|---|---|---|
| | | | | | with exactly one Gene. A Protein is associated with exactly one Gene. A Gene is associated with one to many Gene_Map_Location. A Gene is associated with one to many Client_Gene. A Gene is associated with one to many Seq_Gene_Location. A Gene is associated with one to many Feature_Gene_Location. A Gene is associated with one to many Therapeutic_Gene. A Gene is associated with one to many Gene_Pathway. A Gene is associated with one to many Drug_Target. A Gene is associated with one to many Gene_Class. A Gene is associated with one to many Patent. A Gene is associated with one to many Project_Gene. A Gene is associated with one to many Gene_Hap_Locus. A Gene is associated with one to many Gene_Transcript. A Gene is associated with one to many Gene_Region. A Gene is associated with one to many Gene_Alias. A Gene is associated with one to at least one Protein. A Gene is associated with exactly one Species. A Gene is associated with exactly one Genetic_Feature. A Gene is associated with exactly one Species. A Gene is associated with exactly one Gene_Nomenclature. |
| Gene_ Alias | Descr | No | No | | |
| | Gene_ID | No | Yes | | |
| | Alias_Name | No | No | descriptive name | |
| | Gene_Alias_ ID | Yes | No | id | A Gene_Alias is associated with exactly one Gene. |
| Gene_ Class | Descr | No | No | | |
| | Class_ID | Yes | Yes | gene classification | A Gene_Class is associated with exactly one Gene. |
| | Gene_ID | Yes | Yes | | A Gene_class is associated with exactly one Class_System. |
| Gene_Hap_ Locus | Descr | No | No | HAP association to the gene | |
| | Hap_Locus_ID | Yes | Yes | | A Gene_Hap_Locus is associated with exactly one Gene. |
| | Gene_ID | Yes | Yes | | A Gene_Hap_Locus is associated with exactly one Hap_Locus. |
| Gene_Map _Location | Map_Location | No | No | location of the gene in the genome | |
| | Descr | No | No | | |
| | Chromosome_ ID | No | Yes | the chromosome | A Gene_Map_Location is associated with exactly one Gene. |
| | Map_ID | Yes | Yes | id of the map | A Gene_Map_Location is |

-continued

| Table Name | Field Name | PK | FK | Comments | Relationship Explanation |
|---|---|---|---|---|---|
| | Gene_ID | Yes | Yes | gene | associated with exactly one Chromosome. A Gene_Map_Location is associated with exactly one Genome_Map. |
| Gene_Nomen-clature | Chromosome_ID | No | Yes | the standard literature for the gene | |
| | Descr | No | No | | A Gene_Nomenclature is associated with zero or one Gene_Nomenclature. |
| | Cyto_Location | No | N | cytological location of gene | A Gene_Nomenclature is associated with zero or one Chromosome. |
| | Gene_Description | No | N | | |
| | Gene_Name | No | N | descriptive name | A Gene_Nomenclature exactly 1 Gene. |
| | Gene_Symbol | Yes | N | standard symbol | |
| | Most_Current | No | No | version management of the record | A Gene is associated with exactly one Gene_Nomenclature. |
| | Locus_ID | No | No | id | |
| Gene_Pathway | Descr | No | No | | |
| | Gene_ID | Yes | Yes | | A Gene_Pathway is associated with exactly one Pathway. |
| | Pathway_ID | Yes | Yes | biological pathway | A Gene_Pathway is associated with exactly one Gene. |
| Gene_Region | Region_Type | No | No | genomic region type | A Gene_Region is associated with one to many Polymorphism. |
| | Region_Name | No | No | descriptive name | A Polymorphism is associated with zero or one Gene_Region. |
| | Descr | No | No | | |
| | Gene_ID | No | Yes | gene it belongs to | A Genomic_Region is associated with exactly one Gene_Region. |
| | Region_ID | Yes | Yes | id | A Transcript_Region is associated with exactly one Gene_Region. A Gene_Region is associated with one to many Genomic_Region. A Gene_Region is associated with one to many Transcript_Region. A Gene_Region is associated with exactly one Gene_Feature. A Gene_Region is associated with exactly one Gene. |
| Gene_Transcript | Descr | No | No | | A Gene_Transcript is associated with one to many Splice. |
| | Transcript_Name | No | No | descriptive name | A Gene_Transcript is associated with one to many Transcript_Region. |
| | Gene_ID | No | Yes | gene it belongs to | A Splice is associated with exactly one Gene_Transcript. |
| | Transcript_ID | Yes | Yes | id | A Transcript_Region is associated with exactly one Gene_Transcript. A Gene_Transcript is associated with exactly one Genetic_Feature. A Gene_Transcript is associated with zero or one Gene. |
| Genetic_Accession | Mol_Type | No | No | molecular type of the record | |
| | URL_ID | N | Yes | the URL address on the web | |

-continued

| Table Name | Field Name | PK | FK | Comments | Relationship Explanation |
|---|---|---|---|---|---|
| | Source_Name | No | No | | |
| | Descr | No | No | | |
| | Accession_Code | N | N | the actual accession code | A Genetic_Accession is associated with zero r one URL. |
| | Seq_Version | No | No | sequence version number | |
| | Accession_ID | Yes | Yes | id | A Genetic_Accession is associated with exactly one Genetic_Feature. |
| | GI | No | No | GI number used in GenBank | |
| Genetic_Feature | | | | the high level abstraction of genetic objects | A Genetic_Accession is associated with exactly one Genetic_Feature. A Protein is associated with exactly one Genetic_Feature. A Chromosome is associated with exactly one Genetic_Feature. A Feature_Literature is associated with exactly one Genetic_Feature. A Polymorphism is associated with exactly one Genetic_Feature. A Gene_Region is associated with exactly one Genetic_Feature. A Gene is associated with exactly one Genetic_Feature. A Seq_Feature_Location is associated with exactly one Genetic_Feature. A Feature_Gene_Location is associated with exactly one Genetic_Feature. A Feature_Info is associated with exactly one Genetic_Feature. A Gene_Transcript is associated with exactly one Genetic_Feature. A Seq_Assembly is associated with exactly one Genetic_Feature. |
| | Feature_ID | Yes | No | id | A Unordered_Contig is associated with zero or one Genetic_Feature. |
| | Most_Current | No | No | version management of the record | A Unordered_Contig is associated with zero or one Genetic_Feature. |
| | Feature_Type | No | No | type of the feature | A Unordered_Contig is associated with exactly one Genetic_Feature. |
| | Ref_ID | No | No | parent of a feature in term of positional map | A Genetic_Feature associated with zero or one Genetic_Feature |
| | Start_Pos | No | No | start position of the feature in its parent | An Assembly_Component is associated with zero or one Genetic_Feature. |
| | End_Pos | No | N | end | An Alignment_Component is associated with exactly one Genetic_Feature. |
| | Complement | No | No | whether on the reverse strand | A Contig is associated with exactly one Genetic_Feature. |
| | Descr | No | No | | A Splice is associated with exactly one Genetic_Feature. A Seq_Text is associated with exactly one Genetic_Feature. A Genetic_Feature is associated with one to many Genetic_Accession. A Genetic_Feature is associated with one to exactly 1 Protein. A Genetic_Feature is |

-continued

| Table Name | Field Name | PK | FK | Comments | Relationship Explanation |
|---|---|---|---|---|---|
| | | | | | associated with one to many Chromosome. |
| | | | | | A Genetic_Feature is associated with one to many Feature_Literature. |
| | | | | | A Genetic_Feature is associated with one to many Polymorphism. |
| | | | | | A Genetic_Feature is associated with one to many Gene_Region. |
| | | | | | A Genetic_Feature is associated with one to many Gene. |
| | | | | | A Genetic_Feature is associated with one to at least one Seq_Feature_Location. |
| | | | | | A Genetic Feature is associated with exactly one to many Feature_Gene_Location. |
| | | | | | A Genetic_Feature is associated with one to many Feature_Info. |
| | | | | | A Genetic_Feature is associated with one to many Gene_Transcript. |
| | | | | | A Genetic_Feature associated with one to many Seq_Assembly. |
| | | | | | A Genetic_Feature is associated with one to many Unordered_Contig. |
| | | | | | A Genetic_Feature is associated with one to many Unordered_Contig. |
| | | | | | A Genetic_Feature is associated with one to many Unordered_Contig. |
| | | | | | A Genetic_Feature is associated with one to many Genetic_Feature. |
| | | | | | A Genetic_Feature is association with one to many Assembly_Component. |
| | | | | | A Genetic_Feature is associated with one to many Alignment_Component. |
| | | | | | A Genetic_Feature is associated with one to many Contig. |
| | | | | | A Genetic_Feature is associated with ne to many Splice. |
| | | | | | A Genetic_Feature is associated with one to many Seq_Text |
| | | | | | A Genetic_Feature is associated with zero or one Genetic_Feature. |
| Genome_Map | External_Key | No | No | legendary key | |
| | Descr | No | No | | A Genome_Map is associated with exactly one Species. |
| | Map_Type | No | No | type of the map | A Genome_Map is associated with one to many Gene_Map_Location. |
| | Map_ID | Yes | No | id | A Genome_Map is associated with zero or one Genome_Map. |
| | Map_Name | No | No | descriptive name | |
| | Most_Current | No | No | version management of the record | A Gene_Map_Location is associated with exactly one Genome_Map. |

-continued

| Table Name | Field Name | PK | FK | Comments | Relationship Explanation |
|---|---|---|---|---|---|
| Genomic_Region | Species_ID | No | Yes | species of the map | |
| | Descr | No | No | gene region in terms of DNA organization | |
| | Region_ID | Yes | Yes | id | A Genomic_Region is associated with exactly one Gene_Region. |
| Geo_Ethnicity | Ethnic_Group | No | No | the major ethnic group name | A Disease_Susceptibility is associated with exactly one Geo_Ethnicity. |
| | Descr | No | No | | A Ind_Geo_Ethnicity is associated with exactly one Geo_Ethnicity. |
| | Ethnic_Name | No | No | descriptive name | A Poly_Confirmation is associated with zero or one Geo_Ethnicity. |
| | Ethnic_code | Yes | No | code for a specific ethnic sub-group | A Hap_Confirmation is associated with zero or one Geo_Ethnicity. A Geo_Ethnicity is associated with one to many Disease_Susceptibility. A Geo_Ethnicity is associated with one to many Ind_Geo_Ethnicity. A Geo_Ethnicity is associated with one to many Poly_Confirmation. A Geo_Ethnicity is associated with one to many Hap_Confirmation. |
| Hap_Allele | Descr | No | No | | |
| | Poly_ID | Yes | Yes | polymorphism that constituting the HAP | |
| | Allele_Code | Yes | Yes | the specific allele of that polymorphism | A Hap_Allele is associated with exactly one Haplotype. |
| | Hap_ID | Yes | Yes | HAP | A Hap_Allele is associated with exactly one Allele. |
| Hap_Confirmation | Sample_Size | No | No | sample size in the HAP study | |
| | External_Key | No | No | legendary key | |
| | QC | No | No | quality info | |
| | Descr | No | No | | |
| | Name_Alias | No | No | other names | |
| | Source_Name | Yes | No | where reported | A Hap_Confirmation is associated with zero or one Geo_Ethnicity. |
| | Hap_Locus_ID | Yes | Yes | id | A Hap_Confirmation is associated with exactly one Hap_Locus. |
| | Ethnic_Code | No | Yes | sub-group or population | A Hap_Confirmation is associated with zero or one Discovery_Method. |
| | Method_ID | No | Yes | method used in discovery | |
| Hap_Locus | | | | the HAP built on a locus region | A Haplotype is associated with exactly one Hap_Locus. A Hap_Locus_Poly is associated with exactly one Hap_Locus. A Gene_Hap_Locus is associated with exactly one Hap_Locus. |
| | Descr | No | No | | A Hap_Locus_Subject is associated with exactly one Hap_Locus. |
| | Hap_Locus Name | No | No | descriptive name | A Hap_Locus is associated with zero or one Hap_Locus. |
| | Most_Current | No | No | version management of the record | A Subject_Hap is associated with exactly one Hap_Locus. |
| | Hap_Locus_ID | Yes | No | id | A Hap_Confirmation is associated with exactly one Hap_Locus. A Hap_Locus is associated with zero or one Hap_Locus. A Hap_Locus is associated with one to many Haplotype. A Hap_Locus is associated |

| Table Name | Field Name | PK | FK | Comments | Relationship Explanation |
|---|---|---|---|---|---|
| | | | | | with one to many Hap_Locus_Poly. A Hap_Locus is associated with one to many Gene_Hap_Locus. A Hap_Locus is associated with one to many Hap_Locus_Subject. A Hap_Locus is associated with one to many Hap_Locus. A Hap_Locus is associated with one to many Subject_Hap. A Hap_Locus is associated with one to many Hap_Confirmation. |
| Hap_Locus_Poly | Descr | No | No | HAP to SNP association | |
| | Poly_ID | Yes | Yes | | A Hap_Locus_Poly is ass ciated with exactly one Hap_Locus. |
| | Hap_Locus_ID | Yes | Yes | | A Hap_Locus_Poly is ass ciated with exactly one Polymorphism. |
| Hap_Locus_Subject | Hap_Locus_ID | Yes | Yes | HAP to subject association | |
| | Descr | No | No | | A Hap_Locus_Subject is associated with exactly one Hap_Locus. |
| | Sub_ID | Yes | Yes | | A Hap_Locus_Subject is associated with exactly one Subject. |
| Haplotype | Descr | No | No | | A Subject_Hap is associated with exactly one Haplotype. |
| | Hap_Name | No | No | descriptive name | A Hap_Allele is associated with exactly one Haplotype. |
| | Hap_Locus_ID | No | Yes | HAP locus to which this HAP belongs | A Disease_Susceptibility is associated with zone or one Haplotype. |
| | Hap_ID | Yes | No | id | A Clasper_Clone is associated with exactly one Haplotype. A Haplotype is associated with one to many Subject_Hap. A Haplotype is associated with one to many Hap_Allele. A Haplotype is associated with one to many Disease_Susceptibility. A Haplotype is associated with one to many Clasper_Clone. A Haplotype is associated with exactly one Hap_Locus. |
| Ind_Geo_Ethnicity | Ethic_Code | Yes | Yes | individual's ethnic background | |
| | Ind_ID | Yes | Yes | | An Ind_Geo_Ethnicity is associated with exactly one Individual. |
| | Genetic_Weight | No | No | the weight of different ethnic heritage | A Ind_Geo_Ethnicity is associated with exactly one Geo_Ethnicity. |
| Ind_Medical_History | Descr | No | No | Medical history for an individual | |
| | Ind_ID | Yes | Yes | | An Ind_Medical_History is associated with exactly one Therapeutic_Area. |
| | Therap_ID | Yes | Yes | | An Ind_Medical_History is associated with exactly one Individual. |
| Individual | Descr | No | No | individual info | |
| | YOB | No | No | year of birth | |
| | Gender | No | No | | |

-continued

| Table Name | Field Name | PK | FK | Comments | Relationship Explanation |
|---|---|---|---|---|---|
| | Mother | No | No | | |
| | Father | No | No | | An Ind_Geo_Ethnicity is associated with exactly one Individual. |
| | Species_ID | No | Yes | possible for cross species study | A Family is associated with exactly one Individual. |
| | Ind_Type | N | No | | A Family is ass ciated wit exactly ne Individual. |
| | Ind_Code | No | No | | An Ind_Medical_History is associated with exactly one Individual. |
| | Ind_ID | Yes | No | id | A Subject is associated with exactly one Individual. An Individual is associated with one to many Ind_Geo_Ethnicity. An Individual is associated with one to zero or one Family. An Individual is associated with zero to many Ind_Medical_History. An Individual is associated with zero to one Subject. An Individual is associated with exactly one Species. |
| Literature | Descr | No | No | | |
| | Image_File | No | No | the large multimedia file for the record | A Patent is associated with exactly one Literature. |
| | Source_Name | No | No | | A Publication is associated with exactly one Literature. |
| | Literature_Type | No | No | | Electronic_material is associated with exactly one Literature. |
| | Literature_ID | Yes | No | id | A Feature_Literature is associated with exactly one Literature. |
| | URL_ID | No | Yes | URL address on the web | A Pathway_Literature is associated with exactly one Literature. A Literature is associated with zero or one URL. A Literature zero to many Patent. A Literature is associated with zero many Publication. A Literature is associated with zero many Electronic_Material. Literature is associated with zero many Feature_Literature. A Literature is associated with zero many Pathway_Literature. |
| Locus_Accession | Accession_Type | No | No | the molecule type for the sequence | |
| | Descr | No | No | | |
| | Locus_ID | Yes | No | NCBI locus id | |
| | Accession | No | No | the actual accession code | |
| Med_Thesaurus | Data_Source | No | No | medical terminology | |
| | External_Key | No | No | | |
| | Descr | No | N | | |
| | Term_ID | Yes | No | | A Med_Thesaurus is associated with zero or one URL. |
| | Definition | No | No | | |
| | URL_ID | No | Yes | | |
| | Medical_Term | N | No | | |
| Patent | Instruction | No | No | patent info | |
| | Year | No | No | | |
| | Title | No | No | | A Patent is associated with zero many Patent_Full_Text. |
| | Abstract | No | No | | A Patent is associated with zero many Compound. |

-continued

| Table Name | Field Name | PK | FK | Comments | Relationship Explanation |
|---|---|---|---|---|---|
| | Granted_By | No | No | | A Patent is associated with zero many Poly_Patent. |
| | Descr | No | No | | A Patent is associated with zero or one Gene. |
| | Patent_Claims | No | No | | A Patent is associated with zero or one Company. |
| | Inventors | No | No | | A Patent is associated with exactly one Literature. |
| | Patent_ID | Yes | Yes | | A Patent_Full_Text is associated with exactly one Patent. |
| | Gene_ID | No | Yes | | A Compound is associated with zero or one Patent. |
| | Patent_Num | No | No | | A Poly_Patent is associated with exactly one Patent. |
| | Company_ID | No | Yes | | |
| | Patent_Type | No | No | could be pending, approved, etc. | |
| Patent_Full_Text | Descr | No | No | | |
| | Full_Text | No | No | the full text document | |
| | Patent_ID | Yes | Yes | | A Patent_Full_Text is associated with exactly one Patent. |
| Pathway | Pathway_Name | No | No | biological pathway info | A Gene_Pathway is associated with exactly one Pathway. |
| | Pathway_ID | Yes | No | | A Pathway_Literature is associated with exactly one Pathway. |
| | Descr | No | No | | A Pathway is associated with one to many Gene_Pathway. A Pathway is associated with one to many Pathway_Literature. |
| Pathway_Literature | Descr | | | pathway literature association | |
| | Pathway_ID | Yes | Yes | | A Pathway_Literature is associated with exactly one Literature. |
| | Literature_ID | Yes | Yes | | A Pathway_Literature is associated with exactly one Pathway. |
| Poly_Confirmation | Method_ID | No | Yes | polymorphism confirmation info | |
| | Source_Name | Yes | No | which data source | |
| | Name_Alias | No | No | alias name | |
| | Poly_ID | Yes | Yes | id | |
| | Descr | No | N | | |
| | QC | No | No | quality control info | |
| | External_Key | No | No | legendary key | A Poly_Confirmation is associated with exactly one Polymorphism. |
| | Sample_Size | No | No | size of sample in discovery | A Poly_Confirmati n is associated with zero or one Discovery_Method. |
| | Ethnic_Code | No | Yes | ethnic group info | A Poly_Confirmation is associated with zero or one Geo_Ethnicity. |
| Poly_Patent | Descr | No | No | polymorphism patent association | |
| | Poly_ID | Yes | Yes | | A Poly_Patent is associated with exactly one Patent. |
| | Patent_ID | Yes | Yes | | A Poly_Patent is associated with exactly one Polymorphism. |
| Poly_Pub | Descr | No | No | polymorphism publication association | |
| | Pub_ID | Yes | Yes | | A Poly_Poly is associated with exactly one Publication. |
| | Poly_ID | Yes | Yes | | A Poly_Pub is associated with exactly one Polymorphism. |
| Poly-morphism | Mol_Consequence | No | No | molecular mechanism of the polymorphism | A Subject_Pub is associated with exactly one Polymorphism. |
| | Primer_Pair_ID | No | No | primer used in the discovery | A Poly_Pub is associated with exactly one Polymorphism. |
| | 3Flank_Seq_Text | No | No | flanking sequence on 3' end | A Polymorphism is associated with one to many Subject_Poly. |
| | 5Flank_Seq_ | No | No | flanking sequence on 5' end | A Polymorphism is |

-continued

| Table Name | Field Name | PK | FK | Comments | Relationship Explanation |
|---|---|---|---|---|---|
| | Text | | | | associated with one to many Poly_Pub. |
| | Descr | No | No | | A Polymorphism is associated with one to many Genetic_Feature. |
| | Region_ID | No | Yes | the region where the polymorphism locates | A Disease_Susceptibility is associated with zero or one Polymorphism. |
| | Poly_Length | No | No | length of the variation | A Poly_Patent is associated with exactly one Polymorphism. |
| | Poly_ID | Yes | Yes | id | A Hap_Locus_Poly is associated with exactly one Polymorphism. |
| | Variation_Type | No | No | type of variation | A Allele is associated with exactly one Polymorphism. |
| | System_Name | No | No | systematic name of the polymorphism | A Poly_Confirmation is associated with exactly one Polymorphism. A Polymorphism is associated with zero to many Disease_Susceptibility. A Polymorphism is associated with zero to many Poly_Patent. A Polymorphism R/361 many Hap_Locus_Poly. A Polymorphism is associated with at least one Allele. A Polymorphism is associated with at least one Poly_Confirmation. A Polymorphism is associated with zero or one Gene_Region. |
| Project | Descr | No | No | project info | |
| | Submitter | No | No | | |
| | Project_Manager | No | No | | |
| | Project_Name | No | No | | A Project is associated with on to many Project_Gene. |
| | Project_ID | No | No | | A Project_Gene is associated with exactly one Project. |
| Project_Gene | Descr | No | No | project gene association | |
| | Gene_ID | Yes | Yes | | A Project_Gene is associated with exactly one Project. |
| | Project_ID | Yes | Yes | | A Project_Gene is associated with exactly one Gene. |
| Protein | Descr | No | No | | A Protein is associated with zero to many Drug. |
| | Structure_Handler | No | No | protein structure info handler | A Protein is associated with zero to many Assay_Result. |
| | Gene_ID | No | Yes | gene it belongs to | A Drug is associated with zero or one Protein. |
| | Protein_ID | Yes | Yes | id | An Assay_Result is associated with exactly one Protein. A Protein is associated with exactly one Gene. A Protein is associated with exactly one Genetic_Feature. |
| Publication | Keywords | No | No | | |
| | Abstract | No | No | | |
| | Descr | No | No | | |
| | Title | No | No | | |
| | Institution | No | No | | A Publication is associated with zero to many Poly_Pub. |
| | Year | No | No | | A Publication is associated with exactly one Literature. |
| | Pub_ID | Yes | Yes | | A Poly_Pub is associated with exactly one Publication. |
| | Authors | No | No | | |
| | Journal | No | No | | |
| Seq_ | Assembly_ | No | No | the consensus sequence built from alignment | A Seq_Assembly is |

-continued

| Table Name | Field Name | PK | FK | Comments | Relationship Explanation |
|---|---|---|---|---|---|
| Assembly | Name | | | | associated with one to many Assembly_Component. |
| | Descr | No | No | | A Seq_Assembly is associated with exactly one Genetic_Feature. |
| | Assembly_ID | Yes | Yes | id | An Assembly_Component is associated with exactly one Seq_Assembly. |
| Seq_Text | Descr | No | No | | |
| | Seq_Text | No | No | the actual sequence text | |
| | Seq_ID | Yes | Yes | id | A Seq_Text is associated with exactly one Genetic_Feature. |
| Species | Alias_Name | No | N | ther names | |
| | Species_ID | Yes | No | id | A Gene is associated with exactly on Species. |
| | Descr | No | No | | A Genome_Map is associated with exactly one Species. |
| | System_Name | No | No | systematic name of the species | A Gene is associated with exactly one Species. |
| | Common_Name | No | No | common name | A Chromosome is associated with zero or one Species. |
| | | | | | A Individual is associated with exactly one Species. |
| | | | | | A Species is associated with one to many Gene. |
| | | | | | A Species is associated with zero to many Genome_Map. |
| | | | | | A Species is associated with one to many Gene. |
| | | | | | A Species is associated with one to many Chromosome. |
| | | | | | A Species is associated with one to many Individual. |
| Splice | Component_ID | No | Yes | component involved in the splicing | |
| | Descr | No | No | | |
| | Order_Num | Yes | No | order of the component in the splicing product | A Splice is associated with exactly one Gene_Transcript. |
| | Transcript_ID | Yes | Yes | id for the transcript | A Splice is associated with exactly one Genetic_Feature. |
| | | | | | A Clasper_Clone is associated with zero or one Subject. |
| Subject | | | | this is a subset of individual | A Subject_Poly is associated with exactly one Subject. |
| | Descr | No | No | | A Subject_Hap is associated with exactly one Subject. |
| | External_Key | No | No | | A Subject_Cohort is associated with exactly one Subject. |
| | Clinical_Site_ID | No | Yes | collection site | A Subject_Measurement is associated with exactly one Subject. |
| | Sub_ID | Yes | Yes | id | A Hap_Locus_Subject is associated with exactly one Subject. |
| | | | | | A Subject is associated with zero to many Clasper_Clone. |
| | | | | | A Subject is associated with zero to many Subject_Poly. |
| | | | | | A Subject is associated with zero to many Subject_Hap. |
| | | | | | A Subject is associated with zero to many Subject_Cohort. |
| | | | | | A Subject is associated with zero to many Subject_Measurement. |
| | | | | | A Subject is associated with zero to many Hap_Locus_Subject. |
| | | | | | A Subject is associated with exactly one Clinical_Site. |
| | | | | | A Subject is associated with |

-continued

| Table Name | Field Name | PK | FK | Comments | Relationship Explanation |
|---|---|---|---|---|---|
| | | | | | exactly one Individual. |
| Subject_Cohort | Cohort_ID | Yes | Yes | cohort subject association | |
| | Descr | No | No | | A Subject_Cohort is associated with exactly one Subject. |
| | Sub_ID | Yes | Yes | | A Subject_Cohort is associated with exactly one Cohort. |
| Subject_Hap | Hap_Locus_ID | Yes | Yes | subject HAP typing info | |
| | Copy_Num | Yes | No | identify the copy of the HAP | |
| | QC | No | No | quality control data | A Subject_Hap is associated with exactly one Haplotype. |
| | Descr | No | No | | A Subject_Hap is associated with exactly one Subject. |
| | Hap_ID | No | Yes | id of HAP | A Subject_Hap is associated with exactly one Hap_Locus. |
| | Sub_ID | Yes | Yes | id of subject | |
| Subject_Measurement | Measure_Num | Yes | No | subject clinical measurement | |
| | Measure_Result | No | No | result of the measurement | |
| | Measure_ID | Yes | Yes | id | |
| | Descr | No | No | | |
| | Operator | No | No | who did it | |
| | QC | No | No | quality control data | A Subject_Measurement is associated with exactly one Subject. |
| | Measure_Date | No | No | when it's done | A Subject_Measurement is associated with exactly one Trial_Measurement. |
| | Sub_ID | Yes | Yes | subject being measured | |
| Subject_Poly | Poly_ID | Yes | Yes | subject genotyping info | |
| | Copy_Num | Yes | No | identify the copy of the SNP | |
| | Descr | No | No | | A Subject_Poly is associated with exactly one Subject. |
| | Allele_Code | No | Yes | the allele for the subject | A Subject_Poly is associated with exactly one Allele. |
| | QC | No | No | quality control data | A Subject_Poly is associated with exactly one Polymorphism. |
| | Descr | No | No | | |
| Therap_Drug | Drug_ID | Yes | Yes | drug info for the therapeutical area | A Therap_Drug is associated with exactly one Therapeutic_Area. |
| | Therap_ID | Yes | Yes | | A Therap_Drug is associated with exactly one Drug. A Therap_Drug is associated with exactly one Therapeutic_Area. |
| Therapeutic_Area | Descr | No | No | the look up table for the therapeutic areas | A Therapeutic_Gene is associated with exactly one Therapeutic_Area. |
| | Related_Area | No | N | | A Ind_Medical_History is associated with exactly one Therapeutic_Area. |
| | Therap_Area | No | No | | A Disease_Susceptibility is associated with exactly one Therapeutic_Area. |
| | Therap_ID | Yes | No | | A Clinical_Trial is associated with zero or one Therapeutic_Area. A Therapeutic_Area is associated with zero to many Therap_Drug. A Therapeutic_Area is associated with zero to many Therapeutic_Gene. A Therapeutic_Area is associated with zero to many Ind_Medical_History. A Therapeutic_Area is associated with zero to many |

-continued

| Table Name | Field Name | PK | FK | Comments | Relationship Explanation |
|---|---|---|---|---|---|
| | | | | | Disease_Susceptibility. A Therapeutic_Area is associated with zero to many Clinical_Trial. |
| Therapeutic_Gene | Descr | No | No | gene links to the therapeutic areas | |
| | Therap_ID | Yes | Yes | | A Therapeutic_Gene is associated with exactly one Therapeutic_Area. |
| | Gene_ID | Yes | Yes | | A Therapeutic_Gene is associated with exactly one Gene. |
| Transcript_Region | Descr | No | No | | |
| | Transcript_ID | No | Yes | link between gene region and the transcript | A Transcript_Region is associated with exactly one Gene_Region. |
| | Region_ID | Yes | Yes | | A Transcript_Region is associated with exactly one Gene_Transcript. |
| Trial_Cohort | Descr | No | No | | |
| | Cohort_ID | Yes | Yes | cohort involved in the clinical trial | A Trial_Cohort is associated with exactly one Clinical_Trial. |
| | Trial_ID | Yes | Yes | | A Trial_Cohort is associated with exactly one Cohort. |
| Trial_Drug | Descr | No | No | | |
| | Trial_ID | Yes | Yes | drug used in the clinical trial | A Trial_Drug is associated with exactly one Drug. |
| | Drug_ID | Yes | Yes | | A Trial_Drug is associated with exactly one Clinical_Trial. |
| Trial_Measurement | Measure_Name | No | No | Recording of the clinical measurement | |
| | Measure_Details Descr | No N | No No | measurement result | |
| | Measure_Type | N | N | type | |
| | Measure_Abbrev | No | No | abbreviation from of the measurement name | A Trial_Measurement is associated with one to many Subject_Measurement. |
| | Measure_ID | Yes | No | id | A Subject_Measurement is associated with exactly one Trial_Measurement. |
| | Trial_ID | No | Yes | trial in which the measurement is taken | A Trial_Measurement is associated with exactly one Clinical_Trial. |
| Unordered_Contig | Descr | No | No | a table to handle the unordered sequence pieces | |
| | Uncontig_Seq_ID | No | Yes | the actual sequence corresponding | A Unordered_Contig is associated with exactly one Genetic_Feature. |
| | Uncontig_List_ID | No | Yes | the accession in which it's reported | A Unordered_Contig is associated with zero or one Genetic_Feature. |
| | Uncontig_ID | Yes | Yes | id | A Unordered_Contig is associated with zero or one Genetic_Feature. |
| URL | URL | No | No | the URL address | A Genetic_Accession is associated with zero or one URL. |
| | Most_Current | No | No | version management for the record | A Med_Thesaurus is associated with zero or one URL. |
| | URL_ID | Yes | No | id | A URL is associated with zero or one URL. |
| | Descr | No | No | | A Literature is associated with zero or one URL. A URL is associated with zero or one URL. A URL is associated with zero to many Genetic_Accession. A URL is associated with |

-continued

| Table Name | Field Name | PK | FK | Comments | Relationship Explanation |
|---|---|---|---|---|---|
| | | | | | zero to many Genetic_Accession. A URL is associated with zero to many Med_Thesaurus. A URL is associated with zero to one URL. A URL is associated with zero or one Literature. |

G. Business Models

1. Hap2000 Partnership

The haplotype and other data developed using the methods and/or tools described herein may be used in a partnership of two or more companies (referred to herein as the Partnership) to integrate knowledge of human population and evolutionary variation into the discovery, development and delivery of pharmaceuticals. The partners in the partnership may be classified as pharmaceutical, biopharmaceutical, biotechnology, genomics, and/or combinatorial chemistry companies. One of the partners, referred to herein as the HAP™ Company, will provide the other partner(s) with the tools needed to address drug response problems that are attributable to human diversity.

The HAP™ Company will focus on identifying polymorphisms in genes and/or other loci found in a diverse set of individuals, information on which will be stored in a database (referred to herein as the Isogenomics™ Database). Preferably, the database is designed to store polymorphism information for at least 2000 genes and/or other loci that are important to the pharmaceutical process. In a preferred embodiment the polymorphisms identified are gene specific haplotypes and the genes chosen for analysis will be prioritized by the HAP™ Company by pharmaceutical relevance. Analyzed genes may include, while not being limited to, known drug targets, G-coupled protein receptors, converting enzymes, signal transduction proteins and metabolic enzymes. The database will be accessible through an informatics computer program for epidemiological correlation and evaluation, a preferred embodiment of which is the DecoGen™ application described above.

a. Partnership Benefits i. Isogenomics™ Database

The partners will have non-exclusive access to the Isogenomics™ Database, which contains the frequencies, sequences and distribution of the polymorphisms, e.g., gene haplotypes, found in a diverse set of individuals, referred to herein as the index repository, which preferably represents all the ethnogeographic groups in the world. Haplotypes in the database preferably include polymorphisms found in the promoter, exons, exon/intron boundaries and the 5' and 3' untranslated regions. Preferably, the number of individuals examined in the index repository allows the detection of any haplotype whose frequency is 10% or higher with a 99% certainty.

ii. Informatics Computer Program

The information within the Isogenomics™ Database is part of the HAP™ Company's informatics computer program which is accessible through an intuitive and logical user interface. The informatics program contains algorithms for the reconstruction of relationships among gene haplotypes and is capable of abstracting biological and evolutionary information from the Isogenomics™ Database. The informatics program is designed to analyze whether genes in the Isogenomics™ Database are relevant to a clinical phenotype, e.g., whether they correlate with an effective, inadequate or toxic drug response. In a preferred embodiment, the program also contains algorithms designed for detecting clinical outcomes that are dependent upon cooperative interactions among gene products. In this embodiment, the computer system has the capability to simulate gene interactions that are likely to cause polygenic diseases and phenotypes such as drug response. The informatics computer program will be installed at a site selected by each partner(s). The information in the Isogenomics™ database will be of immediate use to drug discovery teams for target validation and lead prioritization and optimization, to drug development specialists for design and interpretation of clinical trials, and to marketing groups to address problems encountered by an approved drug in the marketplace.

iii. Cohort Haplotyping

In one preferred embodiment, partner(s) can use the genotyping and/or haplotyping capabilities of the HAP™ Company to stratify their clinical cohorts, which will enable the partner(s) to separate cohorts by drug response. For a fixed fee per patient, the HAP™ Company will genotype and/or haplotype Phase II, Phase III, and Phase IV patient cohorts under good laboratory conditions (GLP) conditions that will allow submittal of the data to clinical regulatory authorities. Preferably, the clinical genotype and/or haplotype data is deposited within a component of the informatics computer program that is proprietary to the partner to allow the partner to correlate polymorphisms such as gene haplotypes with drug response.

iv. Isogene Clones

Partner(s) will have access to the physical clones that correspond to each of the haplotypes for a given gene or other locus. These isogene clones can be used in primary or secondary screening assays and will provide useful information on such pharmacological properties as drug binding, promoter strength, and functionality.

v. Gene Selection by Partners

The partners can select genes (or other loci) of their choosing for haplotyping in the index repository. The genes selected can be in the public domain or proprietary to the partner(s). In a preferred embodiment, haplotyping results for a proprietary gene will only be accessible by the owner of that gene until sequence information for the gene enters the public domain.

vi. Patent Dossier

In a preferred embodiment, the Isogenomics™ Database also contains public patent information that is available for each gene in the database. This feature provides the partner(s) with an understanding of the potential proprietary status of any-gene in the database.

vii. Committed Liaison

In a preferred embodiment, the HAP™ Company will assign a Ph.D. level scientist as a liaison to a partner to facilitate communication, technology transfer, and informatics support viii. Special Services: cDNAs and Genomic Intervals In a preferred embodiment, the HAP™ Company will also provide, at an extra charge, special molecular, biological and genomics services to partner(s) who submit cDNAs or ESTs to be haplotyped. cDNAs or ESTs will be utilized to retrieve genomic loci and to create special haplotyping assays that will allow the gene locus at the chromosome level to be haplotyped in the index repository. Genomic intervals containing possible genes of high significance for phenotypic correlations stemming from positional cloning programs can also be submitted by partner(s) for haplotyping.

b. Membership in the Partnership

Each partner(s) will pay the HAP™ Company a fee for membership in the Partnership, preferably for a period of at least two or three years. Companies joining the Partnership may utilize the resources of the informatics computer program and Isogenomics™ Database on a company wide basis, including groups in drug discovery, medicinal chemistry, clinical development, regulatory affairs, and marketing.

c. Envisioned Outcomes from the Partnership

It is contemplated that novel isogenes will be isolated and characterized by the HAP™ Company, as well as methods for the detection of novel SNP's or haplotypes encompassed by the isogenes.

It is also contemplated that associations between clinical outcome and haplotypes (hereinafter "haplotype association") for many of the genes in the Isogenomics™ Database will be discovered. Therefore, it is also contemplated that methods of using the haplotypes and/or isogenes for diagnostic or clinical purposes relating to disease indications supported by the particular association will be discovered.

It is further contemplated there will be successful applications of the data and informatics tools for drug approval and marketing.

A number of different scenarios for using the database and/or analytical tools of the present invention may be envisioned. These include the following:

1. A Partner selects a candidate gene or genes from the HAP™ Company's database that is haplotyped. The Partner provides clinical cohorts for haplotype analysis and provides clinical response data for the cohorts. The HAP™ Company performs haplotype analysis for the candidate gene(s) in the clinical cohorts, finds new haplotypes, if any, and determines the association between one or more haplotypes and clinical response using the informatics computer program.

2. The Partner selects a candidate gene from the HAP™ Company's database that is haplotyped. The Partner provides clinical cohorts for haplotype analysis. The HAP™ Company does haplotype analysis, finds new haplotypes, if any, and sends the haplotype data to the Partner. The Partner determines the association between haplotype and clinical response using the informatics computer program provided by the HAP™ company.

3. Like 1 above, but the Partner performs the haplotype analysis and determines the association between haplotype and clinical response.

4. Like 2 above, but the Partner performs the haplotype analysis.

5. A Partner provides one or more genes to the HAP™ Company for haplotype analysis. The HAP™ Company clones and characterizes isogenes for the gene(s), discovers new polymorphisms in the gene, if any, and determines the haplotypes for the gene(s).

6. Based on polymorphisms observed in a gene or genes, a Partner sends the HAP™ Company clinical cohorts to haplotype and the Partner uses the haplotype data in conjunction with their own clinical response data to determine the association between haplotype and clinical response.

7. A Partner sends the HAP™ Company a cDNA or an expressed sequence tag (EST). The HAP™ Company isolates and characterizes the gene corresponding to the cDNA or EST. The HAP™ Company clones isogenes of the gene and determines the haplotypes embodied within the isogenes.

A more detailed description of how the database and/or analytical tools of the present invention may be used in the context of clinical trials is set forth below.

As a review, the standard routine procedure in premarketing development of a new drug to be used in humans is to conduct pre-clinical animal toxicology studies in two or more species of animals followed by three phases of clinical investigation as follows: Phase I—clinical pharmacology investigations with attention to pharmacokinetics, metabolism, and both single dose and dose-range safety; Phase II—limited size closely monitored investigations designed to assess efficacy and relative safety; Phase III—full scale clinical investigations designed to provide an assessment of safety, efficacy, optimum dose and more precise definition of drug-related adverse effects in a given disease or condition. In other words, Phase I and Phase II are the early stages of the drug's development, when the safety and the dosing level are tested in a small number of patients. Once the safety and some evidence that the drug is effective in treatment have been established, the drug's developer then proceeds to Phase III. In Phase III, many more patients, usually several hundred, are given the new drug to see whether the early findings that demonstrated safety and effectiveness, will be borne out in a larger number of patients. Phase III is pivotal to learning hard statistical facts about a new drug. Larger numbers of patients reveal the percentage of patients in which the drug is effective, as well as give doctors a clearer understanding about the side effects which may occur.

In the research or discovery phase, a Partner's discovery personnel may desire haplotype information for isogenes of a gene, and/or one or more clones containing isogenes of the gene, regardless of whether or not clinical trials (or field trials, in the case of plants) are planned, in progress, or completed. For example, the Partner may be studying a gene (or its encoded protein) and by be interested in obtaining information concerning, e.g., protein structure or mRNA structure, in particular information concerning the location of polymorphisms in the mRNA structure and their possible effect on mRNA transcription, translation or processing, as well as their possible effect on the structure and function of the encoded protein. Such information may be useful in designing and/or interpreting the results of laboratory test results, such as in vitro or animal test results. Such information may be useful in correlating polymorphisms with a particular result or phenotype which may indicate that the gene is likely to be responsible for certain diseases, drug response or other trait. Such information could aid in drug design for pharmaceutical use in humans and animals, or aid in selecting or augmenting plants or animals for desired traits such as increased disease or pest resistance, or increased fertility, for agricultural or veterinary use. The Partner may also be interested in knowing the frequency of the haplotypes. Such information may be used by the Partner to determine which haplotypes are present in the population below a certain frequency, e.g., less than 5%, and the Partner may use this information to exclude studying the isogenes, mRNAs and encoded proteins for these haplotypes and may also use this information to weed out individuals containing these haplotypes from their proposed clinical trials.

When information such as that described above is desired by a Partner, then the HAP™ Company may give access to the Partner to all or part of the data and/or analytical tools exemplified herein by the DecoGen™ Informatics Platform. The Partner may also be given access to one or more clones containing isogenes, e.g., a genome anthology clone (see, e.g., U.S. Patent Application Ser. No. 60/032,645, filed Dec. 10, 1996 and U.S. patent application Ser. No. 08/987,966, filed Dec. 10, 1997).

During a Phase I clinical trial, which is being conducted to determine the safety of a drug (or drugs) in people, a Partner may desire haplotype information for haplotypes of a gene, and/or one or more clones containing isogenes of the gene, in particular when toxicity or adverse reactions to the drug are observed in at least some of the people taking the drug. In that case, the Partner may request that the HAP™ Company obtain, for each person experiencing toxicity or other adverse effect, the haplotypes for one or more genes which are suspected to be associated with the observed toxicity or adverse effect (e.g., a gene or genes associated with liver failure) and determine whether there is a correlation between haplotype and the observed toxicity or adverse effect. If there is a correlation, then the Partner may decide to keep all people having the haplotype correlated with toxicity or other adverse effect out of Phase II clinical trials, or to allow such people to enter Phase II clinical trials, but be monitored more closely and/or given conjunctive therapy to modify the toxicity or other adverse effect. The HAP™ Company may provide a diagnostic test, or have such a test prepared, which will detect the people which have, or lack, the haplotype correlated with toxicity or other adverse effect.

During a Phase II clinical trial, which is being conducted to determine the efficacy of a drug (or drugs) in people, a Partner may desire haplotype information for haplotypes of a gene, and/or one or more clones containing isogenes of the gene, in particular when the results of the trial are ambiguous. For example, the results of a Phase II clinical trial might indicate that 50% of the people given a drug were responders (e.g., they lost weight in a trial for an anti-obesity drug, albeit to different degrees), 49.9% of people were non-responders (e.g., they did not lose any weight) and 0.1% had adverse effects. In such a case, the Partner may, for example, request that the HAP™ Company obtain, for each of person in the Phase II clinical trial, the haplotypes for one or more genes which are suspected to be associated with the drug response. (In general, such gene(s) will be different from the gene associated with the adverse effect, but not necessarily.) A correlation may then be obtained between various haplotypes and the observed level of response to the drug. If a correlation is found, this information may be used to determine those individuals in which the drug will or will not be effective and, therefore, identify who should or should not get the drug. In addition, the information may also be used to develop a model (or test) which will predict, as a function of haplotype, how much of the drug should be used in an individual patient to get the desired result. Again, the HAP™ Company may provide a diagnostic test, or have such a test prepared, which will detect the people which have, or lack, the haplotype correlated with the efficacy or non-efficacy of the drug.

During Phase III clinical trials, which are being conducted to verify the safety and efficacy of a drug (or drugs) in people, a Partner may desire haplotype information for isogenes of a gene, and/or one or more clones containing isogenes of the gene, in particular to use at the beginning of the trial to design cohorts of patients (i.e., a group of individuals which will be treated the same). For example, the drug or placebo can be given to a group of people who have the same haplotype which is expected to be correlated with a good drug response, and the drug or placebo can be given to a group of people who have the same haplotype which is expected to be correlated with no drug response. The results of the trial will confirm whether or not the expected correlation between haplotype and drug response is correct.

During "Phase IV," which involves monitoring of clinical results after FDA approval of a drug to obtain additional data concerning the safety and efficacy of a drug (or drugs) in people, a Partner may desire haplotype information for a gene, and/or one or more clones containing isogenes of the gene, in particular if additional adverse events (or hidden side effects) become apparent. In such a case, the methods described above can be used to identify people who are likely to experience such adverse events.

After clinical trials are successfully completed, a Partner may desire haplotype information for isogenes of a gene, and/or one or more isogene clones, in particular in the situation where the drug is what is known as a "me too" drug, i.e., there are already a number of drugs on the market used to treat the disease or other condition which the Partner's drug is designed to treat. This can be used, e.g., as a marketing or business development tool for the Partner and/or help health care providers, such as doctors and HMOs, to keep drug costs down. For example, the haplotype information and analytical tools of the invention may be used to identify the patients for which the Partner's drug will work and/or for whom the Partner's drug will be superior to (or cheaper than) the other drugs on the market. A test can be developed to identify the target patients. This test can be diagnostic for the condition (e.g., it could distinguish asthma from a respiratory infection) or it could be diagnostic for response to the drug. Preferably the doctor can perform the test in his office or other clinical setting and be able to prescribe the appropriate drug immediately, or after access to part or all of the database or analytical tools of the invention. This will also aid the doctor in that it may provide information about which drugs not to give, since they will not be effective in the patient. Again, this reduces costs for the patient and/or health care provider, and will likely accelerate the time in which the patient will receive effective treatment, since time may be saved by eliminating trial and error administrations of other drugs which would not be expected to work for the disease or condition manifested by the patient.

If clinical trials are unsuccessfully completed, a Partner may desire haplotype information for isogenes, and/or one or more isogene clones containing isogenes of the gene, to correlate drug response with haplotype and to use as an aid in designing an additional clinical trial (or trials), as discussed elsewhere herein.

The database and analytical tools of the invention are envisioned to be useful in a variety of settings, including various research settings, pharmaceutical companies, hospitals, independent or commercial establishments. It is expected users will include physicians (e.g., for diagnosing a particular disease or prescribing a particular drug) pharmaceutical companies, generics companies, diagnostics companies, contract research organizations and managed care groups, including HMOs, and even patients themselves.

However, as discussed above, it is obvious that various aspects of the invention may be useful in other settings, such as in the agricultural and veterinary venues.

The following examples illustrate certain embodiments of the present invention, but should not be construed as limiting its scope in any way. Certain modifications and variations will be apparent to those skilled in the art from the teachings of the foregoing disclosure and the following examples, and these are intended to be encompassed by the spirit and scope of the invention.

2. Mednostics Program

The Mednostics™ program is a program in which one company, i.e., the HAP™ Company, uses HAP Technology to analyze variation in response to drugs currently marketed by third parties, in the hope of conferring a competitive advantage on these companies. It is expected that this technology will provide pharmaceutical companies with information that could lead to the development of new indications for existing drugs, as well as second generation drugs designed to replace existing drugs nearing the end of their patent life. As a result, the Mednostics program will benefit pharmaceutical companies by allowing them to extend the patent life of existing drugs, revitalize drugs facing competition and expand their existing market. Entities such as HMOs and other third-party payers, as well as pharmacy benefit management organizations, may also benefit from the Mednostics program.

The goals of the Mednostics™ program are to find HAP Markers that:

identify individuals who are currently not undergoing therapy for a given disease yet are at risk and will respond well to a given drug. This application would be useful in markets that have high growth potential and involve conditions that are undertreated, such as many central nervous system disorders and cardiovascular disease; and identify individuals who will respond better to one drug within a competitive class than other drugs in the same class or to one competing class of drugs as compared to another class of drugs. This application would allow drugs that are not selling well to gain a greater market share and would be best applied to a drug that was not the first introduced into the market and is having difficulty gaining market share against the established competitors. Alternatively, if multiple drug classes are indicated for the same disease, they could be differentiated by HAP Markers, thus giving drugs within one class a competitive advantage over the other class.

An example of the Mednostics™ program involves the statin class of drugs, which are used to treat patients with high cholesterol and lipid levels and who are therefore at risk for cardiovascular disease. This is a highly competitive market with multiple approved products seeking to gain increased market share. For example, three of the most commonly prescribed statins are pravastatin (sold by Bristol-Myers Squibb Company as Pravacol), atorvastatin (sold by Parke-Davis as Lipitor), and cerivastatin (sold by Bayer AG as Baycol). The statin market is currently approximately $11 billion worldwide and is forecasted to at least double in size by 2005. Identification of genetic markers that would allow the right drug to reach the right patient would allow a company to boost its market share and improve patient compliance, which are both particularly important factors when maximizing profit from drugs that are taken over the course of a lifetime.

H. EXAMPLE 1

Simulated Clinical Trial

For illustration, we will use a particular example that shows how the CTS™ method works, and how the DecoGen™ application is used. For this we have simulated a data set. Polymorphisms for the gene CYP2D6 were obtained from the literature. From those we constructed 10 haplotypes. A set of individual subjects were created and assigned a value of the variable "Test" in the range from 0.0–1.0. They were also assigned 2 of the haplotypes. This data set simulates what would come from a clinical trial in which patients were haplotyped and tested for some clinical variable. Most individuals have a relatively low value of the Test measure, but a small number have a large value. This simulates the case where a small number of individuals taking a medication have an adverse reaction. Our goal is to find genetic markers (i.e. haplotypes) that are correlated with this adverse event.

Step 1. Identify candidate genes. CYP2D6 is the sample candidate gene.

Step 2. Define a Reference Population. A standard population is used. An example is the CEPH families and unrelated individuals whose cell lines are commercially available. (Source Coriell Cell Repositories, URL: http://locus.umdnj.edu/nigms/ceph/ceph.html) Coriell sells cell lines from the CEPH families (a standard set of families from the United States and France for which cells lines are available for multiple members from several generations from several families) and from individuals from other ethnogeographic groups. The CEPH families have been widely studied. The cell lines were originally collected by Foundation Jean DAUSSET (http://landru.cephb.fr/).

Step 3. DNA from this reference population is obtained.

Step 4. Haplotype individuals in the reference population. We use either direct or indirect haplotyping methods, or a combination of both, to obtain haplotypes for the CYP2D6 gene in the reference population. The polymorphic sites and nucleotide positions for these individuals are given in FIGS. 4A and 4B.

Step 5. Get population averages and other statistics. The haplotypes and population distributions are shown using the DecoGen™ application in FIGS. 4A, 4B, 10, and 11. They are determined by the methods and equations descried in Item 5 above.

Step 6. Determine genotyping markers. By examining the linkage data (FIG. 15) we see that all of the sites are tightly linked except 2 and 8. This indicates that this set should be a minimal set for genotyping. From this it was decided to genotype patients in the clinical trial at only these sites.

Step 7. Recruit a trial population. In this case we use the reference population as the clinical population, having only added the simulated values of Test.

Step 8. Treat, test and haplotype patients. All patients are measured for the Test variable. All of the patients were then genotyped at sites 2 and 8 (i.e. unphased haplotypes were found at these sites). Next their haplotypes are found directly (for those individuals who were totally homozygous or heterozygous at any one site) or inferred using maximum likelihood methods based on the observed haplotype frequencies in the reference population.

Step 9. Find correlation's between haplotype pair and clinical outcome. We measure the value of Test.

First we examine the results of the single site regression model (FIG. 21) to determine to sites showing the strongest correlation with Test. From this we see that sites 2 and 8 have a strong correlation, at the 99% o confidence level.

The statistics for each of the sub-haplotype pair groups (using sites 2 and 8) is shown in FIGS. 18, 19, and 22. From this we see that individuals homozygous for TA at sites 2 and 8 have a high value of Test (average of 0.93). One conclusion we can make from this data is that patients homozygous for TA are likely to have an adverse reaction. A typical haplotype pair distribution is shown in detail in FIG. 20.

We can use the ANOVA calculation to see whether grouping individuals by haplotype-pair (or sub-haplotype-pair) helps explain the observed variation in response in a statistically significant way. If ANOVA indicates that there is a significant group-to-group variation, then we can investigate this correlation further using the regression and clinical modeling tools. From FIG. 23, we see that there is a significant level of group-to-group variation even at the 99% confidence level. This says that the haplotype-pair (or sub-haplotype pair) that an individual has for this gene does have a significant impact on that individual's value of Test.

Step 10. Follow-up trials are run. Additional trials should be run to accomplish 2 goals. The first would attempt to prove the correlation between being homozygous for haplotype TA and the high value of Test. One way to do this would be to enroll a group of subjects and break them into 4 cohorts. The first and second would be homozygous for TC. The second and third would have no copies of TC. The first and third group should take the medication causing the high value of Test and the second and fourth should take a placebo. The cohorts and their expected response are shown in the following matrix:

| Cohort 1 | Cohort 2 |
|---|---|
| TC/TC | TC/TC |
| Medication | Placebo |
| Expectation: High value of Test | Expectation: Low value of Test |
| Cohort 3 | Cohort 3 |
| Not-TC/not-TC | Not-TC/not-TC |
| Medication | Placebo |
| Expectation: Low value of Test | Expectation: Low value of Test |

If we see this pattern of response, then the link between TC homozygosity and high value of Test, the correlation is proven.

Step 11. Design a genotyping method to identify a relevant set of patients. Using the Genotype view tool in the DecoGen browser, we found that by genotyping individuals at sites 2 and 8 we could classify the group with high value of Test with 100% certainty. The results are shown in FIG. 14.

I. EXAMPLE 2

1. Provision of Clinical Data

DNA sequence information for a cohort of normal subjects was obtained and entered into the database as described previously. For this example, 134 patients, all of whom came to the clinic having an asthmatic attack, were recruited. Each patient had a standard spirometry workup upon entering the clinic, was given a standard dose of albuterol, and was given a followup spirometry workup 30 minutes later. Blood was drawn from each patient, and DNA was extracted from the blood sample for use in genotyping and haplotyping. Clinical data, in the form of the response of the asthmatic patients to a single dose of nebulized albuterol, was obtained from the asthmatic patients, as described previously (Yan, L., Galinsky, R. E., Bernstein, J. A., Liggett, S. B. & Weinshilboum, R. M. *Pharmacogenetics,* 2000, 10:261–266) The clinical data was entered into the database, and displayed as in FIG. 29B.

2. Determination of ADBR2 Genotypes and Haplotypes

Haplotypes for ADBR2 were determined using a molecular genotyping protocol, followed by the computational HAPBuilder procedure (See U.S. patent application Ser. No. 60/198,340 (inventors: Stephens, et al.), filed Apr. 18, 2000). Comparison of the sequences resulted in the identification of thirteen polymorphic sites.

The ADBR2 gene was selected from the screen shown in FIG. 26. The polymorphism and haplotype data for the ADBR2 gene among normal subjects was as displayed in FIG. 28. Only twelve different haplotypes were observed and/or inferred. Diplotype and haplotype data for the ADBR2 gene among the asthmatic patients was as displayed in FIG. 29A.

The heterozygosity of individual patients at each polymorphic site was as displayed in FIG. 30. At each polymorphic site (SNP), each patient has zero, one, or two copies of a given nucleotide. The same is true of combinations of SNPs: for any collection of two or more SNPs (i.e., a haplotype or sub-haplotype), a patient will have zero, one, or two alleles having that particular combination of SNPs.

3. Correlation of ADBR2 Haplotypes and Haplotype Pairs with Drug Response

The measure of delta % FEV1 pred. was chosen as the clinical outcome value for which correlations with ADBR2 haplotypes were to be sought.

a. Build-Up Procedure (to 4 SNP Limit)

Each individual SNP was statistically analyzed for the degree to which it correlated with "delta % FEV1 pred." The analysis was a regression analysis, correlating the number of occurrences of the SNP in each subject's genome (i.e. 0, 1, or 2), with the value of "delta % FEV1 pred."

"Cut-off" criteria were applied to each SNP in turn, as follows. In this example, a confidence limit of 0.05 was the default value for the tight cutoff, and a limit of 0.1 was the default value of the loose cutoff. The default values were automatically entered into the screen shown in FIG. 39A, in the two boxes labeled "Confidence". A SNP was then chosen from among the SNPs present in the population, and the p value calculated for correlation of this SNP with delta % FEV1 pred. was tested against the tight cutoff. If the value was 0.05 or less, the SNP and associated correlation data were stored for later calculations and for display in the screen shown in FIG. 39A. If the p value was between 0.05 and 0.1, the SNP and associated correlation data were stored without being displayed. Any SNP whose p value was greater than 0.1 was discarded, i.e., it was not considered further in the process. All thirteen ADBR2 SNPs were selected and tested in turn. The individual SNPs at positions 3 and 9 passed the tight cut-off; these were saved for display in FIG. 39A. In addition, the SNP at position 11 passed the loose cut-off and was saved without display.

All possible pair-wise combinations (sub-haplotypes) of the saved SNPs were then generated. The correlations of the newly generated two-SNP sub-haplotypes with delta % FEV1 pred. were calculated by regression analysis, as was done for the individual SNPs. The correlation of each sub-haplotype was tested in turn, as described above, discarding any sub-haplotypes whose p-value did not pass the cut-off criteria and saving those that did pass, with those that passed the tight cut-off stored for display in the screen shown in FIG. 39A. The sub-haplotypes that passed the tight cut-off were ********A*G, A***A, and A*****G; these were saved for display in FIG. 39A. No sub-haplotypes passed only the loose cut-off.

When all the two-SNP sub-haplotypes had been examined, all pair-wise combinations between originally saved SNPs and saved two-SNP sub-haplotypes, and among the saved two-SNP sub-haplotypes, were generated. This produced a collection of three-SNP and four-SNP subhaplotypes. Again, correlations were calculated by regression. A single three-SNP sub-haplotype, A***A*G**, passed the tight cut-off and was saved for display, and no four-SNP sub-haplotype passed. No sub-haplotypes passed only the loose cut-off. Combinations between the saved three-SNP sub-haplotypes and the saved SNPs generated four-SNP subhaplotypes, none of which passed the tight cut-off. No new combinations were possible within the default limit (four) to the number of SNPs permitted in the generated sub-haplotypes. (See FIG. 39A, where "fixed site=4" indicates the 4-SNP limit).

The results of the build-up process are shown in FIG. 39A, where the SNPs and sub-haplotypes that passed the tight cut-off are displayed along with results of the regression analyses. It was discovered that the three-SNP subhaplotype A***A*G has a p-value nearly identical to that of the full haplotype. FIG. 39B shows the regression line (response as a function of number of copies of haplotype A*****A*G**), indicating that the more copies of this marker a patient has, the lower the response.

b. Pare-Down Procedure (to 10 SNP Limit)

Each of the twelve haplotypes observed for the ADBR2 gene is analyzed for the degree to which it correlates with the value of delta % FEV1 pred. by a regression analysis, correlating the number of occurrences of the haplotype in the subject's genome, i.e. 0, 1, or 2, with the value of the clinical measurement A "tight cut-off" criterion is then applied to each haplotype in turn. A first haplotype is selected, and its correlation with delta % FEV1 pred. is tested against the tight cut-off of 0.05. If the value is 0.05 or less, the haplotype and associated correlation data are stored for later calculations and for display in the screen shown in FIG. 39A. If the p value is between 0.05 and 0.1, the haplotype and associated correlation data are stored as well but are not displayed. Any haplotype whose p value is greater than 0.1 is discarded, i.e., it is not considered further in the process. All twelve ADBR2 haplotypes are selected and tested in turn.

From the saved haplotypes, all possible sub-haplotypes in which a single SNP is masked are generated by systematically masking each SNP of all saved haplotypes. The correlations of the newly generated sub-haplotypes with the clinical outcome value are calculated by regression, as was done for the haplotypes themselves. Each newly generated sub-haplotype is tested against the tight and loose cut-offs as described above for the haplotype correlations, discarding sub-haplotypes that do not pass the cut-off criteria and saving those that do pass.

When the first generation of sub-haplotypes, having a single SNP masked, has been tested, a second generation of sub-haplotypes having a two SNPs masked is generated from those of the first generation whose p-values passed the cut-offs. This is done, as before, by systematically masking each of the remaining SNPs. The p-values of the second generation of sub-haplotypes, having two SNPs masked, are tested, and from those that pass the cut-offs a third generation having three SNPs masked is generated.

c. Cost Reduction

The frequencies for each of the twelve haplotypes of the ADBR2 gene were calculated and were found to be as shown in FIG. 28A (eleven of the twelve haplotypes are visible). A list of all 78 genotypes that could be derived from the 12 observed haplotypes was generated. A portion of the list is shown in FIG. 32. The expected frequency of each of these genotypes from the Hardy-Weinberg equilibrium was calculated, and is shown in the third column under each population group. Linkage between the polymorphic sites was as shown in FIG. 33.

A set of masks of the same length as the haplotype, i.e., thirteen sites in length, was created. A portion of the set of masks is shown in FIG. 34, along with a portion of the list of possible genotypes (haplotype pairs) which has been sorted by Hardy-Weinberg frequency.

For each mask, an ambiguity score was calculated as follows: all pairs of genotypes [i,j] that were rendered identical by imposition of the mask were noted, and the geometric mean of their Hardy-Weinberg frequencies ($f_i$ and $f_j$) was calculated. For each mask, all the geometric means of the frequencies of all the ambiguous pairs were added together, and the sum was multiplied by 10 to obtain the ambiguity score for that mask:

$$\text{ambiguity score} = 10\Sigma\sqrt{f_i f_j}$$

Ambiguity scores calculated in this manner are shown in FIG. 34 to the right of each of the displayed masks, along with the genotype pairs rendered ambiguous by the mask. (The genotype numbers refer to the row numbers in the first column of the sorted genotype list.)

From the data visible in FIG. 34, it may be seen that one can mask sites 1, 6, 7, 8, and 10 (five of the thirteen polymorphic sites in the ADBR2 gene) with an ambiguity score of only 0.072. This mask (sixteenth mask from the top) renders four genotypes (sets of haplotype pairs) ambiguous, and three of the four ambiguities are between common and rare haplotype pairs. It is thus discovered that a savings of about 38% in the variable cost of haplotyping this gene can be achieved, simply by measuring eight rather than all thirteen known polymorphic sites, and that the complete haplotype can be inferred with high confidence from this smaller data set.

J. REFERENCES

1) D. L. Hartl and A. G. Clark, "Principles of Population Genetics", Sinauer Associates, (Sunderland Mass.) 3rd Edition, 1997.
2) David H. Mathews, Jeffrey Sabina, Michael Zuker, and Douglas H. Turner; Expanded Sequence Dependence of Thermodynamic Parameters Improves Prediction of RNA Secondary Structure; Journal of Mol. Biol. in Press.
3) Nakamura, Y., Gojobori, T. and Ikemura, T. (1998) Nucl. Acids Res. 26, 334. The most recent human data is found at the web site: http://www.dna.affrc.go.jp/nakamura-bin/showcodon.cgi?species=Homo+sapiens+[gbpri]
4) L. D. Fisher and G. vanBelle, "Biostatistics: A Methodology for the Health Sciences", Wiley-Interscience (New York) 1993.
5) R. Judson, "Genetic Algorithms and Their Uses in Chemistry" in Reviews in Computational Chemistry, Vol. 10, pp. 1–73, K. B. Lipkowitz and D. B. Boyd, eds. (VCH Publishers, New York, 1997).
6) W. H. Press, S. A. Teukolsky, W. T. Vetterling, B. P. Flannery, "Numerical Recipes in C: The Art of Scientific Computing", Cambridge University Press (Cambridge) 1992.

7) E. Rich and K. Knight, "Artificial Intelligence", 2nd Edition (McGraw-Hill, New York, 1991).
8) A. Ecof and B. Smouse, Genetics Vol. 136, pp. 343–359 (1994) Using allele frequencies and geographic subdivision to reconstruct gene trees within species: molecular variance parsimony.
9) G. Ruano, K. Kidd, C. Stephens, Proc. Nat. Acad. Sci., Vol. 87, 6296–6300 (1990), Haplotype of multiple polymorphisms resolved by enzymatic amplification of single DNA molecules.
10) A. G. Clark, et al., Am. J. Hum. Genet., Vol. 63, 595–612 (1998), Haplotype Structure and population genetic inferences from nucleotide-sequence variation in human lipoprotein lipase.

All references cited in this specification, including patents and patent applications, are hereby incorporated in their entirely by reference. The discussion of references herein is intended merely to summarize the assertions made by their authors and no admission is made that any reference constitutes prior art. Applicants reserve the right to challenge the accuracy and pertinency of the cited references.

Modifications of the above described modes for carrying out the invention that are obvious to those of skill in the fields of chemistry, medicine, computer science and related fields are intended to be within the scope of the following claims.

TABLE OF CONTENTS

I. TITLE OF THE INVENTION
II. RELATED APPLICATIONS
III. FIELD OF THE INVENTION
IV. BACKGROUND OF THE INVENTION
V. SUMMARY OF THE INVENTION
VI. BRIEF DESCRIPTION OF THE DRAWINGS
VII. DETAILED DESCRIPTION OF THE INVENTION
  A. DEFINITIONS
  B. METHODS OF IMPLEMENTING THE INVENTION
  C. CTS™ METHODS OF THE INVENTION
    1. Illustration Using The CYP2D6 Gene
    2. Illustration With ADRB2 Gene
  D. IMPROVED METHODS
    1. Improved Method For Finding Optimal Genotyping Sites
    2. Improved Methods For Correlating Haplotypes With Clinical Outcome Variable(s)
      a. Multi-SNP Analysis Method (Build-Up Process)
      b. Reverse SNP Analysis Method (Pare-Down Process)
  E. TOOLS OF THE INVENTION
  F. DATA/DATABASE MODEL
    1. Database Model Version 1
      a. Submodels
      b. Abbreviations
      c. Tables
      d. Fields
    2. Database Model Version 2
      a. Submodels
      b. Abbreviations
      c. Tables
      d. Fields
  G. BUSINESS MODELS
    1. Hap2000 Partnership
      a. Partnership Benefits
        i. Isogenomics™ Database
        ii. Informatics Computer Program
        iii. Cohort Haplotyping
        iv. Isogene Clones
        v. Gene Selection by Partners
        vi. Patent Dossier
        vii. Committed Liaison
        viii. Special Services: cDNAs and Genomic Intervals
      b. Membership in the Partnership
      c. Envisioned Outcomes From The Partnership
    2. Mednostics Program
  H. EXAMPLE 1
  I. EXAMPLE 2
    1. Provision Of Clinical Data
    2. Determination Of ADBR2 Genotypes And Haplotypes
    3. Correlation Of ADBR2 Haplotypes And Haplotype Pairs With Drug Response
      a. Build-Up Procedure (To 4 SNP Limit)
      b. Pare-Down Procedure (To 10 SNP Limit)
      c. Cost Reduction
  J. REFERENCES
II. ABSTRACT OF THE INVENTION

We claim:

1. A method of determining polymorphic sites or sub-haplotypes for a locus that correlate with an outcome of interest, comprising:
(a) providing a haplotype for each allele of the locus for each subject in a cohort of subjects and an outcome value for the outcome of interest for each subject in the cohort of subjects, the locus comprising at least two polymorphic sites;
(b) statistically analyzing each individual polymorphism in the haplotypes for the degree to which it correlates with the outcome of interest and calculating a numerical measure of the degree of correlation;
(c) saving each individual polymorphism whose numerical measure of the degree of correlation meets a first cut-off criterion and its numerical measure of the degree of correlation;
(d) generating all possible pair-wise combinations of the saved individual polymorphisms so as to provide a set of n-site sub-haplotypes where n=2;
(e) statistically analyzing each newly generated n-site sub-haplotype for the degree to which it correlates with the outcome of interest and calculating the numerical measure of the degree of correlation;
(f) saving each n-site sub-haplotype whose numerical measure of the degree of correlation meets the first cut-off criterion and its numerical measure of the degree of correlation;
(g) generating all possible pair-wise combinations among and between the saved individual polymorphisms and saved sub-haplotypes, to produce new sub-haplotypes with increased values of n; and
(h) repeating steps (e) trough (g) until either (i) no new sub-haplotypes can be generated, or (ii) no new sub-haplotypes having n less than a pre-selected limit can be generated.

2. The method of claim 1, further comprising the step of displaying the saved individual polymorphisms and sub-haplotypes whose numerical measure of the degree of correlation meets a second cut-off criterion, wherein the second cut-off criterion is more stringent than the first cut-off criterion.

3. The method of claim 1, wherein the numerical measure of the degree of correlation is a p-value, and the first cut-off criterion is that the p-value is less than or equal to a first cut-off value.

4. The method of claim 3, further comprising the stop of displaying the saved individual polymorphisms and sub-haplotypes whose p-value is less than or equal to a second cut-off value, wherein the second cut-off value is less than the first cut-off value.

5. The method of any one of claims 1–4, further comprising the step of eliminating a complex redundant sub-haplotype generated from smaller saved, sub-haplotypes, wherein the numerical measure of the degree of correlation of each of the smaller saved sub-haplotypes is at least as significant as that of the complex redundant sub-haplotype.

6. The method of claim 2, further comprising displaying the numerical measure of the degree of correlation of each displayed individual polymorphism or sub-haplotype.

7. The method of claim 1, wherein providing comprises determining the haplotype for each allele of the locus for each subject and acquiring the outcome value for the outcome of interest for each subject.

8. A method of determining polymorphic sites or sub-haplotypes for a locus that correlate with an outcome of interest, comprising:
   (a) providing a haplotype for each allele of the locus for each subject in a cohort of subjects and an outcome value for the outcome of interest for each subject in the cohort, the locus comprising at least two polymorphic sites;
   (b) statically analyzing each haplotype for the degree to which it correlates with the outcome of interest, and calculating a numerical measure of the degree of correlation;
   (c) saving each haplotype whose numerical measure of the degree of correlation meets a first cut-off criterion and its numerical measure of the degree of correlation;
   (d) from each haplotype composed of m polymorphic sites, generating all possible sub-haplotypes having a single site masked, so as to provide a set of sub-haplotypes having (m-n) sites, where n=1;
   (e) statistically analyzing each newly generated sub-haplotype for the degree to which it correlates with the outcome of interest, and calculating the numerical measure of the degree of correlation;
   (f) saving each sub-haplotype whose numerical measure of the degree of correlation meets the first cut-off criterion and its numerical measure of the degree of correlation;
   (g) from the saved sub-haplotypes, generating all possible sub-haplotypes having one additional site masked; and
   (h) repeating steps (e) through (g) until either (i) no new sub-haplotypes or (ii) no further sub-haplotypes having more unmasked sites than a pre-selected limit can be generated.

9. The method of claim 8, further comprising the step of displaying those saved haplotypes and sub-haplotypes whose numerical measure of the degree of correlation meets a second cut-off criterion, wherein the second cut-off criterion is more stringent than the first cut off criterion.

10. The method of claim 8, wherein the numerical measure of the degree of correlation is a p-value and the first cut-off criterion is that the p-value is less than or equal to a first selected value.

11. The method of claim 10, further comprising the step of displaying those saved haplotypes and sub-haplotypes whose p-value is less than or equal to a second selected value, wherein the second selected value is less than the first selected value.

12. The method of any one of claims 8–11, further comprising the step of discarding a complex redundant sub-haplotype which is constructed from smaller saved sub-haplotypes, wherein the numerical measure of the degree of correlation of each of the smaller saved sub-haplotypes is at least as significant as that of the complex redundant sub-haplotype.

13. The method of claim 9, further comprising displaying the numerical measure of the degree of correlation of each displayed haplotype or sub-haplotype.

14. The method of claim 8, wherein providing comprises determining the haplotype for each allele of the locus for each subject and acquiring the outcome value for the outcome of interest for each subject.

15. A computer-usable medium having computer-readable program code stored thereon, for causing a computer to execute a method to determine polymorphisms or sub-haplotypes for a locus that correlate with an outcome of interest, the method comprising:
   (a) accessing a database comprising a haplotype for each allele of the locus for each subject in a cohort of subjects, and an outcome value for the outcome of interest for each subject in the cohort of subjects, the locus comprising at least two polymorphic sites;
   (b) statically analyzing each individual polymorphism in the haplotypes for the degree to which it correlates with the outcome of interest and calculating a numerical measure of the degree of correlation;
   (c) storing each individual polymorphism whose numerical measure of the degree of correlation meets a first cut-off criterion and its numerical measure of the degree of correlation;
   (d) generating all possible pair-wise combinations of the saved individual polymorphisms so as to provide a set of n-site sub-haplotypes where n=2;
   (e) statistically analyzing each newly generated n-site sub-haplotype for the degree to which it correlates with the outcome of interest and calculating the numerical measure of the degree of correlation;
   (f) storing each n-site sub-haplotype whose numerical measure of the degree of correlation meets the first cut-off criterion and its numerical measure of the degree of correlation;
   (g) generating all possible pair-wise combinations among and between the saved individual polymorphisms and saved sub-haplotypes, to produce new sub-haplotypes with increased values of n; and
   (h) repeating steps (e) through (g) until either (i) no new sub-haplotypes can be generated, or (ii) no new sub-haplotypes having n less than a pre-selected limit can be generated.

16. The computer-usable medium of claim 15, wherein the method further comprises displaying those saved individual polymorphisms and sub-haplotypes whose numerical measure of the degree of correlation meets a second cut-off criterion, wherein the second cut-off criterion is more stringent than the first cut-off criterion.

17. The computer-usable medium of claim 15, wherein the method further comprises displaying the saved individual polymorphisms and sub-haplotypes whose p-value does not exceed a second cut-off value, wherein the second cut-off value is less than the it cut-off value.

18. The computer-useable medium of claim 15, wherein the method further comprises eliminating a complex redundant subhaplotype generated from smaller saved sub-haplotypes, wherein the numerical measure of the degree of correlation of each of the smaller saved sub-haplotypes is at least as significant as that of the complex redundant sub-haplotype.

19. A computer-usable medium having computer-readable program code stored thereon, for causing a computer to execute a method to determine polymorphic sits or sub-haplotypes for a locus that correlate with an outcome of interest, the method comprising:
(a) accessing a database comprising a haplotype from each allele of the locus for each subject in a cohort of subjects and an outcome value for the outcome of interest for each subject in the cohort of subjects, the locus comprising at least two polymorphic sites;
(b) statistically analyzing each individual polymorphism in the haplotypes for the degree to which it correlates with the outcome of interest and calculating the p-value for the correlation;
(c) storing each individual polymorphism whose p-value does not exceed a first cut-off value and its p-value;
(d) generating all possible pair-wise combinations of the saved individual polymorphisms so as to provide a set of n-site sub-haplotypes where n=2;
(e) statistically analyzing each newly generated n-site sub-haplotype for the degree to which it correlates with the outcome of interest and calculating the p-value for the correlation;
(f) storing each n-site sub haplotype whose p-value does not exceed the first cut-off value and its p-value;
(g) generating all possible pair-wise combinations among and between the saved individual polymorphisms and saved sub-haplotypes, to produce new subhaplotypes with increased values of n; and
(h) repeating steps (e) through (g) until either (i) no new sub-haplotypes can be generated, or (ii) no new sub-haplotypes having n less than a pre-selected limit can be generated.

20. A computer-usable medium having computer-readable program code stored thereon, for causing a computer to execute a method to determine polymorphic sites or sub-haplotypes for a locus that correlate with an outcome of interest, the method comprising:
(a) accessing a database comprising a haplotype for each allele of the locus for each subject in a cohort of subjects and an outcome value for the outcome of interest for each subject in the cohort of subjects, the locus comprising at least two polymorphic sites;
(b) statistically analyzing each haplotype for the degree to which it correlates with the outcome of interest, and calculating a numerical measure of the degree of correlation;
(c) storing each haplotype whose numerical measure of the degree of correlation meets a first cut-off value criterion and its numerical measure of the degree of correlation;
(d) generating, from each haplotype composed of m polymorphic sites, all possible sub-haplotypes having a single site masked, so as to provide a set of m-n site sub-haplotypes where n=1;
(e) statistically analysing each newly generated sub-haplotype for the degree to which it correlates with the outcome of interest, and calculating the numerical measure of the degree of correlation;
(f) storing each sub-haplotype whose numerical measure of the degree of correlation meets the first cut-off criterion and its numerical measure of the degree of correlation;
(g) generating, from the stored sub-haplotypes, all possible sub-haplotypes having one additional site masked; and
(h) repeating steps (e) through (g) until either (i) no new sub-haplotypes, or (ii) no further sub-haplotypes having more unmasked sites than a pre-selected limit can be generated.

21. The computer-usable medium of claim 20, wherein the method further comprises displaying those stored haplotypes and sub-haplotypes whose numerical measure of the degree of correlation meets a second cut-off criterion, wherein the second cut-off criterion is more stringent than the first cut-off criterion.

22. A computer-usable medium having computer-readable program code stored thereon, for causing a computer to execute a method to determine polymorphic sites or sub-haplotypes for a locus that correlate with an outcome of interest, the method comprising:
(a) accessing a database comprising a haplotype for each allele of the locus for each subject in a cohort of subjects and an outcome value for the outcome of interest for each subject in the cohort of subjects, the locus comprising at least two polymorphic sites;
(b) statistically analyzing each haplotype for the degree to which it correlates with the outcome of interest, and calculating the p-value for the correlation;
(c) storing each haplotype whose p-value does not exceed a first cut-off value and its p-value;
(d) generating, for each haplotype composed of m polymorphic sites, all possible sub-haplotypes having a single site masked, so as to provide a set of m-n site sub-haplotypes where n=1;
(e) statistically analyzing each newly generated sub-haplotype for the degree to which it correlates with the outcome of interest, and calculating the p-value for the correlation;
(f) storing those sub-haplotypes whose p-value does not exceed the first out-off value and its p-value;
(g) generating, from the stored sub-haplotypes, all possible sub-haplotypes having one additional site masked; and
(h) repeating steps (e) through (g) until either (i) no new sub-haplotypes, or (ii) no further sub-haplotypes having more unmasked sites than a pre selected limit can be generated.

23. The computer-usable medium of claim 22, wherein the method further comprises displaying those stored haplotypes and sub-haplotypes whose p-value does not exceed a second cut-off value, wherein the second cut-off value is less than the first cut-off value.

24. The computer-usable medium of claim 22, wherein the method further comprises discarding a complex redundant sub-haplotype which is constructed from smaller stored sub-haplotypes, wherein the p-value of each of the smaller sub-haplotypes is at least as significant at that of the complex redundant sub-haplotype.

25. A computer programmed to execute a method to determine polymorphic sites or sub-haplotypes for a locus that correlates with an outcome of interest, the computer comprising a memory having at least one region for storing computer executable program code and a processor for executing the program code stored in memory wherein the method comprises:
(a) accessing a database comprising a haplotype for each allele of the locus for each subject in a cohort of subjects and an outcome value for the outcome of interest for each subject in the cohort of subjects, the locus comprising at least two polymorphic sites;
(b) statistically analyzing each individual polymorphism in the haplotype for the degree to which it correlates with the outcome of interest and calculating a numerical measure of the degree of correlation;

(c) saving each individual polymorphism whose numerical measure of the degree of correlation meets a first cut-off criterion and its numerical measure of the degree of correlation;

(d) generating all possible pair-wise combinations of the saved individual polymorphism so as to provide a set of n-site sub-haplotypes where n=2;

(e) statistically analyzing each newly generated n-site sub-haplotype for the degree to which it correlates with the outcome of interest and calculating the numerical measure of the degree of correlation;

(f) saving each n-site sub-haplotype whose numerical measure of the degree of correlation meets the first cut-off criterion ad its numerical measure of the degree of correlation;

(g) generating all possible pair-wise combinations among and between the saved individual polymorphisms and saved sub-haplotypes, to produce new sub-haplotypes with increased values of n; and (h) repeating steps (e) through (g) until either (i) no new sub-haplotypes can be generated, or (ii) no new sub-haplotypes having n less than a pre-selected limit can be generated.

26. The computer of claim 25, wherein the method further comprises displaying those saved individual polymorphisms and sub-haplotypes whose numerical measure of the degree of correlation meets a second cut-off criterion, wherein the second cut-off criterion is more stringent than the first cut-off criterion.

27. The computer of claim 25, wherein the method further comprises displaying those saved individual polymorphisms and sub-haplotypes whose p-value does not exceed a second cut-off value, wherein the second cut-off value is less than the first cut-off value.

28. The computer of any one of claims 25–26, wherein the method further comprises discarding a complex redundant sub-haplotype which is generated from smaller saved sub-haplotypes, wherein the numerical measure of the degree of correlation of each of the smaller saved sub-haplotypes is at least as significant as that of the complex redundant sub-haplotype.

29. A computer programmed to execute a method to determine polymorphic sites or sub-haplotypes for a locus that correlate with an outcome of interest, the computer comprising a memory having at least one region for storing computer executable program code and a processor for executing the program code stored in memory, wherein the method comprises:

(a) accessing a database comprising a haplotype for each allele of the locus for each subject in a cohort of subjects and an outcome value for the outcome of interest for each subject in the cohort of subjects, the locus comprising at least two polymeric sites;

(b) statistically analyzing each individual polymorphism in the haplotype for the degree to which it correlates with the outcome of interest and calculating a p-value for the correlation;

(c) saving each individual polymorphism whose p-value does not exceed a first cut-off value and its p-value;

(d) generating all possible pair-wise combinations of the saved individual polymorphisms so as to provide a set of n-site sub-haplotypes where n=2;

(e) statistically analyzing each newly generated n-site sub-haplotype for the degree to which it correlates with the outcome of interest and calculating the p-value for the correlation;

(f) saving each n-site sub-haplotype whose p-value does not exceed the first cut-off value and its p-value;

(g) generating all possible pair-wise combinations among and between the saved individual polymorphisms and saved sub-haplotypes, to produce new sub-haplotypes with increased values of n; and (h) repeating steps (e) through (g) until either (i) no new sub-haplotypes can be generated, or (ii) no new sub-haplotypes having n less than a pre-selected limit can be generated.

30. A computer programmed to execute a method to determine polymorphic sites or sub-haplotypes for a locus that correlate with an outcome of interest, the computer comprising a memory having at least one region for storing computer executable program code and a processor for executing the program code stored in memory, wherein the method comprises:

(a) accessing a database comprising a haplotype for each allele of the locus for each subject in a cohort of subjects and an outcome value for the outcome of interest for each subject in the cohort of subjects, the locus comprising at least two polymorphic sites;

(b) statistically analyzing each haplotype for the degree to which it correlates with the outcome of interest, and calculating a numerical measure of the degree of correlation;

(c) saving each haplotype whose numerical measure of the degree of correlation meets a first cut-off criterion and its numerical measure of the degree of correlation;

(d) generating, from each haplotype composed of m polymorphic sites, all possible sub-haplotypes having a single site masked, so as to provide a set of m-n site sub-haplotypes where n=1;

(e) statistically analyzing each newly generated sub-haplotype for the degree to which it correlates with the outcome of interest, and calculating the numerical measure of the degree of correlation;

(f) saving each sub-haplotype whose numerical measure of the degree of correlation meets the first cut-off criterion and its numerical measure of the degree of correlation;

(g) generating, form the saved sub-haplotypes, all possible sub-haplotypes having one additional site masked; and (h) repeating steps (e) through (g) until either (i) no new sub-haplotypes, or (ii) no further sub-haplotypes having more unmasked sites than a pre-selected limit can be generated.

31. The computer of claim 30, wherein the method further comprises displaying those saved haplotypes and sub-haplotypes whose numerical measure of the degree of correlation meets a second cut-off criterion, wherein the second cut-off criterion is more stringent than the first cut-off criterion.

32. A computer programmed to execute a method to determine polymorphic sites or sub-haplotypes for a locus that correlate with an outcome of interest, the computer comprising a memory having at least one region for storing computer executable program code and a processor for executing the program code stored in memory, wherein the method comprises:

(a) accessing a database comprising a haplotype for each allele of the locus for each subject in a cohort of subjects and an outcome value for the outcome of interest for each subject in the cohort of subjects, the locus comprising at least two polymorphic sites;

(b) statistically analyzing each haplotype for the degree to which it correlates with to outcome of interest, and calculating a p-value for the correlation;

(c) saving each haplotype whose p-value does not exceed a first cut-off value and its p-value;

(d) generating, from each haplotype composed of m polymorphic sites, all possible sub-haplotypes having a single site masked, so as to provide a set of m-n site sub-haplotypes where n=1;

(e) statistically analyzing each newly generated sub-haplotype for the degree to which it correlates with the outcome of interest, and calculating the p-value for the correlation;

(f) saving each sub-haplotype whose p-value does not exceed the first cut-off value and its p-value;

(g) generating, from the saved sub-haplotypes, all possible sub-haplotypes having one additional site masked; and (h) repeating steps (e) through (g) until either (i) no new sub-haplotypes or (ii) no further sub-haplotypes having more unmasked sites than a pre-selected limit can be generated.

33. The computer of claim 32, wherein the method further comprises displaying those saved haplotypes and sub-haplotypes whose p-value des not exceed a second cut-off value, wherein the second cut-off value is less than the first cut-off value.

34. The computer of any one of claims 30–31, wherein the method further comprises discarding a complex redundant sub-haplotype which is constructed from smaller saved sub-haplotypes, wherein the numerical measure of the degree of correlation of each of the smaller saved sub-haplotypes is at least as significant as that of the complex redundant sub-haplotype.

35. A method of determining polymorphic sites or sub-haplotypes for a locus that correlate with an outcome of interest, comprising:

(a) providing a haplotype for each allele of the locus for each subject in a cohort of subjects and an outcome value for the outcome of interest for each subject in the cohort of subjects, the locus comprising at least two polymorphic sites;

(b) statistically analyzing each individual polymorphism in the haplotypes for the degree to which it correlates with the outcome of interest and calculating a numerical measure of the degree of correlation;

(c) saving each individual polymorphism whose numerical measure of the degree of correlation meets a first cut-off criterion for statistical significance;

(d) generating all possible pair-wise combinations of the saved individual polymorphisms so as to provide a set of n-site sub-haplotypes where n=2;

(e) statically analyzing each newly generated n-site sub-haplotype for the degree to which it correlates with the outcome of interest and calculating the numerical measure of the degree of correlation;

(f) saving each n-site sub-haplotype whose numerical measure of the degree of correlation meets the first cut-off criterion;

(g) generating all possible pair-wise combinations among and between the saved individual polymorphisms and saved sub-haplotypes, to produce new sub-haplotypes with increased values of n; and (h) repeating steps (e) through (g) until either (i) no new sub-haplotypes or (ii) no new sub-haplotypes having n less than a pre-selected limit can be generated.

36. The method of claim 35, wherein providing comprises determining the haplotype for each allele of the locus for each subject and acquiring the outcome value for the outcome of interest for each subject.

37. The method of claim 35, further comprising saving the numerical measure of the degree of correlation of each saved individual polymorphism or sub-haplotype.

* * * * *